United States Patent
Bohm et al.

(10) Patent No.: US 12,029,560 B2
(45) Date of Patent: Jul. 9, 2024

(54) ANALYTE SENSOR WITH IMPEDANCE DETERMINATION

(71) Applicant: DexCom, Inc., San Diego, CA (US)

(72) Inventors: Sebastian Bohm, San Diego, CA (US); Anna Claire Harley-Trochimczyk, San Diego, CA (US); Daiting Rong, San Diego, CA (US); Rui Ma, San Diego, CA (US); Wenjie Lan, San Diego, CA (US); Minglian Shi, San Diego, CA (US); Disha B. Sheth, Oceanside, CA (US); Nicholas Kalfas, San Diego, CA (US); Vincent P. Crabtree, San Diego, CA (US); Kamuran Turksoy, Clarksburg, MD (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 16/728,765

(22) Filed: Dec. 27, 2019

(65) Prior Publication Data
US 2020/0205702 A1 Jul. 2, 2020

Related U.S. Application Data

(60) Provisional application No. 62/786,116, filed on Dec. 28, 2018, provisional application No. 62/786,127, (Continued)

(51) Int. Cl.
*A61B 5/1495* (2006.01)
*A61B 5/00* (2006.01)
(Continued)

(52) U.S. Cl.
CPC .......... *A61B 5/1495* (2013.01); *A61B 5/0537* (2013.01); *A61B 5/14532* (2013.01);
(Continued)

(58) Field of Classification Search
CPC . A61B 5/1495; A61B 5/0537; A61B 5/14532; A61B 5/14546; A61B 5/1473;
(Continued)

(56) References Cited

U.S. PATENT DOCUMENTS

| | | | |
|---|---|---|---|
| 5,800,420 | A | 9/1998 | Gross et al. |
| 6,001,067 | A | 12/1999 | Shults et al. |

(Continued)

FOREIGN PATENT DOCUMENTS

| | | |
|---|---|---|
| GB | 1505343 A | 3/1978 |
| JP | 2000171431 A | 6/2000 |

(Continued)

OTHER PUBLICATIONS

International Search Report and Written Opinion dated Apr. 16, 2020 for Application No. PCT/US2019/068713.

*Primary Examiner* — Navin Natnithithadha
(74) *Attorney, Agent, or Firm* — Schwegman, Lundberg & Woessner, P.A.

(57) ABSTRACT

Various examples are directed to systems and methods of and using analyte sensors. An example analyte sensor system comprises an analyte sensor and a hardware device in communication with the analyte sensor. The hardware device may be configured to perform operations comprising applying a first bias voltage to the analyte sensor, the first bias voltage less than an operational bias voltage of the analyte sensor, measuring a first current at the analyte sensor when the first bias voltage is applied, and applying a second bias voltage to the analyte sensor. The operations may further comprise measuring a second current at the analyte sensor when the second bias voltage is applied, detecting a plateau bias voltage using the first current and the second (Continued)

current, determining that the plateau bias voltage is less than a plateau bias voltage threshold, and executing a responsive action at the analyte sensor.

18 Claims, 66 Drawing Sheets

Related U.S. Application Data filed on Dec. 28, 2018, provisional application No. 62/786,208, filed on Dec. 28, 2018, provisional application No. 62/786,166, filed on Dec. 28, 2018, provisional application No. 62/786,228, filed on Dec. 28, 2018.

(51) Int. Cl.

| | | |
|---|---|---|
| A61B 5/0537 | (2021.01) | |
| A61B 5/145 | (2006.01) | |
| A61B 5/1473 | (2006.01) | |
| A61B 5/1486 | (2006.01) | |
| G01N 27/22 | (2006.01) | |
| G01N 27/24 | (2006.01) | |
| G01N 33/487 | (2006.01) | |
| G01N 27/02 | (2006.01) | |

(52) U.S. Cl.
CPC ........ *A61B 5/14546* (2013.01); *A61B 5/1473* (2013.01); *A61B 5/1486* (2013.01); *A61B 5/14865* (2013.01); *A61B 5/6844* (2013.01); *G01N 27/221* (2013.01); *G01N 27/24* (2013.01); *G01N 33/48707* (2013.01); *A61B 5/0004* (2013.01); *A61B 5/0031* (2013.01); *A61B 2560/0223* (2013.01); *A61B 2560/0252* (2013.01); *A61B 2560/0276* (2013.01); *G01N 27/026* (2013.01)

(58) Field of Classification Search
CPC . A61B 5/1486; A61B 5/14865; A61B 5/6844; A61B 5/0004; A61B 5/0031; A61B 2560/0252; A61B 2560/0223; A61B 2560/0276; A61B 5/0024; A61B 5/0205; A61B 5/1459; A61B 2560/0214; A61B 2560/028; A61B 2562/168; A61B 5/1468; A61B 5/6832; G01N 27/24; G01N 26/026; G01N 33/48707; G01N 27/221; G01N 27/026; G01N 27/02; G01N 27/3271
USPC .......................................... 600/309, 345–366
See application file for complete search history.

(56) References Cited

U.S. PATENT DOCUMENTS

| | | |
|---|---|---|
| 6,424,847 B1 | 7/2002 | Mastrototaro et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,565,509 B1 | 5/2003 | Say et al. |
| 6,579,690 B1 | 6/2003 | Bonnecaze et al. |
| 7,494,465 B2 | 2/2009 | Brister et al. |
| 8,372,266 B2 | 2/2013 | Biswas et al. |
| 8,682,408 B2 | 3/2014 | Boock et al. |
| 8,834,707 B2 | 9/2014 | Milam et al. |
| 9,044,199 B2 | 6/2015 | Brister et al. |
| 9,481,917 B2 | 11/2016 | Bochiechio et al. |
| 9,808,190 B2 | 11/2017 | Bohm et al. |
| 2002/0098119 A1 | 7/2002 | Goodman |
| 2003/0191376 A1 | 10/2003 | Samuels et al. |
| 2005/0027463 A1 | 2/2005 | Goode, Jr. et al. |
| 2005/0043598 A1 | 2/2005 | Goode, Jr. et al. |
| 2006/0020187 A1 | 1/2006 | Brister et al. |
| 2007/0027385 A1 | 2/2007 | Brister et al. |
| 2007/0128681 A1 | 6/2007 | Barman et al. |
| 2007/0197890 A1 | 8/2007 | Boock et al. |
| 2008/0108942 A1 | 5/2008 | Brister et al. |
| 2008/0119703 A1 | 5/2008 | Brister et al. |
| 2008/0156661 A1 | 7/2008 | Cooper et al. |
| 2010/0196203 A1 | 8/2010 | Sanghera et al. |
| 2011/0024307 A1 | 2/2011 | Simpson et al. |
| 2012/0003687 A1 | 1/2012 | Toner et al. |
| 2012/0004524 A1 | 1/2012 | Van Antwerp et al. |
| 2012/0262298 A1 | 10/2012 | Böhm et al. |
| 2012/0265037 A1 | 10/2012 | Bohm et al. |
| 2013/0245981 A1 | 9/2013 | Estes et al. |
| 2014/0005509 A1 | 1/2014 | Bhavaraju et al. |
| 2015/0351672 A1 | 12/2015 | Vanslyke et al. |
| 2017/0181672 A1 | 6/2017 | Nogueira et al. |
| 2017/0184527 A1 | 6/2017 | Nogueira et al. |
| 2017/0228345 A1 | 8/2017 | Gupta et al. |
| 2017/0281092 A1 | 10/2017 | Burnette et al. |
| 2017/0311852 A1 | 11/2017 | Morgan |
| 2018/0279928 A1 | 10/2018 | Previl |
| 2018/0325430 A1 | 11/2018 | Vaddiraju et al. |
| 2018/0372667 A1 | 12/2018 | Gupta |
| 2019/0004005 A1 | 1/2019 | Oja et al. |
| 2019/0227022 A1 | 7/2019 | Harley-Trochimczyk et al. |

FOREIGN PATENT DOCUMENTS

| | | | | |
|---|---|---|---|---|
| JP | 2015509803 A | * | 4/2015 | ............. G01N 33/66 |
| WO | 2012154548 A1 | | 11/2012 | |
| WO | 2019007842 A1 | | 1/2019 | |

* cited by examiner

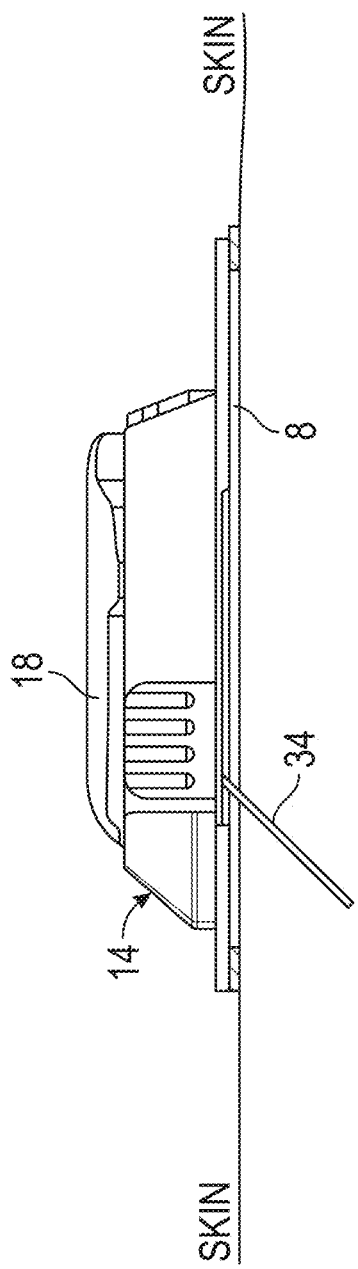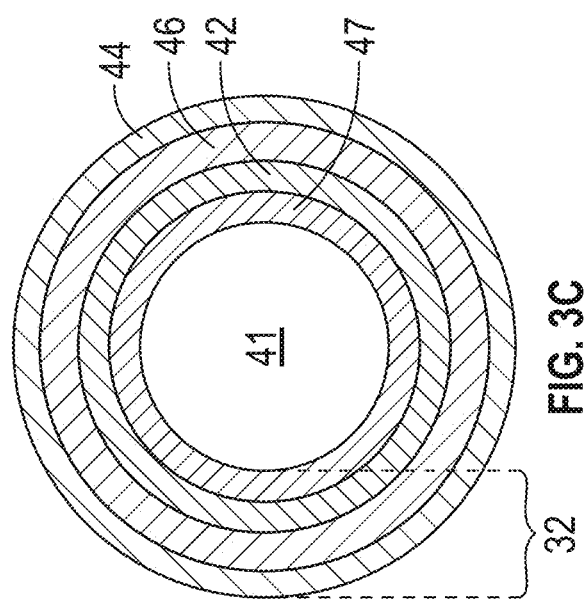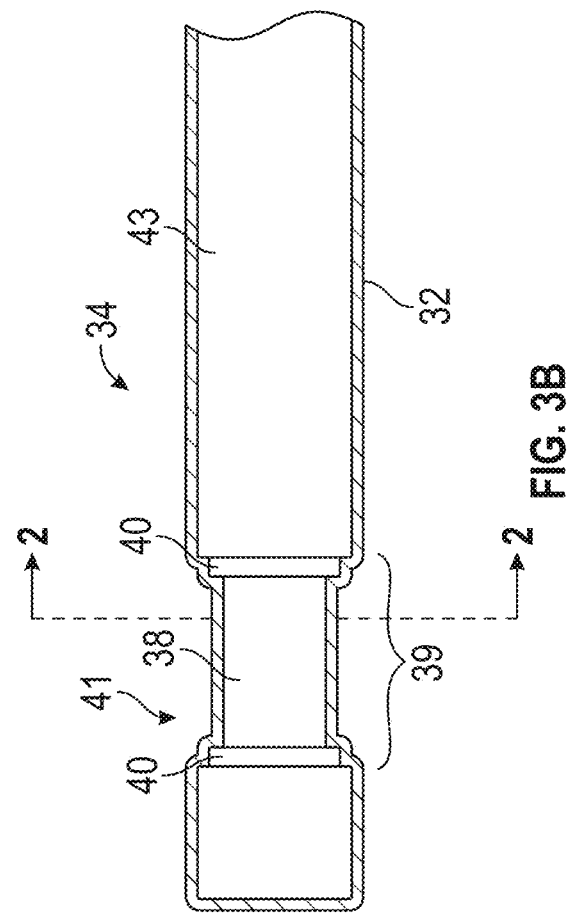

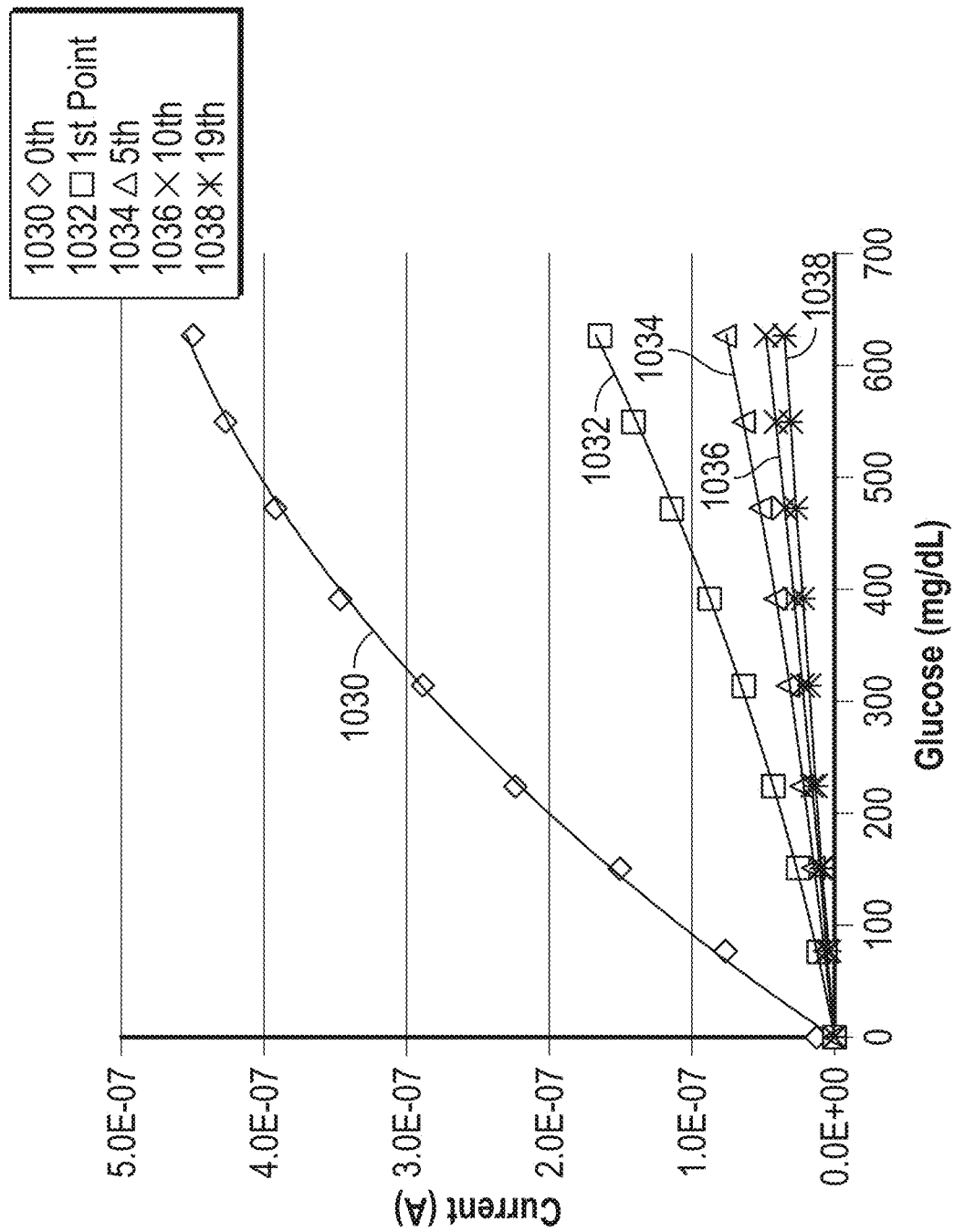

Damage Level 0
(No Damage)

Damage Level 1

Damage Level 4

Damage Level 7

Damage Level 8

Simplified Equivalent Circuit of Sensor

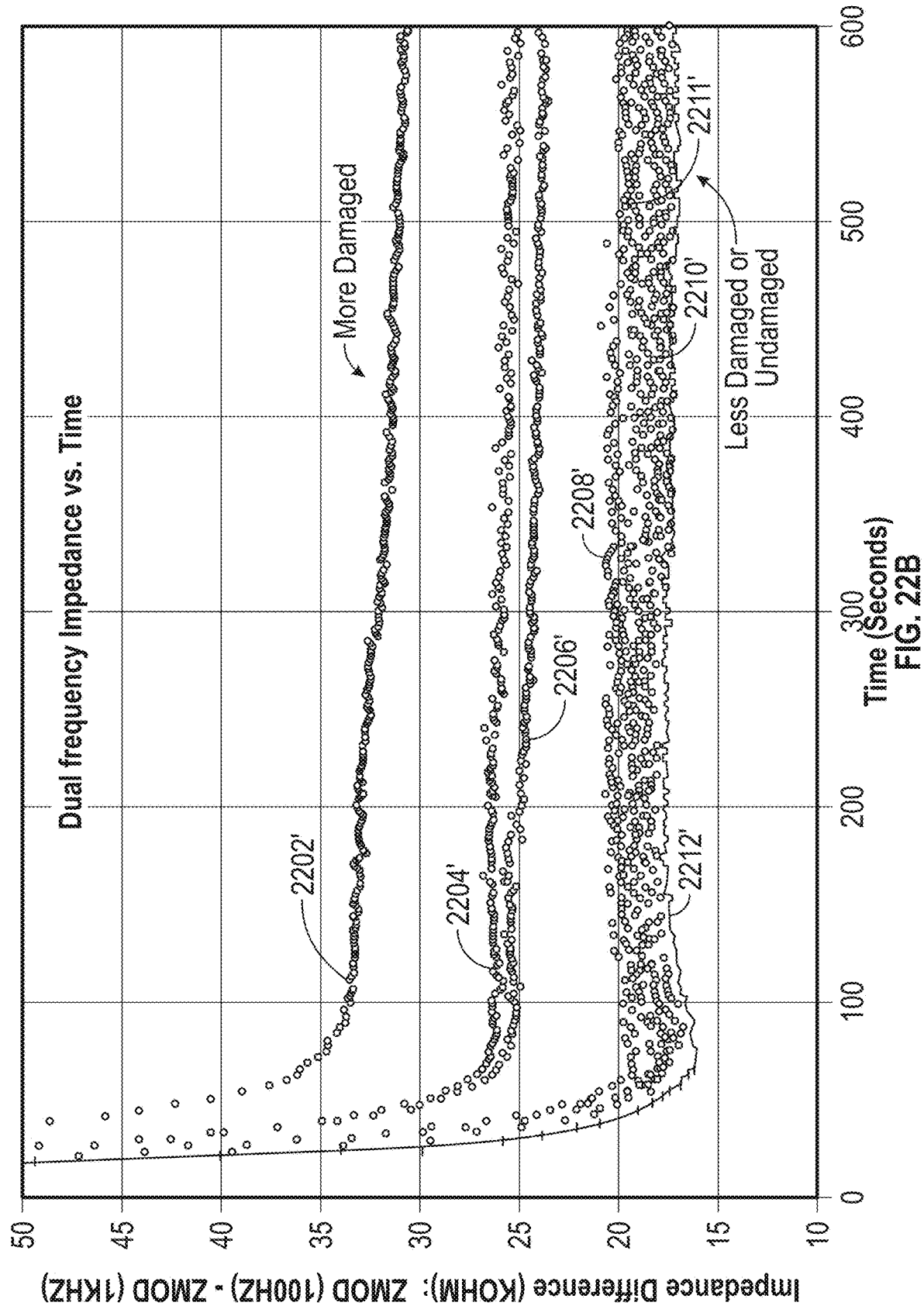

| Algo | MARD Percentiles | | | RMSE (pA/mg/dL) | % RMSE |
|---|---|---|---|---|---|
| | 2.5%-tile | Median | 97.5%-tile | | |
| FC | 10.21 | 11.66 | 13.38 | 4.88 | 15.36 |
| FC Local | 8.98 | 10.20 | 11.33 | 4.30 | 14.62 |
| Impd | 9.12 | 10.29 | 11.53 | 4.35 | 14.84 |
| Impd+cc | 8.92 | 10.12 | 11.29 | 4.27 | 14.55 |
| Impd+T | 8.70 | 9.87 | 11.14 | 4.28 | 14.60 |
| Impd+T+cc | 8.04 | 9.38 | 10.69 | 4.11 | 13.97 |

902610_022_351_223PVX_5238322_815042B_TEST1_062718_150854

ANALYTE SENSOR WITH IMPEDANCE DETERMINATION

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application Ser. No. 62/786,166, filed on Dec. 28, 2018, U.S. Provisional Application Ser. No. 62/786,116, filed on Dec. 28, 2018, U.S. Provisional Application Ser. No. 62/786,208, filed on Dec. 28, 2018, U.S. Provisional Application Ser. No. 62/786,127, filed on Dec. 28, 2018, and U.S. Provisional Application Ser. No. 62/786,228, filed on Dec. 28, 2018. Each of the aforementioned applications is incorporated by reference herein in its entirety, and each is hereby expressly made a part of this specification.

TECHNICAL FIELD

The present development relates generally to medical devices such as analyte sensors, and more particularly, but not by way of limitation, to systems, devices, and methods that use impedance measurements in a continuous glucose monitoring system.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A continuous glucose monitor may provide the wearer (patient) with information, such as an estimated blood glucose level or a trend of estimated blood glucose levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This present application discloses, among other things, systems, devices, and methods for use of impedance or conductance measurements or estimates in an analyte sensor, such as a glucose sensor.

Example 1 is a method comprising disconnecting an analyte sensor from a measurement circuit and reconnecting the analyte sensor to the measurement circuit after an accumulation period. The subject matter of Example 1 may also comprise receiving a signal from the analyte sensor, where the signal is indicative of an amount of charge accumulated on the analyte sensor during the accumulation period. The subject matter of Example 1 may further comprise determining an estimated analyte concentration level based on the received signal.

In Example 2, the subject matter of Example 1 optionally includes using a gate circuit to disconnect and reconnect the analyte sensor.

In Example 3, the subject matter of any one or more of Examples 1-2 optionally includes determining a membrane status based on the analyte signal received after reconnection of the analyte sensor to the measurement circuit.

In Example 4, the subject matter of any one or more of Examples 1-3 optionally includes wherein the disconnection and reconnection of the analyte sensor improves a signal to interference ratio of the analyte sensor.

In Example 5, the subject matter of any one or more of Examples 1-4 optionally includes measuring an open cell potential during the accumulation period and determining a membrane status based on one or more open cell potentials.

In Example 6, the subject matter of any one or more of Examples 3-5 optionally includes wherein the membrane status includes an interference status.

In Example 7, the subject matter of any one or more of Examples 3-6 optionally includes wherein the membrane status includes a damage or defect status.

In Example 8, the subject matter of Example 7 optionally includes monitoring a current profile after reconnecting the analyte sensor and detecting a membrane fault using the current profile.

In Example 9, the subject matter of any one or more of Examples 7-8 optionally includes determining an impedance characteristic and detecting a membrane fault responsive to the impedance characteristic satisfying a condition.

In Example 10, the subject matter of Example 9 optionally includes wherein the impedance characteristic is an estimated membrane impedance, a first derivative of impedance, a second derivative impedance, or a fitted curve.

Example 11 is a continuous analyte sensor comprising an analyte sensor, and sensor electronics operatively coupled to the analyte sensor to receive a signal indicative of glucose concentration from the analyte sensor. The sensor electronics may comprise a measurement circuit. The sensor electronics may disconnect the measurement circuit from the analyte sensor and reconnect the analyte sensor to the measurement circuit after an accumulation period. The measurement circuit may measure an accumulated charge from the analyte sensor after reconnection of the analyte sensor to the measurement circuit.

In Example 12, the subject matter of Example 11 optionally includes the sensor electronics determining an estimated analyte concentration level based on the measurement of the accumulated charge.

In Example 13, the subject matter of any one or more of Examples 11-12 optionally includes the sensor electronics comprising a gate circuit to disconnect and reconnect the analyte sensor from the measurement circuit.

In Example 14, the subject matter of any one or more of Examples 11-13 optionally includes the sensor electronics determining a membrane status based on a profile of an analyte signal received after reconnection of the analyte sensor to the measurement circuit.

In Example 15, the subject matter of any one or more of Examples 11-14 optionally includes the disconnection and reconnection of the analyte sensor improving a signal to interference ratio of the analyte sensor.

In Example 16, the subject matter of any one or more of Examples 11-15 optionally includes the sensor electronics measuring an open cell potential during a period of time that the analyte sensor is disconnected and determining a membrane status based on a profile of the open cell potential.

In Example 17, the subject matter of any one or more of Examples 14-16 optionally includes the membrane status including an interference status.

In Example 18, the subject matter of any one or more of Examples 14-17 optionally includes the membrane status including a damage or defect status.

In Example 19, the subject matter of Example 18 optionally includes the sensor electronics monitoring a current profile of the signal received from the analyte sensor after reconnecting the analyte sensor and detecting a membrane fault using the current profile.

In Example 20, the subject matter of any one or more of Examples 18-19 optionally includes the sensor electronics determining an impedance characteristic and detect a membrane fault responsive to the impedance characteristic satisfying a condition.

Example 21 is a method comprising applying a biphasic pulse to a continuous analyte sensor circuit, integrating a current response to the biphasic pulse, and determining an estimated impedance using the integrated current response.

In Example 22, the subject matter of any one or more of Examples 1-21 optionally includes compensating a sensor sensitivity using the determined impedance.

In Example 23, the subject matter of Example 22 optionally includes determining impedance using a signal at a frequency that avoid an effect of a double-layer membrane capacitance on the impedance.

In Example 24, the subject matter of any one or more of Examples 22-23 optionally includes wherein compensation is based on impedance and one or more additional factors.

In Example 25, the subject matter of Example 24 optionally includes the one or more additional factors including temperature, a calibration curve, or both.

In Example 26, the subject matter of Example 25 optionally includes the compensation using a transmitter temperature, and the transmitter temperature is filtered using Greene's function.

In Example 27, the subject matter of any one or more of Examples 1-26 optionally includes using the determined impedance to determine humidity of an environment of the sensor.

In Example 28, the subject matter of Example 27 optionally includes detection of humidity during transportation of the sensor.

In Example 29, the subject matter of any one or more of Examples 27-28 optionally includes detection of humidity during storage of the sensor.

In Example 30, the subject matter of any one or more of Examples 27-29 optionally includes compensating a sensor sensitivity based upon the determined humidity.

In Example 31, the subject matter of any one or more of Examples 27-30 optionally includes declaring an alert based upon a determined humidity.

In Example 32, the subject matter of Example 31 optionally includes delivering an alert using a smart device to alert a user that a sensor should not be used due to excessive humidity exposure.

Example 33 is a method of assessing sensor membrane integrity using sensor electronics may comprise determining an impedance parameter of an analyte sensor and determining a membrane integrity state of the analyte sensor based on the impedance parameter.

In Example 34, the subject matter of Example 33 optionally includes wherein determining the membrane integrity state includes determining whether an impedance condition has been satisfied.

In Example 35, the subject matter of Example 34 optionally includes wherein determining whether the impedance condition has been satisfied includes determining when the impedance parameter is below a specified threshold.

In Example 36, the subject matter of any one or more of Examples 34-35 optionally includes alerting a user to replace a sensor responsive to the impedance condition being satisfied.

In Example 37, the subject matter of any one or more of Examples 33-36 optionally includes wherein determining the membrane integrity state includes determining a level of membrane damage or abnormality.

In Example 38, the subject matter of Example 37 optionally includes compensating an estimated analyte concentration level based at least in part on a determined level of membrane damage or abnormality.

In Example 39, the subject matter of Example 38 optionally includes compensating the estimated analyte concentration level by adjusting a sensitivity value based on the determined level.

In Example 40, the subject matter of any one or more of Examples 33-39 optionally includes determining the impedance parameter at a specified frequency.

In Example 41, the subject matter of Example 40 optionally includes determining the impedance parameter at a frequency above 100 Hz.

In Example 42, the subject matter of Example 41 optionally includes determining the impedance at a frequency between 100 Hz and 10,000 Hz.

In Example 43, the subject matter of any one or more of Examples 33-42 optionally includes the determined impedance parameter being an impedance of the analyte sensor after hydration.

In Example 44, the subject matter of any one or more of Examples 33-43 optionally includes the determined impedance parameter being a determined impedance of a membrane portion of an analyte sensor after hydration.

In Example 45, the subject matter of any one or more of Examples 33-44 optionally includes the determined impedance parameter being based on a comparison of an impedance at a first frequency and an impedance at a second frequency.

In Example 46, the subject matter of Example 45 optionally includes the comparison between an impedance at the first frequency and the impedance at the second frequency becoming stable, after hydration, before the impedance at the first frequency or the impedance at the second frequency becomes stable.

In Example 47, the subject matter of any one or more of Examples 45-46 optionally includes the first frequency and second frequency providing a relatively pronounced impedance difference.

In Example 48, the subject matter of any one or more of Examples 45-47 optionally includes the comparison between the impedance at the frequency and the impedance at the second frequency being a difference between the impedance at the first frequency and the impedance at the second frequency.

In Example 49, the subject matter of any one or more of Examples 45-48 optionally includes wherein the comparison includes determining an existence or amount of a kickback of in a dual frequency impedance vs time relationship.

In Example 50, the subject matter of any one or more of Examples 33-49 optionally includes determining the impedance parameter based on a measurement a specified time after hydration of the sensor.

In Example 51, the subject matter of Example 50 optionally includes the specified time being between 5 and 600 seconds after hydration.

In Example 52, the subject matter of any one or more of Examples 66-51 optionally includes determining the impedance parameter based on a measurement after a measured parameter has reached a steady state condition.

In Example 53, the subject matter of any one or more of Examples 66-52 optionally includes the impedance parameter being a first derivative of impedance with respect to time.

In Example 54, the subject matter of Example 53 optionally includes determining the membrane integrity state based on a shape of a first derivative vs. time curve.

In Example 55, the subject matter of any one or more of Examples 66-54 optionally includes wherein the impedance parameter is a second derivative of impedance with respect to time.

In Example 56, the subject matter of any one or more of Examples 66-55 optionally includes wherein determining the membrane integrity state is based at least in part on a fitted membrane resistance determined using a constant phase element model.

In Example 57, the subject matter of any one or more of Examples 66-56 optionally includes wherein determining a membrane integrity state includes performing a template match.

In Example 58, the subject matter of Example 57 optionally includes determining a best fit from a plurality of templates.

In Example 59, the subject matter of Example 58 optionally includes determining a best fit using dynamic time warping.

Example 60 is an analyte sensor system comprising an analyte sensor sized and shaped for insertion into a host, and sensor electronics coupled to the analyte sensor. The sensor electronics may be to determine an impedance parameter of the analyte sensor and determine a membrane integrity state of the analyte sensor based on the impedance parameter.

In Example 61, the subject matter of Example 60 optionally includes the impedance parameter being an impedance value and the sensor electronics determining whether the impedance value is below a threshold, wherein an impedance value below the threshold indicates a presence of damage or abnormality in a sensor membrane portion of the analyte sensor.

In Example 62, the subject matter of any one or more of Examples 60-61 optionally includes the sensor electronics determining a level of membrane damage or abnormality based on the impedance parameter and compensate an estimated analyte concentration level based at least in part on the level of membrane damage or abnormality.

In Example 63, the subject matter of any one or more of Examples 60-62 optionally includes the sensor electronics determining the impedance parameter by applying a voltage signal at a specified frequency.

In Example 64, the subject matter of Example 63 optionally includes the sensor electronics determining the impedance parameter at frequency between 100 Hz and 10,000 Hz.

In Example 65, the subject matter of any one or more of Examples 63-64 optionally includes the sensor electronics comparing an impedance at a first frequency and an impedance at a second frequency.

In Example 66, the subject matter of Example 67 optionally includes wherein the impedance parameter is a difference between an impedance at a first frequency and an impedance at a second frequency.

In Example 67, the subject matter of any one or more of Examples 65-67 optionally includes the sensor electronics determining an existence or amount of kickback in a dual frequency impedance vs. time relationship; and determining the existence or amount of membrane damage based on the existence or amount of kickback.

In Example 68, the subject matter of any one or more of Examples 61-67 optionally includes the sensor electronics determining a first derivative of impedance with respect to time and determine the membrane integrity state based on a value of the first derivative or a shape of a first derivative vs. time curve.

In Example 69, the subject matter of any one or more of Examples 61-68 optionally includes wherein the sensor electronics determining a second derivative of impedance with respect to time and determining the membrane integrity state based on a value of the second derivative.

In Example 70, the subject matter of any one or more of Examples 61-69 optionally includes the sensor electronics matching an impedance curve to a template.

In Example 71, the subject matter of Example 70 optionally includes the sensor electronics performing dynamic time warping to determine a template match.

Example 72 is a method of operating analyte sensor comprising determining an impedance parameter of an analyte sensor and determining an insertion state of the analyte sensor based on the impedance parameter.

In Example 73, the subject matter of Example 72 optionally includes wherein determining the insertion state includes detecting a dislodgment of a sensor from an insertion position in a host.

In Example 74, the subject matter of Example 73 optionally includes detecting that a sensor has been at least partially pulled out of an initial insertion position.

In Example 75, the subject matter of any one or more of Examples 73-74 optionally includes detecting dislodgement based upon an increase in impedance.

Example 76 is an analyte sensor system comprising an analyte sensor sized and shaped for insertion into a host, and sensor electronics coupled to the analyte sensor. The sensor electronics are to determine an impedance parameter of an analyte sensor and determine an insertion state of the analyte sensor based on the impedance parameter.

In Example 77, the subject matter of Example 76 optionally includes the sensor electronics detecting a dislodgement of a sensor based at least in part on an increase in the impedance parameter.

Example 78 is a method of operating an analyte sensor system comprising determining an impedance parameter of an analyte sensor; determining membrane state based on the impedance parameter; and compensating an analyte concentration level based on the membrane state.

In Example 79, the subject matter of Example 78 optionally includes wherein the impedance parameter is an estimated membrane impedance.

In Example 80, the subject matter of any one or more of Examples 78-79 optionally includes wherein the impedance parameter is an impedance at a specified frequency.

In Example 81, the subject matter of any one or more of Examples 78-80 optionally includes wherein the impedance parameter is a dual frequency impedance.

In Example 82, the subject matter of any one or more of Examples 78-81 optionally includes determining when the impedance parameter is in a steady state and compensating based on the impedance parameter in the steady state.

In Example 83, the subject matter of any one or more of Examples 78-82 optionally includes determining an existence or amount of a kickback of in a dual frequency impedance vs. time relationship and determining an amount of compensation based on the existence or amount of kickback.

In Example 84, the subject matter of any one or more of Examples 78-83 optionally includes wherein the impedance parameter is a first derivative of impedance with respect to time.

In Example 85, the subject matter of any one or more of Examples 78-84 optionally includes wherein the impedance parameter is a second derivative of impedance with respect to time.

Example 86 is an analyte sensor system comprising an analyte sensor sized and shaped for insertion into a host, and sensor electronics coupled to the analyte sensor. The sensor electronics are to determine an impedance parameter of an analyte sensor and compensate an analyte concentration level based on the impedance parameter to compensate for damage or abnormality in a membrane.

In Example 87, the subject matter of Example 86 optionally includes wherein the impedance parameter is an estimated membrane impedance.

In Example 88, the subject matter of any one or more of Examples 86-87 optionally includes wherein the impedance parameter is an impedance at a specified frequency.

In Example 89, the subject matter of any one or more of Examples 86-88 optionally includes wherein the impedance parameter is a dual frequency impedance.

In Example 90, the subject matter of any one or more of Examples 86-89 optionally includes wherein the impedance parameter is a first derivative of impedance with respect to time.

In Example 91, the subject matter of any one or more of Examples 86-90 optionally includes wherein the impedance parameter is a second derivative of impedance with respect to time.

In Example 92, the subject matter of any one or more of Examples 86-91 optionally includes wherein the sensor electronics determine when the impedance parameter is in a steady state and compensate based on the steady state impedance parameter.

In Example 93, the subject matter of any one or more of Examples 86-92 optionally includes the sensor electronics determining an existence or amount of a kickback of in a dual frequency impedance vs. time relationship and determine an amount of compensation based on the existence or amount of kickback.

Example 94 is a method of calibrating damage to impedance in a population of analyte sensors comprising damaging a first sensor and damaging a second sensor. The method also comprises determining an impedance parameter for the first sensor using a first process and determining an impedance parameter for the second sensor using a second process. The second process may be different than the first process. The method also comprises determining an impedance parameter for a third sensor and estimating a damage state of the third sensor based at least in part on the determined impedance parameter for the first sensor, the determined impedance parameter for the second sensor, and the determined impedance parameter for the third sensor.

In Example 95, the subject matter of Example 94 optionally includes determining a damage curve based at least in part on the determined impedance parameter for the first sensor and the determined impedance parameter for the second sensor and estimating the damage state of the third sensor based upon the determined impedance parameter for the third sensor and the damage curve.

In Example 96, the subject matter of any one or more of Examples 94-95 optionally includes wherein damaging the first sensor comprises scratching the first sensor against an abrasive surface a specified number of times and damaging the second sensor comprises scratching the second sensor against an abrasive surface a specified number of times.

Example 97 is a method of operating an analyte sensor system using sensor electronics. The method comprises applying a bias voltage change to an analyte sensor bias voltage and measuring a current value for each of a plurality of time periods after application of the bias voltage change. The method also comprises determining an estimated impedance using the current values for the plurality of time periods and determining a characteristic of the analyte sensor using the estimated impedance. The method further comprises receiving from the analyte sensor a signal indicative of an analyte concentration and determining an estimated analyte concentration level using the determined characteristic of the analyte sensor and the received signal.

In Example 98, the subject matter of Example 97 optionally includes wherein measuring the current includes integrating a charge over each of the specified time periods.

In Example 99, the subject matter of any one or more of Examples 97-98 optionally includes wherein determining an impedance includes fitting a curve using the determined currents for the plurality of time periods, and determining the impedance based on the fitted curve.

In Example 100, the subject matter of Example 99 optionally includes wherein fitting the curve includes fitting an exponential curve, wherein the exponential curve accounts for the impact of double-layer capacitance on the measured current response.

In Example 101, the subject matter of any one or more of Examples 97-100 optionally includes wherein determining a characteristic of the analyte sensor includes determining a sensitivity of the analyte sensor to an analyte concentration.

In Example 102, the subject matter of Example 101 optionally includes compensating for sensor drift using the determined impedance or the determined sensitivity.

In Example 103, the subject matter of any one or more of Examples 97-102 optionally includes wherein determining a characteristic of the analyte sensor includes determining a level of damage or defect of the sensor.

In Example 104, the subject matter of any one or more of Examples 97-103 optionally includes wherein determining a characteristic of the analyte sensor includes determining a compensation for the sensor.

In Example 105, the subject matter of any one or more of Examples 97-104 optionally includes wherein applying a change to an analyte sensor bias voltage includes applying a step in the bias voltage.

Example 106 is an analyte sensor system comprising an analyte configured to provide a sensor signal indicative of an analyte concentration level, and sensor electronics coupled to the analyte sensor. The sensor electronics are to apply a change to an analyte sensor bias voltage, measure a plurality of current response levels for each of a plurality of respective time periods after application of the change to the bias voltage, determine an estimated impedance using the plurality of current response levels, receive a signal indicative of an analyte concentration from the analyte sensor, and determine an estimated analyte concentration level based upon the received signal and the estimated impedance.

In Example 107, the subject matter of Example 106 optionally includes wherein measuring a plurality of current response levels includes integrating charge over each of the plurality of respective time periods.

In Example 108, the subject matter of any one or more of Examples 106-107 optionally includes wherein determining an estimated impedance includes fitting a curve using the measured current response levels and determining the estimated impedance using the fitted curve.

In Example 109, the subject matter of Example 108 optionally includes wherein fitting the curve includes fitting an exponential curve, wherein the exponential curve account for the impact of double-layer capacitance on the measured current response.

In Example 110, the subject matter of any one or more of Examples 106-111 optionally includes wherein the sensor electronics are configured to determine a sensor sensitivity to the analyte using the estimated impedance and determine the estimated analyte concentration level using the sensor sensitivity.

In Example 111, the subject matter of Example 110 optionally includes wherein determining a sensor sensitivity includes determining a sensor compensation based on the estimated impedance.

In Example 112, the subject matter of any one or more of Examples 106-111 optionally includes wherein determining an estimated impedance using the plurality of current response levels accounts for a double-layer membrane capacitance of the sensor.

Example 113 is a method of operating an analyte sensor system using sensor electronics to correct for an error from double-layer capacitance of a sensor membrane. The method comprises applying a change to an analyte sensor bias voltage and measuring a current value for each of a plurality of time periods after application of the bias voltage change. The method also comprises determining a current at the time of the bias voltage change using the current values for the plurality of time periods and determining an estimated impedance using the determined current at the time of the bias voltage change. The method further comprises determining a characteristic of the analyte sensor using the estimated impedance, receiving from the analyte sensor a signal indicative of an analyte concentration, and determining an estimated analyte concentration level using the determined characteristic of the analyte sensor and the received signal.

In Example 114, the subject matter of Example 113 optionally includes fitting the current values for the plurality of time periods to an exponential curve, and extrapolating the fitted curve to determine the current at the time of the bias voltage change.

In Example 115, the subject matter of any one or more of Examples 113-114 optionally includes wherein determining the characteristic of the analyte sensor includes determining a sensor sensitivity.

In Example 116, the subject matter of Example 115 optionally includes updating sensor sensitivity to account for drift by applying the change to the bias voltage at a second time, measuring the currents for a second plurality of time periods, extrapolating to determine the current at the second time, determining the estimated impedance based on the current at the second time, and determining the characteristic of the sensor at the second time based on the estimated impedance at the second time.

Example 117 is an analyte sensor system comprising an analyte sensor sized and shaped for insertion into a host and configured to generate a sensor signal indicative of an analyte concentration level and sensor electronics coupled to the analyte sensor. The sensor electronics are to apply a change to an analyte sensor bias voltage; measure a current value for each of a plurality of time periods after application of the bias voltage change; extrapolate to determine a current at the time of the bias voltage change using the current values for the plurality of time periods; determine an estimated impedance using the determined current at the time of the bias voltage change; determine a characteristic of the analyte sensor using the estimated impedance; receive from the analyte sensor a signal indicative of an analyte concentration; and determine an estimated analyte concentration level using the determined characteristic of the analyte sensor and the received signal.

In Example 118, the subject matter of Example 117 optionally includes the sensor electronics fitting the current values for the plurality of time periods to an exponential curve and extrapolate the fitted curve to determine the current at the time of the bias voltage change.

In Example 119, the subject matter of any one or more of Examples 117-118 optionally includes the sensor electronics determining a sensor sensitivity.

In Example 120, the subject matter of Example 119 optionally includes the sensor electronics updating the sensor sensitivity to account for drift by applying the change to the bias voltage at a second time, measuring the currents for a second plurality of time periods, extrapolating to determine the current at the second time, determining the estimated impedance based on the current at the second time, and determining the characteristic of the sensor at the second time based on the estimated impedance at the second time.

Example 121 is a method of operating an analyte sensor system using sensor electronics. The method comprises applying a change to an analyte sensor bias voltage, measuring a current for one or more time periods after application of the bias voltage change, and determining an estimated impedance based on the current and a double-layer capacitance value. The method also comprises determining a characteristic of the analyte sensor using the estimated impedance, receiving from the analyte sensor a signal indicative of an analyte concentration, and determining an estimated analyte concentration level using the determined characteristic of the analyte sensor and the received signal.

In Example 122, the subject matter of Example 121 optionally includes wherein the double-layer capacitance is a specified double-layer capacitance estimate for the sensor.

In Example 123, the subject matter of any one or more of Examples 121-122 optionally includes increasing the bias voltage and measuring a current response to increasing the bias voltage, decreasing the bias voltage and measuring a current response to decreasing the bias voltage, and determining the double-layer capacitance using the current response to increasing the bias voltage and the current response to decreasing the bias voltage.

In Example 124, the subject matter of any one or more of Examples 121-123 optionally includes measuring currents for a plurality of time periods after changing the bias voltage and determining the double-layer capacitance based on the currents for the plurality of time periods.

Example 125 is an analyte sensor system comprising an analyte sensor sized and shaped for insertion into a host and configured to generate a sensor signal indicative of an analyte concentration level, and sensor electronics coupled to the analyte sensor. The sensor electronics are to apply a change to an analyte sensor bias voltage, measure a current for one or more time periods after application of the bias voltage change, and determine an estimated impedance based on the current and a double-layer capacitance value. The sensor electronics are also to determine a characteristic of the analyte sensor using the estimated impedance, receive from the analyte sensor a signal indicative of an analyte concentration, and determine an estimated analyte concentration level using the determined characteristic of the analyte sensor and the received signal.

In Example 126, the subject matter of Example 125 optionally includes wherein the double-layer capacitance is a specified double-layer capacitance estimate for the sensor.

In Example 127, the subject matter of any one or more of Examples 125-126 optionally includes wherein the sensor electronics increase the bias voltage and measuring a current response to increasing the bias voltage, decrease the bias voltage and measure a current response to decreasing the bias voltage, and determine the double-layer capacitance using the current response to increasing the bias voltage and the current response to decreasing the bias voltage.

In Example 128, the subject matter of any one or more of Examples 125-127 optionally includes wherein the sensor electronics measure currents for a plurality of time periods after changing the bias voltage and determine the double-layer capacitance based on the currents for the plurality of time periods.

Example 129 is an analyte sensor system, comprising an analyte sensor comprising a working electrode and a reference electrode. The reference electrode comprises a material that is depleted during use of the analyte sensor. The analyte sensor system also comprises a hardware device in communication with the analyte sensor. The hardware device is configured to perform operations comprising applying a first bias voltage to the analyte sensor and measuring a first current at the analyte sensor when the first bias voltage is applied. The first bias voltage is less than an operational bias voltage of the analyte sensor. The operations further comprise applying a second bias voltage to the analyte sensor and measuring a second current at the analyte sensor when the second bias voltage is applied. The operations may further comprises detecting a plateau bias voltage using the first current and the second current, determining that the plateau bias voltage is less than a plateau bias voltage threshold, and executing a responsive action at the analyte sensor.

In Example 130, the subject matter of Example 129 optionally includes wherein applying the first bias voltage and applying the second bias voltage comprises continuously sweeping the bias voltage of the analyte sensor along a range including the first bias voltage and the second bias voltage.

In Example 131, the subject matter of any one or more of Examples 129-129 optionally includes wherein detecting the plateau bias voltage comprises determining that the first current is less than a current threshold.

In Example 132, the subject matter of any one or more of Examples 129-131 optionally includes the operations further comprising determining a current response of the analyte sensor using the first current and the second current, wherein detecting the plateau bias voltage comprises determining a bias voltage at which a slope of the current response is about zero.

In Example 133, the subject matter of any one or more of Examples 129-132 optionally includes the operations further comprising: determining stage of life data for the analyte sensor using the plateau bias voltage; and displaying the stage of life data at a user interface.

In Example 134, the subject matter of any one or more of Examples 129-133 optionally includes wherein the responsive action comprises applying a compensation to a third sensor current generated by the sensor.

In Example 135, the subject matter of any one or more of Examples 129-134 optionally includes wherein the responsive action comprises: ceasing to provide a bias current to the analyte sensor; and displaying at a user interface an indication that a sensor session for the analyte sensor is ended.

Example 136 is a method of operating an analyte sensor, comprising applying a first bias voltage to the analyte sensor where the first bias voltage less than an operational bias voltage of the analyte sensor. The method may also comprise measuring a first current at the analyte sensor when the first bias voltage is applied. The method further comprises applying a second bias voltage to the analyte sensor and measuring a second current at the analyte sensor when the second bias voltage is applied. The method also comprises detecting a plateau bias voltage using the first current and the second current, determining that the plateau bias voltage is less than a plateau bias voltage threshold, and executing a responsive action at the analyte sensor.

In Example 137, the subject matter of Example 136 optionally includes wherein applying the first bias voltage and applying the second bias voltage comprises continuously sweeping the bias voltage of the analyte sensor along a range including the first bias voltage and the second bias voltage.

In Example 138, the subject matter of any one or more of Examples 136-137 optionally includes wherein detecting the plateau bias voltage comprises determining that the first current is less than a current threshold.

In Example 139, the subject matter of any one or more of Examples 136-138 optionally includes determining a current response of the analyte sensor using the first current and the second current, wherein detecting the plateau bias voltage comprises determining a bias voltage at which a slope of the current response is about zero.

In Example 140, the subject matter of any one or more of Examples 136-139 optionally includes determining stage of life data for the analyte sensor using the plateau bias voltage and displaying the stage of life data at a user interface.

In Example 141, the subject matter of any one or more of Examples 136-140 optionally includes wherein the responsive action comprises applying a compensation to a third sensor current generated by the sensor.

In Example 142, the subject matter of any one or more of Examples 136-141 optionally includes wherein the responsive action comprises ceasing to provide a bias current to the analyte sensor and displaying at a user interface an indication that a sensor session for the analyte sensor is ended.

Example 143 is a method of trimming an analyte sensor comprising an integrated current amplifier comprising a first component and a second component. The method comprises exposing the analyte sensor to a first buffer having a first concentration of the analyte and removing material from the first component of the integrated current amplifier to generate an output current having a predetermined characteristic.

In Example 144, the subject matter of Example 143 optionally includes wherein the predetermined characteristic is a predetermined offset.

In Example 145, the subject matter of Example 144 optionally includes exposing the analyte sensor to a second buffer having a second concentration of the analyte greater than the first concentration and removing material from the second component of the integrated current amplifier to generate an output current in the second buffer having a second predetermined characteristic.

In Example 146, the subject matter of any one or more of Examples 143-145 optionally includes wherein the predetermined characteristic is a predetermined gain.

Example 147 is an analyte sensor system, comprising an analyte sensor comprising a working electrode and a reference electrode. The analyte sensor system also comprises a hardware device in communication with the analyte sensor. The hardware device is configured to perform operations comprising receiving an analyte sensor current signal generated by the analyte sensor, the analyte sensor current signal indicative of an analyte concentration in a host, determining that the analyte sensor current exhibits a rate of reduction greater than a rate of reduction threshold, determining that a membrane impedance meets a membrane impedance condition, and executing a compression low response action.

In Example 148, the subject matter of Example 147 optionally includes wherein the compression low response comprises suspending reporting of analyte concentration values from the analyte sensor.

In Example 149, the subject matter of any one or more of Examples 147-148 optionally includes wherein the compression low response comprises applying a compensation to generate analyte concentration values from the analyte sensor.

In Example 150, the subject matter of any one or more of Examples 147-149 optionally includes wherein determining that the membrane impedance meets the membrane impedance condition comprises determining that the membrane impedance is less than a threshold impedance.

In Example 151, the subject matter of any one or more of Examples 147-150 optionally includes wherein determining that the membrane impedance meets the membrane impedance condition comprises determining that a rate of reduction of the membrane impedance is greater than an impedance rate threshold.

Example 152 is a method for monitoring an analyte concentration in a host using an analyte sensor. The method comprises receiving an analyte sensor current signal generated by the analyte sensor. The analyte sensor current signal is indicative of the analyte concentration in the host. The method further comprises determining that the analyte sensor current exhibits a rate of reduction greater than a rate of reduction threshold, determining that a membrane impedance meets a membrane impedance condition, and executing a compression low response action.

In Example 153, the subject matter of Example 152 optionally includes wherein the compression low response comprises suspending reporting of analyte concentration values from the analyte sensor.

In Example 154, the subject matter of any one or more of Examples 152-153 optionally includes wherein the compression low response comprises applying a compensation to generate analyte concentration values from the analyte sensor.

In Example 155, the subject matter of any one or more of Examples 152-154 optionally includes wherein determining that the membrane impedance meets the membrane impedance condition comprises determining that the membrane impedance is less than a threshold impedance.

In Example 156, the subject matter of any one or more of Examples 152-155 optionally includes wherein determining that the membrane impedance meets the membrane impedance condition comprises determining that a rate of reduction of the membrane impedance is greater than an impedance rate threshold.

An example (e.g., "Example 9") of subject matter (e.g., a system or apparatus) may optionally combine any portion or combination of any portion of any one or more of Examples 1-8 to include "means for" performing any portion of any one or more of the functions or methods of Examples 1-8.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments described in the present document.

FIG. 3A is an illustration of an example analyte sensor system.

FIG. 3B is an enlarged view of an example analyte sensor portion of the analyte sensor system shown in FIG. 3A.

FIG. 3C is a cross-sectional view of the analyte sensor of FIG. 3B.

FIGS. 10D and 10E are graphs showing sensitivity of the example current responses illustrated in FIG. 10C.

FIG. 22B is a graph that shows the dual frequency impedance for 100 Hz and 1000 Hz for the same sensors as shown in FIG. 22A.

FIG. 30G provides data that shows the performance improvement achieved by various compensation techniques described above.

DETAILED DESCRIPTION

Figure 1:
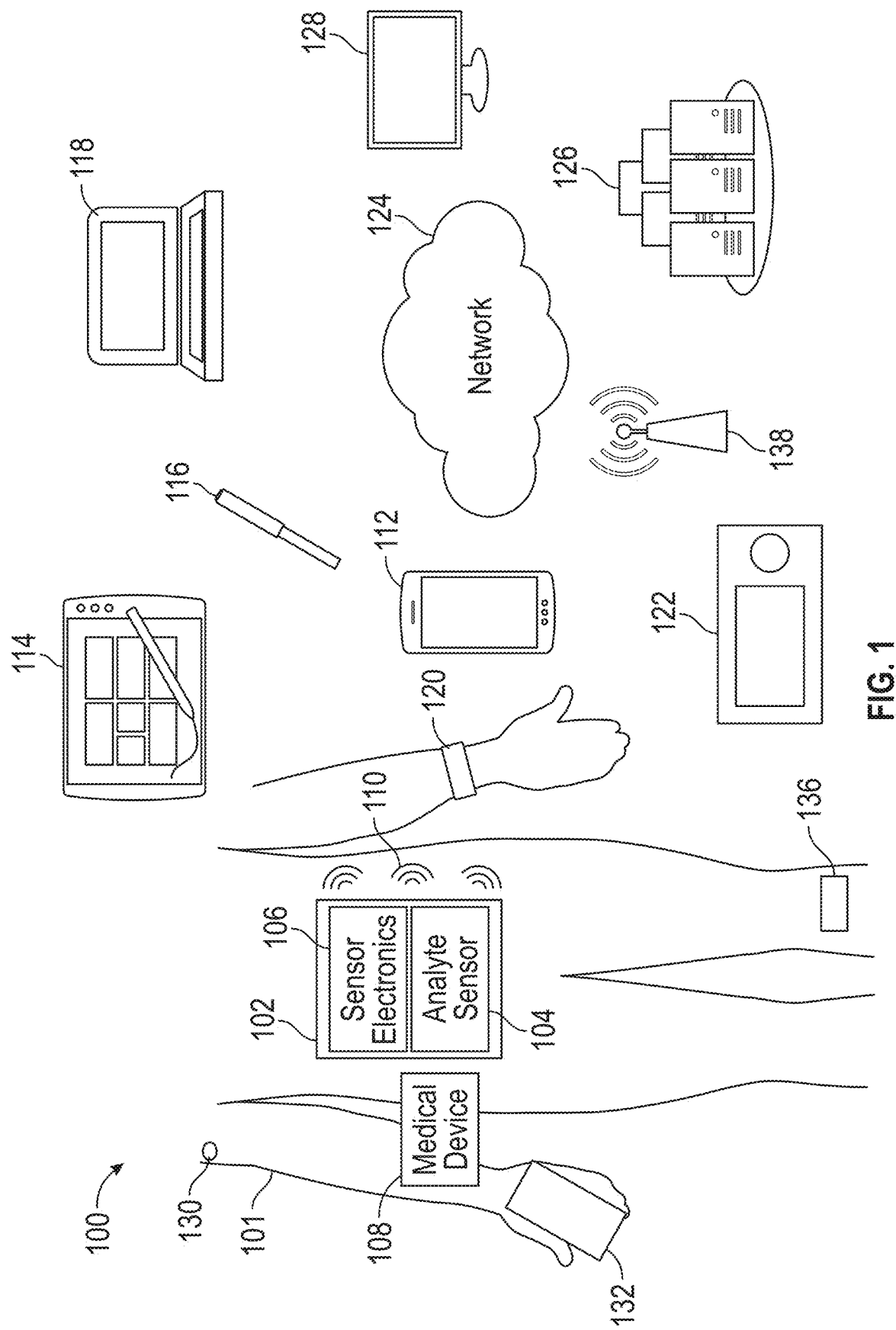
FIG. 1 is an illustration of an example medical device system.

The present inventors have recognized, among other things, that measurements or estimates of impedance in an analyte sensor system may be used to improve the operation of the analyte sensor system. For example, impedance may be used to improve the performance (e.g., accuracy or precision) of an analyte sensor system, or to detect damage or a fault in a sensor. In some examples, an estimate of the impact (e.g., effective capacitance) of a membrane layer interface may be determined.

Overview

An estimate of an impedance of a sensor (e.g., double-layer impedance of a membrane) may be determined using electronic measurements. The impedance estimate may be used, for example, to calibrate a sensor, compensate for drift, identify a damaged sensor, compensate for damage or deviation from a performance standard (e.g., default sensitivity curve).

Impedance may also be used to reduce or eliminate a need for in vivo sensor calibration using blood glucose meter (e.g., "finger stick") data. An analyte sensor, such as a glucose sensor, may be calibrated during manufacture ("factory calibration"), to provide a predictable analyte response curve. For example, a sensor's response to the presence of an analyte (e.g., a glucose concentration) may be checked during (or after) manufacture to assure that the sensor's response to the analyte (e.g., the current signal generated in response to exposure to a known glucose concentration) is within an acceptable range. After implantation in the body, the analyte sensitivity of a sensor is subject to change over time, i.e. "drift." One approach to accounting for in vivo drift is to periodically calibrate the sensor using information from a blood glucose meter (i.e., "finger stick" blood glucose measurements). However, it may be desirable to avoid use of blood glucose meter data or reduce the number or frequency of such in-vivo calibration events. For reasons described in detail below, determining one or more impedance values (e.g., for the circuit 400 shown in FIG. 4) may reduce or eliminate the need to rely on blood glucose meter information. In some examples, impedance may allow for factory calibration, without further in vivo calibration events.

An analyte sensor may include a number of domains or layers, which may include a diffusion resistance domain (e.g., domain 44 shown in FIG. 3C). In a glucose sensor, for example, the diffusion coefficient of electrically neutral glucose molecules in the resistance layer may be a direct correlate or determinant of glucose sensitivity. The electrochemical impedance of the resistance layer is a measure of the mobility of electrically charged ions in the resistance layer. Although the diffusion coefficient and electrochemical impedance are two fundamentally different physical properties associated with two different agents (glucose vs. ions), bench experiments have shown these properties to correlate with each other. As a result, the electrochemical impedance may be used as a surrogate to estimate the diffusion coefficient, which may allow for compensations in in vivo drift of glucose sensitivity. For example, a sensor compensation may be based upon a membrane impedance determined from circuit measurements made in vivo or prior to implantation.

As further described in detail below, the impedance of the membrane (e.g., the electrochemical impedance of the resistance layer) may be determined or estimated based on electrical measurements by sensor electronics or other instrumentation. In various examples, an impedance measurement may be obtained using a sine-wave approach, a step response function approach, or an impulse response function approach. A sine-wave approach may include imposing sinusoidal perturbations in the bias voltage over the RL and measuring the amplitudes of sinusoidal response currents: a scan through a band of frequencies may be performed, and the ratio between the voltage and current excursions may be taken as the impedance at a specific frequency. In step response function approach, a square step change in the bias may be imposed and held, and a perturbation in the sensor current may be measured: the ratio between the Fourier or Laplace transform of the step voltage and that of the transient current is the impedance of the membrane. In an impulse response function approach, a short square wave pulse in the bias voltage may be imposed, and a perturbation in the sensor current may be measured. The impedance may be determined from the current perturbation and the applied bias voltage pulse.

The sensor sensitivity ($m_t$) correlates linearly with the reciprocal of the membrane impedance (ZRL,t), i.e. ZRL, $t*m_t$=constant. This relationship can be employed to make use of impedance for estimating in vivo sensitivity in real time:

$$\hat{m}_t = Z_{RL,t}^{-1} \cdot \text{constant}$$

Based on this relationship, a sensor may be calibrated in vivo, which may allow for compensation for drift after deployment in a host.

In some examples, a sensor elapsed time (t) since insertion and an impedance ($R_t$) determined from measurements at the elapsed time may be used as input for a function to estimate sensitivity, e.g., sensitivity ($m_t$) of the sensor may be provided by the function $m_t=f(t)/R_t$. In some examples, an initial calibration curve (CC) may also be used to determine an estimated sensor sensitivity, e.g., $m_t=f(CC, t)/R_t$.

An estimated sensor sensitivity may be used to determine an estimated analyte concentration (e.g., estimated glucose concentration) based upon sensor output (e.g., a current or charge count from a working electrode measured using sensor electronics) and the sensor sensitivity ($m_t$) estimated using the impedance.

Testing and experimentation have been conducted to establish and verify techniques for improving performance of analyte sensor systems, mitigating the effect of double-layer capacitance effects, and detecting, quantifying, or compensating for damage or abnormalities in a sensor membrane. Data, charts, and examples are provided to assist with describing the present subject matter.

Impedance characteristics of a sensor may be used to detect or determine (e.g., quantify) an amount of damage or manufacturing abnormality (e.g., membrane imperfection) in a sensor. A sensor may be functional even though a membrane may include minor imperfections that may be identifiable under a microscope. Some sensors with extensive damage or major manufacturing abnormalities may provide unacceptable performance. Identification of such sensors may provide an opportunity to remove a sensor from circulation or compensate an estimated analyte concentration based on an understanding of impedance characteristics of the sensor. In some examples, a combination of characteristics may be used to assess the integrity of a sensor membrane, e.g., to identify sensors with damage or abnormality, or characterize the extent of sensor abnormality or damage. For example, impedance may be used in combination with dual frequency impedance (e.g., impedance 100 Hz and 1000 Hz), or impedance may be used in combination with an impedance trend or time-based variable (e.g., impedance difference at different points in time), or impedance difference at different frequencies may be used in combination with impedance difference at different points in time (e.g., 72 seconds and 180 seconds or low point and a stable point.) In other examples, other variables, such as signal variability (e.g., perceived noise level), or response to a voltage change (e.g., rate of impedance change) may also be used in combination with any of the above factors and combinations.

In certain situations, such as accidently bumping an analyte sensor, catching a sensor base on an object, or "tenting" of an adhesive patch (e.g., when portions of the adhesive patch are not completely adhered to the skin) to which a sensor is attached, an analyte sensor may be partially pulled out of the skin or otherwise dislodged, which may result in an inaccurate sensor reading. Such an event may be detected based upon a change in impedance.

Sensor impedance may depend on the insertion depth of the sensor into a host. If a sensor is retracted a significant distance, a step change in sensor impedance may be observed.

In an example, an impedance may be measured after insertion, and subsequently measured after insertion. For example, the impedance may be measured recurrently, or may be measured responsive to detection of an event, such as a potential dislodgement event, which may for example be detected using an accelerometer in sensor electronics, or from other sensor information. A sudden change in impedance may indicate dislodgment. For example, a determined impedance change greater than a predetermined impedance change (e.g., in ohms) over a predetermined time period may indicate a dislodgement event. In some examples, a system may declare an alert or raise a "replace sensor" alarm" responsive to detection of a sudden change in impedance.

In some examples, factory calibration may be improved by using impedance for factory calibration. Impedance may be used to determine a calibration value or curve for a sensor, or verification that a sensitivity of the sensor is within acceptable limits. Without use of impedance, calibration may require sequentially exposing a sensor to immersion in fluid baths having varying levels of analyte concentration (e.g., varying glucose concentrations), while applying a bias potential, which may be complicated, time consuming, expensive, or difficult to scale. In some examples, impedance may be used as a replacement (or compliment) to such soaking in analyte solutions.

In an example, a sensor may be pre-soaked in a solution to facilitate measurement of impedance. An impedance measurement may then be made. In an example, the impedance determination (e.g., using current measurements described above) may take one minute, or less, in contrast to a typical one-hour measurement process of current measurements in response to analyte concentrations. This approach may be desirable, for example, because the process does not require application of a bias potential, and a large number of sensors may be soaked simultaneously. In an example, an eight-channel potentiostat may be used to simultaneously measure the impedance of eight sensors on a single fixture. In some examples, the determined impedance values may be used to determine a sensor sensitivity or confirm that the sensor sensitivity or impedance is within defined limits, or to predict drift or later estimate in vivo drift, e.g., using in vivo impedance determinations, which may be compared to the factory impedance values or a default value or range.

In some examples, a sensor may be pre-screened using an impedance procedure, so that damaged sensors may be identified and removed from a production process, which may improve sensor accuracy statistics (e.g., reduce MARD), or improve process efficiency by reducing the number of sensors that proceed through a conventional bath calibration process.

Example System

FIG. 1 is an illustration of an example system 100. The system 100 may include an analyte sensor system 102 that may be coupled to a host 101. The host 101 may be a human patient. The patient may, for example, be subject to a temporary or permanent diabetes condition or other health condition for which analyte monitoring may be useful.

The analyte sensor system 102 may include an analyte sensor 104, which may for example be a glucose sensor. The glucose sensor may be any device capable of measuring the concentration of glucose. For example, the analyte sensor 104 may be fully implantable, or the analyte sensor 104 may be wearable on the body (e.g., on the body but not under the skin), or the analyte sensor 104 may be a transcutaneous device (e.g., with a sensor residing under or in the skin of a host). It should be understood that the devices and methods described herein can be applied to any device capable of detecting a concentration of glucose and providing an output signal that represents the concentration of glucose (e.g., as a form of analyte data).

The analyte sensor system 102 may also include sensor electronics 106. In some examples, the analyte sensor 104 and sensor electronics 106 may be provided as an integrated package. In other examples, the analyte sensor 104 and sensor electronics 106 may be provided as separate components or modules. For example, the analyte sensor system 102 may include a disposable (e.g., single-use) base that may include the analyte sensor 104, a component for attaching the sensor 104 to a host (e.g., an adhesive pad), or a mounting structure configured to receive another component. The system 102 may also include a sensor electronics package, which may include some or all of the sensor electronics 106 shown in FIG. 2. The sensor electronics package may be reusable.

An analyte sensor 104 may use any known method, including invasive, minimally-invasive, or non-invasive sensing techniques (e.g., optically excited fluorescence, microneedle, transdermal monitoring of glucose), to provide a data stream indicative of the concentration of the analyte in a host 101. The data stream may be a raw data signal, which may be converted into a calibrated and/or filtered data stream that is used to provide a useful value of the analyte (e.g., estimated blood glucose concentration level) to a user, such as a patient or a caretaker (e.g., a parent, a relative, a guardian, a teacher, a doctor, a nurse, or any other individual that has an interest in the wellbeing of the host 101).

Analyte sensor 104 may, for example, be a continuous glucose sensor, which may, for example, include a subcutaneous, transdermal (e.g., transcutaneous), or intravascular device. In some embodiments, such a sensor or device may recurrently (e.g., periodically or intermittently) analyze sensor data. The glucose sensor may use any method of glucose measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™, (e.g., the DexCom G5™ sensor or Dexcom G6™ sensor or any variation thereof), from Abbott™ (e.g., the Libre™ sensor), or from Medtronic™ (e.g., the Enlite™ sensor).

In some examples, analyte sensor 104 may be an implantable glucose sensor, such as described with reference to U.S. Pat. No. 6,001,067 and U.S. Patent Publication No. US-2005-0027463-A1, which are incorporated by reference. In some examples, analyte sensor 104 may be a transcutaneous glucose sensor, such as described with reference to U.S. Patent Publication No. US-2006-0020187-A1, which is incorporated by reference. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007, all of which are incorporated by reference. In some examples, the continuous glucose sensor may include a transcutaneous sensor such as described in U.S. Pat. No. 6,565,509 to Say et al., which is incorporated by reference. In some examples, analyte sensor 104 may be a continuous glucose sensor that includes a subcutaneous sensor such as described with reference to U.S. Pat. No. 6,579,690 to Bonnecaze et al. or U.S. Pat. No. 6,484,046 to Say et al., which are incorporated by reference. In some examples, the continuous glucose sensor may include a refillable subcutaneous sensor such as described with reference to U.S. Pat. No. 6,512,939 to Colvin et al., which is incorporated by reference. The continuous glucose sensor may include an intravascular sensor such as described with reference to U.S. Pat. No. 6,477,395 to Schulman et al., which is incorporated by reference. The continuous glucose sensor may include an intravascular sensor such as described with reference to U.S. Pat. No. 6,424,847 to Mastrototaro et al., which is incorporated by reference.

The system 100 may also include a second medical device 108, which may, for example, be a drug delivery device (e.g., insulin pump or insulin pen). In some examples, the medical device 108 may be or include a sensor, such as another analyte sensor 104, a heart rate sensor, a respiration sensor, a motion sensor (e.g. accelerometer), posture sensor (e.g. 3-axis accelerometer), acoustic sensor (e.g. to capture ambient sound or sounds inside the body). In some examples, medical device 108 may be wearable, e.g., on a watch, glasses, contact lens, patch, wristband, ankle band, or other wearable item, or may be incorporated into a handheld device (e.g., a smartphone). In some examples, the medical device 108 may include a multi-sensor patch that may, for example, detect one or more of an analyte level (e.g., glucose, lactate, insulin or other substance), heart rate, respiration (e.g., using impedance), activity (e.g., using an accelerometer), posture (e.g., using an accelerometer), galvanic skin response, tissue fluid levels (e.g., using impedance or pressure).

The analyte sensor system 102 may communicate with the second medical device 108 via a wired connection, or via a wireless communication signal 110. For example, the analyte sensor system 102 may be configured to communicate using via radio frequency (e.g., Bluetooth, Medical Implant Communication System (MICS), Wi-Fi, NFC, RFID, Zigbee, Z-Wave or other communication protocols), optically (e.g., infrared), sonically (e.g., ultrasonic), or a cellular protocol (e.g., CDMA (Code Division Multiple Access) or GSM (Global System for Mobiles)), or via a wired connection (e.g., serial, parallel, etc.).

The system 100 may also include a wearable sensor 130, which may include a sensor circuit (e.g., a sensor circuit configured to detect a glucose concentration or other analyte concentration) and a communication circuit, which may, for example, be a near field communication (NFC) circuit. In some examples, information from the wearable sensor 130 may be retrieved from the wearable sensor 130 using a user device 132 such as a smart phone that is configured to communicate with the wearable sensor 130 via NFC when the user device 132 is placed near the wearable sensor 130 (e.g., swiping the user device 132 over the sensor 130 retrieves sensor data from the wearable sensor 130 using NFC). The use of NFC communication may reduce power consumption by the wearable sensor 130, which may reduce the size of a power source (e.g., battery or capacitor) in the wearable sensor 130 or extend the usable life of the power source. In some examples, the wearable sensor 130 may be wearable on an upper arm as shown. In some examples, a wearable sensor 130 may additionally or alternatively be on the upper torso of the patient (e.g., over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 such as a watch, and an additional wearable sensor 130 may communicate with one another via wired or wireless (e.g., Bluetooth, MICS, NFC or any of the other options described above,) communication. The additional wearable sensor 130 may be any of the examples described above with respect to medical device 108. The analyte sensor system 102, medical device 108, and additional sensor 130 on the host 101 are provided for the purpose of illustration and description and are not necessarily drawn to scale.

The system 100 may also include one or more peripheral devices, such as a hand-held smart device (e.g., smartphone) 112, tablet 114, smart pen 116 (e.g., insulin delivery pen with processing and communication capability), computer 118, a wearable device 120 such as a watch, or peripheral medical device 122 (which may be a proprietary device such as a proprietary user device available from DexCom), any of which may communicate with the analyte sensor system 102 via a wireless communication signal 110, and may also communicate over a network 124 with a server system (e.g., remote data center) 126 or with a remote terminal 128 to facilitate communication with a remote user (not shown) such as a technical support staff member or a clinician.

The wearable device 120 may include an activity sensor, a heart rate monitor (e.g., light-based sensor or electrode-based sensor), a respiration sensor (e.g., acoustic- or electrode-based), a location sensor (e.g., GPS), or other sensors.

The system 100 may also include a wireless access point (WAP) 138 that may be used to communicatively couple one or more of analyte sensor system 102, network 124, server system 126, medical device 108 or any of the peripheral devices described above. For example, WAP 138 may provide Wi-Fi and/or cellular connectivity within system 100. Other communication protocols (e.g., Near Field Communication (NFC) or Bluetooth) may also be used among devices of the system 100. In some examples, the server system 126 may be used to collect analyte data from analyte sensor system 102 and/or the plurality of other devices, and to perform analytics on collected data, generate or apply universal or individualized models for glucose levels, and communicate such analytics, models, or information based thereon back to one or more of the devices in the system 100.

Figure 2:
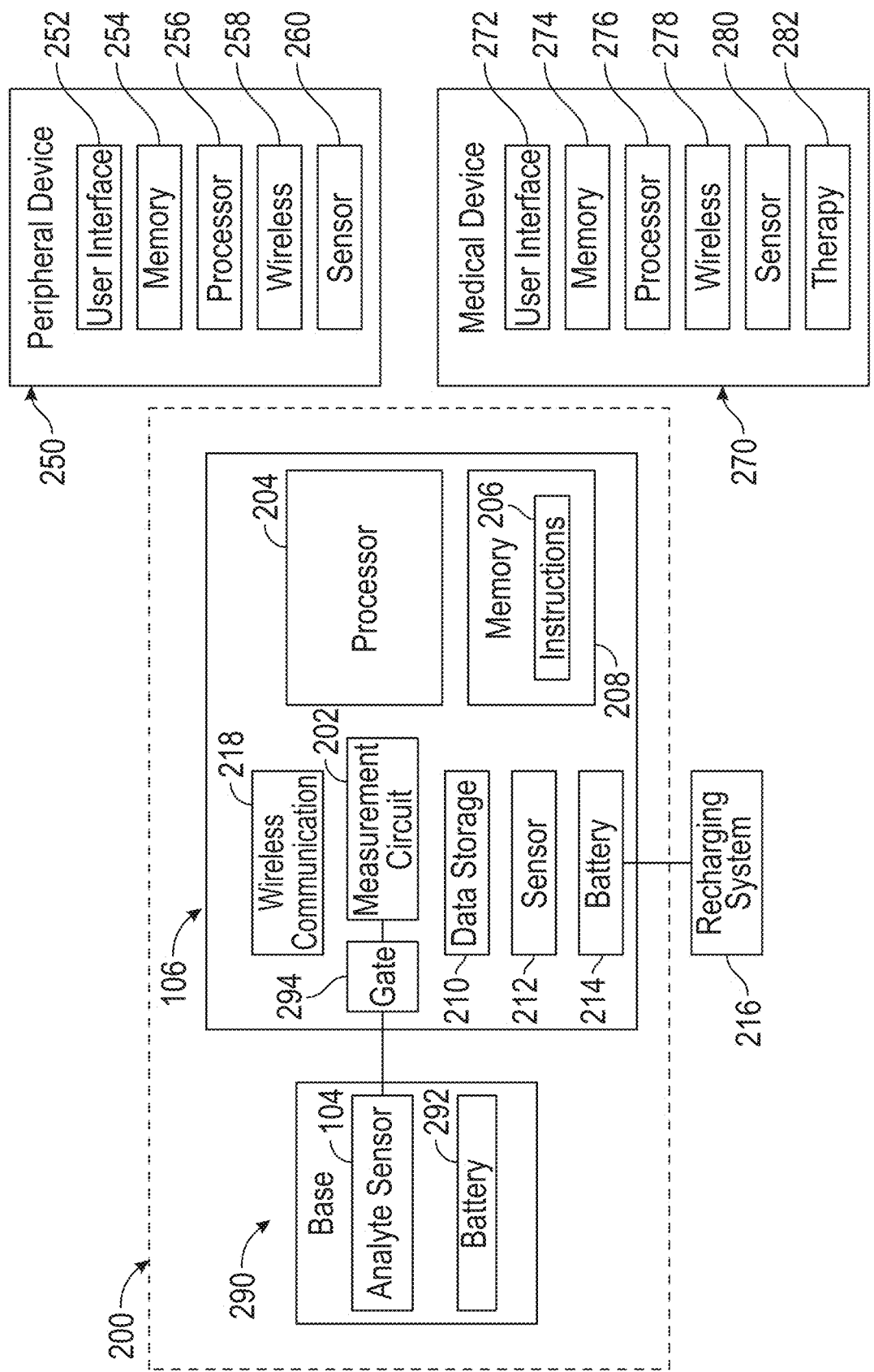
FIG. 2 is a schematic illustration of various example electronic components that may be part of the medical device system shown in FIG. 1.

FIG. 2 is a schematic illustration of various example electronic components that may be part of a medical device system 200. In an example, the system 200 may include sensor electronics 106 and a base 290. While a specific example of division of components between the base 290 and sensor electronics 106 is shown, it is understood that some examples may include additional components in the base 290 or in the sensor electronics 106, and that some of the components (e.g., a battery or supercapacitor) that are shown in the sensor electronics 106 may be alternatively or additionally (e.g., redundantly) provided in the base 290.

In an example, the base 290 may include the analyte sensor 104 and a battery 292. In some examples, the base 290 may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as sensor data, and generate transformed sensor data and displayable sensor information. The sensor electronics 106 may, for example, include electronic circuitry associated with measuring, processing, storing, or communicating continuous analyte sensor data, including prospective algorithms associated with processing and calibration of the sensor data. The sensor electronics 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

As shown in FIG. 2, the sensor electronics 106 may include a measurement circuit 202 (e.g., potentiostat), which may be coupled to the analyte sensor 104 and configured to recurrently obtain analyte sensor readings using the analyte sensor 104, for example by continuously or recurrently measuring a current flow indicative of analyte concentration. The sensor electronics 106 may include a gate circuit 294, which may be used to gate the connection between the measurement circuit 202 and the analyte sensor 104. In an example, the analyte sensor 104 accumulates charge over an accumulation period, and the gate circuit 294 is opened so that the measurement circuit 202 can measure the accumulated charge. Gating the analyte sensor 104 may improve the performance of the sensor system 102 by creating a larger signal to noise or interference ratio (e.g., because charge accumulates from an analyte reaction, but sources of interference, such as the presence of acetaminophen near a glucose sensor, do not accumulate, or accumulate less than the charge from the analyte reaction). The sensor electronics 106 may also include a processor 204, which may retrieve instructions 206 from memory 208 and execute the instructions 206 to determine control application of bias potentials to the analyte sensor 104 via the potentiostat, interpret signals from the sensor 104, or compensate for environmental factors. The processor 204 may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor 204. The sensor 212 may be a temperature sensor, accelerometer, or another suitable sensor. The sensor electronics 106 may also include a power source such as a capacitor or battery 214, which may be integrated into the sensor electronics 106, or may be removable, or part of a separate electronics package. The battery 214 (or other power storage component, e.g., capacitor) may optionally be rechargeable via a wired or wireless (e.g., inductive or ultrasound) recharging system 216. The recharging system 216 may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component).

The sensor electronics 106 may also include one or more supercapacitors in the sensor electronics package (as shown), or in the base 290. For example, the supercapacitor may allow energy to be drawn from the battery 214 in a highly consistent manner to extend the life of the battery 214. The battery 214 may recharge the supercapacitor after the supercapacitor delivers energy to the communication circuit or to the processor 204, so that the supercapacitor is prepared for delivery of energy during a subsequent high-load period. In some examples, the supercapacitor may be configured in parallel with the battery 214. A device may be configured to preferentially draw energy from the supercapacitor, as opposed to the battery 214. In some examples, a supercapacitor may be configured to receive energy from a rechargeable battery for short-term storage and transfer energy to the rechargeable battery for long-term storage.

The supercapacitor may extend an operational life of the battery 214 by reducing the strain on the battery 214 during the high-load period. In some examples, a supercapacitor removes at least 10% of the strain off the battery during high-load events. In some examples, a supercapacitor removes at least 20% of the strain off the battery during high-load events. In some examples, a supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor 204 and may be configured to wirelessly communicate with one or more peripheral devices or other medical devices, such as an insulin pump or smart insulin pen.

A peripheral device 250 may, for example, be a wearable device (e.g., activity monitor), such as a wearable device 120. In other examples, the peripheral device 250 may be a hand-held smart device 112 (e.g., smartphone or other device such as a proprietary handheld device available from Dexcom), a tablet 114, a smart pen 116, or special-purpose computer 118 shown in FIG. 1.

The peripheral device 250 may include a user interface 252, a memory circuit 254, a processor 256, a wireless communication circuit 258, a sensor 260, or any combination thereof. The peripheral device 250 may also include a power source, such as a battery. The peripheral device 250 may not necessarily include all of the components shown in FIG. 2. The user interface 252 may, for example, include a touch-screen interface, a microphone (e.g., to receive voice commands), or a speaker, a vibration circuit, or any combination thereof, which may receive information from a user (e.g., glucose values) or deliver information to the user such as glucose values, glucose trends (e.g., an arrow, graph, or chart), or glucose alerts. The processor 256 may be configured to present information to a user, or receive input from a user, via the user interface 252. The processor 256 may also be configured to store and retrieve information, such as communication information (e.g., pairing information or data center access information), user information, sensor data or trends, or other information in the memory circuit 254. The wireless communication circuit 258 may include a transceiver and antenna configured to communicate via a wireless protocol, such as Bluetooth, MICS, or any of the other options described above. The sensor 260 may, for example, include an accelerometer, a temperature sensor, a location sensor, biometric sensor, or blood glucose sensor, blood pressure sensor, heart rate sensor, respiration sensor, or other physiologic sensor. The peripheral device 250 may, for example, be a hand-held smart device 112 (e.g., smartphone or other device such as a proprietary handheld device available from Dexcom), tablet 114, smart pen 116, watch or other wearable device 120, or computer 118 shown in FIG. 1.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the user interface 252 (e.g., via visual display, sound, or vibration). In some examples, the peripheral device 250 may be configured to display or otherwise communicate the sensor information as it is communicated from the sensor electronics 106 (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level). In other examples, the peripheral device 250 may process or interpret the received information (e.g., to declare an alert based on glucose values or a glucose trend). In various examples, the peripheral device 250 may receive information directly from sensor electronics 106, or over a network (e.g., via a cellular or Wi-Fi network that receives information from the sensor electronics 106 or from a device that is communicatively coupled to the sensor electronics 106).

Referring again to FIG. 2, the medical device 270 may include a user interface 272, a memory circuit 274, a processor 276, a wireless communication circuit 278, a sensor 280, a therapy circuit 282, or any combination thereof. The user interface 272 may, for example, include a touch-screen interface, a microphone, or a speaker, a vibration circuit, or any combination thereof, which may receive information from a user (e.g., glucose values, alert preferences, calibration coding) or deliver information to the user, such as e.g., glucose values, glucose trends (e.g., an arrow, graph, or chart), or glucose alerts. The processor 276 may be configured to present information to a user, or receive input from a user, via the user interface 272. The processor 276 may also be configured to store and retrieve information, such as communication information (e.g., pairing information or data center access information), user information, sensor data or trends, or other information in the memory circuit 274. The wireless communication circuit 278 may include a transceiver and antenna configured communicate via a wireless protocol, such as Bluetooth, Medical Implant Communication System (MICS), Wi-Fi, Zigbee, or a cellular protocol (e.g., CDMA (Code Division Multiple Access) or GSM (Global System for Mobiles)). The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one sensor 280 is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof. In various examples, the medical device 270 may be the medical device 108, peripheral medical device 122, wearable device 120, wearable sensor 130, or wearable sensor 136 shown in FIG. 1.

In examples where the peripheral medical device 122 or medical device 270 is an insulin pump, the pump and analyte sensor system 102 may be in two-way communication (e.g., so the pump can request a change to an analyte transmission protocol, e.g., request a data point or request data on a more frequent schedule), or the pump and analyte sensor system 102 may communicate using one-way communication (e.g., the pump may receive analyte concentration level information from the analyte sensor system). In one-way communication, a glucose value may be incorporated in an advertisement message, which may be encrypted with a previously-shared key. In a two-way communication, a pump may request a value, which the analyte sensor system 102 may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the system 100 shown in FIG. 1 may include two or more peripheral devices that each receives information directly or indirectly from the analyte sensor system 102. Because different display devices provide many different user interfaces, the content of the data packages (e.g., amount, format, and/or type of data to be displayed, alarms, and the like) may be customized (e.g., programmed differently by the manufacturer and/or by an end user) for each particular device. For example, in the embodiment of FIG. 1, a plurality of different peripheral devices may be in direct wireless communication with a sensor electronics module (e.g., such as an on-skin sensor electronics 106 that is physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system 102 and relay (i.e., share) information to other devices directly or through a server system (e.g., a network-connected data center) 126.

FIG. 3A is a side view of an analyte sensor system, illustrating an analyte sensor 34 implanted into a host. A mounting unit 14 may be adhered to the host's skin using an adhesive pad 8. The adhesive pad 8 may be formed from an extensible material, which may be removably attached to the skin using an adhesive. The sensor electronics 106 may mechanically couple to the adhesive pad 8.

FIG. 3B is an enlarged view of a distal portion of the analyte sensor 34. The analyte sensor 34 may be adapted for insertion under the host's skin and may be mechanically coupled to the mounting unit 14 and electrically coupled to the sensor electronics 106. The example analyte sensor 34 shown in FIG. 3B includes an elongated conductive body 41. The elongated conductive body 41 can include a core with various layers positioned thereon. A first layer 38 that at least partially surrounds the core and includes a working electrode, for example located in window 39). In some examples, the core and the first layer 38 are made of a single material (such as, for example, platinum). In some examples, the elongated conductive body 41 is a composite of two conductive materials, or a composite of at least one conductive material and at least one non-conductive material. A membrane system 32 is located over the working electrode and may cover other layers and/or electrodes of the sensor 34, as described herein.

The first layer 38 may be formed of a conductive material. The working electrode (at window 39) is an exposed portion of the surface of the first layer 38. Accordingly, the first layer 38 is formed of a material configured to provide a suitable electroactive surface for the working electrode. Examples of suitable materials include, but are not limited to, platinum, platinum-iridium, gold, palladium, iridium, graphite, carbon, a conductive polymer, an alloy, and/or the like.

A second layer 40 surrounds at least a portion of the first layer 38, thereby defining boundaries of the working electrode. In some examples, the second layer 40 serves as an insulator and is formed of an insulating material, such as polyimide, polyurethane, parylene, or any other suitable insulating materials or materials. In some examples, the second layer 40 is configured such that the working electrode (of the layer 38) is exposed via the window 39.

In some examples, the sensor 34 further includes a third layer 43 comprising a conductive material. The third layer 43 may comprise a reference electrode. In some examples, the third layer 43, including the reference electrode, is formed of a silver-containing material that is applied onto the second layer 40 (e.g., an insulator). The silver-containing material may include various materials and be in various forms such as, for example, Ag/AgCl-polymer pasts, paints, polymer-based conducting mixtures, inks, etc.

The analyte sensor 34 may include two (or more) electrodes, e.g., a working electrode at the layer 38 and exposed at window 39 and at least one additional electrode, such as a reference electrode of the layer 43. In the example arrangement of FIG. 1B, the reference electrode also functions as a counter electrode, although other arrangements can include a separate counter electrode. While the analyte sensor 34 may be used with a mounting unit in some examples, in other examples, the analyte sensor 34 may be used with other types of sensor systems. For example, the analyte sensor 34 may be part of a system that includes a battery and sensor in a single package, and may optionally include, for example, a near-field communication (NFC) circuit.

FIG. 3C is a cross-sectional view through the sensor 34 of FIG. 3B on plane 2-2 illustrating a membrane system 32. The membrane system 32 may include a number of domains (e.g., layers). In an example, the membrane system 32 may include an enzyme domain 42, a diffusion resistance domain 44, and a bioprotective domain 46 located around the working electrode. In some examples, a unitary diffusion resistance domain and bioprotective domain may be included in the membrane system 32 (e.g., wherein the functionality of both the diffusion resistance domain and bioprotective domain are incorporated into one domain).

The membrane system 32, in some examples, also includes an electrode layer 47. The electrode layer 47 may be arranged to provide an environment between the surfaces of the working electrode and the reference electrode that facilitates the electrochemical reaction between the electrodes. For example, the electrode layer 47 may include a coating that maintains a layer of water at the electrochemically reactive surfaces of the sensor 34.

In some examples, the sensor 34 may be configured for short-term implantation (e.g., from about 1 to 30 days). However, it is understood that the membrane system 32 can be modified for use in other devices, for example, by including only one or more of the domains, or additional domains. For example, a membrane system may include a plurality of resistance layers, or a plurality of enzyme layers. In some example, the resistance domain 44 may include a plurality of resistance layers, or the enzyme domain 42 may include a plurality of enzyme layers.

The diffusion resistance domain 44 may include a semipermeable membrane that controls the flux of oxygen and glucose to the underlying enzyme domain 42. As a result, the upper limit of linearity of glucose measurement is extended to a much higher value than that which is achieved without the diffusion resistance domain 44.

In some examples, the membrane system 32 may include a bioprotective domain 46, also referred to as a domain or biointerface domain, comprising a base polymer as described in more detail elsewhere herein. However, the membrane system 32 of some examples can also include a plurality of domains or layers including, for example, an electrode domain, an interference domain, or a cell disruptive domain, such as described in more detail elsewhere herein and in U.S. Pat. Nos. 7,494,465, 8,682,408, and 9,044,199, which are incorporated herein by reference in their entirety.

It is to be understood that sensing membranes modified for other sensors, for example, may include fewer or additional layers. For example, in some examples, the membrane system 32 may comprise one electrode layer, one enzyme layer, and two bioprotective layers, but in other examples, the membrane system 32 may comprise one electrode layer, two enzyme layers, and one bioprotective layer. In some examples, the bioprotective layer may be configured to function as the diffusion resistance domain 44 and control the flux of the analyte (e.g., glucose) to the underlying membrane layers.

In some examples, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some examples, the sensing membrane can be deposited on the electroactive surfaces of the electrode material using known thin or thick film techniques (for example, spraying, electro-depositing, dipping, or the like). The sensing membrane located over the working electrode does not have to have the same structure as the sensing membrane located over the reference electrode 30; for example, the enzyme domain 42 deposited over the working electrode does not necessarily need to be deposited over the reference or counter electrodes.

Although the examples illustrated in FIGS. 3B-3C involve circumferentially extending membrane systems, the membranes described herein may be applied to any planar or non-planar surface, for example, the substrate-based sensor structure of U.S. Pat. No. 6,565,509 to Say et al., which is incorporated by reference.

In an example in which the analyte sensor 34 is a glucose sensor, glucose analyte can be detected utilizing glucose oxidase, which produces hydrogen peroxide ($H_2O_2$) as a byproduct of the reaction of glucose with glucose oxidase. The hydrogen peroxide reacts with the surface of the working electrode, producing two protons ($2H^+$), two electrons ($2e^-$) and one molecule of oxygen ($O_2$), which produces an electronic current that may be detected by the sensor electronics 106. The amount of current is a function of the glucose concentration level. A calibration curve may be used to provide an estimated glucose concentration level based on a measured current. The amount of current is also a function of the diffusivity of glucose through the sensor membrane. The glucose diffusivity may change over time, which may cause the sensor glucose sensitivity to change over time, or "drift."

Figure 4:
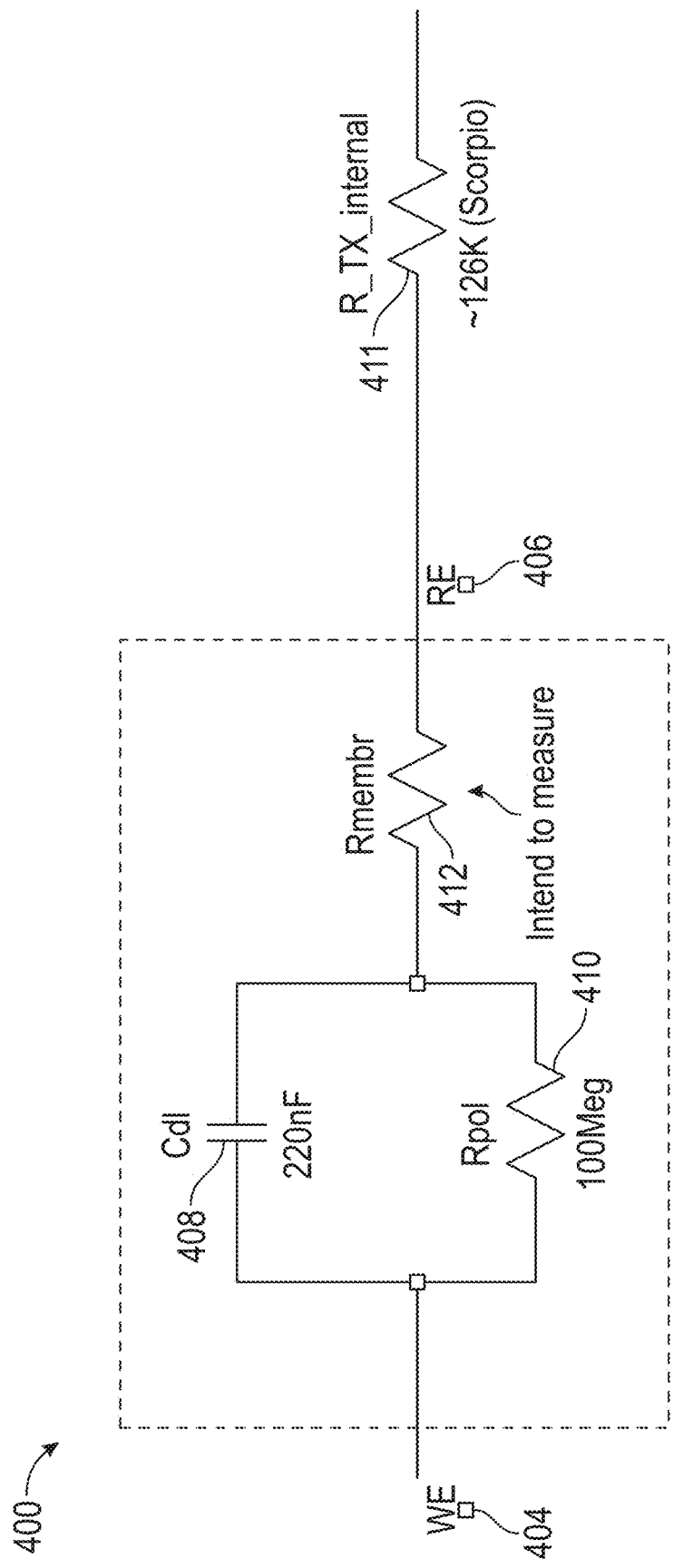
FIG. 4 is a schematic illustration of a circuit that represents the behavior of an analyte sensor.

FIG. 4 is a schematic illustration of a circuit 400 that represents the behavior of an analyte sensor, such as the sensor 34 shown in FIGS. 3A-3C. As described above, the interaction of hydrogen peroxide (generated from the interaction between glucose analyte and glucose oxidase) and working electrode (WE) 404 produces a voltage differential between the working electrode (WE) 404 and reference electrode (RE) 406, which drives a current that may be measured by sensor electronics 106 and used to estimate a glucose concentration level. The circuit 400 also includes a double-layer capacitance (Cdl) 408, which occurs at an interface between the working electrode (WE) 404 and the adjacent membrane (not shown, see description above).

In a typical in vivo analyte sensor, a double-layer capacitance (Cdl) may occur at the interface between the working electrode 404 and the adjacent membrane due to the presence (e.g., during application of an applied voltage between the working electrode 404 and reference electrode) of two layers of ions with opposing polarity. The equivalent circuit 400 may also include a polarization resistance (Rpol) 410, which may be relatively large, and may be modeled, for example, as a static value (e.g., 100 mega-Ohms), or as a variable quantity that varies as a function of glucose concentration level.

An estimated analyte concentration level may be determined based upon A) a measured current (charge) flow through the analyte sensor membrane 412 when a voltage is applied to the sensor circuit and B) a glucose sensitivity of the sensor, which correlates a detected current flow to a glucose concentration level.

The change in glucose diffusivity over time presents a problem, in that two unknown variables (glucose concentration around the membrane 412 and glucose diffusivity in the membrane 412) are present in the system. For example, frequent blood glucose meter calibrations may be used to account for the drift, but this need for meter calibrations may be undesirable for a variety of reasons (e.g., inconvenience to the patient, cost, the potential for inaccurate blood glucose meter data, etc.).

With reference to the equivalent circuit 400, when a voltage is applied across the working and reference electrodes 404 and 406, a current may be considered to flow (forward or backward depending on polarity) through the internal electronics of transmitter (represented by R_Tx_internal) 411; through the reference electrode (RE) 406 and working electrode (WE) 404, which may be designed to have a relatively low resistance; and through the sensor membrane 412 (Rmembr, which is relatively small). Depending on the state of the circuit, current may also flow through, or into, the relatively large polarization resistance 410 (which is indicated as a fixed resistance, but may also be a variable resistance that varies with the body's glucose level, where a higher glucose level provides a smaller polarization resistance), or into the double-layer capacitance 408 (i.e., to charge the double-layer membrane capacitor formed at the working electrode 404), or both.

The impedance (or conductance) of the membrane (Rmembr) 412 is related to electrolyte mobility in the membrane, which is in turn related to glucose diffusivity in the membrane. As the impedance goes down (i.e., conductance goes up, as electrolyte mobility in the membrane 412 goes up), the glucose sensitivity goes up (i.e., a higher glucose sensitivity means that a particular glucose concentration will produce a larger signal in the form of more current or charge flow). Impedance, glucose diffusivity, and glucose sensitivity are further described in U.S. Patent Publication No. US2012/0262298, which is incorporated by reference in its entirety.

Determination of Impedance by Measuring Current or Charge Count.

The relationship between impedance (or conductance) of an analyte sensor circuit and analyte diffusivity (e.g., glucose diffusivity) may allow for determination of an accurate glucose sensitivity based upon a determined impedance value of the sensor circuit. In a situation (e.g., in vivo implantation) where the sensor sensitivity is not precisely known, but impedance can be determined from measurements (e.g., using Ohm's law), a predicted sensitivity may be determined based on a correlation between impedance (or conductivity) and glucose sensitivity.

Figure 5A:
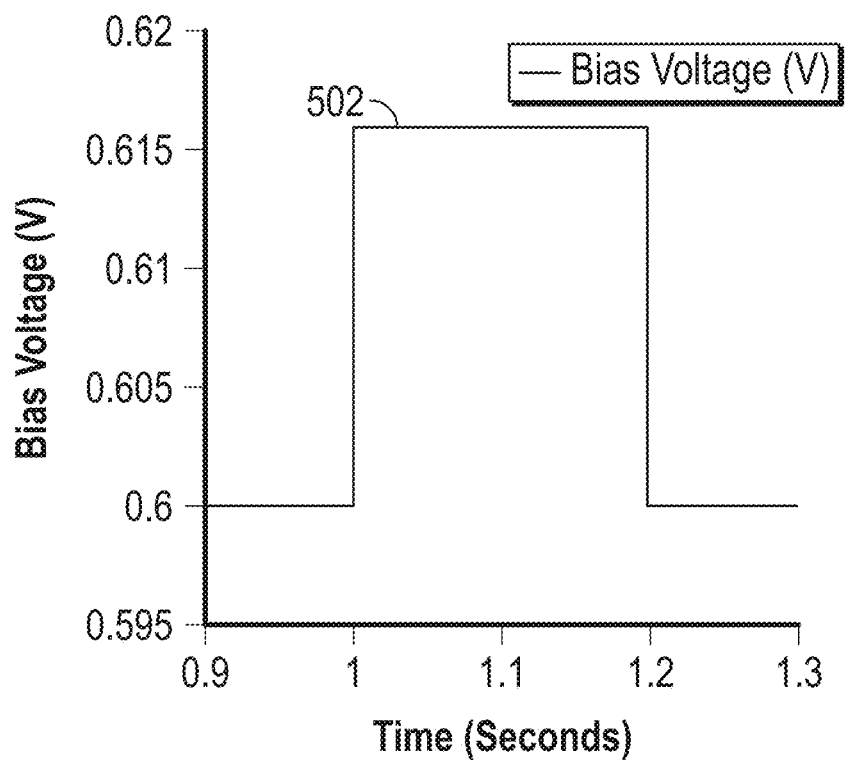
FIG. 5A is a graph that shows a bias voltage step.
Figure 5B:
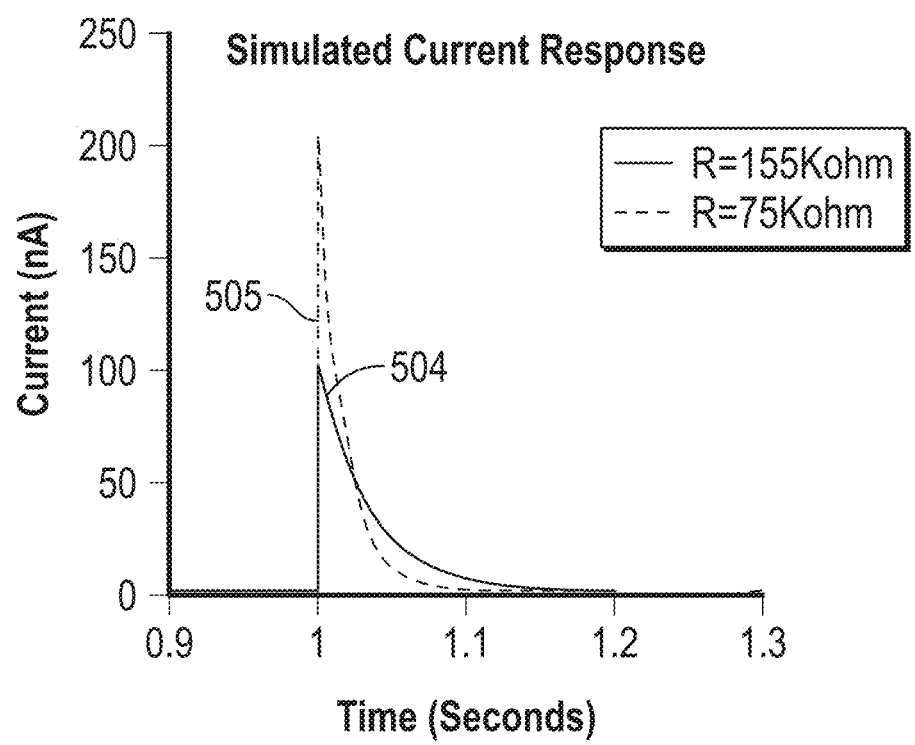
FIG. 5B is a graph that shows a simulated current response to the voltage step shown in FIG. 5A.

In some examples, impedance may be determined based upon application of a known voltage (or voltage step) and measurement of current flow (e.g., integrating charge count over time). In a typical analyte sensor, a sensor bias voltage is applied to a sensor circuit to enable accurate sensing using a sense amplifier. FIG. 5A is a chart that shows a bias voltage 502 stepped up from 0.600 Volts to 0.616 Volts. FIG. 5B shows the corresponding simulated response 504, 505 for a circuit having a 155 kiloohm impedance and a circuit having a 75 kiloohm impedance. As shown in FIG. 5B, the current for the 75 kiloohm circuit rises to a peak current value of over 200 nanoamps, and the response current for the 155 kiloohm circuit rises to about 100 nanoamps. The response current for both circuits then decays as the double-layer capacitance adjusts to the change in applied bias (e.g., as the Cdl in FIG. 4 charges). It should be noted that both FIGS. 5A and 5B illustrate the change in sensor current in response to the transient voltage step. Accordingly, what is shown is the incremental delta current riding on top of an already-existing non-zero glucose current under 0.6V bias.

In a sensor system, a circuit with 155 kiloohm impedance may be differentiated from a circuit with 75 kiloohm impedance based on the magnitude of the current response. In some examples, the impedance may be determined based on the current response, and the resistance attributable to the membrane (Rmembr 412 in FIG. 4) may be determined based upon knowledge (or estimates) of the other impedances in the circuit (e.g., R_TX_internal may be estimated) and Kirchoff's law.

Figure 5C:
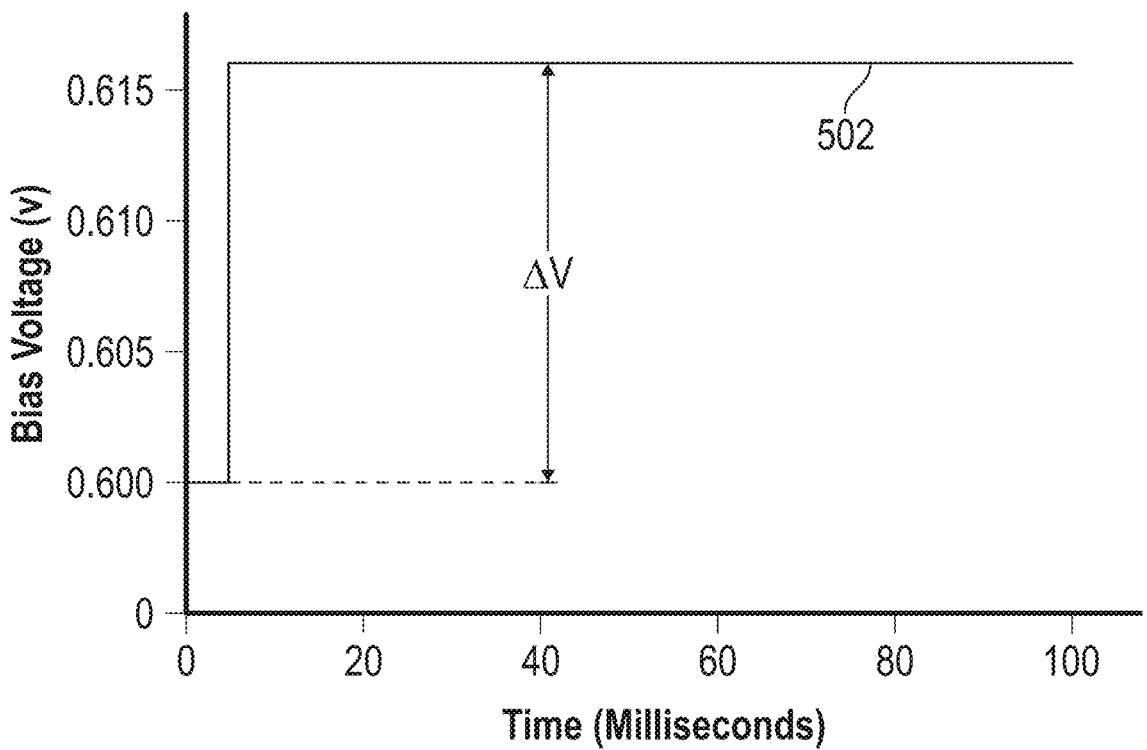
FIG. 5C is a graph that shows the voltage step of FIG. 5A with a time axis in milliseconds.
Figure 5D:
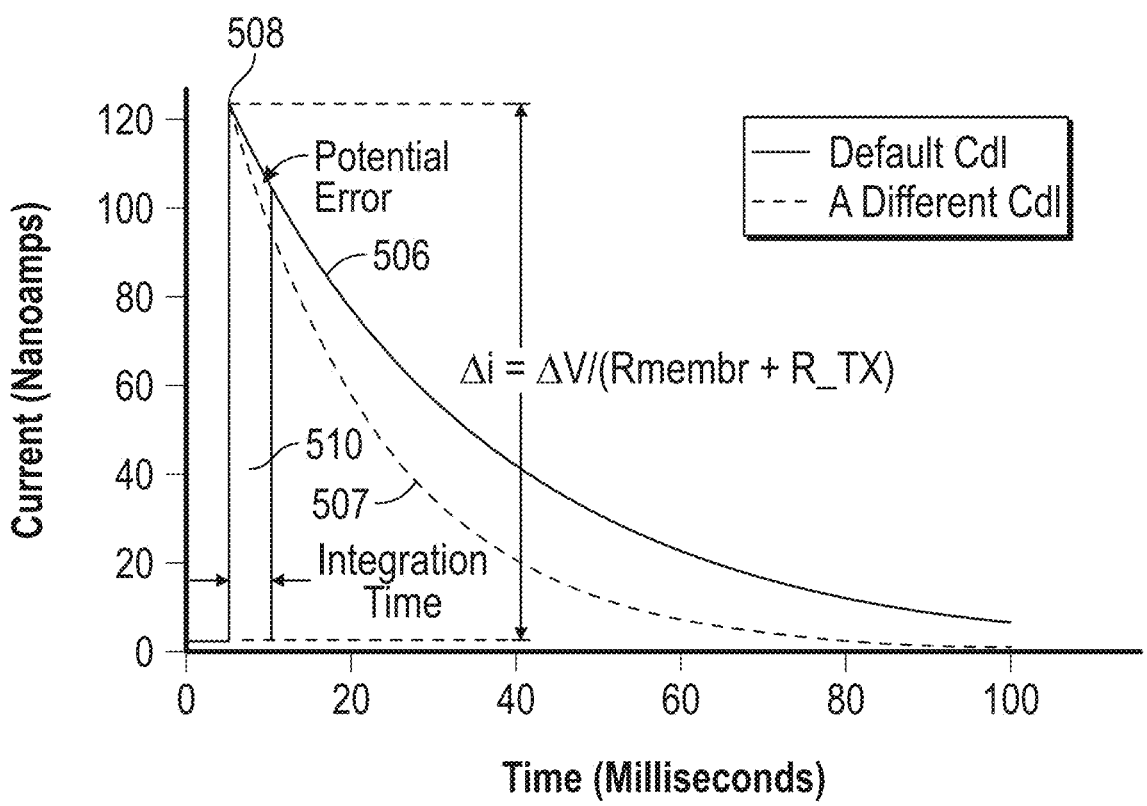
FIG. 5D is a graph that shows the current response to the step of FIG. 5C, with a time axis in milliseconds.

FIG. 5C is a chart that shows a bias voltage 502 stepped up from 0.600 Volts to 0.616 Volts. FIG. 5D shows the current response 506 to the step-up in voltage plotted against time in milliseconds. As shown in FIG. 5D, the sensed current quickly rises to a peak current value 508 (e.g., 120 nA), and then decays as the double-layer capacitance adjusts to the change in applied bias (e.g., as the Cdl 408 in FIG. 4 charges). FIG. 5D also shows a response current 507 for a second sensor with a different double-layer capacitance value, which is described below.

In an analyte sensor, the peak current value 508 may not be measurable directly, but it may be determined by measuring the accumulated charge over an Integration Time 510 (which may, for example, be e.g., 3.9 ms, or a value between 3-5 ms, or a value between 2 and 20 ms, or a value between 2 and 40 ms) after the step-up of the bias voltage, which is the equivalent of integrating under the current response curve for the area A indicated in FIG. 5D.

Simply dividing the integrated current by the specified period of time yields an average current over the integration time, which may be used as an approximation of the peak current, but this approximation is less than the actual peak due to the current decay caused by the double-layer capacitance. A more accurate determination of the peak current may be obtained by assuming a value (e.g., an experimentally determined value) for the double-layer capacitance (Cdl), which allows for derivation of a peak value based upon the integrated current (PI) and the assumed value for Cdl.

Because the capacitance of the membrane (not shown in FIG. 4) may be much smaller than the double-layer capacitance (Cdl), the polarization resistance (Rpol) may be very high (>1 megaOhm), and the capacitive resistance of the membrane is initially very large after the voltage step, substantially all of the current flows through Rmembr 412 and Cdl 408. In a short period (e.g., 5 ms) after the voltage step, the total sensor resistance may be estimated as the membrane resistance (Rmembr 412). The membrane resistance (Rmembr 412) may thus be estimated using Ohm's law: $\Delta i=\Delta V/(Rmembr+R\_TX)$. After the peak current is determined (e.g., based up integrated charge for a short period after the voltage step), this equation may be solved for the resistance of the membrane (Rmembr 412).

An estimate of the integrated pulse current may be obtained by integrating over a small portion of the current decay curve, as shown for example, in FIG. 5D. An integration over a short integration time after the voltage step may be used to estimate peak current. The integration time may be relatively short compared to the time it takes the current response to a step voltage to decay (i.e., compared to the capacitor charge time for the double-layer capacitor after application of the step in bias voltage). For example, an integration time of four milliseconds (4 ms) may be used to estimate peak current. Other important parameters may include the rise time of the voltage step (or bias pulse), the impedance of sensor electronics (which may be measured and consistently controlled in manufacturing), the pulse potential (e.g., a 16 mV step may be applied), and alignment of the current integration with the rising edge of the voltage step (which may be controlled by a clock in the sensor electronics, e.g., the start of the current integration may be one clock cycle after the beginning of a voltage step), and duty cycle (e.g., a five percent duty cycle may be used to allow a sensor membrane capacitance to discharge to a consistent pre-pulse state). In some examples, a voltage step may be applied before each glucose measurement, or recurrently (e.g., before every second glucose measurement, or every third, fourth, or fifth glucose measurement, or once an hour, or once or twice or more times per day).

Figure 5E:
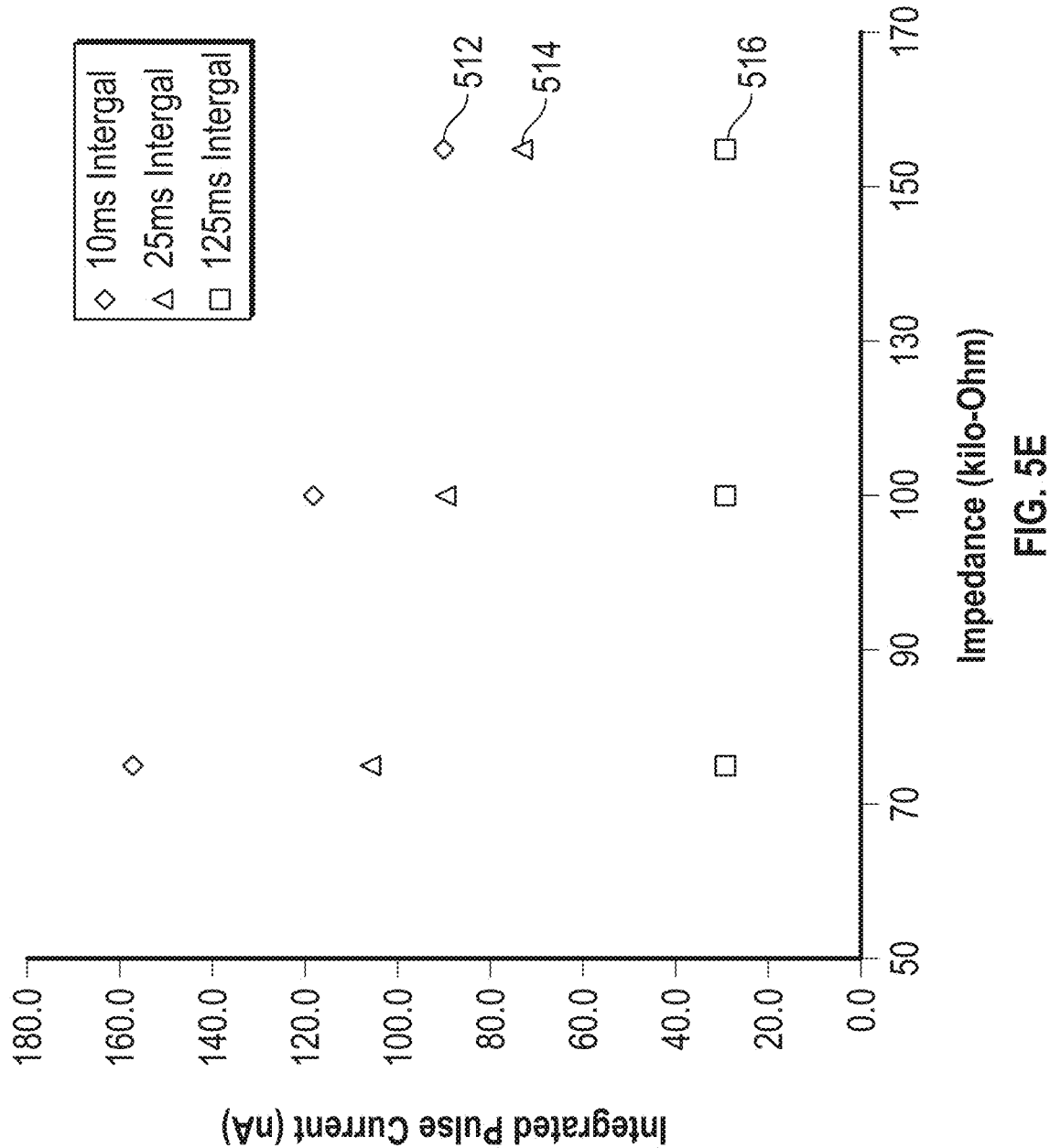
FIG. 5E is a graph that shows integrated pulse current plotted against impedance for three different integration times.

FIG. 5E shows integrated pulse current 512, 514, 516 plotted against impedance for three different integration times (10 milliseconds, 25 milliseconds, and 125 milliseconds). For the 125 millisecond integration time, the integrated pulse current is approximately the same for three different impedance values (75 kOhm, 110 kOhm, 155 kOhm). Because the current is averaged over all or most of the current decay curve (i.e., the current reaches or approaches zero (or a baseline current) within 125 ms), the sensor circuits with different impedances all result in an integrated pulse current of about 30 nanoamps. This approximate equivalence in integrated pulse current for the three different impedance values would prevent determination of an accurate impedance estimate from the integrated pulse currents. In contrast, an integration time of 25 milliseconds results in different values of integrated pulse current for the three different impedance values. As a result, a sensor that integrates over a 25 millisecond integration time would allow for differentiation between sensor circuits having 75 kOhm, 110 kOhm, 155 kOhm impedance values or estimation of an impedance based on integrated pulse current. Using a 10 millisecond integration time provides even greater variation in integrated pulse current for different impedance values, which would improve performance in determining an impedance estimate.

While the description above in some instances discloses absolute current and absolute voltage, it is understood that the methods may also be used with respect to a change in current ($\Delta i$), change in voltage ($\Delta V$), or change in impedance ($\Delta R$). For example, in some analyte sensors, the baseline current may not be zero, because of the presence of a steady bias voltage.

Figure 5F:
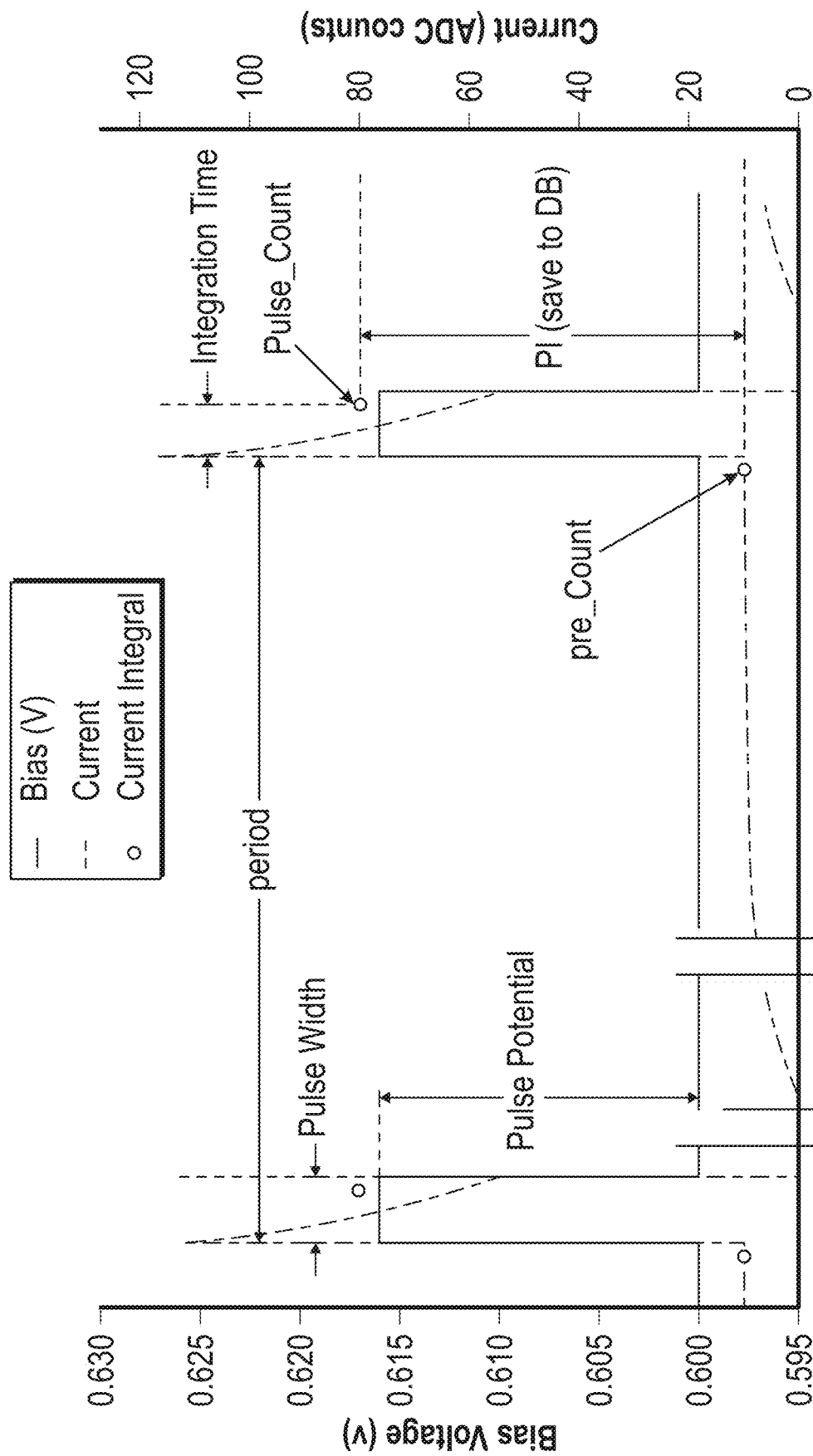
FIG. 5F is a graph that shows bias voltage overlaid onto the current response to a voltage step.

In some examples, a step voltage may be recurrently (e.g., periodically) applied to a sensor circuit. The step voltage may be maintained for a period that is as long or longer than the entire current decay curve, as shown in FIG. 5C, or the step voltage may be returned to a baseline value before the current has decayed to a steady state value, as shown in FIG. 5F. FIG. 5F shows bias voltage overlaid onto the current response to a voltage step ("Pulse Potential"). The step voltage step (e.g., increased from 0.600 Volts to 0.616) may be applied and maintained for a segment of time (Integration Time), and the bias voltage may then be returned to the level it was at prior to the step (e.g., returned to 0.600 Volts). A Current Integral for the Integration Time may be determined based on a difference in a charge count (e.g., obtained using a Coulomb counter) between a count value (Pulse_Count) at the end of the Integration Time and a count value (Pre_Count) at the beginning of the Integration Time. The Current Integral amounts to an accumulated charge for the pulse (PI), which may be stored in a database (DB) for comparison with past or future impedance values or may be used in a compensation algorithm to provide a more accurate estimated analyte concentration value.

When the bias voltage returns to its normal baseline level (e.g., when the Integration Time period expires and the bias voltage drops from 0.616 Volts back to 0.600 Volts), the capacitor begins to discharge (to move back to a 0.6 Volt charge state), and the observed current drops below the baseline value (because the capacitor is supplying some of the potential to maintain the bias voltage). Eventually, the current transitions back to its baseline (steady state) value.

After a period of time has expired, a second voltage step may be applied, and a second PI value may be determined in the manner described above.

Averaging of Charge Count Values Over Multiple Sampling Periods.

Figure 6A:
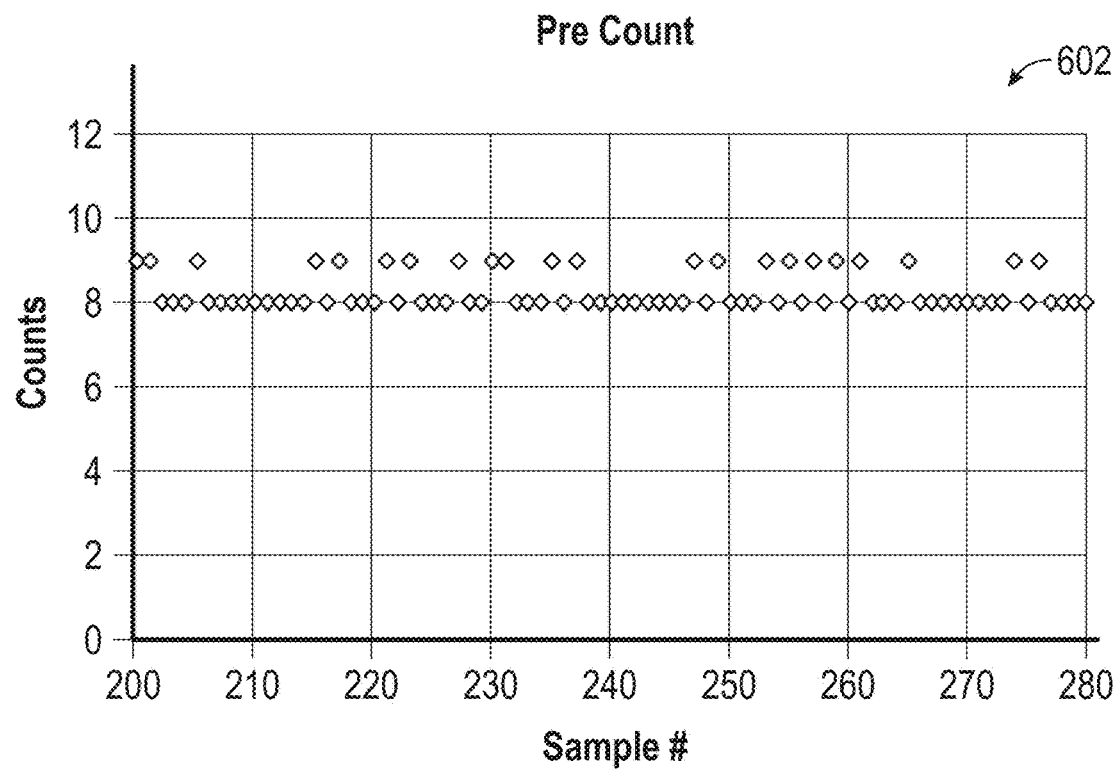
FIG. 6A is a graph that shows count values at the beginning of the Integration Time (Pre_Count) and at the end of the Integration Time (Pulse_Count) for a plurality of samples by a sensor.
Figure 6B:
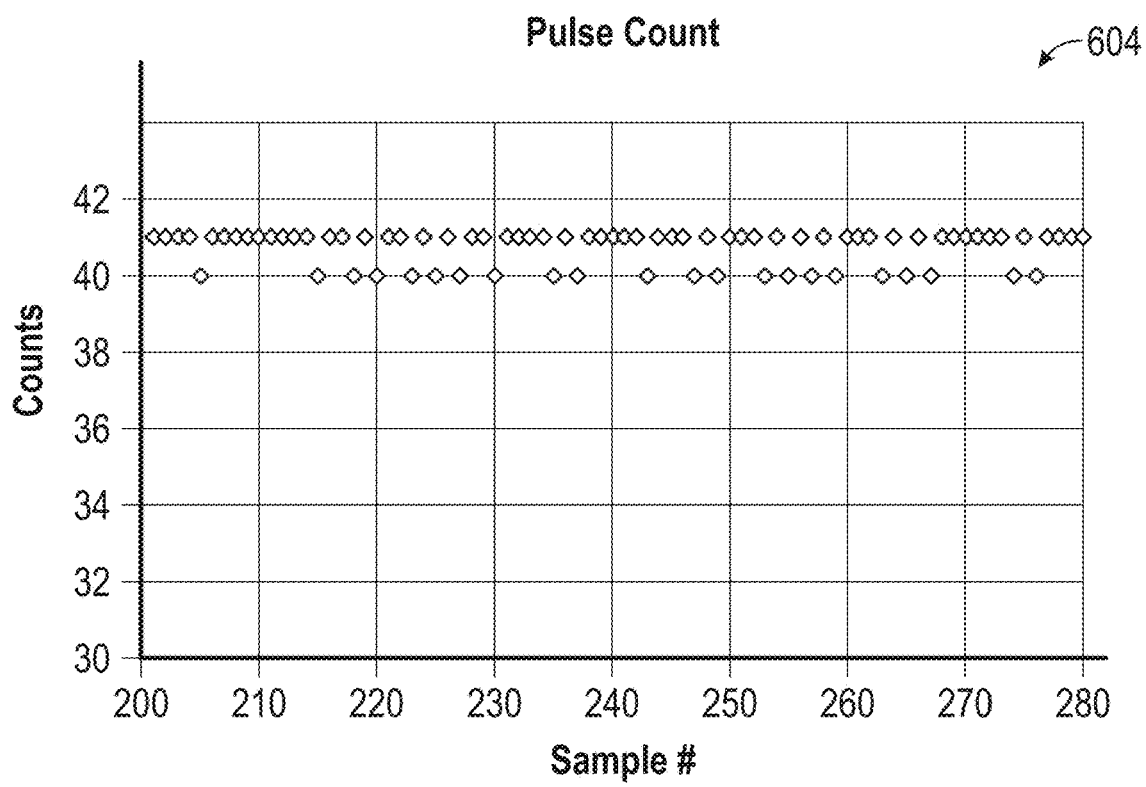
FIG. 6B is a graph that shows count values at the beginning of the Integration Time (Pre_Count) and at the end of the Integration Time (Pulse_Count) for the plurality of sensor samples of FIG. 6A.
Figure 6C:
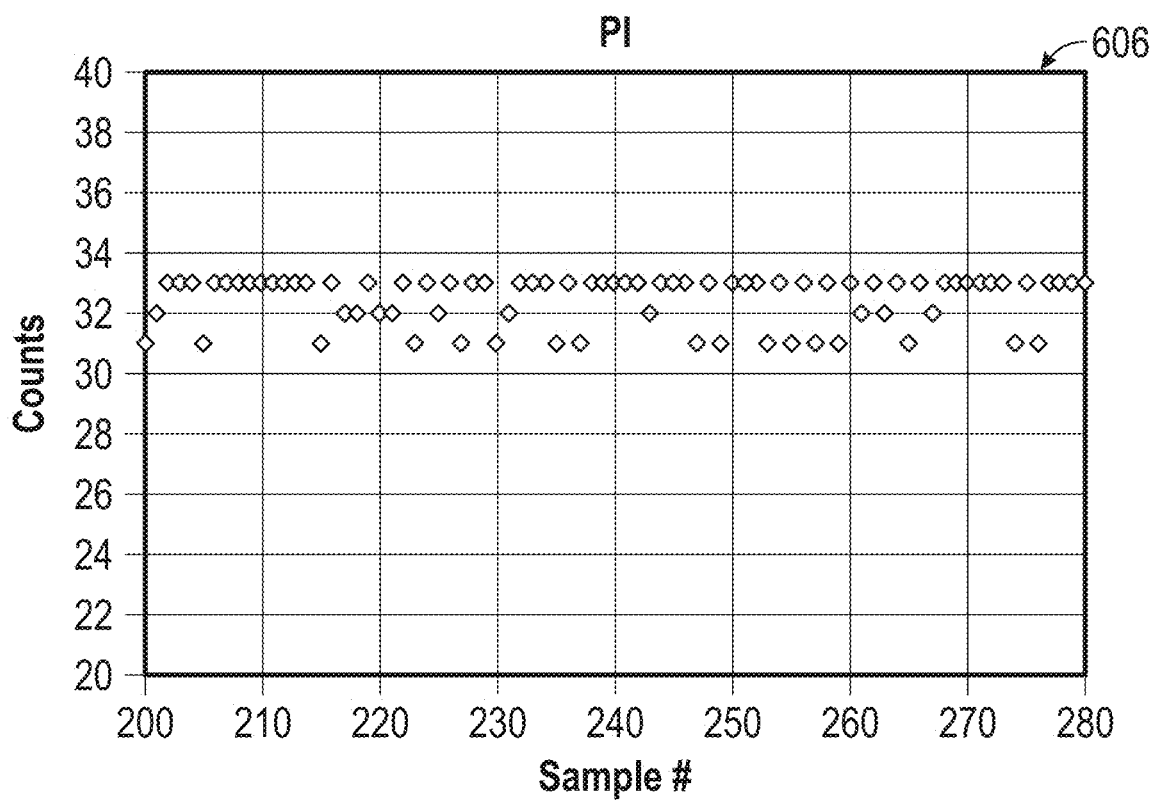
FIG. 6C is a graph that shows integrated charge count (PI) for the samples of FIGS. 6A and 6B.
Figure 6D:
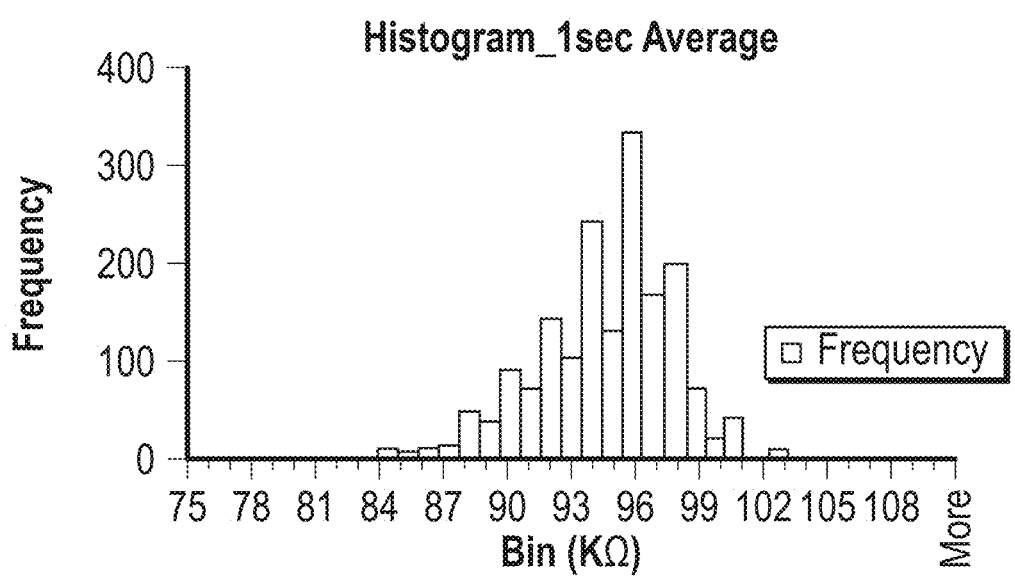
FIG. 6D is a histogram plot of determined impedance for a sensor, where charge count was averaged over a plurality of one-second sampling periods.
Figure 6E:
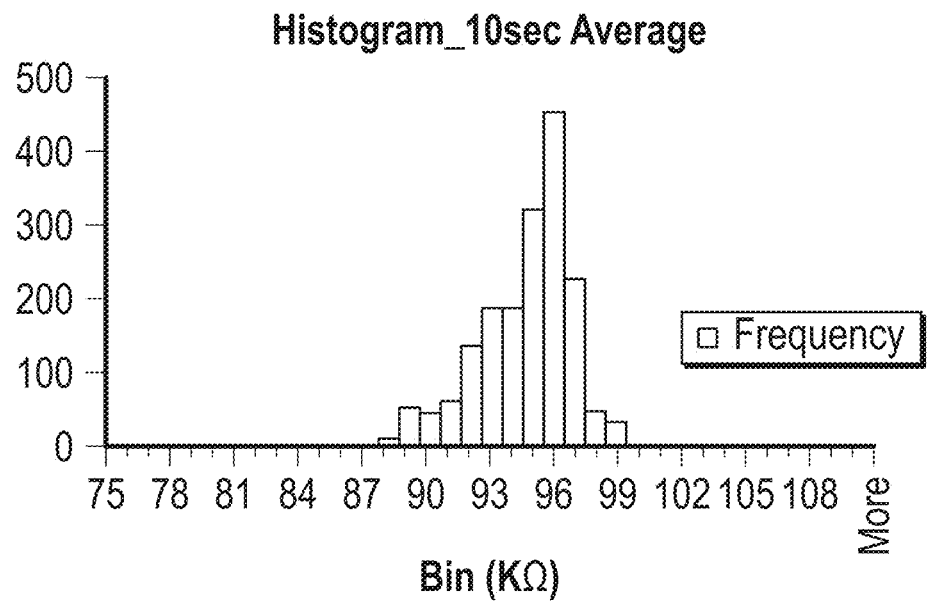
FIG. 6E is a histogram plot of determined impedance for a plurality of ten-second sampling periods.
Figure 6F:
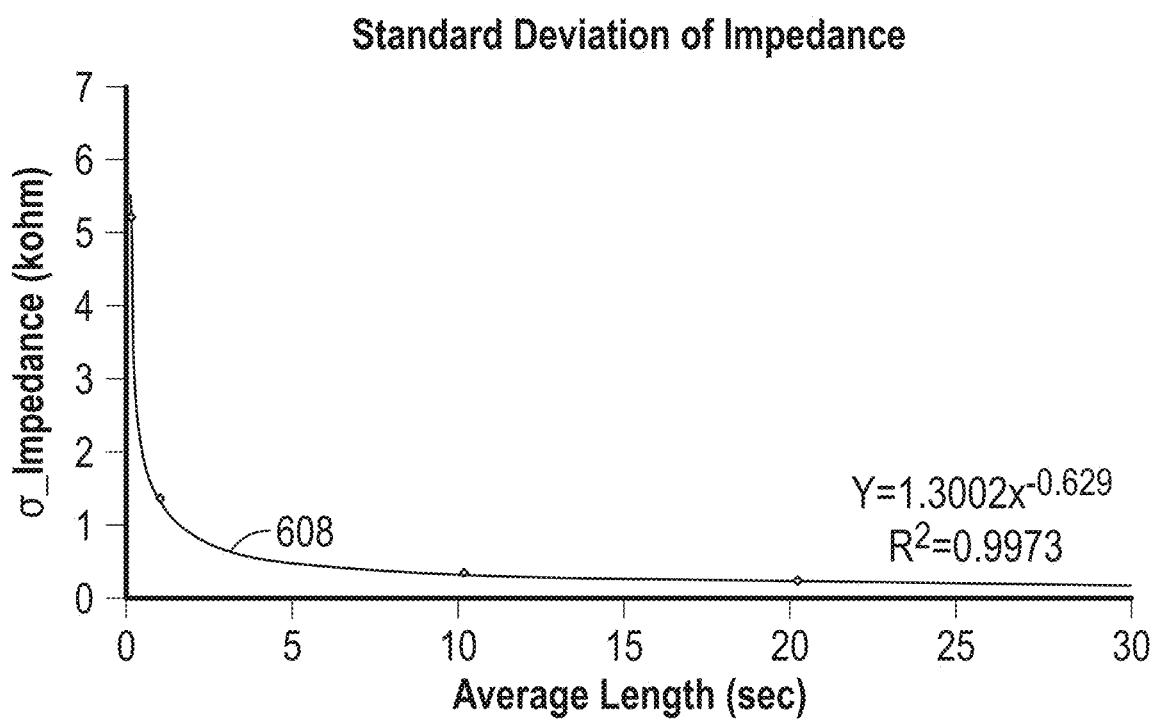
FIG. 6F is a graph that shows the standard deviation of determined impedance values for a sensor plotted against a length of time over which current (e.g., integrated charge count) was measured or determined.

FIGS. 6A and 6B show respective count values 602, 604 at the beginning of the Integration Time (Pre_Count) and at the end of the Integration Time (Pulse_Count) for a plurality of samples by a sensor. FIG. 6C shows the integrated charge count (PI) 606 for the Integration Time (Pulse_Count–Pre_Count.) The counts for multiple Integration Times in a sampling interval (e.g., 1 second, 10 seconds, 12 seconds, or 20 seconds) maybe be averaged to determine an average (e.g., mean or median) integrated charge count (PI), which may increase the accuracy of the charge count (PI) or increase the accuracy of an impedance or sensitivity derived therefrom. FIG. 6D shows a histogram plot of determined impedance for a sensor, where charge count was averaged over a plurality of one-second sampling periods (e.g., at a rate of one sample every 5 milliseconds during the sampling period). FIG. 6E is a histogram plot of determined impedance for a plurality of ten-second sampling periods. The histogram based on ten-second sampling periods provides a tighter distribution (e.g., more clustering around 96 kΩ and a tighter standard deviation). While using an average value from a plurality of Integration Times may improve the accuracy of the integrated charge count (PI) and impedance or sensitivity derived therefrom, obtaining a large data set may have an adverse impact on battery life due to energy consumed in applying the voltage step and processing the resulting current. FIG. 6F shows the standard deviation of determined impedance values 608 for a sensor plotted against a length of time over which current (e.g., integrated charge count) was measured or determined. In some examples, an averaging time of about 1 second (e.g., 0.5 to 1.5 seconds, or 0.5 to 3 seconds) is used, to provide a set of determined impedance values having a standard deviation of less than 2 Ohms. In some examples, an averaging time of about 10 seconds or 12 seconds (e.g., 5 to 15 seconds, or 8 to 12 seconds, or 10 to 14 seconds) is used to collect current (e.g., integrated charge count) values, which may provide a set of determined impedance values with a standard deviation of less than 1 Ohm.

The Relationship Between Impedance and Sensitivity.

Figure 7A:
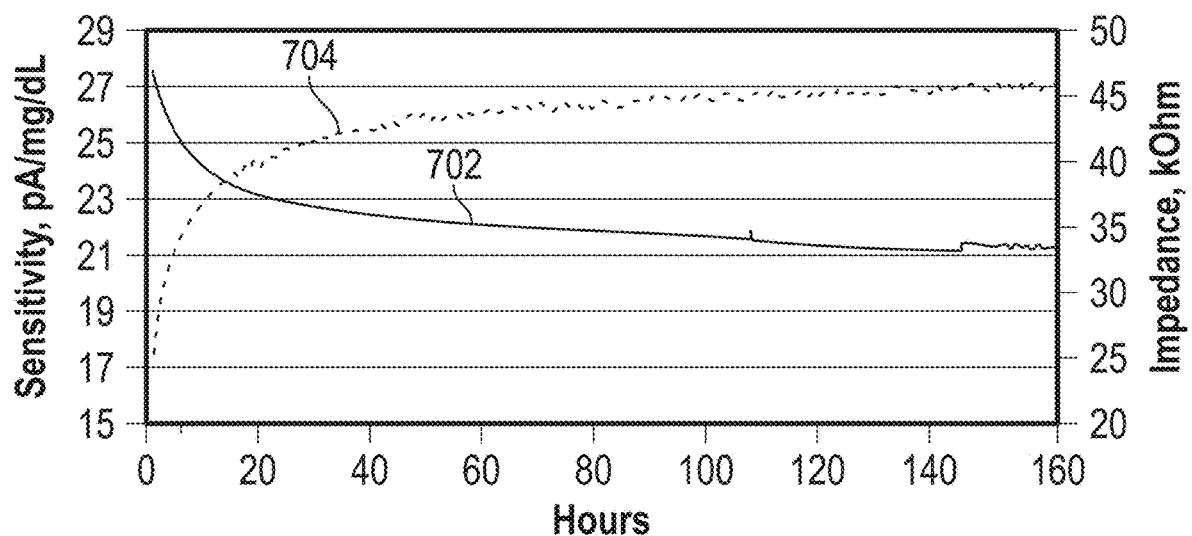
FIG. 7A is a graph that shows experimental data plotted against time, where impedance was measured from a tested sensor, and sensitivity was determined by placing the tested sensor in a solution having a known glucose concentration (e.g., a known mg/dL of glucose) and measuring a current.
Figure 7B:
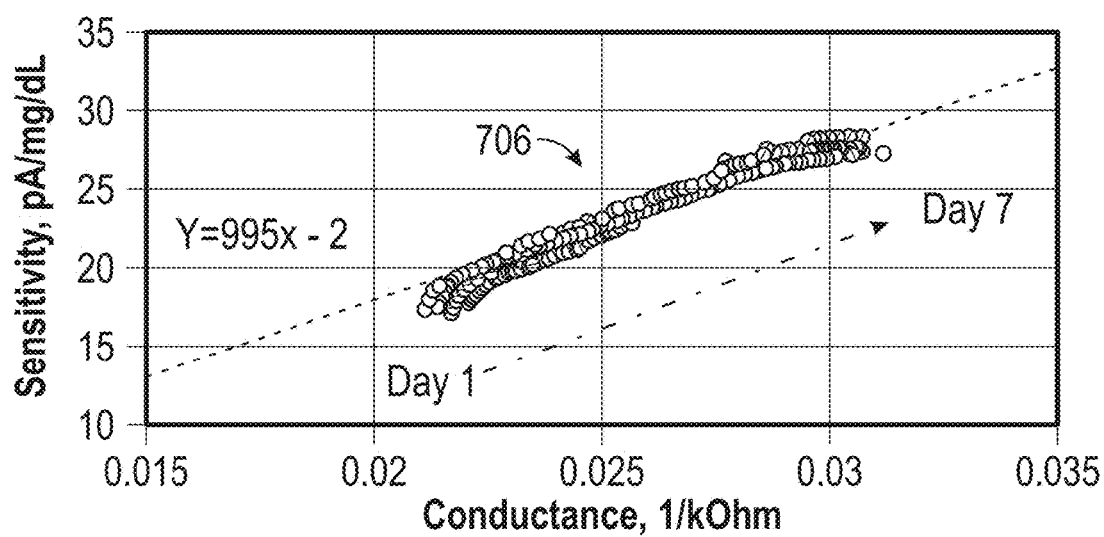
FIG. 7B is a graph that shows sensitivity plotted against conductance.

A correlation has been observed between the estimated impedance (e.g., resistance in a DC circuit) and the glucose sensitivity of a sensor. FIG. 7A shows experimental data plotted against time, where impedance 702 was measured from a tested sensor, and sensitivity 704 was determined by placing the tested sensor in a solution having a known glucose concentration (e.g., a known mg/dL of glucose) and measuring a current (e.g., in pA) in the tested sensor circuit (e.g., using sensor electronics). As can be seen from the graph, impedance 702 falls over time and glucose sensitivity 704 rises. FIG. 7B shows sensitivity 706 plotted against conductance (which is the inverse of impedance) for a number of sensors. A linear relationship between sensitivity and conductance (e.g., y=995x−2, or Sensitivity=995(Conductance)−2) may be observed from the data in FIG. 7B. The relationship between sensitivity and conductance may be used to determine a sensitivity in a sensor (e.g., an implanted sensor) having an unknown sensitivity and a conductance determined from a sensor measurement (e.g., the inverse of a measured impedance as described above). In some examples a functional range of the relationship may be defined. For example, a function range may be defined as in which the relationship between conductance and sensitivity is linear or approximately linear, such as 0.023 to 0.030 in FIG. 7B.

Double-Layer Capacitance Mitigation

While an impedance may be determined by assuming a default value for double-layer capacitance, such an assumption may introduce an error due to a difference between an actual double-layer capacitance and the assumed default capacitance. In some examples, the assumed default capacitance is the capacitance of a text unit for calibrating an analyte sensor transmitter on the bench.

In reference to FIG. 5D, the current response 506 may represent an assumed (e.g., default) double-layer capacitance (Cdl), which has a first current decay rate. As the capacitor charges, the current flow falls off. The second current response 507 shown in FIG. 5D may represent an actual current response of a particular sensor that has a double-layer capacitance that is smaller than the assumed double-layer capacitance. The observed current response 507 decays more quickly than current response 506, due to the smaller capacitance of the sensor associated with current response 507. As a result, the integrated charge during the Integration Time will be lower (i.e., the area under the curve is smaller) for current response 507 of the sensor than for a sensor having the assumed capacitance that produces the current response 506. When sensor electronics determine an impedance for a sensor that has current response 507, but the computations assume the current response 506, the resulting determined impedance will include an error, i.e., the inferred peak will be lower than it actually is, and the determined impedance (based on the erroneously low peak current value) will be higher than it would be if the true double-layer impedance and resulting current response 507 were used in the determination. In other words, failing to account for the actual double layer capacitance (Cdl), which varies from sensor to sensor, will result in inaccurate estimates of the membrane resistance (Rmembr.)

Figure 8A:
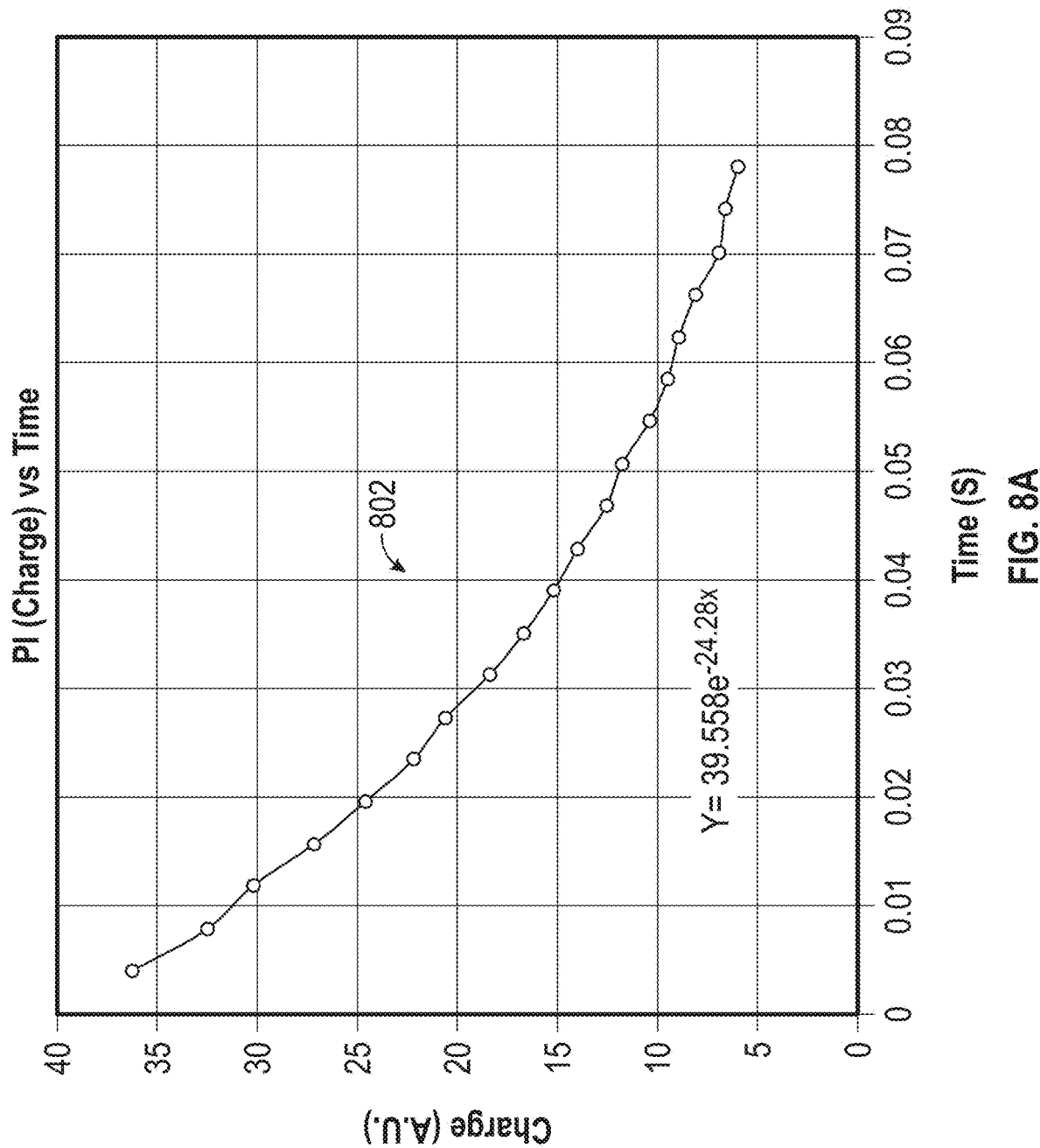
FIG. 8A is a graph that shows integrated charge for a number of sequential time periods.

In some examples, the current response 506 may be estimated by repeated integrations of charge (current) over a number of Integration Time periods during the current decay. For example, charge may be integrated over sequential Integration Time periods to construct a decay curve. FIG. 8A shows an example in which integrated charge 802 for a number of sequential Integration Time periods (e.g., 3.9 ms) is plotted against time to produce a decay curve. Theoretically, the current response i(t) is described by the equation: $i(t)=(Vstep)/Rmember * e^{(-t/Rcoat*Cdl)}$. By fitting the curve to an exponential trend (e.g., $y=39.558e^{-24.28x}$), the 1/Rmembr*Cdl factor can be extracted (e.g., 1/Rmembr*Cdl=1/24.8=40 ms in the illustrated example). The current level at the time at which the step was applied (i.e., time zero) may not be known from measurement, as the integration takes a period of time (e.g., 3.9 ms), so the measured current flow for the first period represents an average over the first period. The current value at time zero may be determined as the factor in front of the exponential in the fitted equation (curve). For example, in the equation above, the current flow at time zero is 39.558, which represents the intercept obtained by extrapolating the curve back to the zero seconds point (T=0) on the curve. By reconstructing the current response curve, the intercept at t=0 can be estimated, yielding a more accurate value for Rmembrane.

Figure 8B:
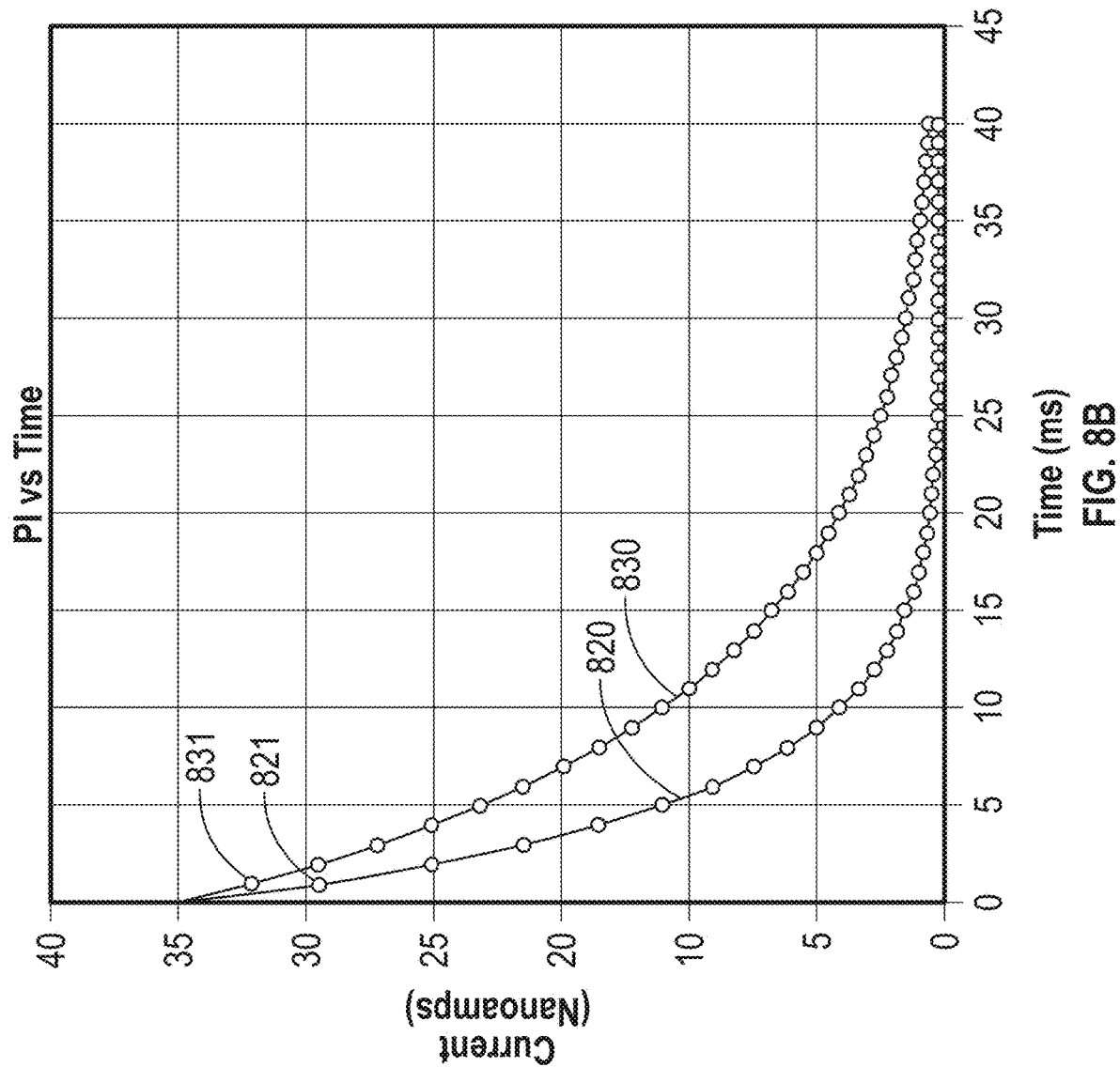
FIG. 8B is a graph that shows two current response curves with the same peak (35 nanoAmps) but a different decay rate.

FIG. 8B shows two current response curves 820, 830 with the same peak (35 nanoAmps) but a different decay rate. The first curve 820 may represent a sensor at a first time after implantation in a host, and the second curve 830 may represent the same sensor at a second time. For example, the sensor may have a membrane resistance (Rmembr) of 50 kiloOhms, the first curve 820 may reflect a double layer capacitance of 100 nanoFarads, and the second curve 830 may represent a double layer capacitance of 200 nanoFarads. The intercept at time zero (t=0) is the same.

Figure 8D:
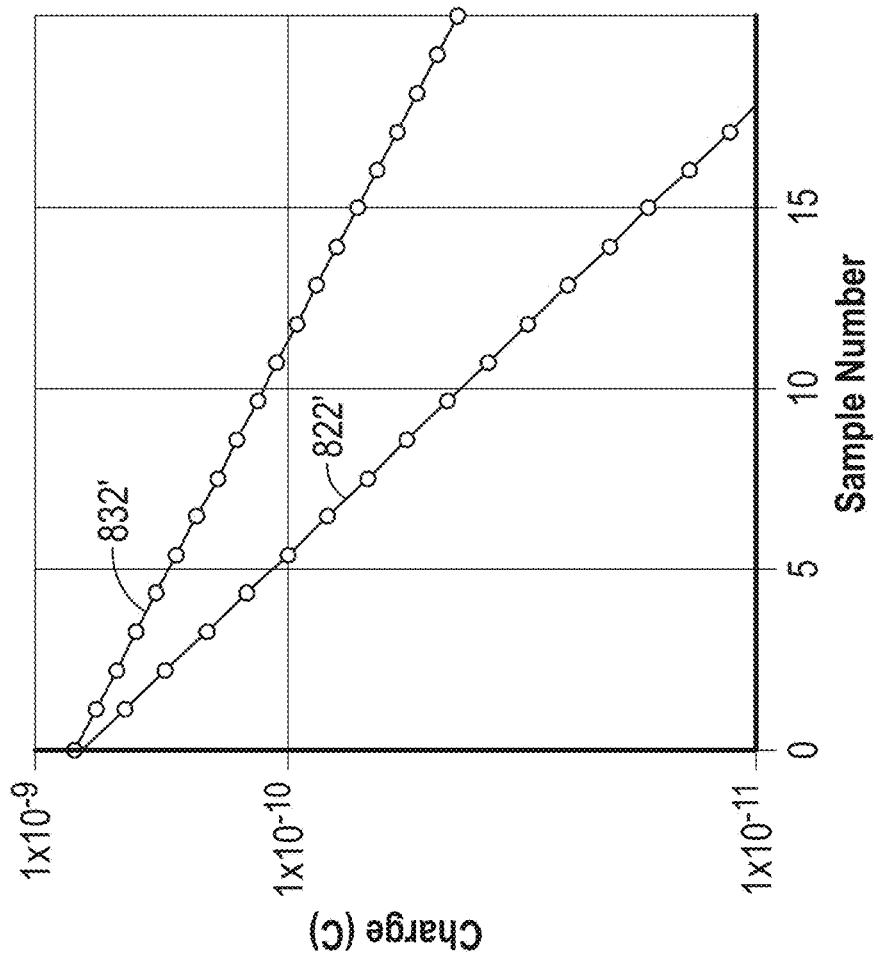
FIG. 8D is a graph that shows charge plotted on a logarithmic scale against sample number.
Figure 8C:
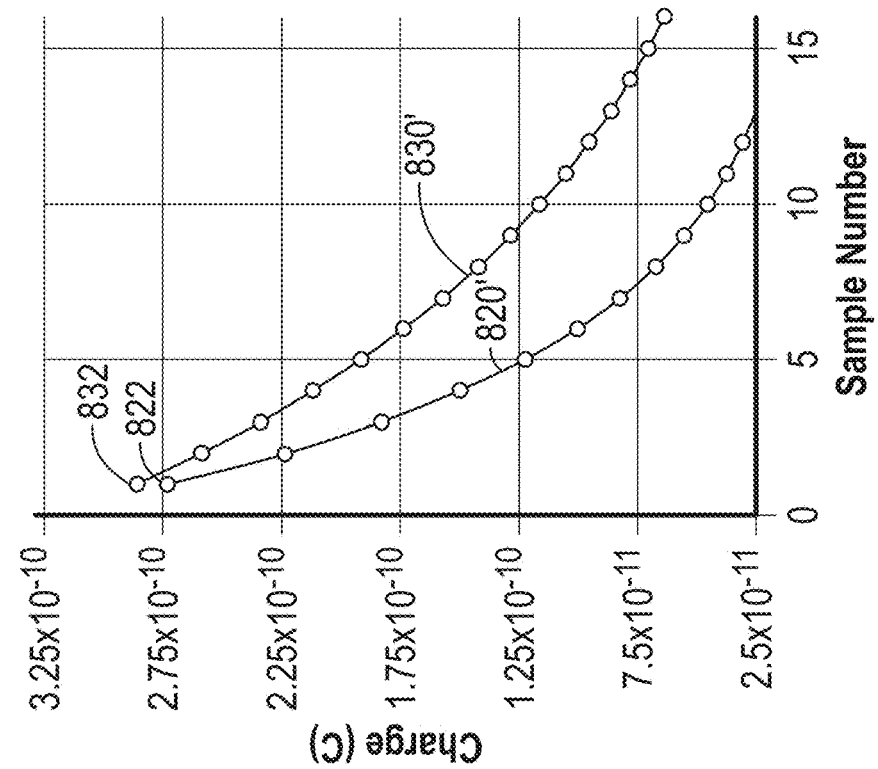
FIG. 8C is a graph that shows integrated charge for a plurality of equivalent Integral Time periods for two sensors having different decay rates.

FIG. 8C shows integrated charge for a plurality of sequential equivalent Integral Time periods for the first curve 820' and the second curve 830' (which means that the Sample Number axis is in effect a time axis). As can be seen from FIG. 8C, if an integral is taken only for the first Interval Time period (e.g., with reference to FIG. 8B, charge or current integrated to point 821 on the first curve 820 and integrated to point 831 on the second curve 830), the resulting integrated charge 832 for curve 830' is larger than the resulting integrated charge 822 for curve 820' because curve 820' has a higher decay rate as a result of a lower double-layer capacitance of the sensor membrane. If impedance is determined from the integrated charge or measured current (e.g., if the capacitance and decay rates are ignored), this difference in integrated charge (or current) would result in a difference in determined impedance. Sensitivities determined based on the impedances determined from the two curves would also be different, reflecting the error caused by capacitance.

In contrast, sampling more points and fitting an exponential trendline (as described above) produces the same estimated intercept (or approximately the same and much more accurate than a single integral) at t=0 e.g., 3e–10 C) for both curves. From this value, the membrane resistance (Rmembr) may be calculated as: Rmembr=integration time*(Vstep/integrated charge)=0.001*0.015/3e–10=50 kOhm.

FIG. 8D shows integrated charge values 822', 832' plotted on a logarithmic scale against sample number (which correlates with time because the samples are taken at regular intervals), which produces a linear relationship between current (or charge) and the sample number.

Another example method of correcting for differences in double-layer capacitance between an assumed default capacitance and the double-layer capacitance of a sensor is illustrated by the following equation:

$$\hat{R}_M = -\frac{\Delta t}{C_{dl} \times \ln\left(1 - \frac{PI}{V \times C_{dl}}\right)}$$

In the above equation, PI is the integration of a pulse current recorded by a transmitter or other sensor electronics associated with a sensor. V is a transient excursion bias voltage. For example, referring again to FIG. 5A, the transient excursion bias voltage in the illustrated example is 16 mV (e.g., a pulse from 600 mV to 616 mV). $C_{dl}$ is the double-layer capacitance of the membrane. $\Delta t$ is the duration of the integration of the current from the sensor. The relationships indicated by the equation above can be used to determine the membrane impedance for a sensor or a combination of a sensor and sensor electronics in circumstances in which the double-layer capacitance is known. In some examples, the relationships indicated by the equation above can also be used to characterize the membrane impedance in an in vivo sensor in which both membrane impedance and double-layer capacitance are unknown. For example, the sensor electronics can apply multiple transient bias pulses and measure the integrated pulse current (PI) over each of the transient pulses. Data from multiple pulses and multiple integrations can be used to solve for membrane impedance in an in vivo scenario where double-layer capacitance is also unknown.

Pulsed Amperometric Response

Figure 9:
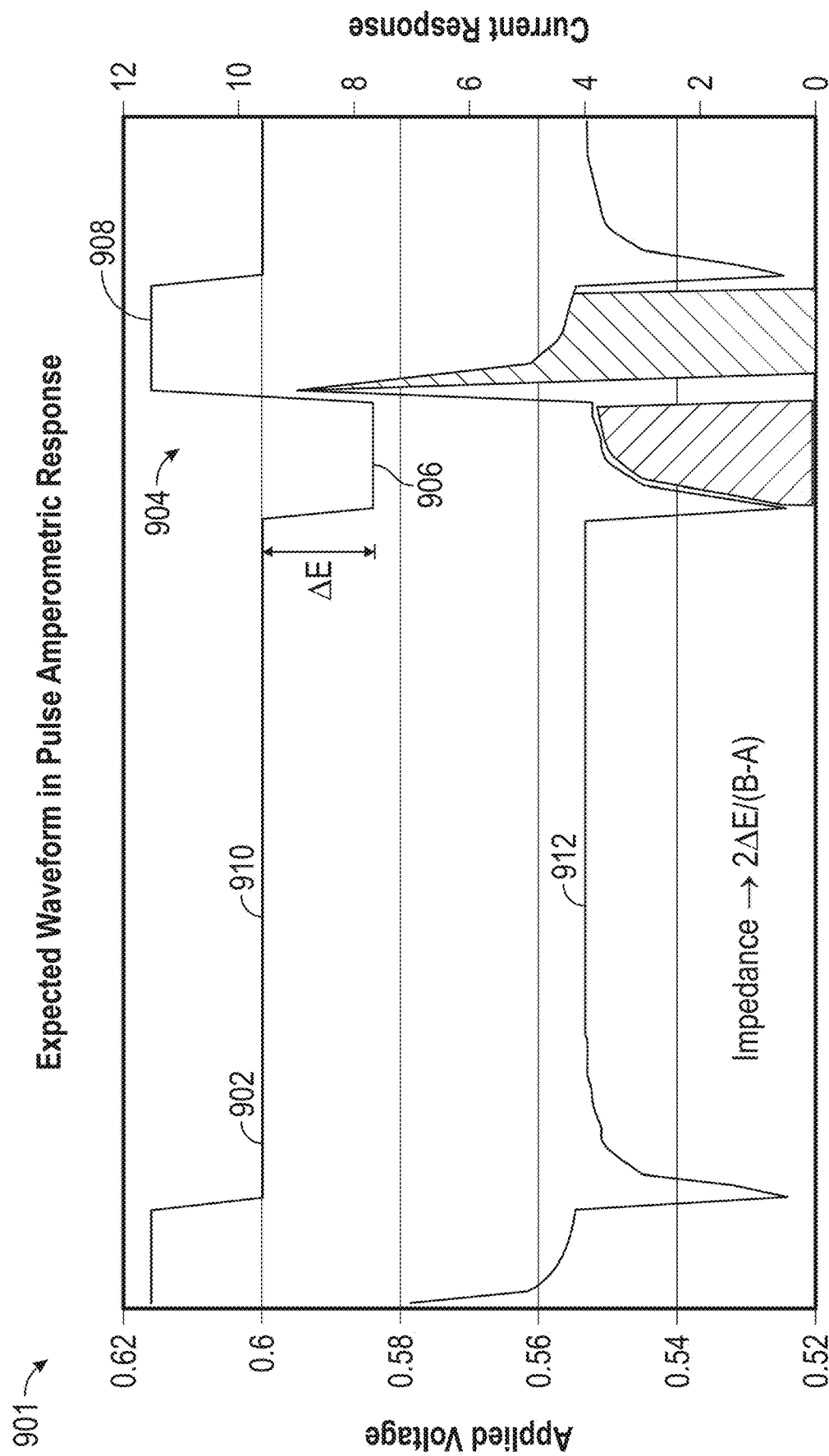
FIG. 9 is graph that shows an applied bias voltage with a biphasic pulse, plotted against time.

In some examples, an analyte sensor may apply a pulse instead of a voltage step. In some examples, the pulse may be a step pulse, as shown in FIG. 5E, in which, for example, a bias voltage is stepped up, and then eventually, after a relatively long period of time, the bias voltage is returned to a steady state value. In other examples, a pulse may be a biphasic pulse, as shown in FIG. 9. More complex pulse shapes are also possible.

FIG. 9 is a graph 901 that shows an applied bias voltage 902 with a biphasic pulse 904, plotted against time. While a square pulse shape is shown, other pulse shapes, such as a sine wave, are also possible. In the illustrated example, the bias voltage 902 has a baseline 910 that corresponds to a steady state (e.g., 0.6 Volts). In a first portion 906 of the pulse 904, the bias voltage 902 drops below the baseline 910 (e.g., from 0.6 Volts to 0.584 Volts) by an amount labeled $\Delta E$, and then returns to the baseline 910. In a second portion 908 of the pulse 904, the bias voltage 902 rises (e.g., from 0.6 Volts to 0.616 Volts). The pulse 904 is illustrated as symmetric, i.e., in the first portion 906 the voltage 902 drops by value $\Delta E$, and in the second portion 908 the voltage 902 rises by value $\Delta E$, but other examples may use an asymmetric pulse.

The lower portion of the graph 901 shows the current response 912 in nanoamps. When the bias voltage 902 is dropped, the observed current response also drops (e.g., from 4 nanoamps to about 02 nanoamps). The observed current response then rises as the capacitor discharges a portion of its stored energy. In the example shown, the second portion 908 of the pulse 904 is timed to occur at (or around) the time the current response reaches a new steady state (e.g., slightly less than the original steady state, as determined by Ohm's law I=V/R). In other examples, the second portion of the pulse may occur sooner (i.e., the period of the pulse may be shorter than the illustrated example) or the second of the pulse may occur later (i.e., the period of the pulse may be longer).

The impedance may be determined from the change in voltage and the change in current in response to the voltage change. For example, for the pulse shown (with equal size pulses), the membrane impedance (Imemb) may be estimated from the voltage change ($2\Delta E$) and the integrated change in current ($\Delta I$). Additional signal processing techniques may be applied to improve the accuracy of the impedance estimate. For example, where the double-layer capacitance is estimated (as described above) or assumed to be a specified value, the determination of impedance may account for the double-layer capacitance.

Gated Amperometric Detection

In some examples, an analyte sensor circuit may be recurrently turned off and turned back on. During a period in which the sensor is turned off, an analyte (e.g., glucose) continues to interact with a sensor enzyme, which develops a signal that may be sensed. For, when a sensor circuit is off, glucose continues to react with glucose oxidase enzyme to produce hydrogen peroxide, which accumulates. When the sensor circuit is turned on, the accumulated hydrogen peroxide creates a much stronger signal than occurs without accumulation. Importantly, some interference materials, such as uric acid and acetaminophen, do not exhibit such an accumulation effect, so the signal-to-noise (or background or interference) ratio is improved. Thus, while the presence of acetaminophen (or other interference materials) may cause an error in a glucose sensor estimate (because the acetaminophen impacts the raw signal observed from the sensor), the impact of acetaminophen may be reduced by gating the analyte sensor circuit to increase the signal-to-noise ratio between the glucose signal and the interfering material. In an example, a test was performed using a sensor using gated and non-gated amperometry. A sensor in a solution with a glucose concentration of 156 mg/dL was exposed to acetaminophen to test the effect of gating the amperometry. With normal (non-gated) amperometry, a concentration of 1 mg/dL of acetaminophen resulted in an error of 3.19 mg/dL in the estimated glucose concentration. With normal gated amperometry, a concentration of 1 mg/dL of acetaminophen resulted in an error of 2.683 mg/dL in the estimated glucose concentration, which indicates that gating provides a system with greater acetaminophen tolerance (e.g., reduces the error due to the presence of acetaminophen at the sensor membrane).

Figure 10A:
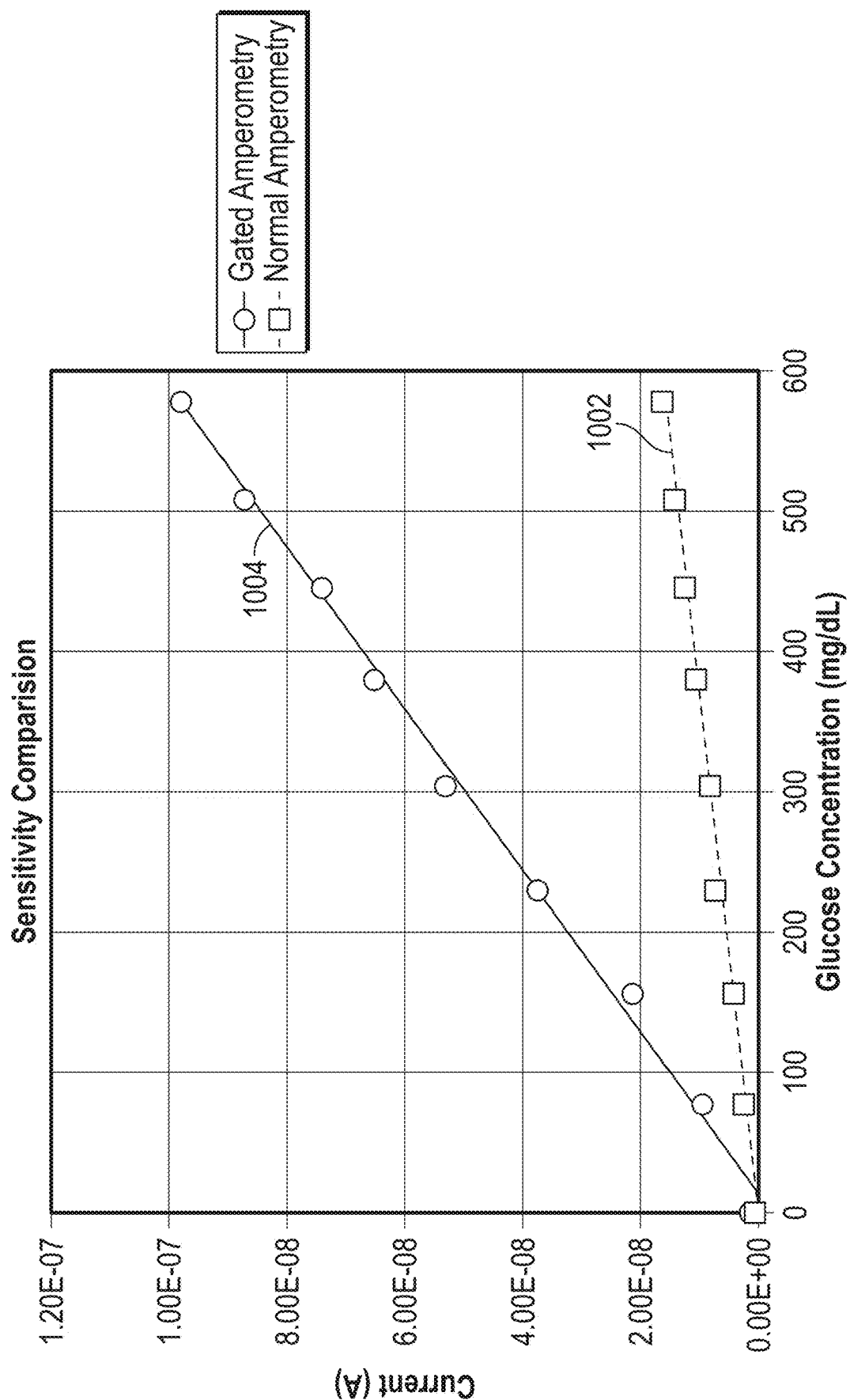
FIG. 10A is a graph that shows current plotted against glucose concentration for a sensor using a normal amperometry technique and a gated amperometry technique.

FIG. 10A shows current plotted against glucose concentration for a sensor. Data points were measured for a sensor using gated amperometry and normal (non-gated) amperometry across a range of glucose concentrations. The data shows the larger current response (which may be detected by an analyte sensor system) for gated amperometry than for normal amperometry. The data for normal amperometry shows a linear relationship between current and glucose concentration, indicated by line 1002. The data for gated amperometry also shows a linear relationship between current and glucose concentration (indicated by line 1004), but the slope is steeper, and the values are higher for gated amperometry. The steeper slope may allow for more effective differentiation between glucose concentration levels.

Figure 10B:
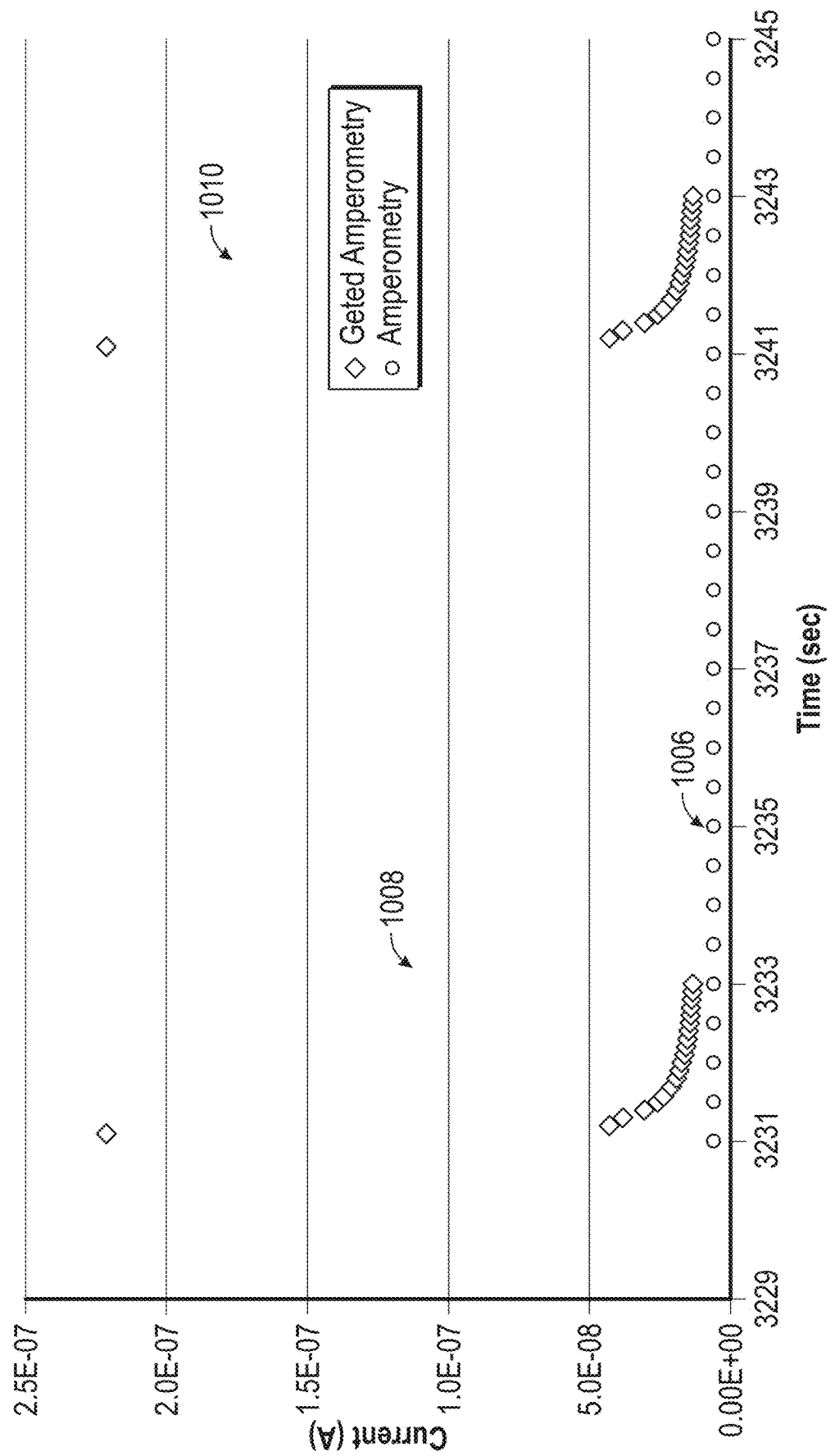
FIG. 10B is a graph that shows an example implementation of gated amperometry in an analyte sensor.

FIG. 10B is a graph that shows an example implementation of gated amperometry in an analyte sensor. The graph of FIG. 10B indicates time on the horizontal or x-axis and measured current from the analyte sensor on the vertical or y-axis. The data illustrated at FIG. 10B was captured with an analyte sensor in the presence of a constant concentration of analyte. A series 1006 of samples indicate current responses of the analyte sensor measured using standard amperometry. In the illustrated example, the series 1006 of samples are captured at rate of 2.5 samples per second. As shown, the series 1006 of samples returns a constant current.

Series 1008 and 1010 show current responses of the analyte sensor according to gated amperometry. In this example, the bias voltage is applied to the analyte sensor for a two-second period and then removed for an eight-second period. For example, the series 1008 of samples shows the current response of the sensor when the bias voltage is applied at 3231 seconds and then removed again at 3233 seconds. As shown, the initial sample of the series 1008 returns a high current (~225 nA) that decays towards the current value of the standard amperometry series 1006. Similarly, the series 1010 of samples includes an initial sample at a high current (~224 nA) that also decays towards the current value of the standard amperometry series 1006. The high initial current, for example, may be the result of the analyte sensor detecting hydrogen-peroxide generated from reactions at the sensor while the bias voltage was turned off. As the excess hydrogen-peroxide is reacted with the now-biased sensor, the sensor current decays towards the steady-state value indicated by the standard amperometry series 1006.

Figure 10C:
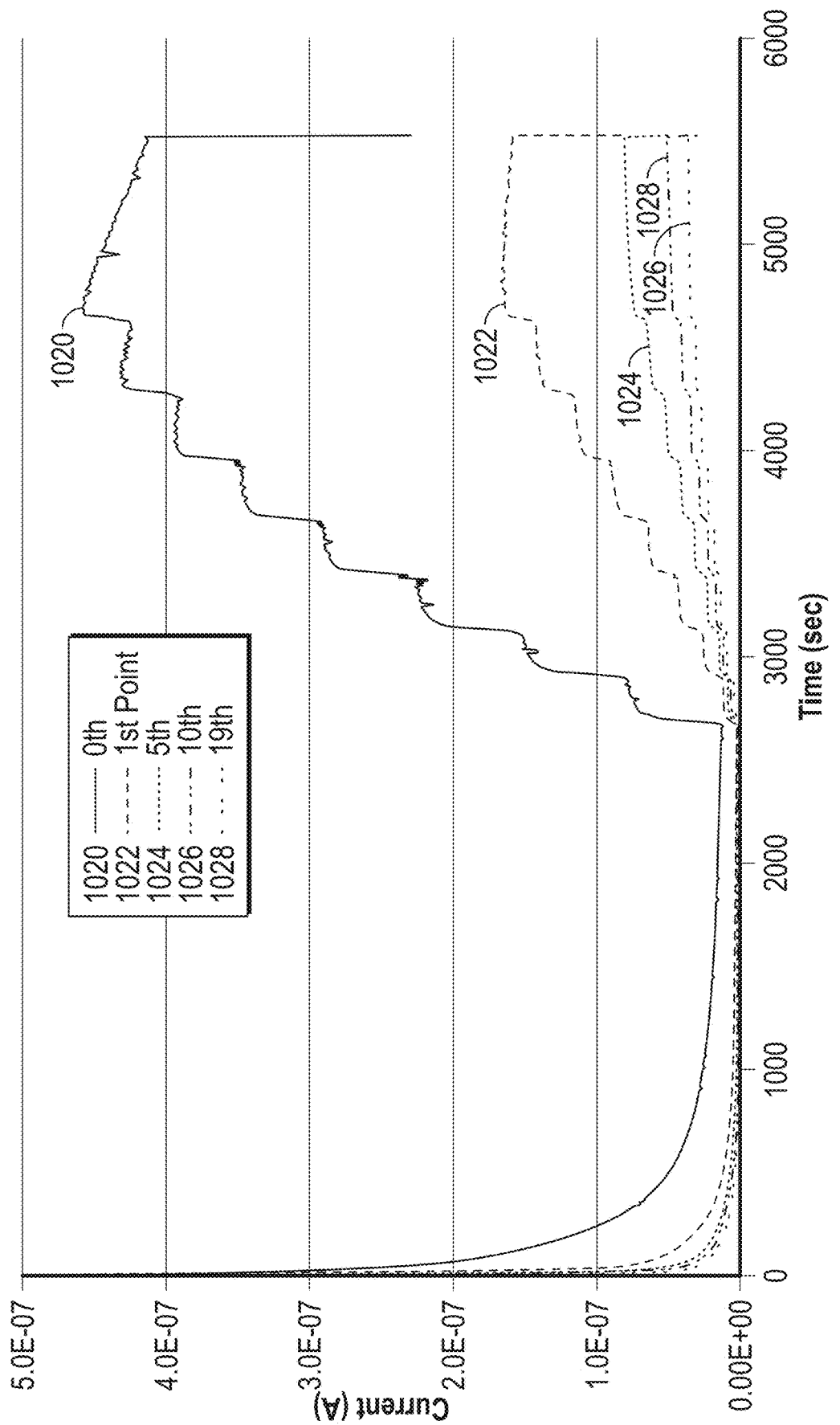
FIG. 10C is a graph showing example current responses of an analyte sensor operated using gated amperometry.

FIG. 10C is a graph showing example current responses of an analyte sensor operated using gated amperometry. The graph of FIG. 10C indicates time on the horizontal or x-axis and measured current from the analyte sensor on the vertical or y-axis. In the example of FIG. 10C, an analyte sensor was subjected to break-in in a buffer material having a constant analyte concentration. At about 2600 seconds, the analyte sensor was exposed to buffer materials with increasingly higher analyte concentrations. In this sample, the analyte sensor was exposed to each respective analyte concentration for about 200 seconds.

In the example of FIG. 10C, the analyte sensor was operated using gated amperometry in the manner indicated by FIG. 10B with the bias voltage applied for a two second period and then turned off for an eight second period. During the two second periods in which the bias voltage was applied, the current at the sensor was sampled at about 10 Hz (e.g., $\frac{1}{100}$ ms). The curves 1020, 1022, 1024, 1026, 1028 in FIG. 10C show the current response of the analyte sensor.

Curve 1020 shows the response of the $0^{th}$ point indicating the first sample captured during each period in which the bias voltage is applied. Curve 1022 shows the response of the $1^{st}$ point indicating the second sample captured during each period in which the bias voltage is applied. Curve 1024 shows the response of the $5^{th}$ point indicating the sixth sample captured during each period in which the bias voltage is applied. Curve 1026 shows the response of the $10^{th}$ point indicating the eleventh sample captured during each period in which the bias voltage is applied. Curve 1028 shows the response of the $19^{th}$ point indicating the twentieth sample captured during each period in which the bias voltage is applied. As shown, the current level corresponding to early points is high and then decays with later-captured points. FIG. 10C also shows that various different points exhibit a dependence on the analyte concentration present at the sensor.

Figure 10E:
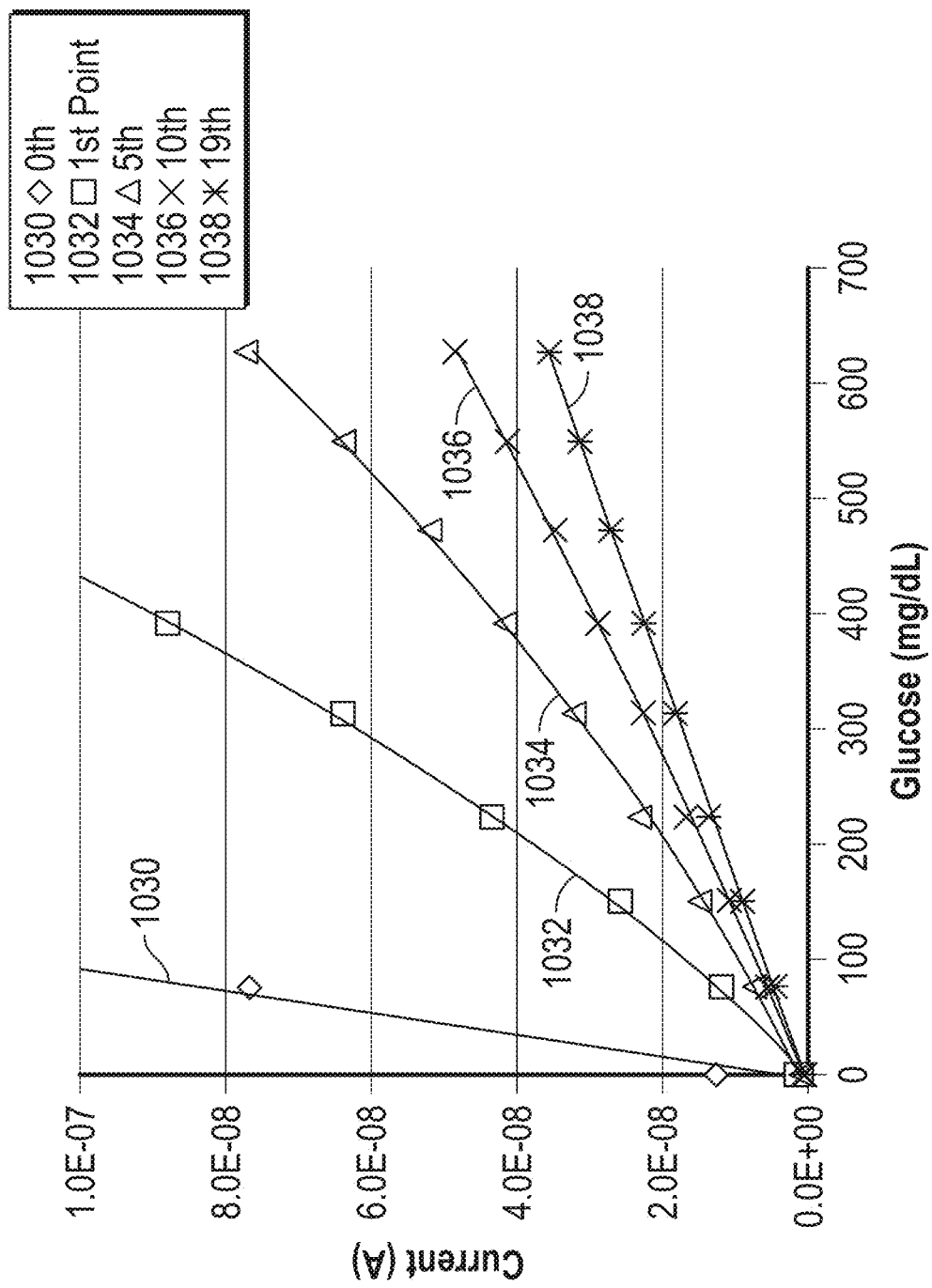

FIGS. 10D and 10E are graphs showing sensitivity of the example current responses illustrated in FIG. 10C. The graph of FIGS. 10D and 10E indicate analyte concentration (glucose in this example) on the horizontal or x-axis and measured current from the analyte sensor on the vertical or y-axis. A curve 1030 shows the sensitivity of the $0^{th}$ point or first sample captured during each period in which the bias voltage is applied. A curve 1032 shows the sensitivity of the $1^{st}$ point or second sample captured during each period in which the bias voltage is applied. A curve 1034 shows the sensitivity of the $5^{th}$ point or sixth sample captured during each period in which the bias voltage is applied. A curve 1036 shows the sensitivity of the $10^{th}$ point or eleventh sample captured during each period in which the bias voltage is applied. A curve 1038 shows the sensitivity of the $19^{th}$ point or twentieth sample captured during each period in which the bias voltage is applied. FIGS. 10D and 10E show the curves 1030, 1032, 1034, 1036, 1038 on different scales. For example, in FIG. 10D, the scale of the vertical axis indicating current is from zero to about 500 nA. In FIG. 10E, the scale of the vertical axis indicating current is from zero to about 100 nA.

Figure 10F:
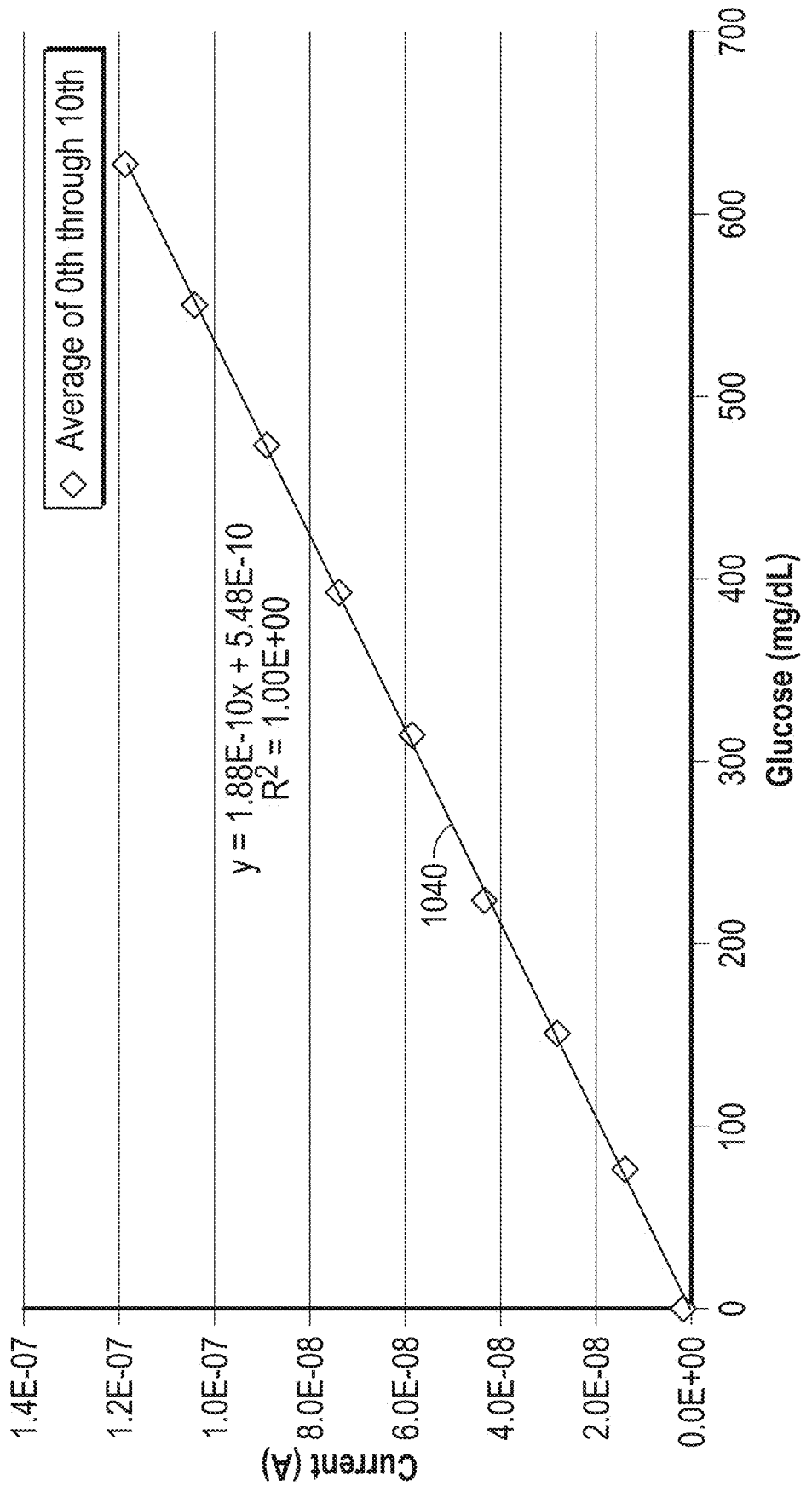
FIG. 10F is a graph showing sensitivity of the example current responses illustrated in FIG. 10C averaged over the 0th through the 10th point.

FIG. 10F is a graph showing sensitivity of the example current responses illustrated in FIG. 10C averaged over the $0^{th}$ through the $10^{th}$ point. The graph of FIG. 10F indicates analyte concentration (glucose in this example) on the horizontal or x-axis and measured current from the analyte sensor on the vertical or y-axis. A curve 1040 shows the sensitivity of an average of the $0^{th}$ point through the $10^{th}$ point. In some examples, gated amperometry can be used to measure analyte concentration using an average of samples gathered while a bias voltage is applied in this way. Although the $0^{th}$ through the $10^{th}$ points are used herein, other combinations can also be used.

Figure 10G:
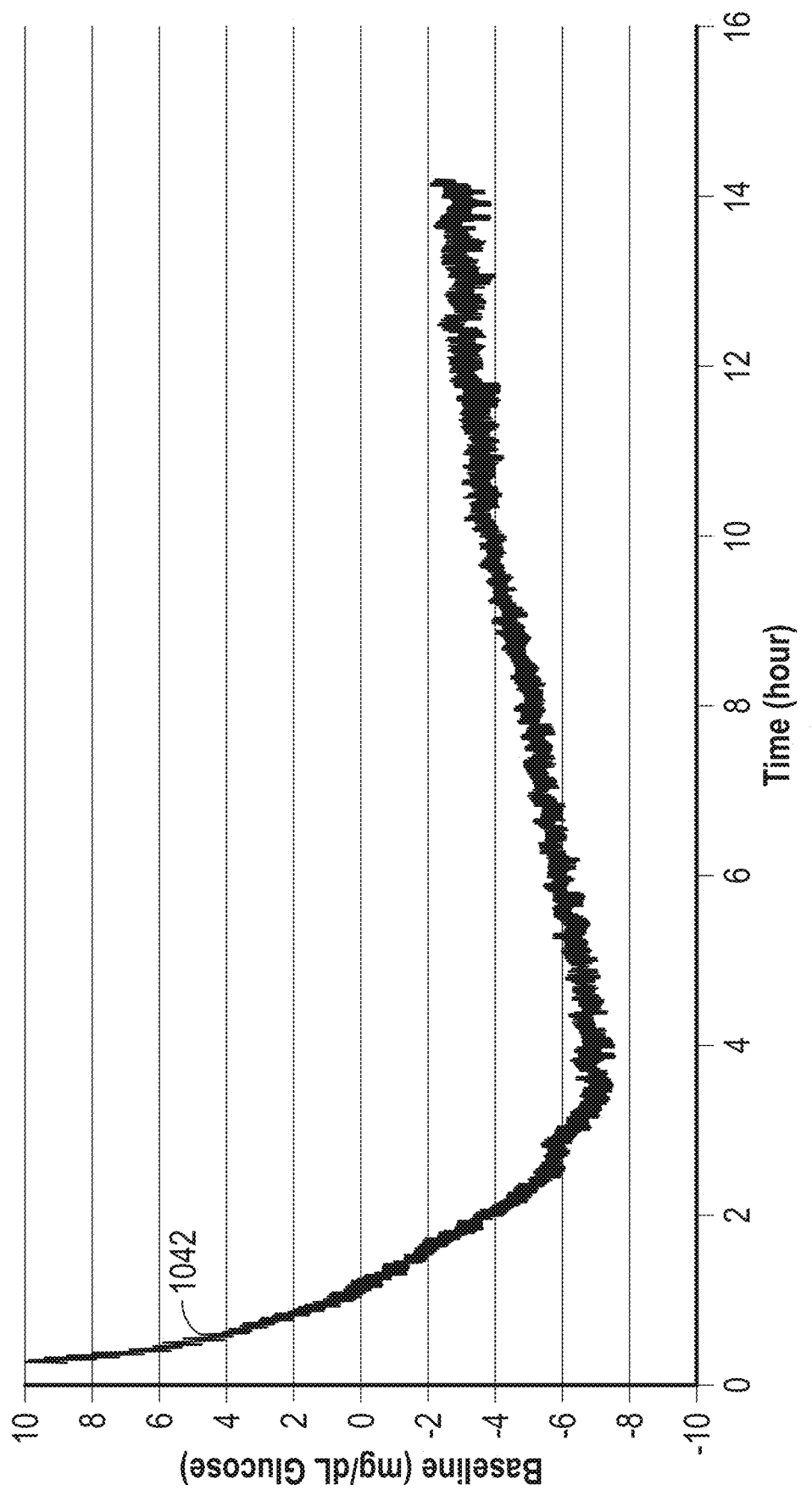
FIG. 10G is a graph showing a baseline curve derived from the example current responses of FIG. 10C averaged over the 0th through the 10th point.

FIG. 10G is a graph showing a baseline curve 1042 derived from the example current responses of FIG. 10C averaged over the $0^{th}$ through the $10^{th}$ point. The graph of FIG. 10G indicates time on the horizontal or x-axis and baseline analyte concentration on the vertical or y-axis. The baseline analyte concentration is a concentration of analyte (glucose in this example) corresponding to a zero level of current at the analyte sensor. As shown by the curve 1042, the gated amperometry methods described herein can result in a relatively constant baseline concentration after about 2 hours.

Figure 10H:
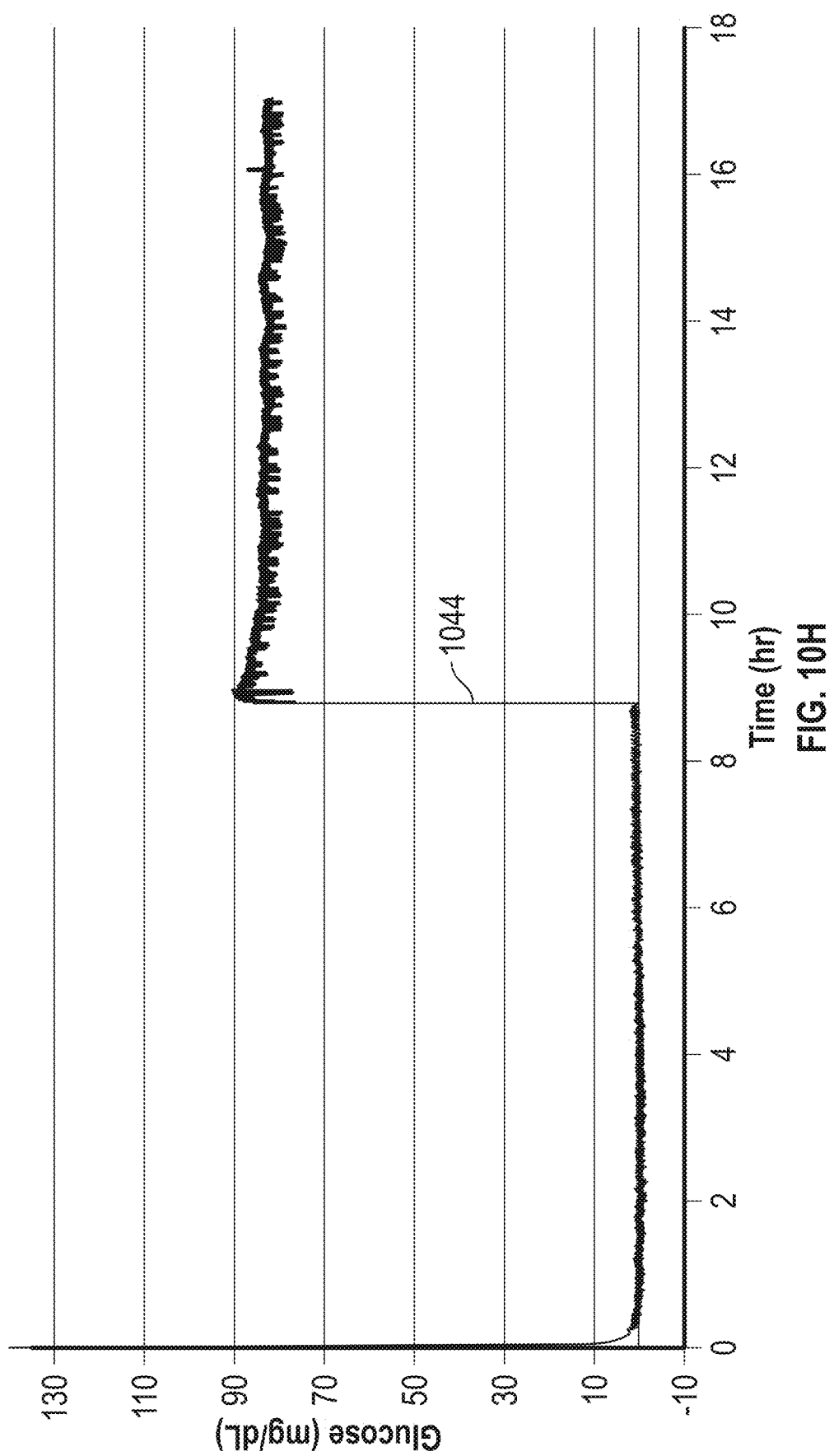
FIG. 10H is a graph showing a span curve of an analyte sensor operated using gated amperometry as described herein.

FIG. 10H is a graph showing a span curve 1044 of an analyte sensor operated using gated amperometry as described herein. The graph of FIG. 10H indicates time on the horizontal or x-axis and analyte concentration on the vertical or y-axis (in this example, glucose concentration). The span curve 1044 indicates the glucose concentration values received from the analyte sensor based on the average of the $0^{th}$ through the $10^{th}$ point as described herein. In this example, the analyte sensor was initially exposed to a buffer having a glucose concentration of zero. At about 9 hours, the analyte sensor was exposed to a buffer having an analyte concentration of about 85 ml/dL. As shown, the analyte concentration values provided by the analyte sensor remain roughly constant.

Figure 10I:
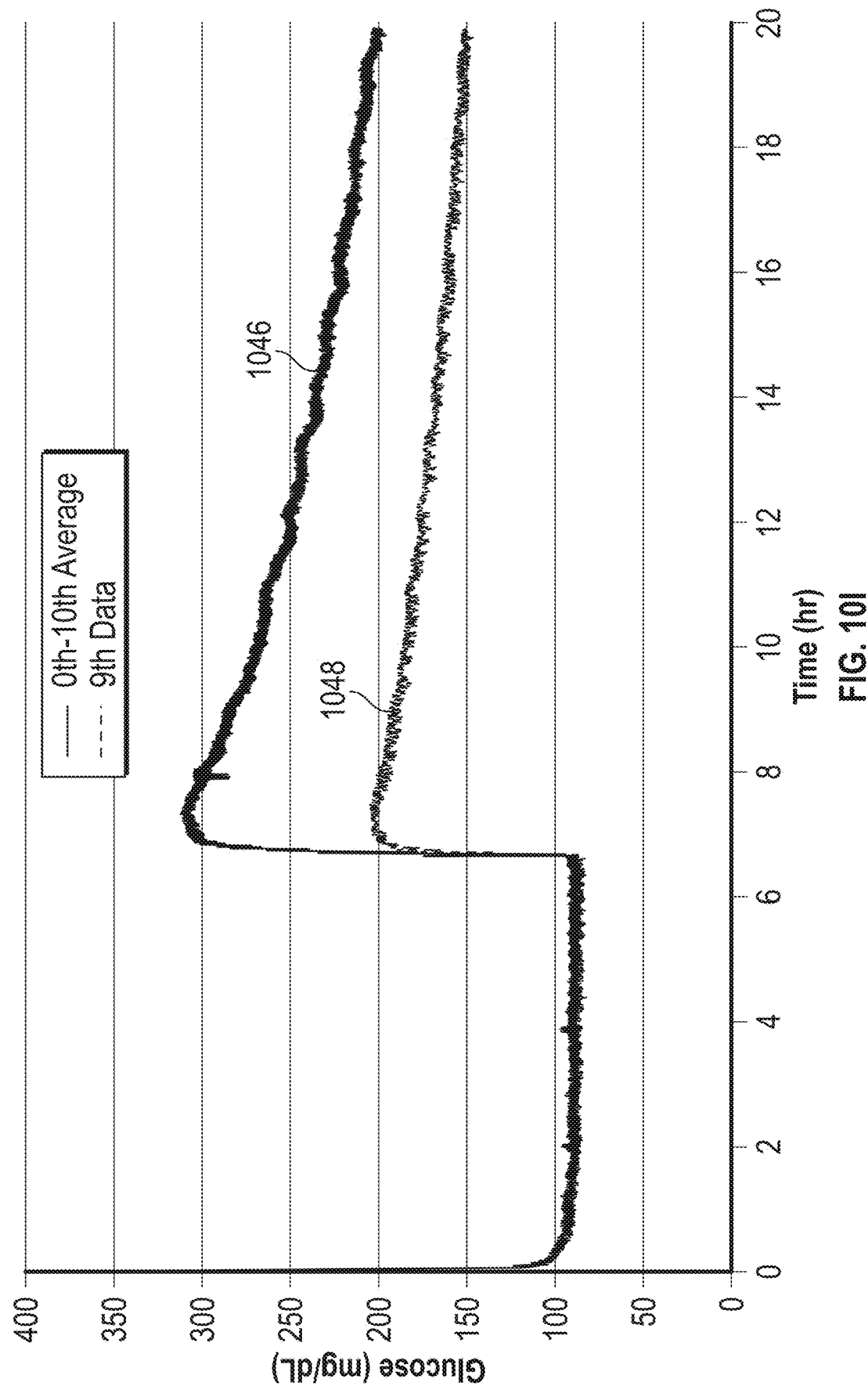
FIG. 10I is a graph showing span curves of an analyte sensor operated using gated amperometry in the presence of acetaminophen.

FIG. 10I is a graph showing span curves 1046, 1048 of an analyte sensor operated using gated amperometry in the presence of acetaminophen. The span curve 1046 shows the response of the $19^{th}$ point sample, as described herein. The span curve 1048 shows an average of the $0^{th}$ through the $10^{th}$ point samples, as described herein. Because the sensor current decays towards the steady state voltage, the $19^{th}$ point is closer to the steady state glucose reading (e.g., using standard amperometry). In the example of FIG. 10I, the analyte sensor was exposed to a buffer with a glucose concentration of about 85 ml/dL until about 6.5 second after which the analyte sensor was exposed to a buffer with a glucose concentration of about 150 ml/dL. As shown, the span curve 1048 for the average of the $0^{th}$ through $10^{th}$ points is flatter than the span curve 1046 for the $19^{th}$ point.

Humidity Detection

An estimated impedance of a moisture-sensitive portion of an analyte sensor may be used to detect humidity. For example, an estimated membrane impedance (e.g., an estimated membrane impedance determined as described above) may provide an indication of exposure of an analyte sensor to a relatively humid environment (compared to a baseline relative humidity). Environments with varying humidity may occur, for example, in manufacturing, storage, transportation (e.g., between manufacturing steps, or en route to a distributor or end user), or with an end user (e.g., if a sensor package is opened but the sensor is not used for a substantial period of time after opening).

An analyte sensor (such as the sensor shown in FIGS. 3A-3C, described above) typically includes an anode (e.g., working electrode), a cathode (e.g., reference electrode), and at least one membrane covering the anode, cathode, or both. The membrane typically includes hydrophilic domains, in which ions may reside and move, which makes the membrane electrically conductive. The membrane conductivity (or resistivity or impedance) may be indicative of the humidity of the environment to which the membrane has been exposed (e.g., because the membrane absorbs water vapor, which makes it more conductive). An impedance measurement may be made by applying a small amplitude (e.g., 1-200 millivolts) excitation pulse or AC signal to a sensor circuit. An impedance estimate may be determined from an observed current response in the sensor circuit, in combination with one or more known voltage characteristics of the injected signal or pulse (e.g., an impedance estimate may be determined based on Ohms law).

In some examples, a plurality of impedance estimates (or measurements from which an impedance estimate may be determined) may be tracked over time, which may provide an indication of the humidity of the environment to which the sensor has been exposed, or the relative humidity of the sensor environment, or both.

The exposure of an analyte sensor to humidity may impact the performance of the sensor. In some examples, a sensor system parameter (e.g., a glucose sensitivity, or glucose sensitivity profile over time) may be adjusted based upon an estimated humidity exposure (e.g., the sensor system output may be compensated for pre-implantation humidity exposure). In some examples, a system may generate an alert or warning indicating that a sensor has been exposed to excessive humidity, or to excessively dry conditions. For example, a system may inform a user that a sensor should not be used.

Figure 11:
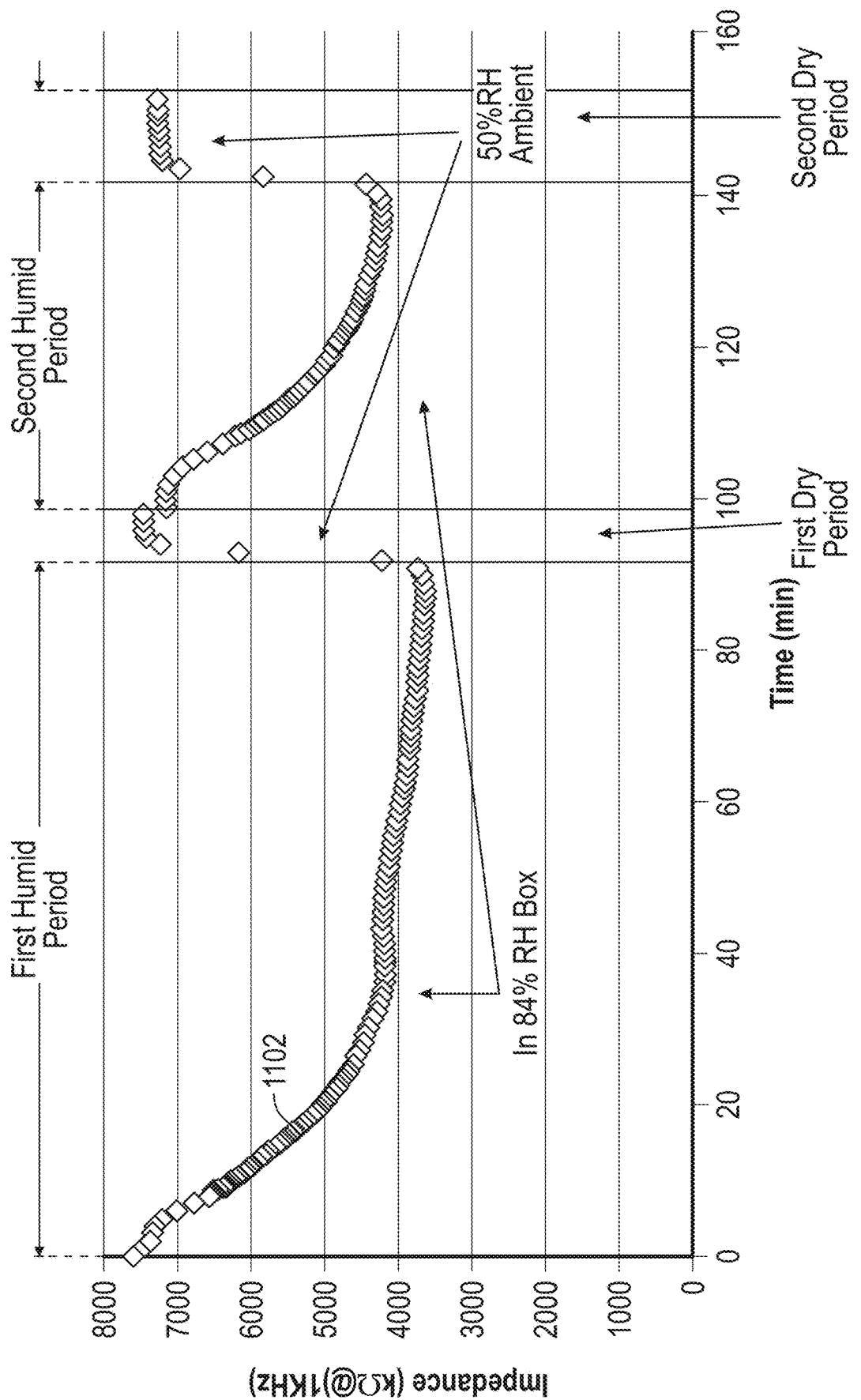
FIG. 11 is a graph that shows measured impedance values plotted against time.

FIG. 11 is a graph that shows measured impedance values 1102 plotted against time. The impedance values 1102 are plotted against minutes, but in other examples may be plotted against days or weeks. The data is from a benchtop experiment, with controlled-humidity environments at 84% relative humidity and 50% relative humidity but is representative of the response of a sensor in actual environments.

At the beginning of a first humid period (which extends from 0 to 93 minutes), the analyte sensor has an estimated impedance (e.g., derived using voltage and current measurements, and Ohm's law) of about 7700 kiloohms (k$\Omega$), at 1 kilohertz. As the sensor absorbs moisture, the impedance during the first period trends downward until it reaches about 3800 kiloohms at 93 minutes. At 93 minutes, the analyte sensor was exposed to a 50% relative humidity ambient environment during a first dry period (from 93 minutes to 98 minutes). As the sensor dried out (e.g., as water evaporated from the sensor membrane and entered the relatively dry ambient environment), the impedance of the sensor quickly trends back up to about 7500 kiloohms. After the first dry period, the sensor was reintroduced to an 84% relative humidity environment for a second humid period (from 98 minutes until 140 minutes), and the sensor impedance fell back down to about 4200 kiloohms. At 140 minutes, the sensor was again exposed to a 50% relative humidity ambient environment, and the estimated impedance rose to over 7000 kiloohms. The data in FIG. 11 illustrates that impedance may be used to track exposure to humidity. Humidity information, such as the humidity information shown in FIG. 10, may be used to determine an alert or warning (e.g., "Sensor damaged") or to adjust the performance of the sensor (e.g., compensate for impedance changes caused by humidity). In some examples, an impedance prior to implantation may be used to compensate an analyte sensitivity (e.g., glucose sensitivity).

While the sensor is generally referred to in this disclosure as an analyte sensor, in other examples, the sensor (e.g., the sensor 34 in FIGS. 3A-3B) may be used as a humidity sensor.

In some examples, a sensor may be integrated into "smart" packaging (of an analyte sensor, or of another device), and humidity in the package, or outside or around the package, may be sensed or tracked.

In some examples, an analyte sensor system or smart packaging may include a memory circuit, which may store impedance information. The impedance information may be stored with time information, which may provide a history of the humidity exposure of the device or packaging. In various examples, impedance may be detected and stored several times a minute, once a minute, several times an hour, once an hour, several times a day (e.g., every six hours), once a day, on a multi-day interval (e.g., every two days, three days, five days, or ten days), once a week, several times a month (e.g. semi-monthly), or once a month. The humidity history information may be used to determine an alert or alarm (e.g., declare that a product is damaged or potentially damaged), or may be presented on a user interface for evaluation by a user, or may be sent over a network (such as the network shown in FIG. 1) for remote processing or evaluation.

Assessment of Membrane Integrity

Measurements by sensor electronics may be used to assess the integrity of a sensor membrane. An analyte sensor may deviate from a performance standard (e.g., deviate from a default sensitivity curve) due to manufacturing variability, damage, or both. In some examples, such a performance variance may be detected or quantified using a determined impedance for a sensor. For simplicity of explanation, in the examples described in this present application a sensor may be referred to as "damaged" to indicate an abnormality in the sensor membrane composition, but references to a "damaged" sensor should be interpreted as also applying to a sensor that has an abnormality (e.g., an abnormality that is a result of a manufacturing process or damage inflicted by handling of the sensor).

An analyte sensor (such as a CGM sensor) typically includes one or more functional membranes, which may include abnormalities or suffer damage during sensor assembly, deployment, or other handling of the sensor. Membrane damage may, for example, include a scratch, puncture, or delamination. When a membrane is damaged, it may produce extra passages for an analyte (such as glucose for a CGM sensor) to reach an underlying electrode surface, which may inflate a sensor's output signal (e.g., increase the sensitivity to glucose), or produce a signal that is noisier or less consistent than normal.

It may be desirable to detect a sensor with a damaged or abnormal membrane, so the sensor can be rejected (e.g., during manufacturing), replaced (e.g., by an end user), or compensated (e.g., a compensation factor may be applied to address minor damage or abnormality). In varying examples, an impedance measurement based on electronic measurements may be used to detect a damage or abnormality early in a manufacturing process to avoid further processing of non-viable sensors, or late in a manufacturing process as a final check to assure that the sensor was not damaged during handling, or prior to or concurrent with insertion into a host, to avoid inconvenience for the user or potential reliance on an inaccurate sensor output.

Damage or an abnormality in a sensor may be identified or quantified using an estimated impedance, such as a membrane impedance as described above. One or more membranes on an analyte sensor are designed to restrict the mobility of molecules and ions. If a membrane is damaged by scratch, puncture, or delamination, ions can move relatively freely in those areas/sections compared to inside the membrane. Therefore, membrane damage may correspond to decrease of impedance (increase of admittance, or conductance).

Membrane damage or abnormalities may take a variety of forms. For example, one or more sensor coating layers may be thinner or different than a surrounding area on the membrane, or a coating layer may be damaged or missing, or, when a sensor coating is badly damaged, an electrode may be exposed.

Figure 12A:
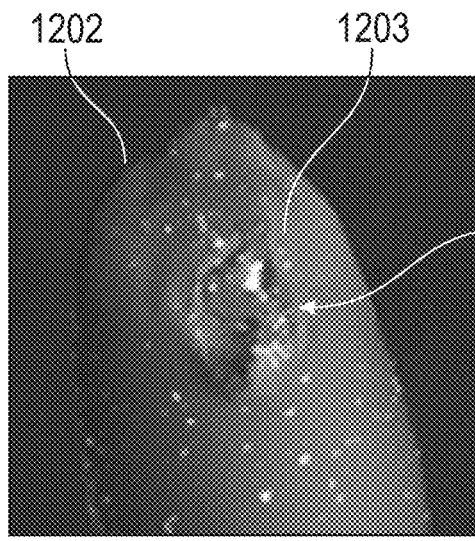
FIG. 12A is an image of an example sensor that has a damaged or abnormal portion.
Figure 12B:
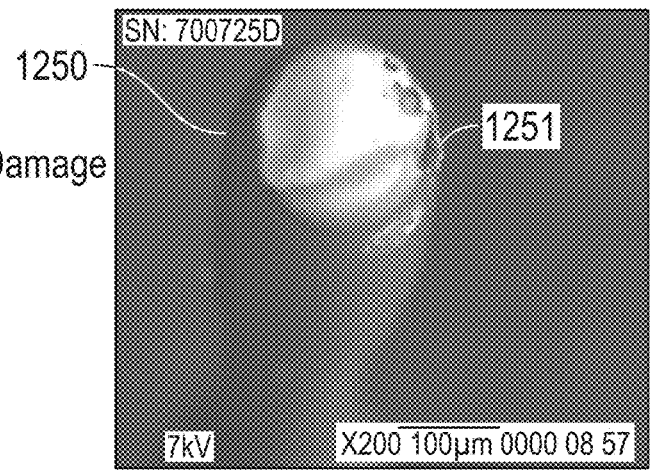
FIGS. 12B and 12C show other examples of damage or abnormality.
Figure 12C:
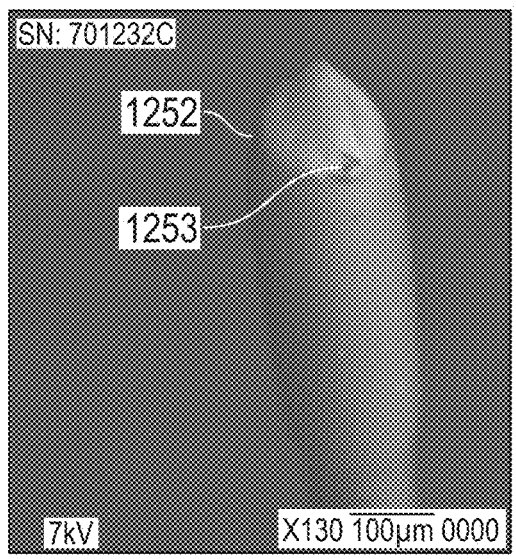

FIG. 12A is an image of an example sensor 1202 that has a damaged or abnormal portion 1203 on the membrane. The imperfection in the sensor membrane may affect the electrical behavior of the sensor 1202 in response to changes in glucose concentration. For example, the sensor 1202 may exhibit a higher sensitivity to glucose (compared to a sensor without the imperfection) due to increased glucose diffusivity through the sensor coating layers. FIGS. 12B and 12C show other examples of damage or abnormality 1251, 1253 from manufacturing of the sensors 1250, 1252.

The determination of whether a membrane is healthy or excessively damaged or abnormal is necessarily a matter of degree, as all sensor membranes will have some degree of variation in membrane thickness or composition. For example, damage to a sensor coating may range from a slight abnormality (e.g., a thin or missing layer in a small portion of the sensor) to severe damage that exposes the working electrode. A sensor with minor coating damage may function properly, but the sensitivity of the sensor may be slightly increased. In some examples, a sensor may have a relatively large area of damage, but the damage may be relatively shallow, so that the sensor performs acceptably well. In other examples, a sensor may have a relatively small area of damage, but the damage may be relatively deep, e.g., the damage may extend most or all of the way to the electrode, in which case the sensor performance may be excessively compromised even though the damage affects a relatively small portion of the surface area of the sensor.

Figure 12D:
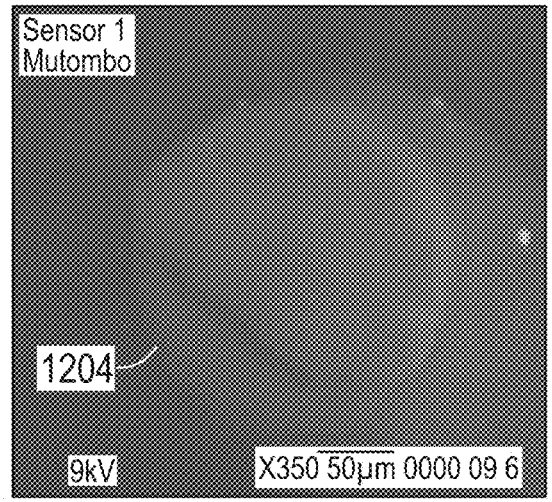
FIGS. 12D through 12H show sensors with damage ranging from none to heavy damage.
Figure 12E:
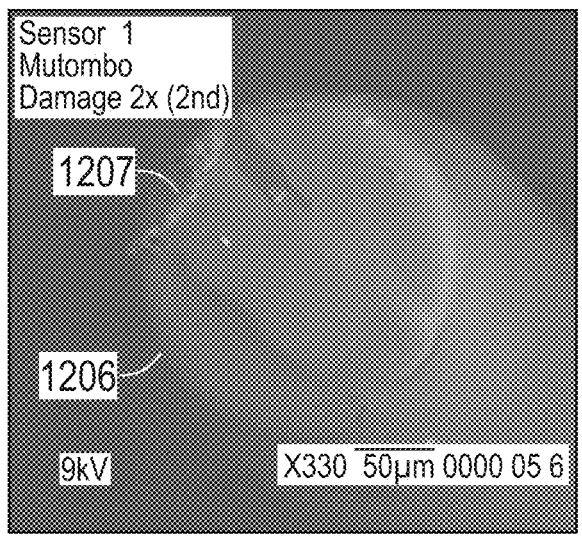
Figure 12F:
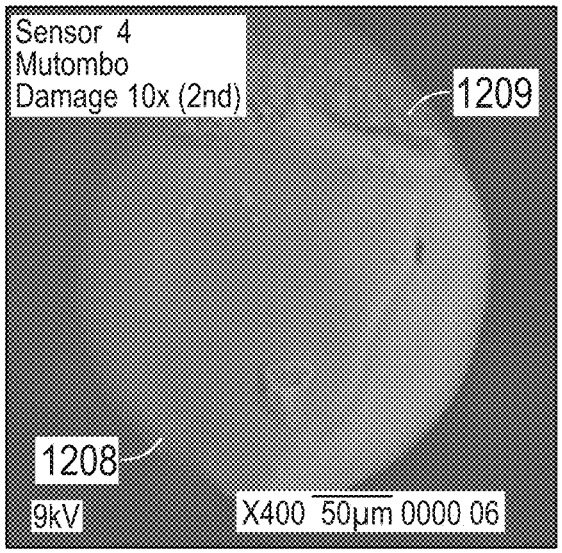
Figure 12G:
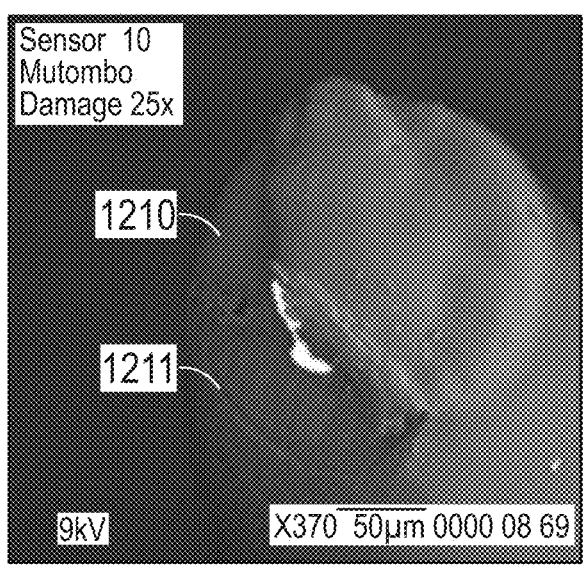
Figure 12H:
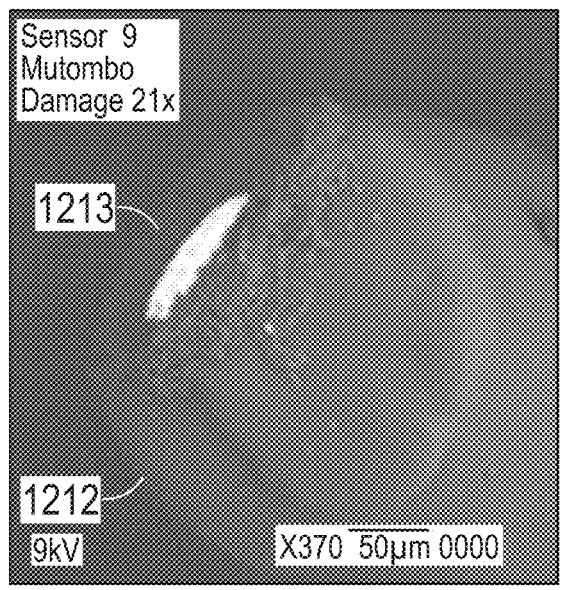

Sensors may be categorized according to a membrane damage scale to quantify the extent of damage. For example, a numerical scale may be developed, where 0 indicates no damage (i.e., a healthy sensor), 1 indicates very minor damage, 4 indicates a moderately damaged sensor, and 8 indicates a heavily damaged sensor (with numbers in between correlated to a continuous scale of damage). FIGS. 12D through 12H show sensors with damage ranging from none to heavy damage. The damage was created by rubbing the sensors on sandpaper to create a spectrum of damaged sensors (with minor to heavy damage) to enable testing of impedance and other characteristics. FIG. 12D shows a microscope image of a healthy sensor 1204, with no damage. FIG. 12E shows a sensor 1206 that has a portion 1207 with minor damage. FIG. 12F shows a sensor 1208 that has a portion 1209 with moderate damage. FIG. 12G shows a sensor 1210 with a portion 1211 that has moderately severe damage. FIG. 12H shows a sensor 1212 that has a portion 1213 with severe damage.

Figure 13:
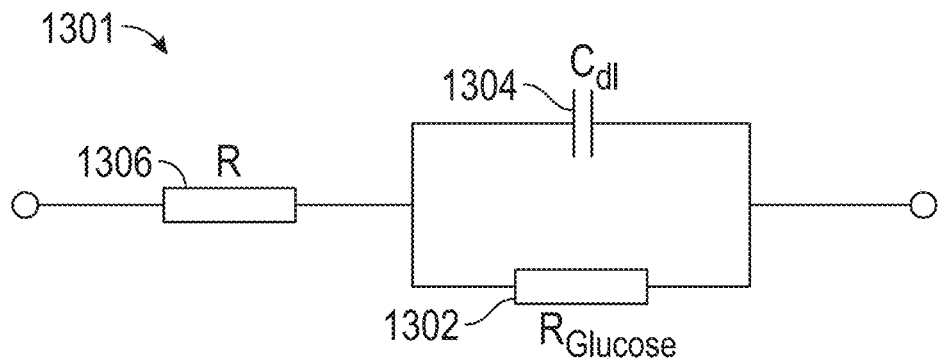
FIG. 13 is a schematic illustration of a simplified equivalent circuit of an analyte sensor.

The presence or extent of damage in a sensor may be evaluated using electrical measurement, such as a determination of impedance. FIG. 13 is a schematic illustration of a simplified equivalent circuit 1301 of an analyte sensor. The circuit 400 shown in FIG. 4 (or other variants) may also be used for sensor analysis, but for simplicity reference will be made to the circuit 1301 shown in FIG. 13. The resistor 1302 represents the polarization resistance (RGlucose, labeled Rpol in FIG. 4) and capacitor 1304 represents the double-layer capacitance (Cdl). The resistor (R) 1306 represents the combined resistance of the membrane (Rmembr in FIG. 4), the electrodes, and the internal resistance in sensor electronics (R_Tx_internal in FIG. 4). Using Ohm's law (I=V/R), impedance of the resistor (R) may be measured, which can indicate the presence or extent of membrane damage or abnormality.

A sensor with excessive damage or abnormality (as determined using impedance, for example), may be identified and excluded from use in a host. For example, an excessively damaged sensor may be identified after implantation in a host, in which case an alert may be delivered to a user to notify the user of the damage (e.g., "Damaged sensor detected. Please replace sensor."). In some examples, a sensor system may apply compensation to account for the minor damage to the sensor. For example, a sensitivity for the sensor may be adjusted (e.g., based on a determined impedance) to provide an accurate estimated analyte concentration level despite the abnormality or damage in a sensor coating.

Figure 14:
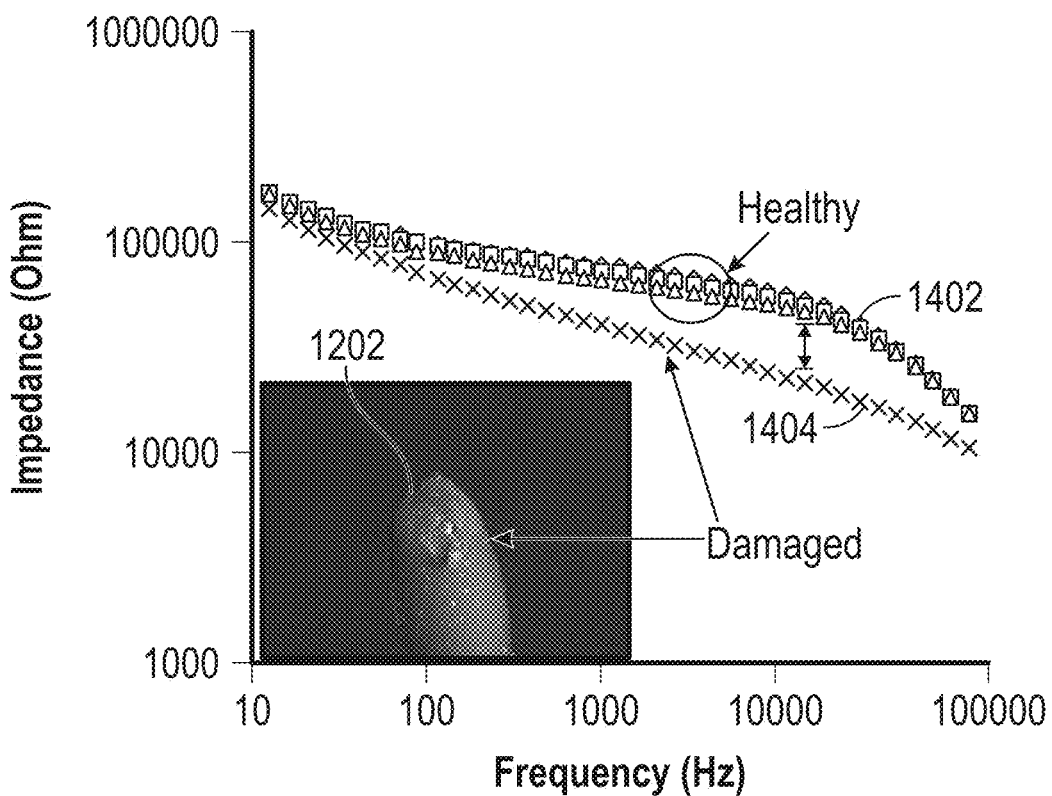
FIG. 14 is a graph that shows impedance plotted against frequency (Hz) for a damaged or abnormal sensor and healthy (non-damaged) sensors.

In some examples, a sensor with damage or an abnormality in the sensor membrane may be more easily differentiated from a healthy sensor by comparing the impedance at a frequency that accentuates the difference in impedance. FIG. 14 is a plot of impedance (Ohms) vs. frequency (Hz) for a damaged or abnormal sensor (such as sensor 1202) and healthy (non-damaged) sensors. Both the X and Y axes are logarithmic scales. It can be seen from the plot that the difference between impedance of a damaged sensor 1404 and the impedance of healthy sensors 1402 varies with frequency. For example, at 100 Hz and 100 kHz the impedance of a damaged sensor 1404 is relatively close to the impedance of healthy sensors 1402. In comparison, at 10 kHz the difference in impedance between a damaged sensor 1404 and healthy sensors 1402 is relatively large, as indicated by the arrow in FIG. 14.

In an example, a sensor with damage or an abnormality may be identified by measuring impedance at a frequency (e.g., 5,000 Hz or 10,000 Hz, or somewhere in the range of 1000 to 30000 Hz) where there is a relatively large gap between impedance of a damaged sensor and that of a healthy sensor.

In another example, a plurality of impedance measurements may be taken over a range of frequencies, and a damaged or abnormal sensor may be differentiated from a healthy sensor using impedance spectroscopy. For example, a damaged sensor may be differentiated from a healthy sensor, or an extent of damage (or abnormality) may be determined or estimated based on attributes of the impedance-frequency curve, such as shape, impedance value, derivative (slope), or second derivative (curvature). In some examples, the impedance or estimated damage/abnormality level may be used to compensate for the slight damage or abnormality.

Figure 15A:
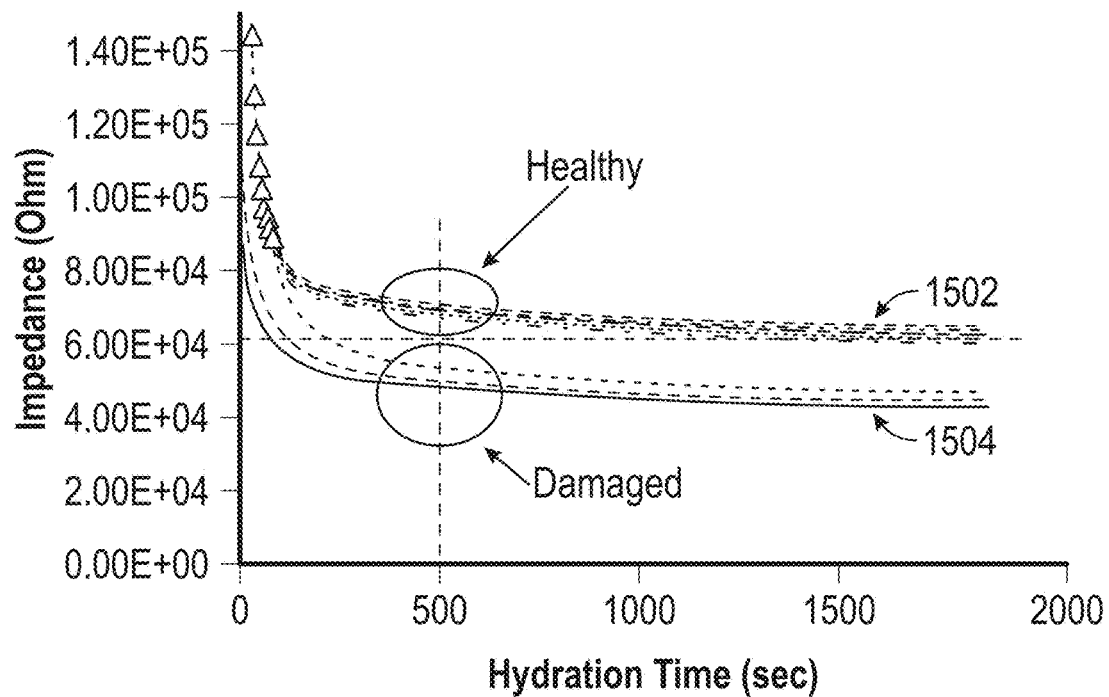
FIG. 15A is a plot of impedance vs. hydration time for a number of sensors.

FIG. 15A is a plot of impedance vs. hydration time for a number of sensors, at 5000 Hz. After sufficient hydration time (e.g., 400 seconds), the damaged sensors produce an impedance 1504 that is significantly smaller than the impedance 1502 of healthy sensors. This impedance difference for healthy vs. damaged sensors may be used to identify damaged or abnormal sensors. For example, a sensor that has an impedance lower than 60000 Ohm after 400 seconds may be deemed abnormal or damaged, or may require compensation, depending on the amount of damage or abnormality, which may be inferred from the impedance. For example, a first threshold may identify sensors that require compensation, and a second threshold may identify sensors that are deemed excessively damaged and excluded from a population of usable sensors. FIG. 15A illustrates an example in which a threshold has been set at 60 kiloohms at 500 seconds of hydration time, which clearly differentiates excessively damaged sensors from healthy sensors.

Figure 15B:
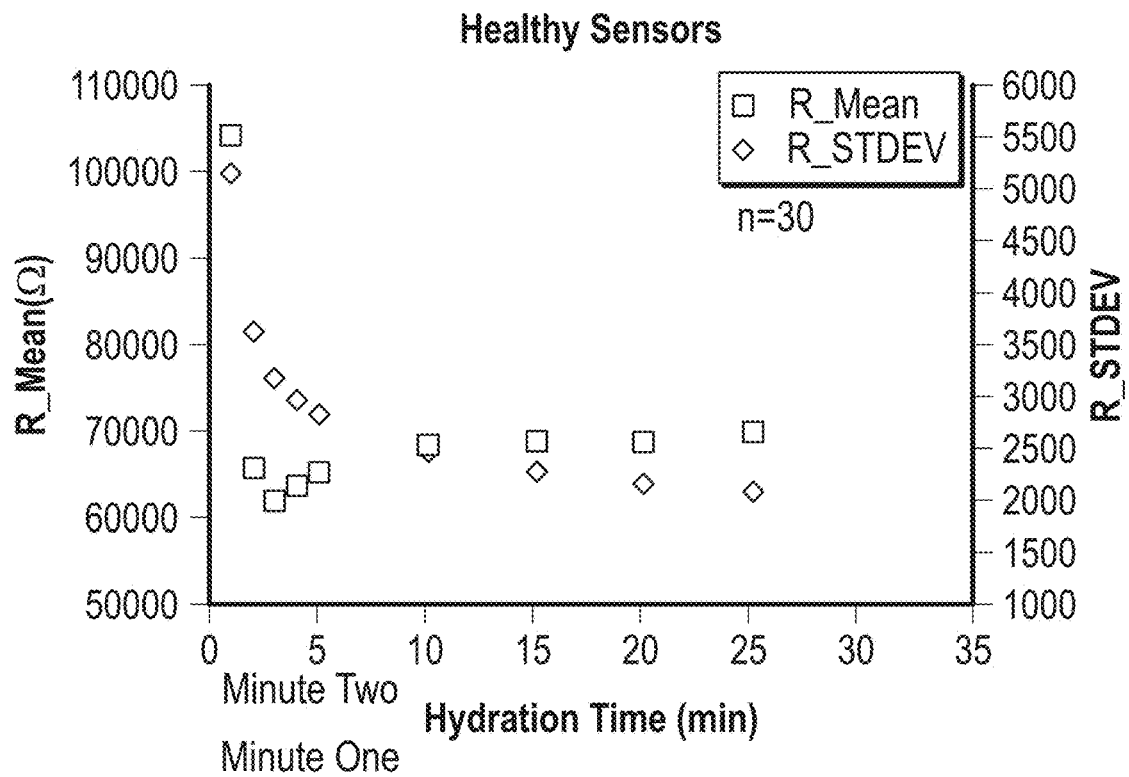
FIG. 15B is a plot of the mean impedance and standard deviation of impedance against hydration time.

FIG. 15B is a plot of the mean impedance (R_mean, indicated by a diamond) and standard deviation (R_STDEV, indicated by a square) of impedance (R_mean) for a number of hydration times. It can be seen from the plot that the standard deviation drops significantly from minute one (R_STDEV over 5000) to minute two (R_STDEV under 2500) and stays below 3000 through minute 30. A damage determination may be made based on an impedance value that is measured after the standard deviation has dropped, e.g., to more effectively assure that a particular sensor is healthy, as opposed to damaged or abnormal.

Figure 16A:
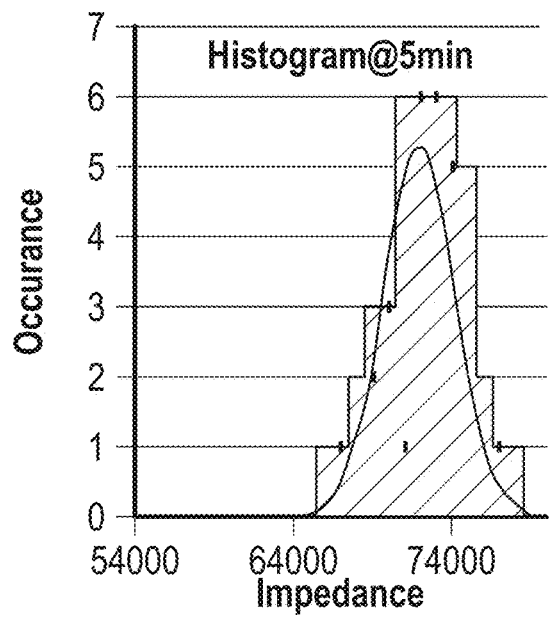
FIGS. 16A-C are graphs that show impedance distributions of sensors at 5 minutes, 10 minutes, and 30 minutes of hydration, respectively.
Figure 16B:
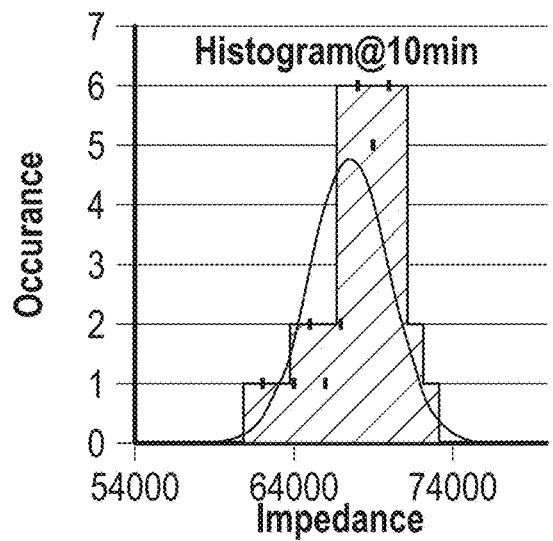
Figure 16C:
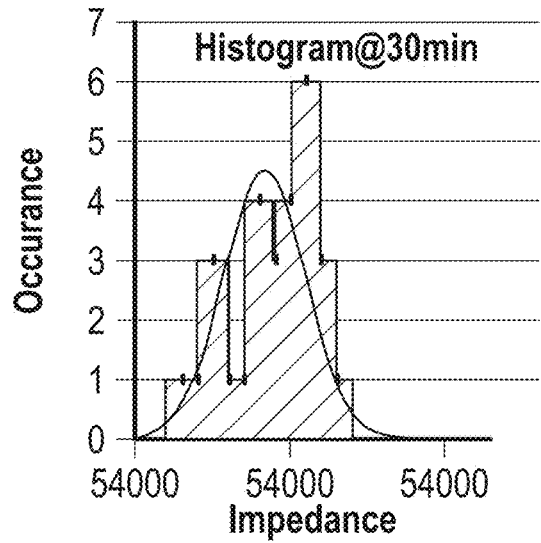

FIGS. 16A-C are histogram plots of determined sensor impedance for healthy sensors at 25 kHz. FIG. 16A shows the impedance distribution at 5 minutes, FIG. 16B shows the impedance distribution at 10 minutes, and FIG. 16C shows the impedance distribution at 30 minutes. The standard deviation of impedance at five minutes is 2.3 kiloohms. The standard deviation of impedance at thirty minutes is 2.7 kiloohms. It may be desirable to measure impedance early (e.g., five minutes of hydration time, or less), as waiting until the 30 minute point does not improve the standard deviation of the impedance distribution. In some examples, an impedance accuracy of one kiloohm is sufficient to identify healthy sensors (e.g., an impedance that deviates from a defined value (e.g., the mean, or a specified value that approximates the mean) may be taken as an indication that a sensor has damage or an abnormality).

Figure 17A:
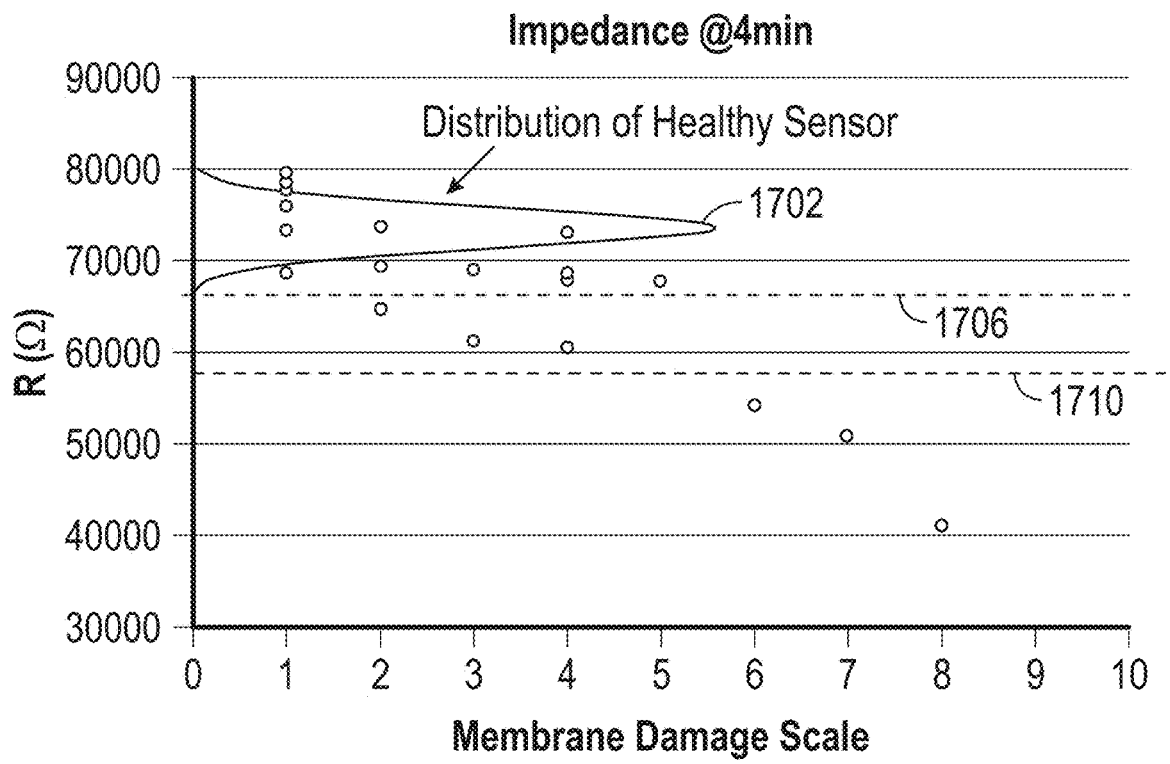
FIGS. 17A and 17B are graphs that shows impedance plotted against the membrane damage scale used to classify the damage on the sensor membranes shown in FIGS. 12B through 12H. The impedance values in FIG. 17A are based on measurements 4 minutes after hydration and the impedance values in 17B are based on measurements 10 minutes after hydration.
Figure 17B:
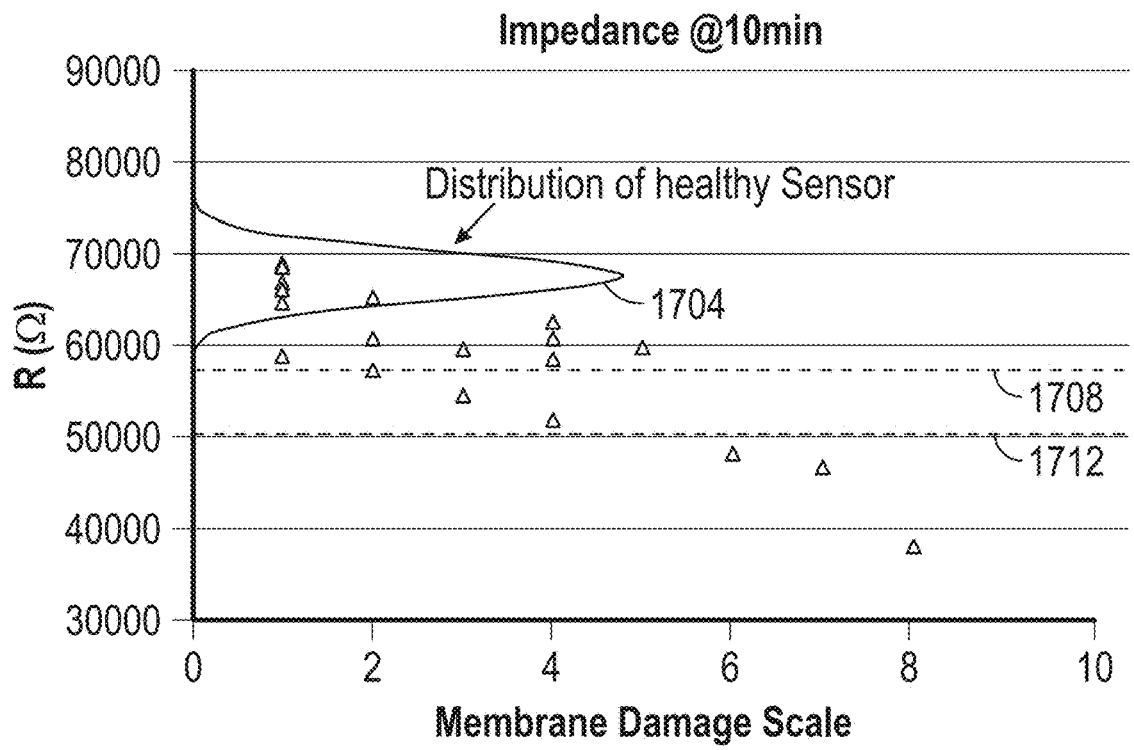

FIGS. 17A and 17B show impedance plotted against the membrane damage scale used to classify the damage on the sensor membranes shown in FIGS. 12B through 12H. For FIG. 17A, the impedance measurements were taken at four minutes of hydration time, and for FIG. 17B, the impedance measurements were taken at 10 minutes of hydration time. The impedance measurements were taken at 25 kHz. The distributions of healthy sensors 1702, 1704 from FIGS. 17A and 17B have also been overlaid onto the figures (with the X-axis indicating frequency of occurrence for the healthy sensor distribution). Sensors with damage of greater than five on the damage scale may be identified based upon the lower impedance values associated with those heavily-damaged sensors (e.g., data points with a damage rating 6, 7, and 8 are far below the impedance of the healthy sensors). Sensors with slight to moderate damage had a measured impedance that overlapped with healthy sensors, but the impedance generally tended to be lower than the impedance range for healthy sensors. In some examples, an impedance threshold may be used to differentiate healthy sensors from excessively damaged sensors. For example, a threshold 1706 of 67 kiloohms may be used to identify damaged sensors (that have an impedance below 67 kHz) at four minutes as shown in FIG. 17A, or a threshold 1708 of 58 kiloohms may be used to identify damaged sensors at ten minutes, as shown in FIG. 17B. In another example, a threshold 1710 (e.g., 58 kiloohms in FIG. 17A) or 1712 (e.g., 50 kiloohms in FIG. 17B) may be used to identify heavily-damaged sensors (e.g., sensors that have a rating of greater than five on the damage scale referenced above). In some examples, a first threshold 1706 or 1708 may be used to identify sensors that should be compensated, and a second threshold 1710 or 1712 may be used to identify a sensor in which the damage or abnormality is large enough that the sensor should not be used.

It may be desirable to quickly identify a sensor that has excessive damage or abnormality. For example, after a sensor is implanted in a host, it may be desirable to make a sensor damage assessment within a minute or within a few minutes, so that a damaged sensor may be replaced. A rapid sensor damage assessment may be more convenient for the wearer of the sensor. For example, making a quick assessment increases the likelihood that the wearer is still in a location or situation where a sensor can be replaced if needed. A long assessment delay may increase the likelihood that the wearer has departed for work, gone to school, left the company of a caregiver, or otherwise experienced an environmental change that makes it more difficult to access a sensor or replace a sensor. It thus may be desirable to base a sensor damage or abnormality assessment upon an impedance determination that provides sufficient spread between healthy and excessively damaged sensors to enable differentiation and is also made reasonably early after sensor hydration (e.g., implantation in subcutaneous fluid). For example, with reference to FIG. 15A-B, impedance values at or before 500 seconds, 400 seconds, or 300 seconds (five minutes) may be used to differentiate excessively damaged or abnormal sensors from healthy sensors. The data shown in FIGS. 16A-C also suggests that a hydration time of about four or five minutes is sufficient to differentiate sensors based on impedance.

Figure 18A:
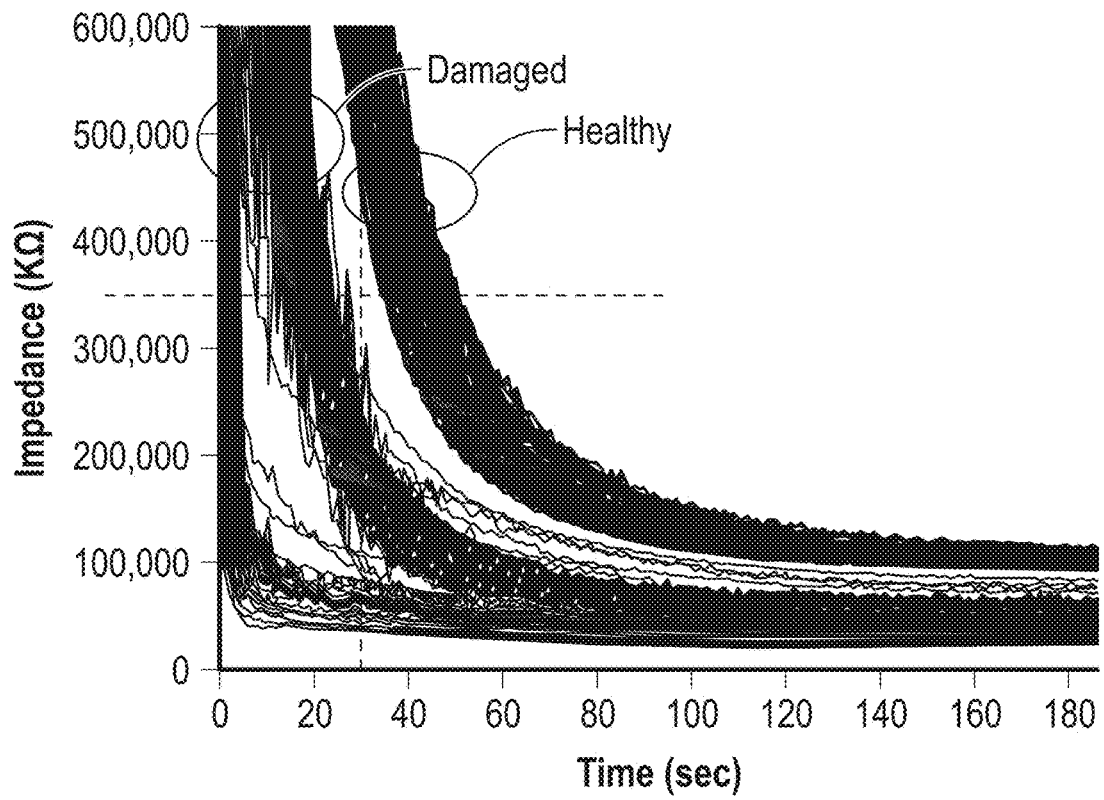
FIG. 18A is a graph that shows impedance plotted against time for a number of sensors.

It may be desirable to differentiate damaged or abnormal from healthy sensors even more quickly. FIG. 18A shows impedance plotted against time for 180 seconds (1.5 minutes) for a number of sensors. Due to membrane hydration, impedance drops quickly during the first minute, and then continues to drift down at a slower rate. The impedance for damaged sensors drops more quickly than the impedance for healthy sensors.

In some examples, in situations where the hydration time is known with sufficient precision (e.g., in systems that control sensor insertion or have a way to capture a time stamp when insertion occurs), a threshold time may be defined for a sensor to reach a particular impedance level. For example, a sensor may be deemed healthy if the impedance is above a threshold (e.g., 350 kiloohms) at a specified time (e.g., 30 seconds) after insertion. In another example, a plurality of impedance determinations may be made (e.g., one per second), and a sensor may be deemed to be healthy if none of the sensor readings falls below a threshold (e.g., none falls below 350 kiloohms in the first 30 seconds after implantation).

Figure 18B:
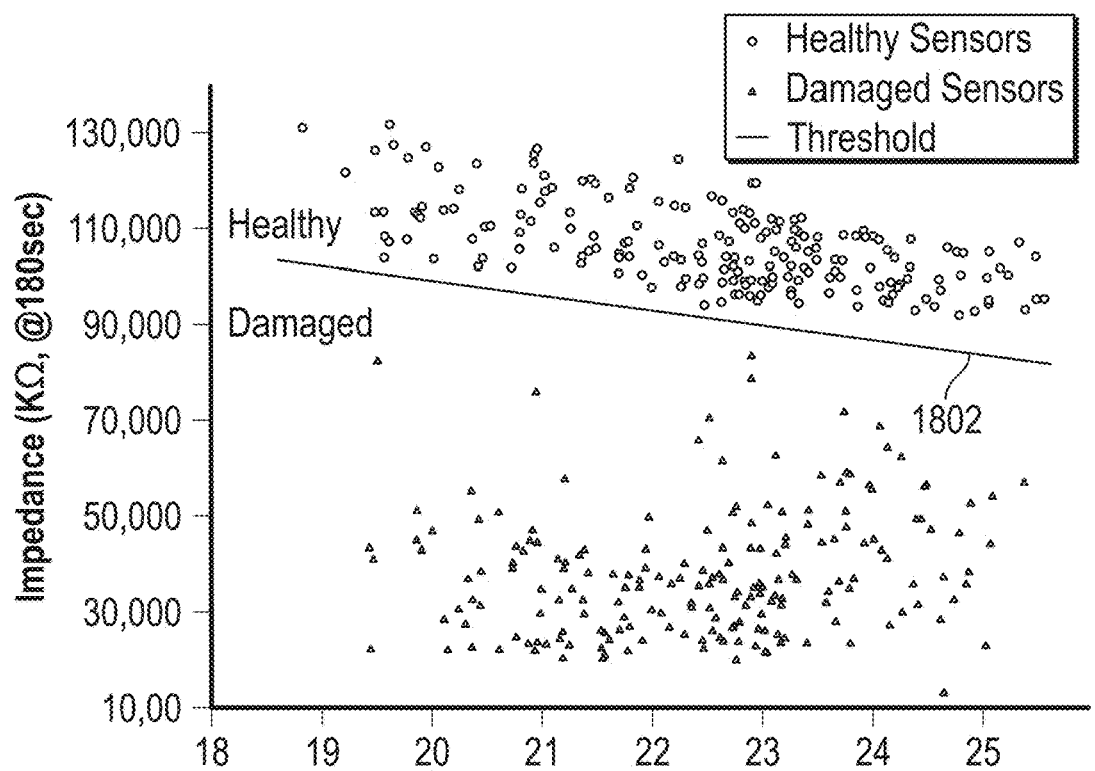
FIG. 18B is a graph of impedance plotted against sensor sensitivity to glucose concentration.

FIG. 18B is a graph of impedance plotted against sensor sensitivity to glucose concentration (in picoamps per milligram per deciliter), which may be determined for example during a factory calibration step or may be predefined or may be based on user calibration. In an example, a threshold 1802 may vary based upon the sensitivity of the sensor. For example, the threshold may be defined to have a linear relationship with sensitivity, as shown in FIG. 18B. In other examples, a threshold may be defined to have a different (e.g., polynomial) relationship with sensitivity, or a single threshold (e.g., 90,000 kiloohms for the data shown in FIG. 18B) may be used for all sensor sensitivities.

Figure 19A:
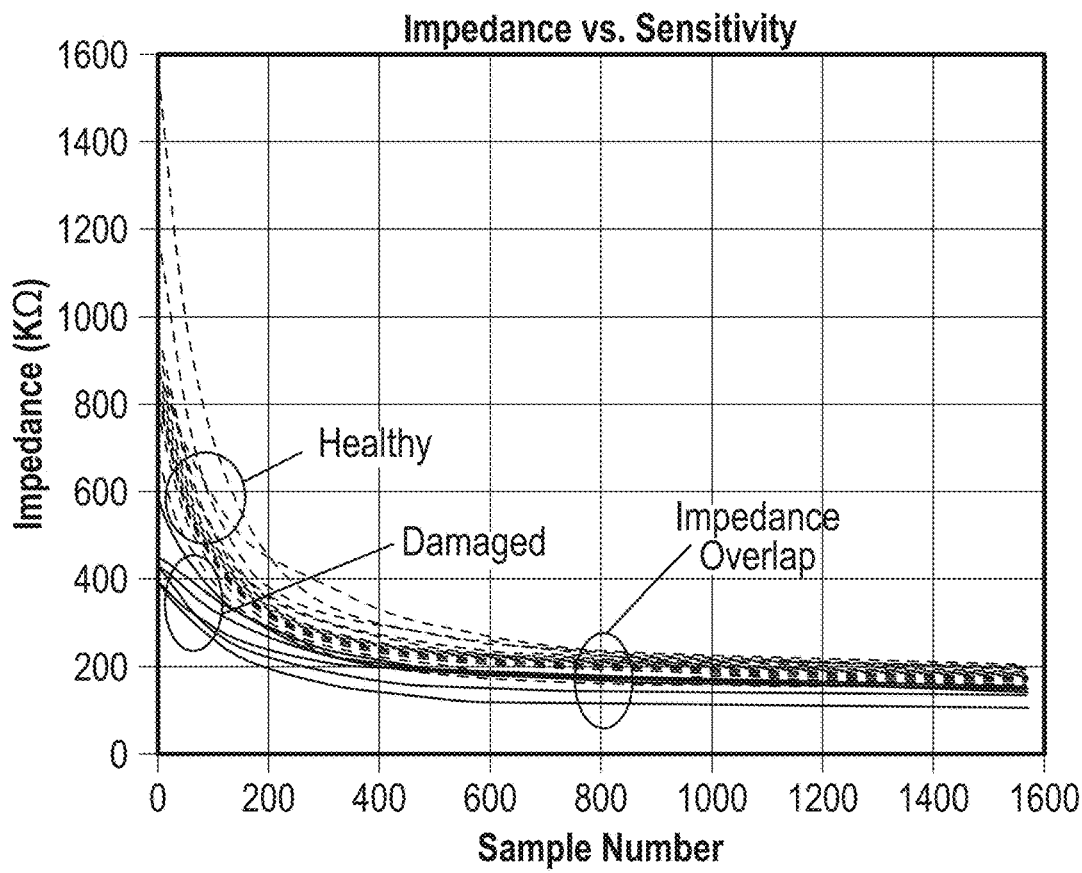
FIG. 19A is a graph that shows impedance plotted against sample number.

In some situations, the actual insertion time for a sensor may not be known. FIG. 19A is a plot of impedance against sample number. The samples are taken sequentially, but the time since insertion is not known, so zero point on the sample axis (X-axis) does not necessarily correspond to time zero. When a sensor is implanted into a wearer, there is typically a delay between sensor insertion into interstitial fluid and assembly of sensor electronics onto the sensor, at which point impedance determination and time measurement may begin. Because the delay is unknown, it may be difficult to differentiate a healthy sensor from an excessively damaged or abnormal sensor based solely on impedance values, because the values may overlap. Moreover, the full impedance trend shown in FIG. 19A may not be available: only a portion of the impedance trend may be captured, based upon timing of connection of the sensor electronics, or other factors.

Figure 19B:
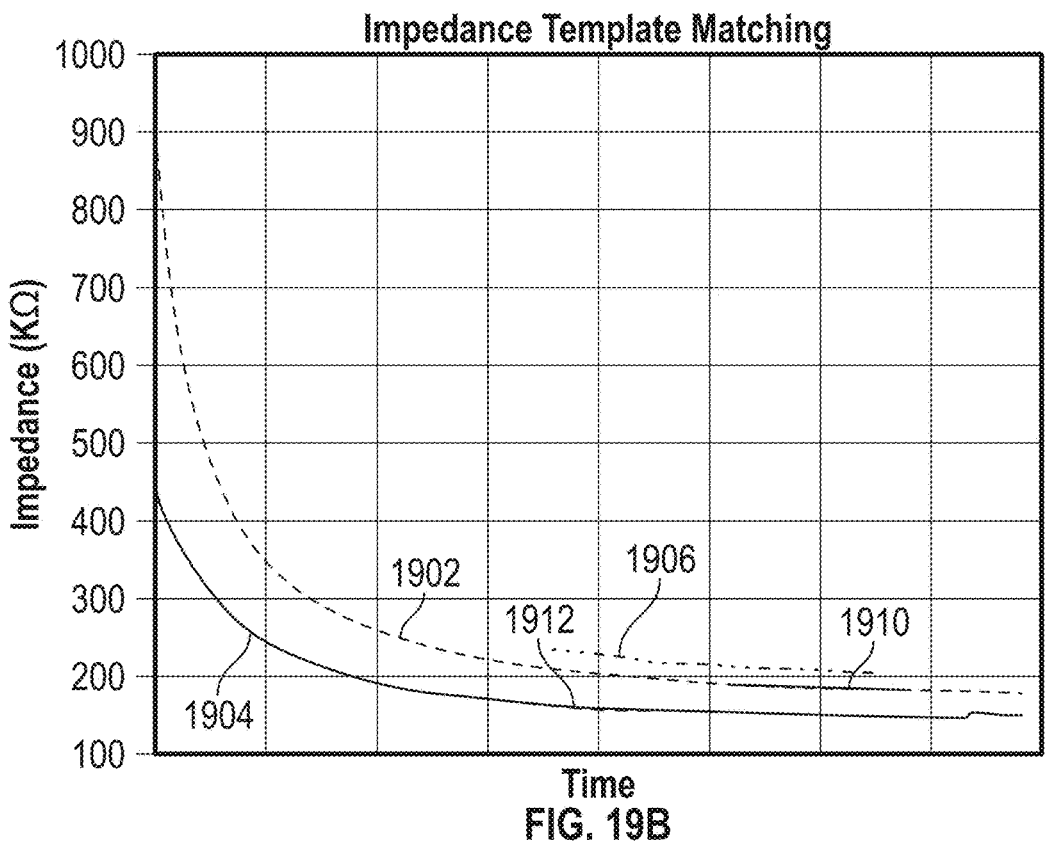
FIG. 19B shows a healthy sensor template, a damaged sensor template, and an impedance sample for a sensor-of-interest.

In some examples, to address these problems, impedance data for a sensor may be compared to one or more templates. For example, impedance may be compared to a healthy sensor template, or a damaged sensor template, or both. FIG. 19B shows a healthy sensor template 1902, a damaged sensor template 1904, and an impedance sample 1906 that is based on measurements of a sensor-of-interest. The impedance sample 1906 may be compared to a template to determine a template sequence (i.e., segment) that is most similar to the impedance sample (e.g., determine which part of the template curve best fits the impedance sample). In some examples, a template sequence match is identified for each template, and a determination is made as to which template sequence is more similar to the impedance sample. For examples, with reference to FIG. 19B, the impedance sample 1906 may be matched to sequence 1910 on healthy sensor template 1902 and matched to sequence 1912 on damaged sensor template 1904. If the impedance sequence is more similar to the sequence 1910 on the healthy sensor template 1902 than to the sequence on damaged sensor template 1904, the sensor corresponding to the impedance sample 1906 may be declared a healthy sensor.

In some examples, multiple reference templates may be used. For example, a plurality of reference templates may be used, where each reference template corresponds to a different damage level.

Dynamic Time Warping

A dynamic time warping (DTW) may be applied to address variations in the timing of impedance data. For example, an impedance sample may match the general shape or pattern of a template, but the time axis may be distorted, e.g., an impedance sample may show characteristics of a template that suggest a healthy (or damaged) sensor, but the rate of change of impedance may be different from the template. This issue may be addressed using a dynamic time warping technique. In some examples, a dynamic time warping (DTW) technique may be used to determine which template is most similar to an impedance sequence. Dynamic time warping may be particularly useful when the impedance sequence is discontinuous.

In an example, dynamic time warping may be applied to find similarities between a real-time measured sequence of impedance values and a reference template. For example, a DTW process may locally translate, compress, and expand the patterns so that similar features in the patterns are matched. In some examples, application of DTW may nonlinearly warp two trajectories in such a way that similar events are aligned and a minimum distance between them is obtained. Scaling may be performed prior to implementation of DTW to improve performance of DTW.

In an example, xa and xt may be the reference and test signal trajectories with data lengths and respectively. DTW may be applied to find a sequence F* of L points on an impedance vs. time (R×T) grid, e.g.:

$$F=[f(1), f(2), \ldots f(k), \ldots f(L)]$$

$$\max(ii, T) < L < R+T$$

where f(k)=[i(k), j(k)] is an ordered pair indicating a position on the grid, k is the number of the grid points along a path between two trajectories, i and j are the sample points (which go up to R and T for the reference and test trajectories, respectively). The sequence F* (among all possible F sequences) is a path on the grid that optimally matches each vector in both trajectories so that a normalized distance between them is minimized. DTW defines the Euclidean distance d between each point of the two trajectories as:

$$d(i(k), j(k)) = [x_r - (i(K)) - x_T(J(k))]^2$$

The total distance between two trajectories is defined as $$D(R, T) = \sum_{\kappa=1}^{L} d(i(\kappa), j(\kappa))$$

The optimal path and minimum total distance is found as the solution of the following optimization problem:

$$F^* = \min_{F} D(R, T)$$

An elegant and effective solution to this problem is dynamic programming, which guarantees to find the optimum path without having to calculate the distance along all possible paths:

$$D_F(i, j) = d(i, j) + \min \begin{cases} D_F(i-1, j) \\ D_F(i-1, j-1) \\ D_F(i, j-1) \end{cases}$$

With respect to some local and global constraints $$D_F(b^*, T) = \min_{b \in [1:R]} D(b, T)$$

$$D_F(a^*, 1) = \max_{a \in [1:R]} a$$

$$i(\kappa + 1) \geq i(\kappa)$$

$$j(\kappa + 1) \geq j(\kappa)$$

In an experiment (using the data shown in FIG. 19A), the DTW method demonstrated good sensitivity and specificity. A population of sensors included nineteen healthy sensors and seven damaged sensors. The method identified 16 of the nineteen healthy sensors as healthy, and three of nineteen healthy sensors were identified as having damage. Six of seven damaged sensors were identified as damaged, and one of seven damaged sensors was identified as healthy. Application of DTW may improve the performance of a sensor system at differentiating between damaged and healthy sensors.

In some examples, derivative dynamic time warping may be used. A smooth derivative may be obtained, for example, using a Savitzky-Golay Filter.

Continuous Impedance Measurements

In another example, if continuous impedance measurements are available, matching may be accomplished using the equations:

$$V_d(k) = \sum_{i=k}^{k+N_{test}-1} (x_{test}(i-k+1) - x_{damaged}(i))^2$$

$$k = 1, \ldots, N_{damaged} - N_{test}$$

$$V_h(k) = \sum_{i=k}^{k+N_{test}-1} (x_{test}(i-k+1) - x_{healthy}(i))^2$$

$$k = 1, \ldots, N_{healthy} - N_{test}$$

$$\text{outcome} = \min(\min(V_d(k)) \min(V_h(k)))$$

where Ntest, Ndamaged, and Nhealthy are the size of real-time measured impedance sequence, reference damaged template, and reference healthy template, respectively.

Impedance—Frequency Characteristics

In some examples, the impedance of a sensor at a specified frequency, or at two or more frequencies, may be used to ascertain information about the sensor. For example, the difference between impedance at two different frequencies, or the shape (e.g., slope) of an impedance-frequency curve, may be used to determine information about a sensor, such as a damage state. Measuring impedance or sensor damage at higher frequencies (e.g., 1 kilohertz or above) may improve the accuracy of measurements, because the double membrane capacitance has less of an effect on the circuit behavior at higher frequencies (e.g., the sensor circuit acts like a high-pass filter).

Figure 20:
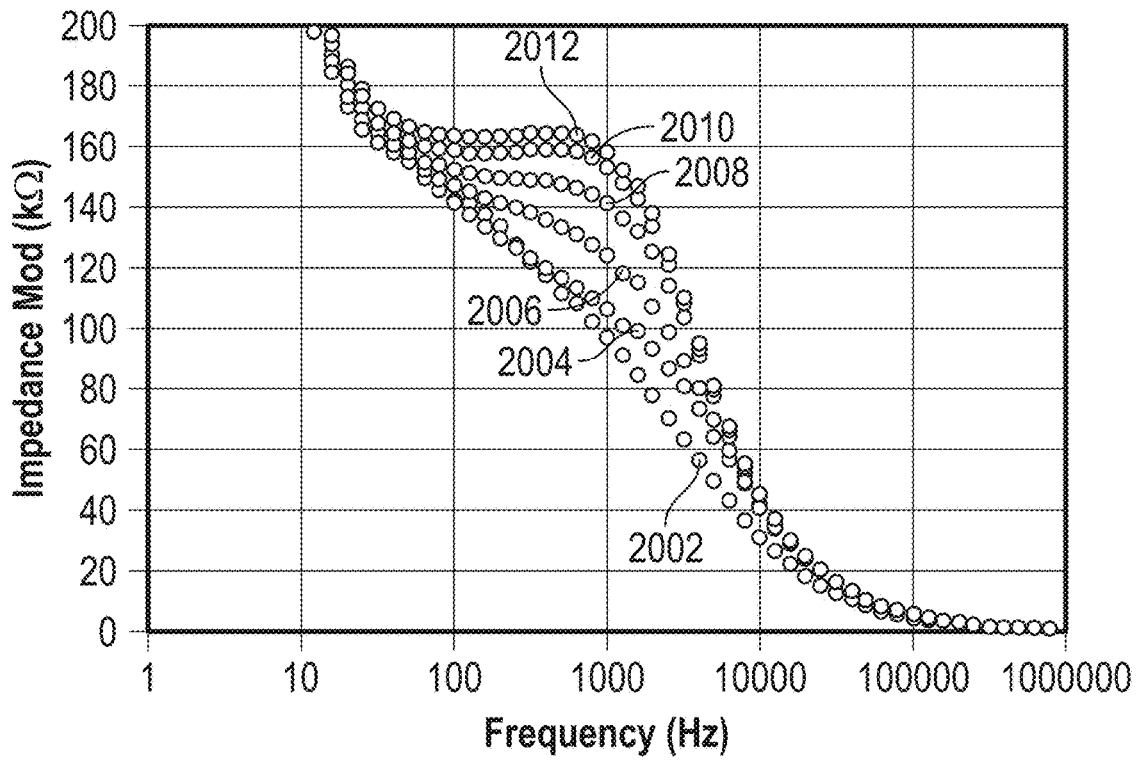
FIG. 20 is a graph that shows impedance plotted against frequency for six sensors.

FIG. 20 is an illustration of impedance plotted against frequency for six sensors. For each sensor, a plurality of impedance measurements were taken across a range of frequencies. To obtain a spectrum of damage levels, the sensors were subject to different levels of physical damage by scratching the sensor against sandpaper. The scratching involved dragging a sensor a distance across sand paper a number of times. The same grade of sandpaper was used for scratching each sensor. A first curve 2002 corresponds to a sensor that was scratched 20 times. A second curve 2004 corresponds to a sensor that was scratched 10 times. A third curve 2006 corresponds to a sensor that was scratched five times. A fourth curve 2008 corresponds to a sensor that was scratched one time. A fifth curve 2010 corresponds to a sensor that was dragged half way through the distance (i.e., subjected to "half a scratch" compared to the sensor that corresponds to the fourth curve). A sixth curve 2012 corresponds to a sensor that was not scratched (not damaged.)

The impedance curves 2002, 2004, 2006, 2008, 2010, 2012 have relatively closely-grouped impedance values below 100 kHz and above 10,000 Hz, but the impedance values spread out between 100 Hz and 10,000 Hz. For example, at 1000 Hz, the first curve 2002 (corresponding to the most damaged sensor) has an impedance value of about 100 kΩ, the second curve 2004 has an impedance value of about 105 kΩ, the third curve 2006 has an impedance value of about 122 kΩ, the fourth curve 2008 has an impedance value of about 140 kΩ, the fifth curve 2010 has impedance value of about 155 kΩ, and the sixth curve 2012 (corresponding to the undamaged sensor) has an impedance value of about 160 kΩ.

In some examples, measuring impedance at a portion of the impedance-frequency curve where the impedance spread is present may allow for characterization of an amount of damage to a sensor. For example, impedance may be determined for a sensor at above 250 Hz, e.g., at 1000 kHz, and the impedance may be compared to a reference value or look-up table to ascertain a damage state of the sensor or to determine a sensitivity of the sensor to an analyte (e.g., glucose). Determining impedance at a relatively high frequency (e.g., over 250 Hz, or at 1000 Hz) may avoid effects from the double-layer capacitance, because the membrane acts like a high-pass filter.

In some examples, a sensor may be characterized by a difference in impedance values at two different frequencies. For example, a difference between the impedance at 1000 Hz and the impedance at 100 Hz may be used to determine an extent of damage to a sensor membrane. This difference between impedance values for a sensor at two difference frequencies will be referred to as the "dual frequency impedance," to avoid confusion with the difference in impedance between healthy and damaged sensors (described above), or with the difference in impedance of a particular sensor at two points in time (described below).

Figure 21:
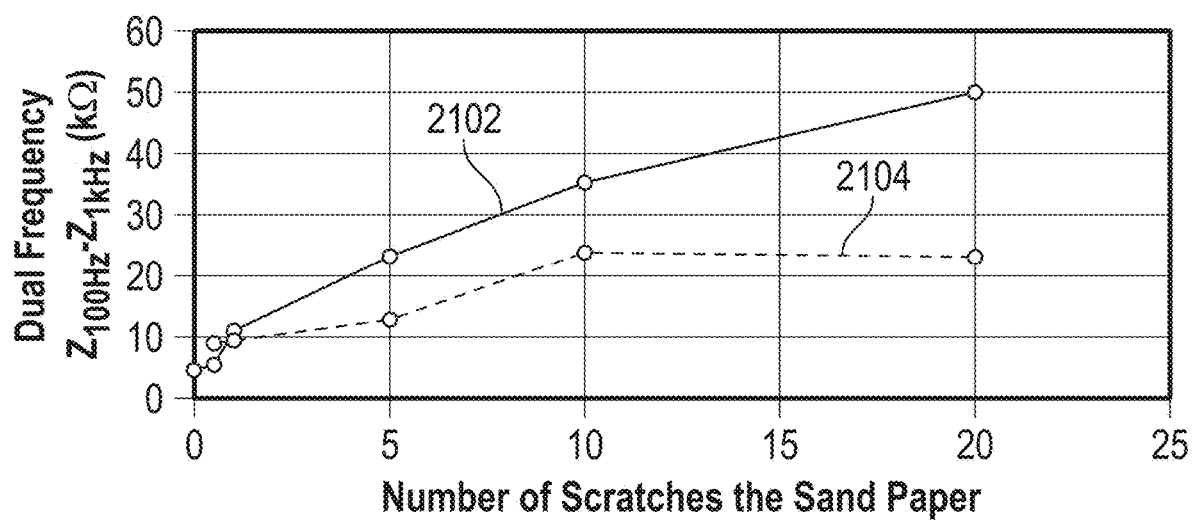
FIG. 21 is a graph that shows dual frequency impedance plotted against the number of scratches through sandpaper to which a sensor was exposed.

FIG. 21 is a graph that shows the dual frequency impedance (in this case, the impedance at 100 Hz minus the impedance at 1 kHz) plotted against the number of scratches through sandpaper to which a sensor was exposed, which correlates with the amount of damage to the sensor. A first curve 2102 indicates the dual frequency impedance measured immediately after the sensor was brought in contact with a solution. A second curve 2104 indicates the dual frequency impedance measured after soaking overnight in a solution. The dual-frequency impedance is larger immediately after the sensor is immersed in solution than after the overnight soak. This indicates that dual frequency impedance based on measurements taken during a manufacturing process, without an extending soaking period, may be used to identify abnormal or damaged sensors. It also indicates that a dual frequency impedance based on impedance measurements taken soon after insertion of a sensor into interstitial fluid in a host may be used to assess sensor health (e.g., quickly determine whether a sensor is damaged, so it may be replaced).

Figure 22A:
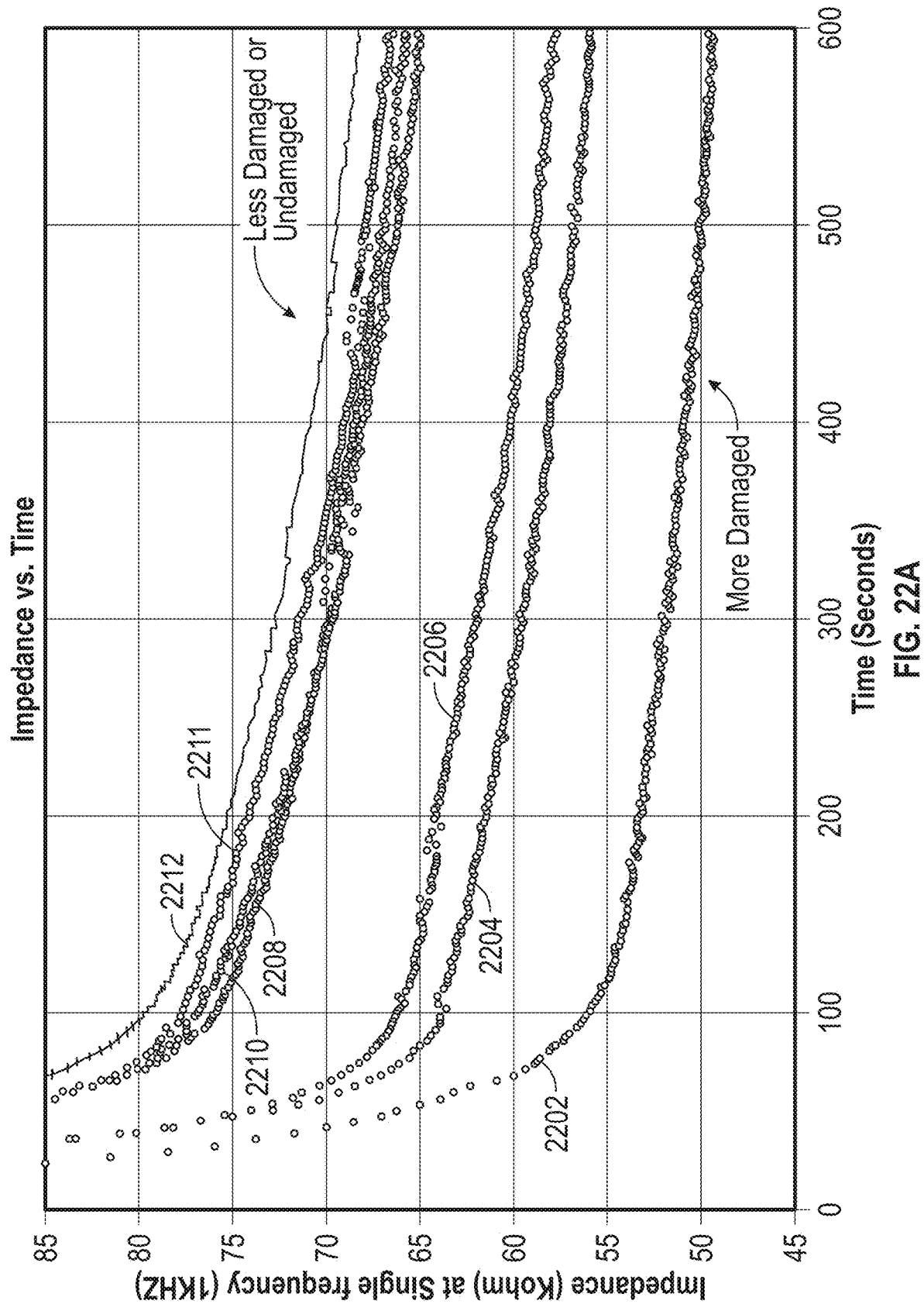
FIG. 22A is a graph that shows impedance at 1 kHz plotted against time for a number of sensors with varying degrees of damage.

FIG. 22A shows impedance at 1 kHz plotted against time for a number of sensors with varying degrees of damage. The impedance was determined using methods described above (e.g., based on current measurements and an applied voltage). The time indicates the amount of elapsed time after insertion in a hydrating solution. Curve 2202 corresponds to a sensor with a relatively large degree of damage. Curve 2212 corresponds to a sensor with no damage. The curves in between correspond to sensors with varying degrees of damage, with more-damaged sensors being closer to curve 2202. Curve 2202 corresponds to a sensor that was scratched 20 times (as described above). Curve 2204 corresponds to a sensor that was scratched 12 times. Curve 2206 corresponds to a sensor that was scratched 8 times. Curve 2208 corresponds to a sensor that was scratched 4 times. Curve 2210 corresponds to a sensor that was scratched 2 times. Curve 2211 corresponds to a sensor that was scratched one time. FIG. 22A shows that, for each sensor (damaged, slightly damaged, and undamaged) the impedance drops rapidly in the first 100 seconds after immersion, and then continues to drop at a slower rate for the next 500 seconds.

FIG. 22B shows the dual frequency impedance for 100 Hz and 1000 Hz (i.e., the difference in impedance at 100 Hz and the impedance at 1000 Hz) for the same sensors as shown in FIG. 22A. Curve 2202', for example, represents the dual frequency impedance for the same sensor as curve 2200 in FIG. 22A, and curve 2212' represents the dual frequency impedance for the undamaged sensor corresponding to curve 2212. FIG. 22B shows that, for each sensor (damaged, slightly damaged, and undamaged), the dual frequency impedance drops rapidly in the first 100 seconds after immersion. The undamaged and slightly damaged sensors (e.g., as represented by curves 2212', 2210', 2211') reach a dual frequency impedance low point at about 75 seconds, after which the dual frequency impedance is relatively stable. The impedance values are relatively stable after 100 seconds, with more damaged sensors showing a slowly dropping dual frequency impedance over time. The relatively stable dual frequency impedance values over the 100 to 600 second time period may allow for differentiation or characterization of sensor damage based on the impedance value, with little sensitivity to the exact time of measurement or temporal variations in sensor response to immersion. The position of the dual frequency impedance value on a dual frequency impedance spectrum may be used to determine the presence or severity of damage. For example, with reference to FIG. 22B, a sensor with a dual frequency impedance of greater than 65 kOhm may be taken as severely damaged (or having a severe manufacturing abnormality), a sensor having an dual frequency impedance below 55 kOhm may be taken as undamaged, or very slightly damaged (and therefore usable, potentially with compensation), and sensors with an dual frequency impedance between 55 kOhm and 65 kOhm may be taken as moderately damaged (and potentially usable with compensation).

Because the dual frequency impedance stabilizes more quickly after contact with solution than simple impedance, the dual frequency impedance may be more preferred than impedance as measure of sensor damage. For example, a predictable steady state range may be determined more easily using dual frequency impedance, or a measurement may be taken over a shorter dwell time because dual frequency impedance stabilizes more quickly than impedance.

Dual frequency impedance may be particularly useful in evaluating sensor health after insertion in a host. When a sensor is inserted into a host, the exact insertion time may not be known if the sensor does not have its own clock or sensor electronics to track time. For example, sensor electronics may be coupled to an inserted sensor an unknown period of time after sensor insertion (i.e., the user may insert the sensor, but may not immediately couple sensor electronics (e.g., a transmitter) to the inserted sensor). As a result, the exact dwell time may not be known. The dwell time (after insertion) may be a few seconds, or a minute, or a few minutes, or longer, depending on the habits or behavior of the user. The sensor impedance data may eventually become available when the sensor electronics are attached, but the length of time since insertion may be unknown, which means that impedance may not be indicative of the amount of sensor damage. For example, with reference to FIG. 22A, an impedance value of 70 kOhm at 1 kHz could correspond to any of the plotted sensors (e.g., heavily damaged sensor curve 2202 has a value of about 70 kOhm at about 60 seconds, and undamaged sensor curve 2212 has a value of 70 kOhm at about 450 seconds).

Because the precise dwell time may not be known, it may be desirable to detect a failed or damaged sensor without using a precise time-since-insertion value as an input. For example, it may be desirable to use a steady-state parameter that is reliably steady a short time after sensor insertion. In some examples, it may be preferable to determine sensor health based on dual frequency impedance (shown in FIG. 22B) as opposed to impedance (shown in FIG. 22A) to take advantage of the relatively stable values after a short period of time. In an example, a sensor system may use a dual frequency impedance value determined a specified period of time (e.g., 72 seconds or 100 seconds) after connection of a sensor to sensor electronics (which may start a clock) to assure that the sensor has reached a stable point in the dual impedance curve.

Figure 23A:
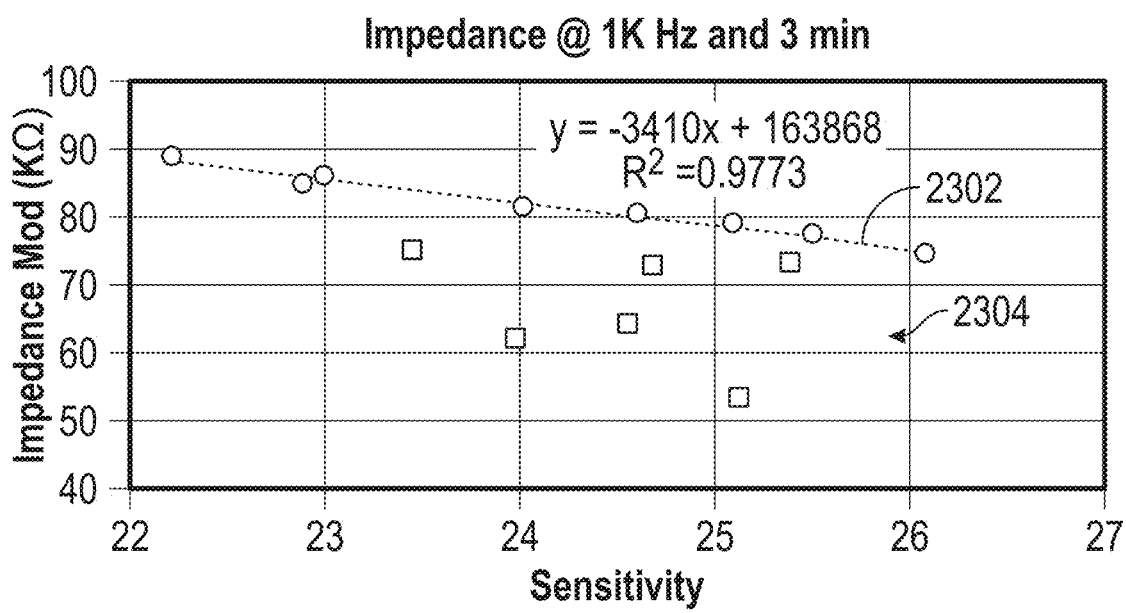
FIG. 23A is a graph that shows sensor impedance at 1000 Hz plotted against a sensitivity for a number of sensors, with measurements taken three minutes after sensor insertion.

FIG. 23A shows sensor impedance at 1000 Hz plotted against a sensitivity (e.g., nA/mg/dL) for a number of sensors, with measurements taken three minutes after sensor insertion. Healthy sensors, which have little or no damage, are indicted by circles, and unhealthy (e.g., significantly damaged) sensors are indicated by squares. The healthy sensors 2302 fall near a line determined by a linear function. The unhealthy sensors 2304 fall below the line. The relative placement of a particular sensor impedance on the chart shown in FIG. 23A may be used to identify unhealthy sensors. For example, damaged sensors may be identified based upon the distance from the healthy sensor line.

Figure 23B:
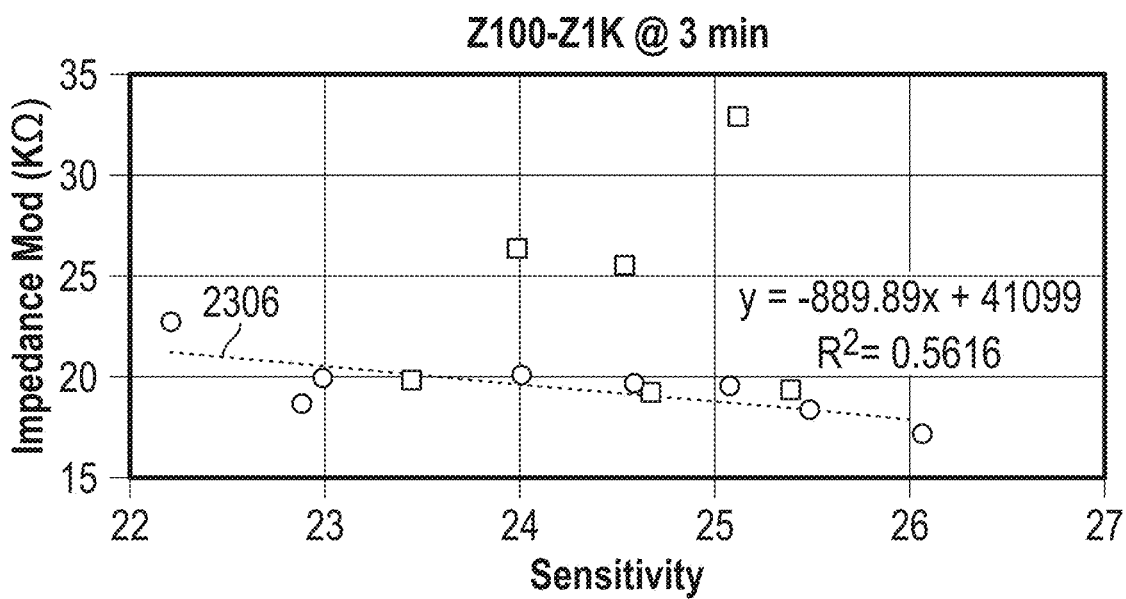
FIG. 23B is a graph that shows dual frequency impedance plotted against sensitivity, for measurements taken three minutes after immersion in fluid.

FIG. 23B shows dual frequency impedance plotted against sensitivity, for measurements taken three minutes after immersion in fluid. Sensors that are displaced from a healthy sensor line 2306 (e.g., above a defined range) may be identified as damaged or abnormal. FIG. 23B suggests that a damage assessment based on the position of a sensor on a dual-frequency impedance vs. sensitivity has good specificity (all three sensors that are spaced from the healthy sensor line are damaged or abnormal) but moderate sensitivity (only three out of six damaged sensors were identified). Dual frequency and impedance and sensitivity may be used alone to identify damaged sensors, or in combination with one or more other techniques, which may identify the other three abnormal sensors that are "missed" (not clearly identifiable as abnormal) in the FIG. 23B plot.

Figure 24A:
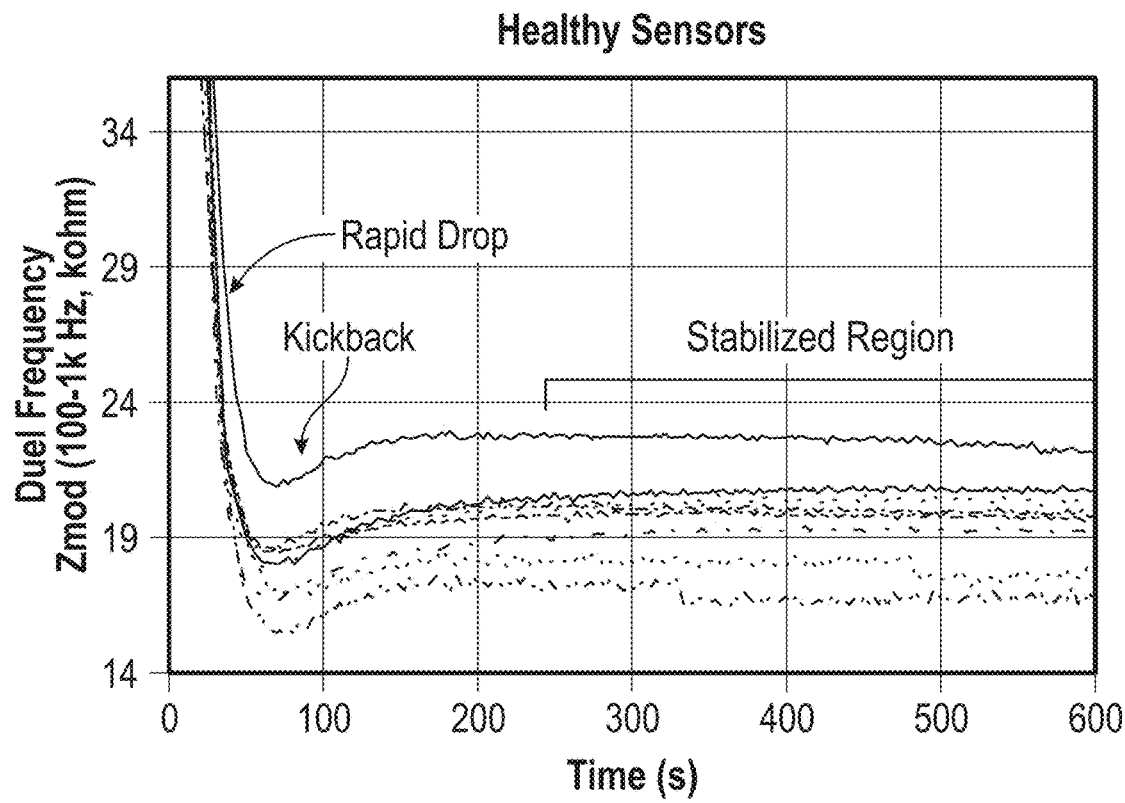
FIG. 24A is a graph that shows dual frequency impedance plotted against time for a number of healthy sensors.

FIG. 24A shows dual frequency impedance plotted against time for a number of healthy sensors. As with the previous disclosure, the dual frequency impedance is the impedance at 100 Hz minus the impedance at 1000 Hz. Other frequencies may also be used, as described in reference to FIG. 20. FIG. 24A shows that the dual frequency impedance drops quickly in the first 50 seconds and then increases slightly ("kickback") before reaching a stabilized state.

Figure 24B:
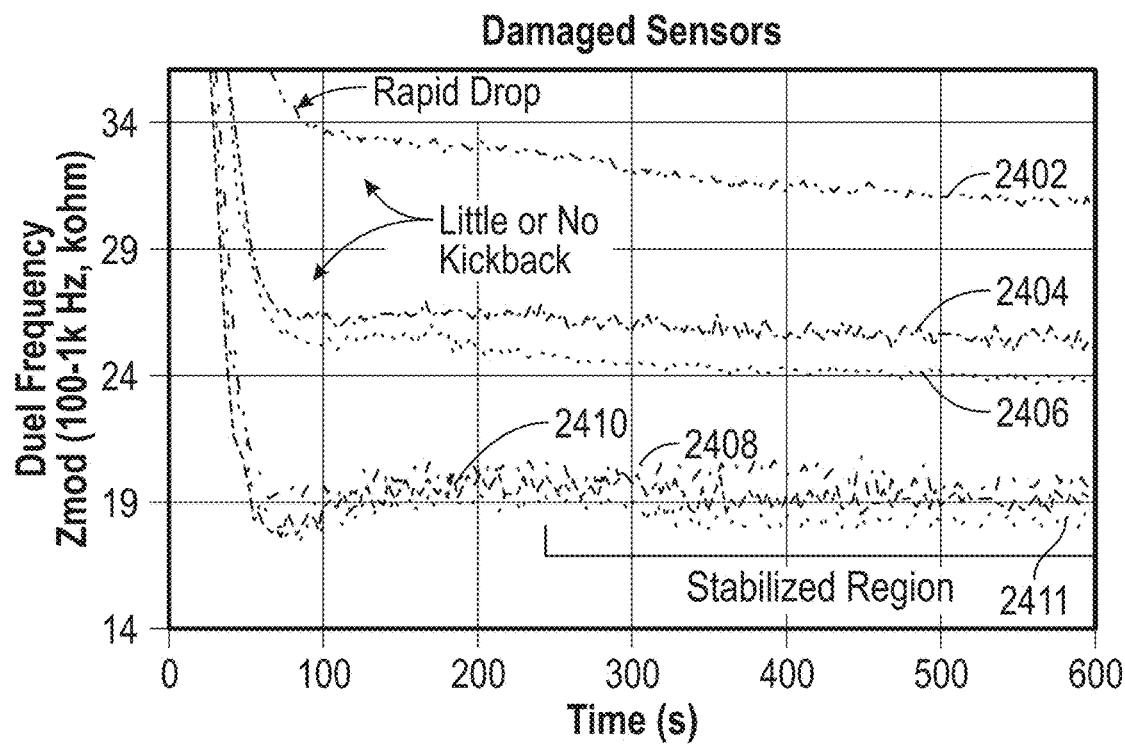
FIG. 24B is a graph that shows dual frequency impedance plotted against time since immersion for a number of damaged sensors.

FIG. 24B shows dual frequency impedance plotted against time since immersion for a number of damaged sensors. The moderately damaged sensors (indicated by curves 2406, 2408, 2410, 2411) show less pronounced kickback, and heavily damaged sensors (indicated by curves 2402, 2404) show little to no kickback. In some examples, the presence or amount of damage in a sensor may be determined based at least in part on the presence or amount of kickback present in a dual frequency impedance curve. For example, a difference between a dual frequency impedance at a specified time after insertion (which may be selected for example based upon the typical low point in the curve shown in FIGS. 24A and 24B) may be compared to a dual frequency impedance at a later time (or earlier time). In some examples, a plurality of impedance values may be measured at two or more frequencies and sequential times, so that a low point on a dual frequency impedance curve may be identified or estimated for a specific sensor being assessed, and a later dual frequency impedance may be compared to a low point to assess the amount or presence of kickback, from which an amount or presence of damage may be inferred.

Figure 24C:
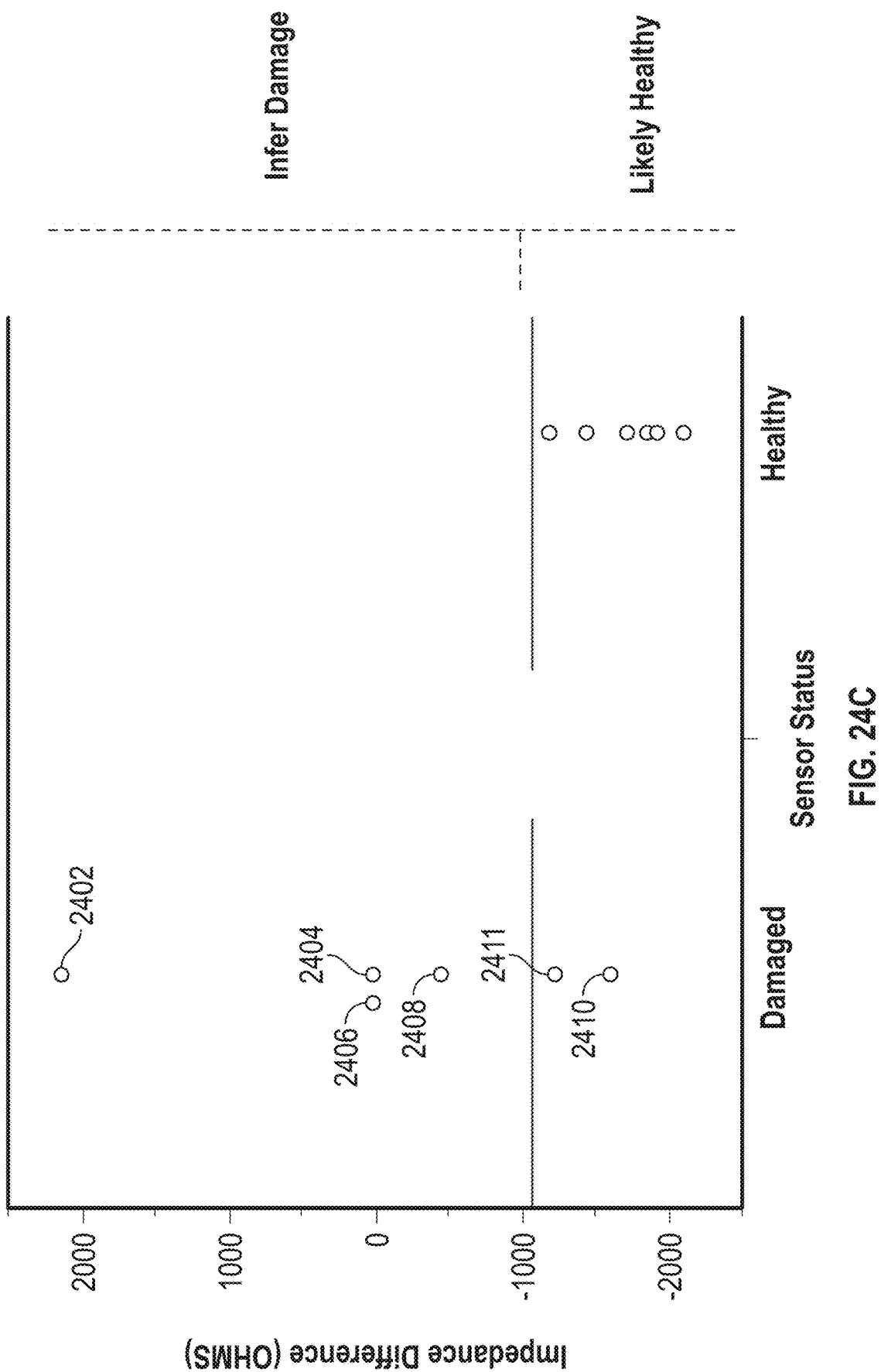
FIG. 24C is a graph that shows the difference between dual-frequency impedance at 72 seconds after immersion and at 180 seconds after immersion, for the healthy sensors of FIG. 24A and the damaged sensors of FIG. 24B.

FIG. 24C shows the difference between dual-frequency impedance at 72 seconds after immersion and at 180 seconds after immersion, for the healthy sensors of FIG. 24A and the damaged sensors of FIG. 24B. The low-point of dual-frequency impedance for both groups of sensors (healthy and damaged) is approximately 72 seconds after immersion. At 180 seconds, the dual frequency impedance has stabilized in both groups. Sensor data points for damaged sensors in FIG. 24C are labeled with reference numbers to indicate the respective corresponding curves on FIG. 24B.

FIG. 24C shows that a difference between dual frequency impedance at a low point (e.g., 72 seconds) and a dual frequency impedance at a steady state (e.g., 180 seconds) may be used to identify damaged sensors. For example, a threshold may be defined, and sensors having a difference in dual-frequency impedance for specified measurement times (e.g., 72 seconds and 180 seconds for the illustrated data) that exceeds the threshold may be deemed damaged (or excessively damaged). In various examples, sensors having an difference in dual-frequency impedance that is below (less than) the threshold may be deemed healthy, or likely healthy (e.g., not damaged, or having minimal damage or abnormality that does not prevent use of the sensor), or in need of further evaluation to ascertain status (e.g., a second technique may be used to identify the sensors corresponding to curves 2410, 2411 that were not identified as damaged).

With reference to FIG. 24C, the threshold may, for example, be negative one-thousand ohms (~1050Ω). The specific impedance-difference threshold may be determined experimentally using a group of sensors with known damaged states (e.g., as determined by a microscope inspection or deliberate damage to the sensors). The threshold may depend at least in part on the design of the sensor (e.g., sensor size), the membrane (e.g., membrane thickness or composition), the specified measurement times (e.g., 72 seconds and 180 seconds were selected for the example data). The precise measurement time may differ, or may be a range, or may be determined from sensor data. For example, the measurement time may be an estimated low point in a dual-frequency impedance curve, and a specified amount of time later (e.g., 108 seconds after the low point).

The chart in FIG. 24C shows good specificity for identifying damaged sensors and reasonably good sensitivity (four out of six) for damaged sensors. In some examples, additional information may be combined with the dual frequency impedance to improve the performance, e.g., to increase the sensitivity of a system to identification of an excessively damaged sensor. For example, a sensor assessment may be based on two or more of: sensor impedance at one or more specified times after a specified event; an impedance difference at two different times; a dual frequency impedance; a difference in dual frequency impedance at two different times; a first derivative of impedance, impedance difference, or dual-frequency impedance; a second derivative of impedance, impedance difference or frequency impedance; a higher order derivative of impedance or impedance difference; or a variability in a signal or variability in a derivative of a signal. A sensor assessment also be based on more than two frequencies, or more than two measurement times.

Figure 25A:
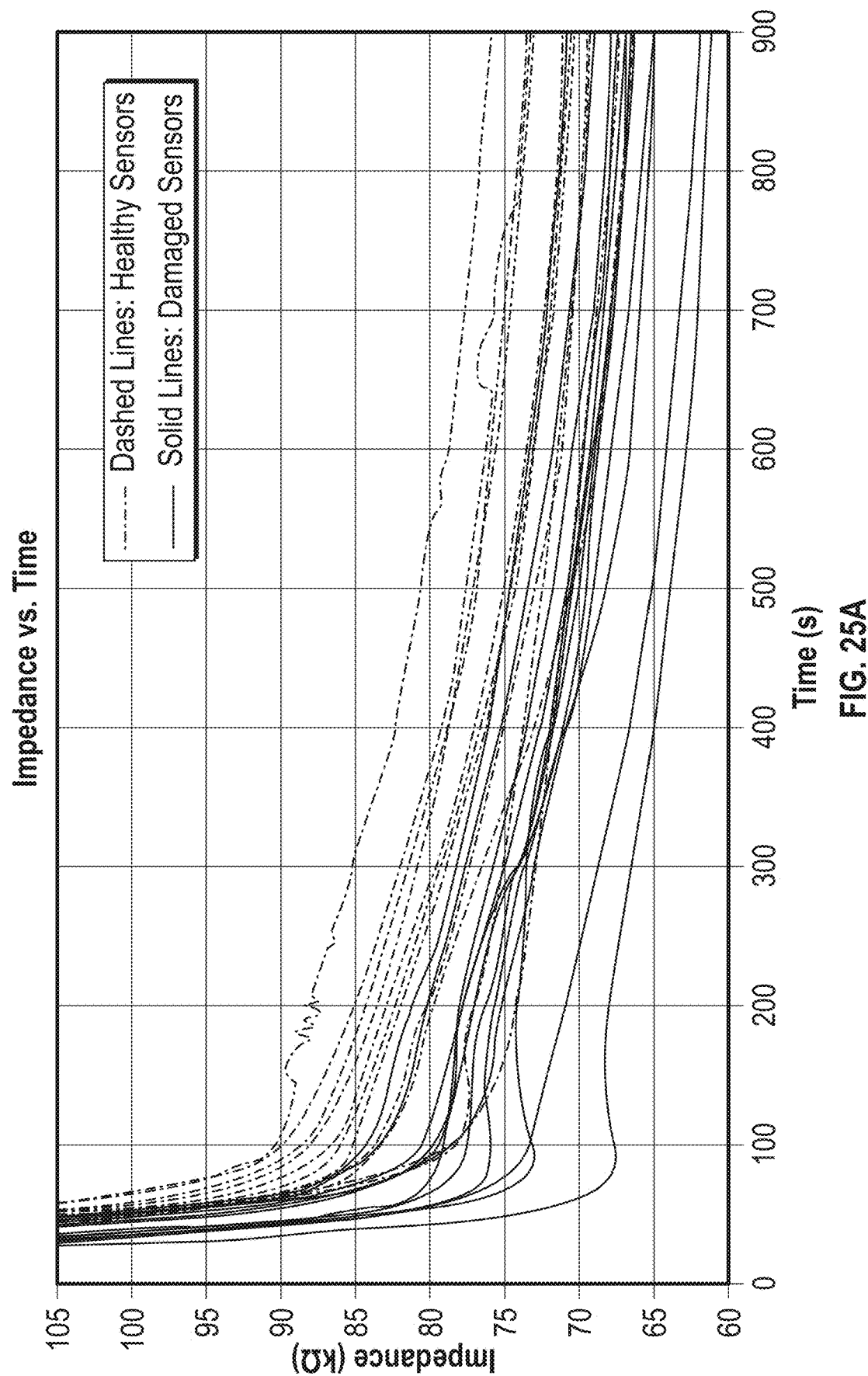
FIG. 25A is a graph that shows impedance plotted against time for healthy sensors (indicated by dashed lines) and damaged sensors (indicated by solid lines).

FIG. 25A shows impedance plotted against time for healthy sensors (indicated by dashed lines) and damaged sensors (indicated by solid lines.) The data in FIGS. 25A-25H was obtained using sensors that were damaged by scraping across sandpaper, as described above. FIG. 25A shows that impedance tends to be lower for damaged sensors, with some overlap at the outer bounds of the impedance distribution. Between 100 seconds and 900 seconds after immersion in fluid, some damaged sensors have an impedance that is higher than some of the healthy sensors.

Figure 25B:
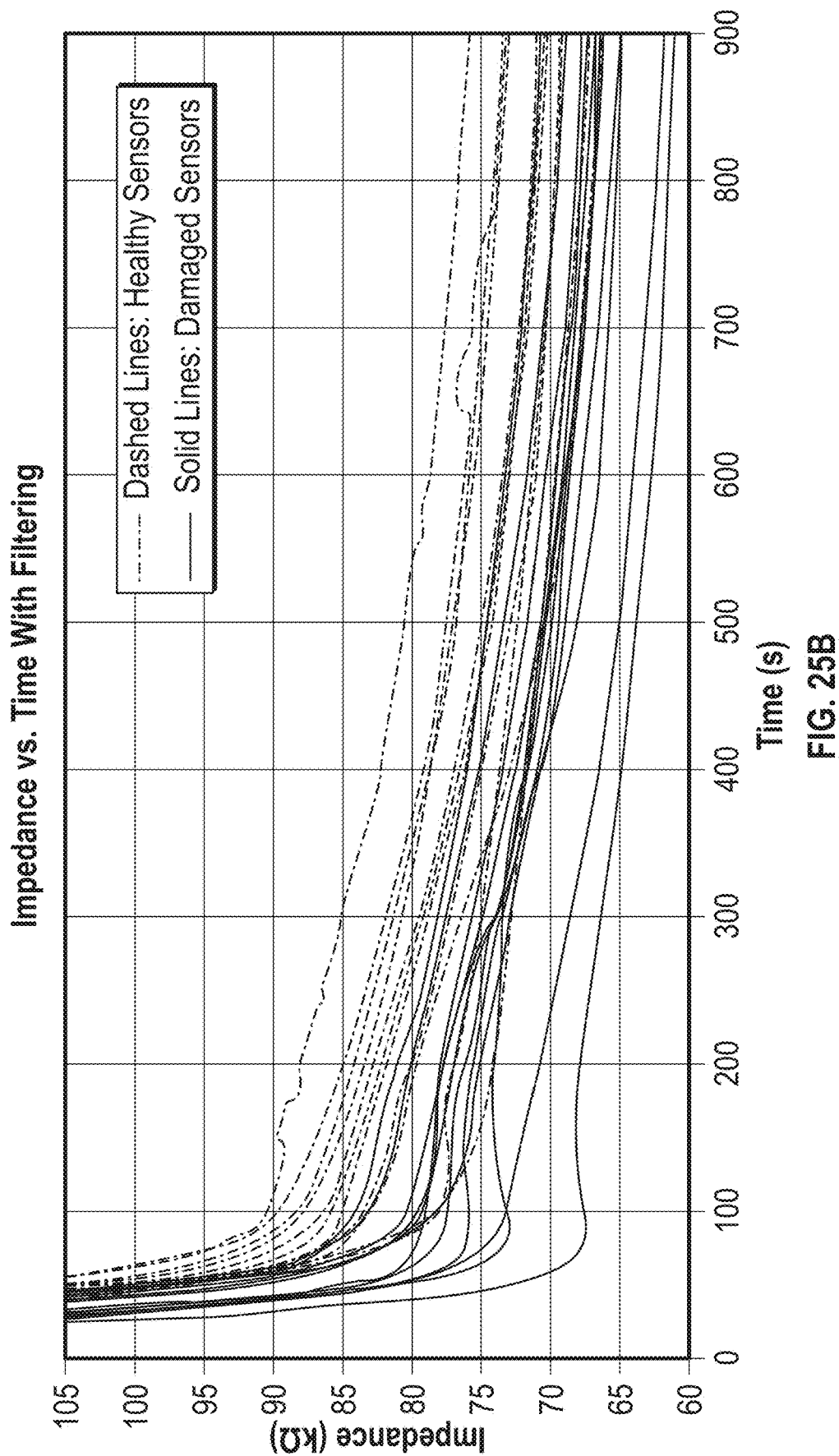
FIG. 25B is a graph that shows impedance plotted against time, with filtering applied to the data.

FIG. 25B shows impedance plotted against time for the same group of sensors, with filtering applied to the data. It can be seen, for example, that some signal variability (e.g., noise) has been removed for several of the healthy sensors between 100 and 200 seconds after immersion. Filtering may be accomplished, for example, using Savitzky-Golay filtering, which was applied to produce the plot shown in FIG. 25B.

Figure 25C:
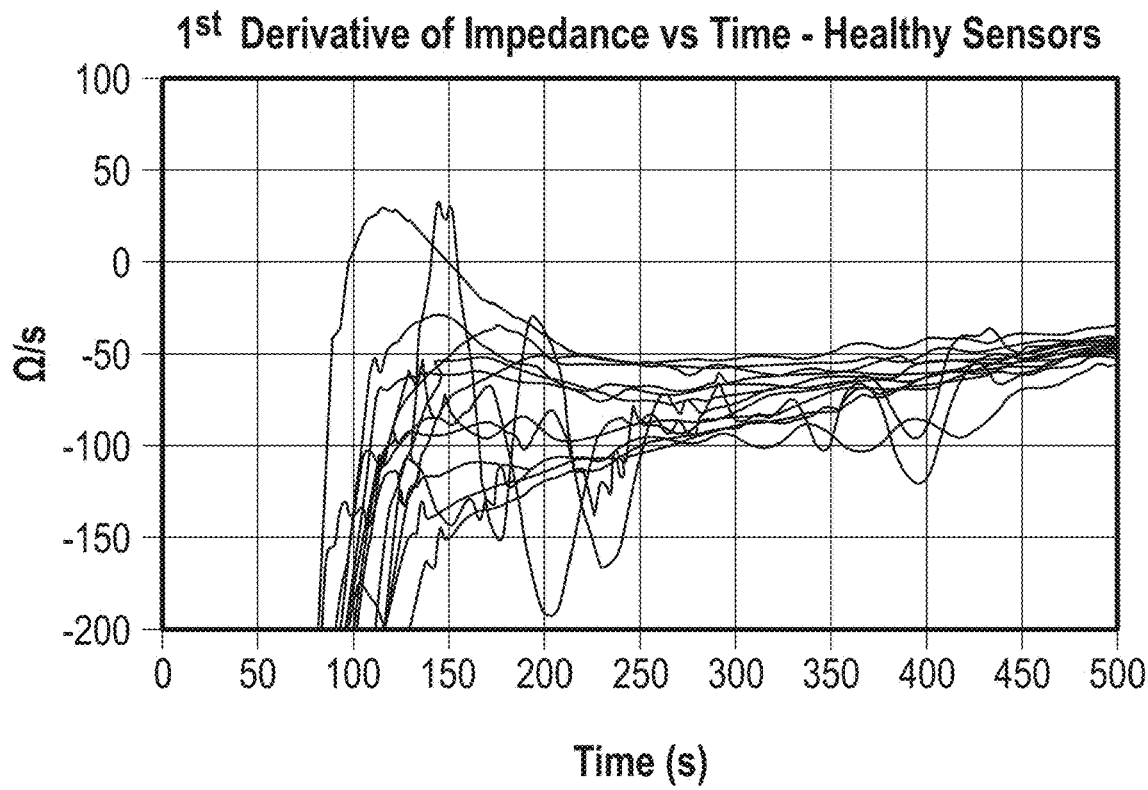
FIG. 25C is a graph that shows the first derivative of filtered impedance (from FIG. 25B) plotted against time, for healthy sensors.
Figure 25D:
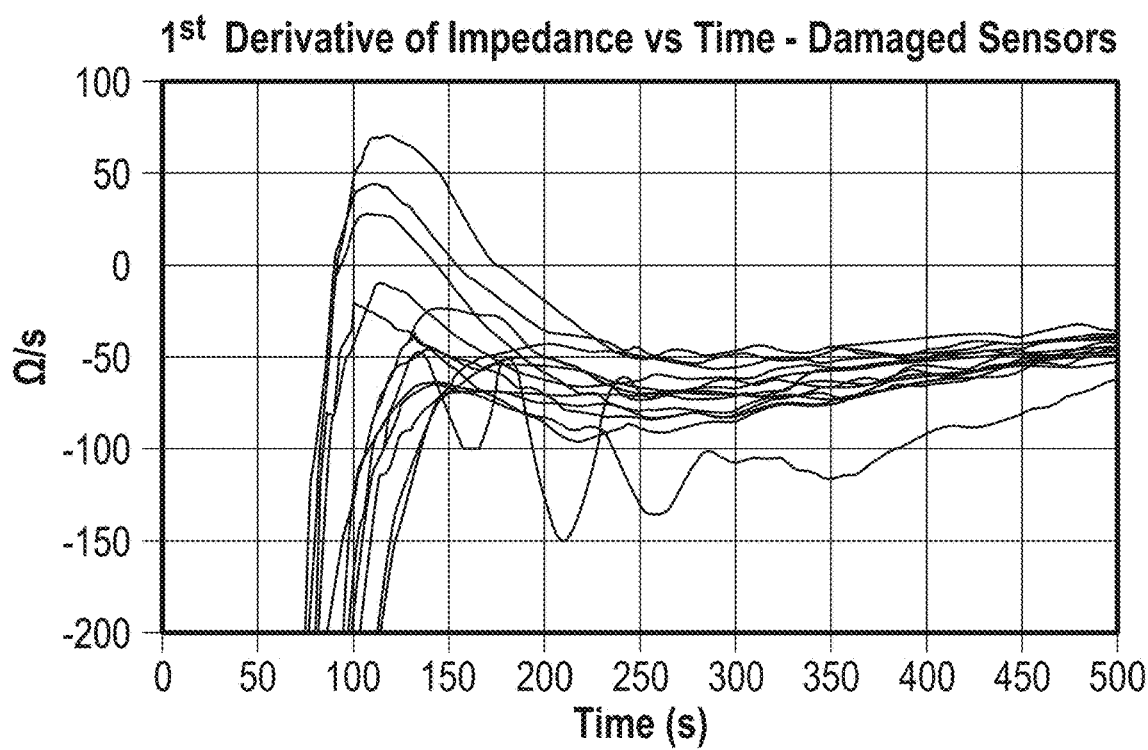
FIG. 25D is a graph that shows the first derivative of filtered impedance plotted against time for damaged sensors.
Figure 25E:
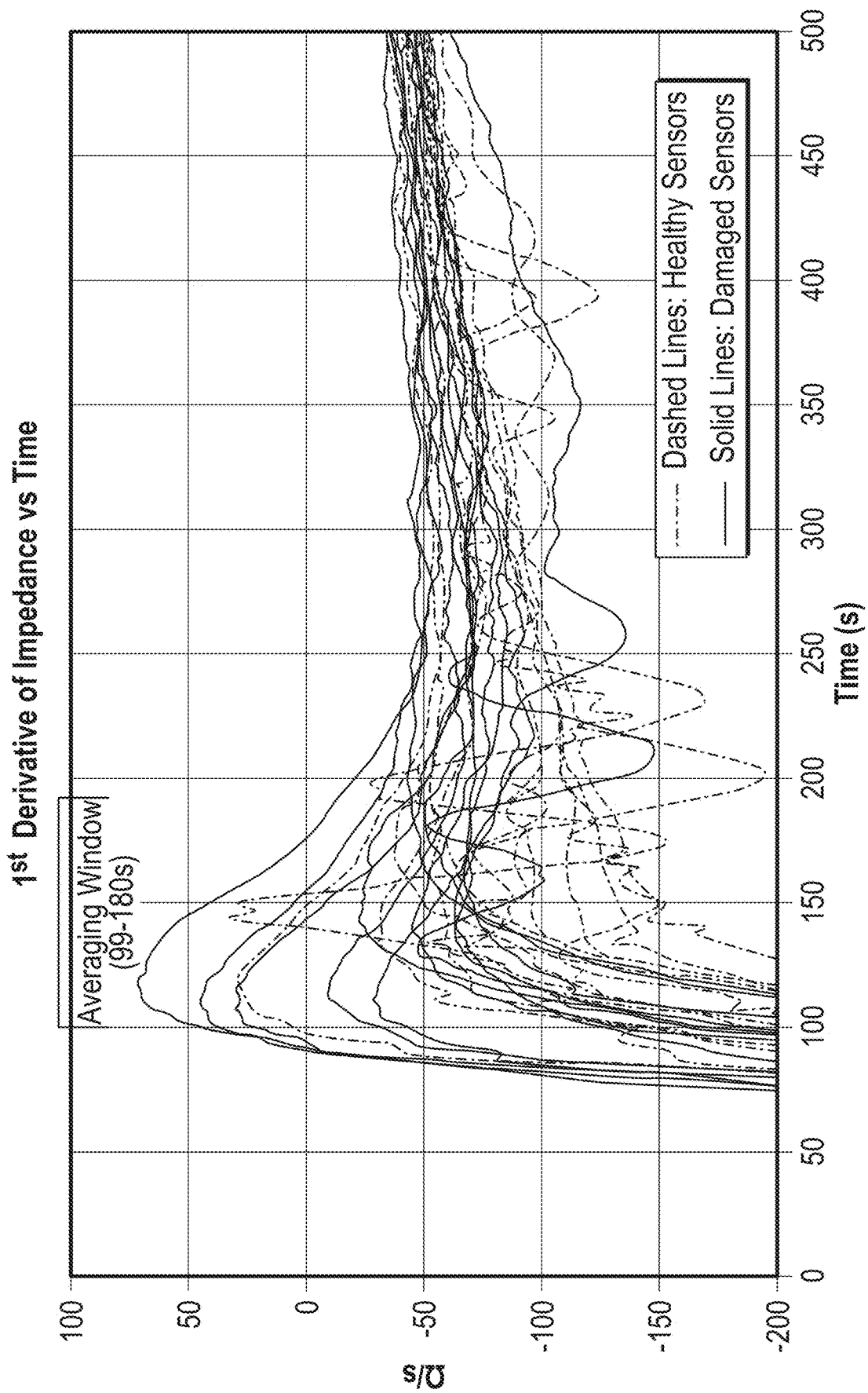
FIG. 25E is a graph that shows the first derivative of filtered impedance for damaged sensors and healthy sensors.

FIG. 25C shows the first derivative of filtered impedance (from FIG. 25B) plotted again time, for healthy sensors. FIG. 25D shows the first derivative of filtered impedance plotted against time for damaged sensors. FIG. 25E shows the first derivative of filtered impedance for damaged sensors and healthy sensors on the same graph (i.e., FIG. 25D overlaid over FIG. 25C).

Differences in features of the first derivative vs. time plot for healthy and damaged sensors may be used to differentiate healthy sensors from damaged sensors. For example, statistical analysis shows that the average of the first derivative values between 99 seconds and 180 second for the damaged sensors is significantly different (p<0.05) from the average for healthy sensors over the same averaging window. FIG. 25I shows the average of the first derivative of filtered impedance for this time window (99 to 180 seconds) for a plurality of damaged and healthy sensors. The healthy sensors have a significantly lower average than damaged sensors. While only a fraction of the damaged sensors (5 or 6 out of 14) may be distinguished from healthy sensors using the first derivative method, the method may be combined with other detection methods to increase the success rate of damage detection.

Other averaging time windows may be used, in place of the 99-180 second example described above. In some examples, the end points of an averaging time window may be selected, for example, as a low point for impedance, and a later time point at which the impedance has stabilized (e.g., determined from data as shown in FIGS. 24A and 24B). In other examples, the averaging time window may be determined from experimental data and a first derivative or second derivative of impedance or dual frequency impedance.

Other features of the first derivative data may also be used to differentiate damaged and healthy sensors. For example, the variability of the first derivative may be used as an indicator of sensor health, with lower variability correlated with sensor damage (i.e., sensors with higher variability over a window (e.g., 72 to 180 seconds) are more likely to be healthy).

Figure 25F:
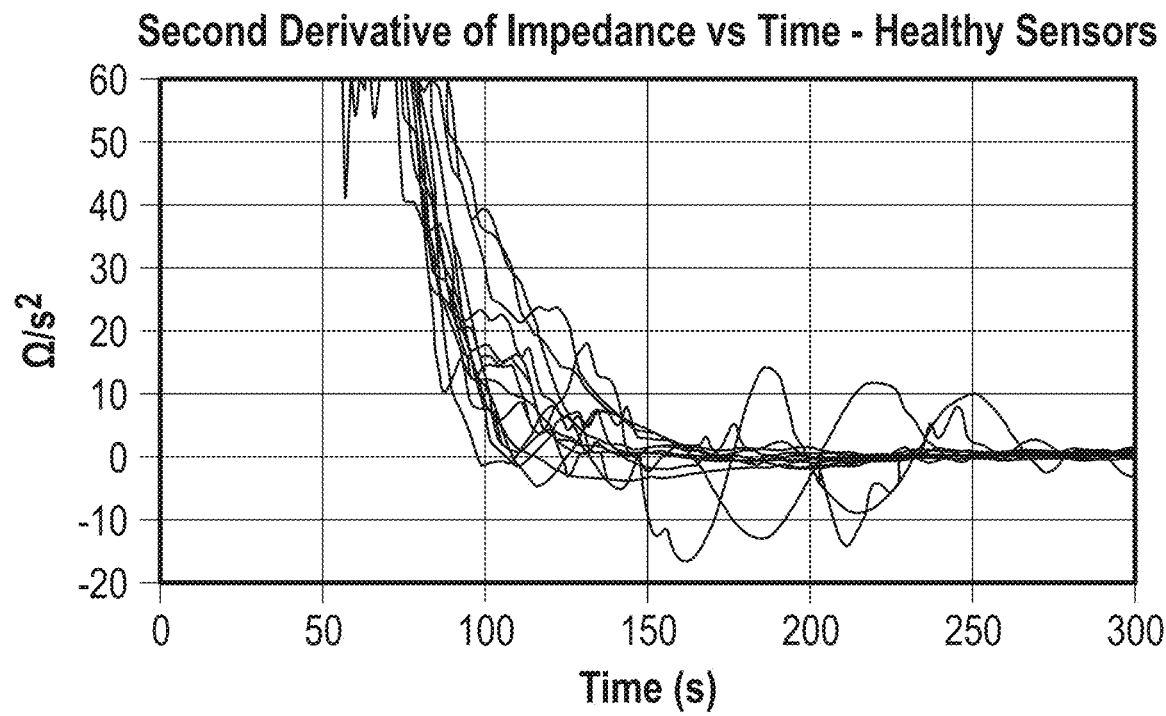
FIG. 25F is a graph that shows the second derivative of impedance plotted against time for healthy sensors.
Figure 25G:
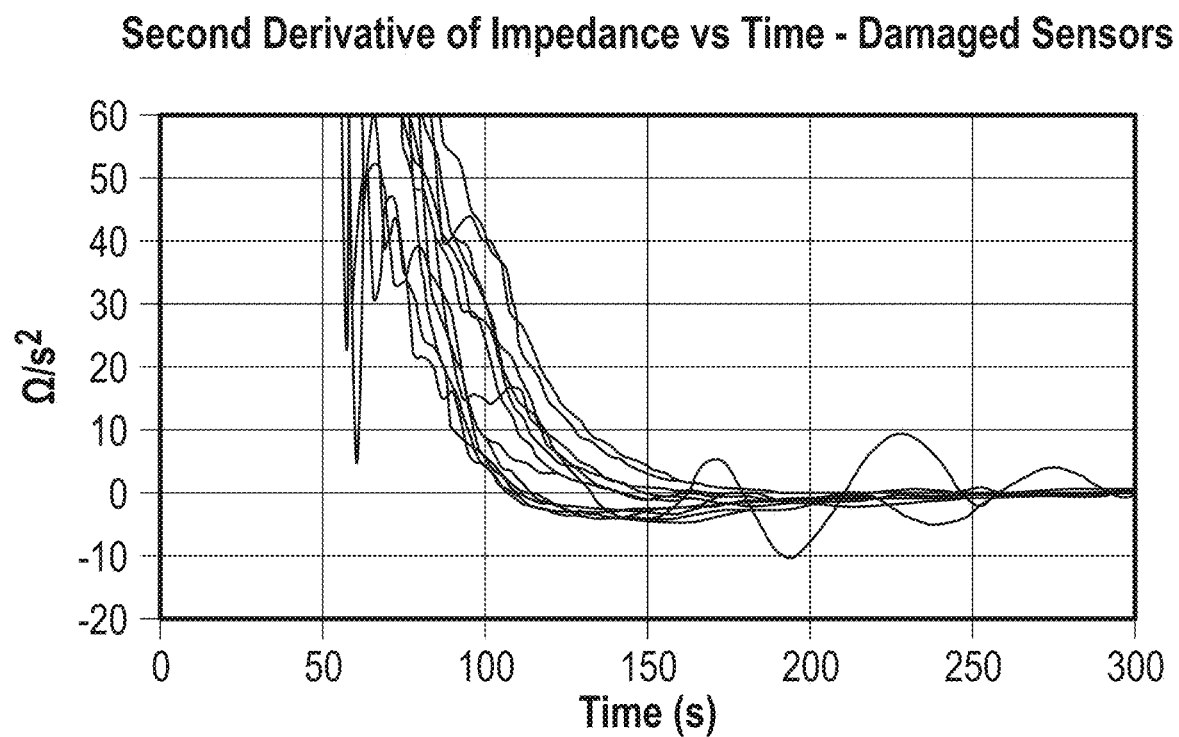
FIG. 25G is a graph that shows the second derivative of impedance plotted against time for damaged sensors.
Figure 25H:
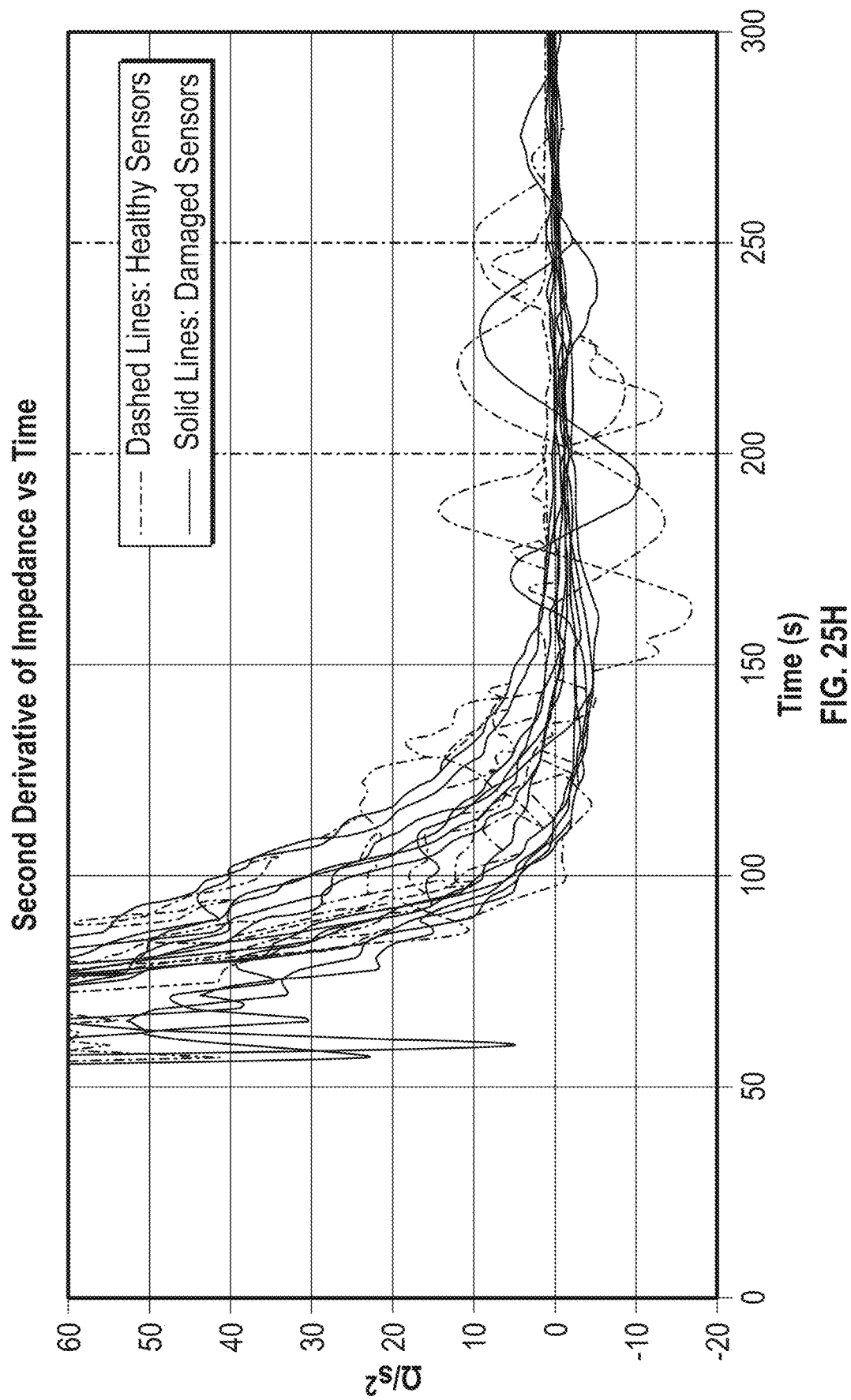
FIG. 25H is a graph that combines the information shown in FIG. 25F and FIG. 25G on the same chart.
Figure 25I:
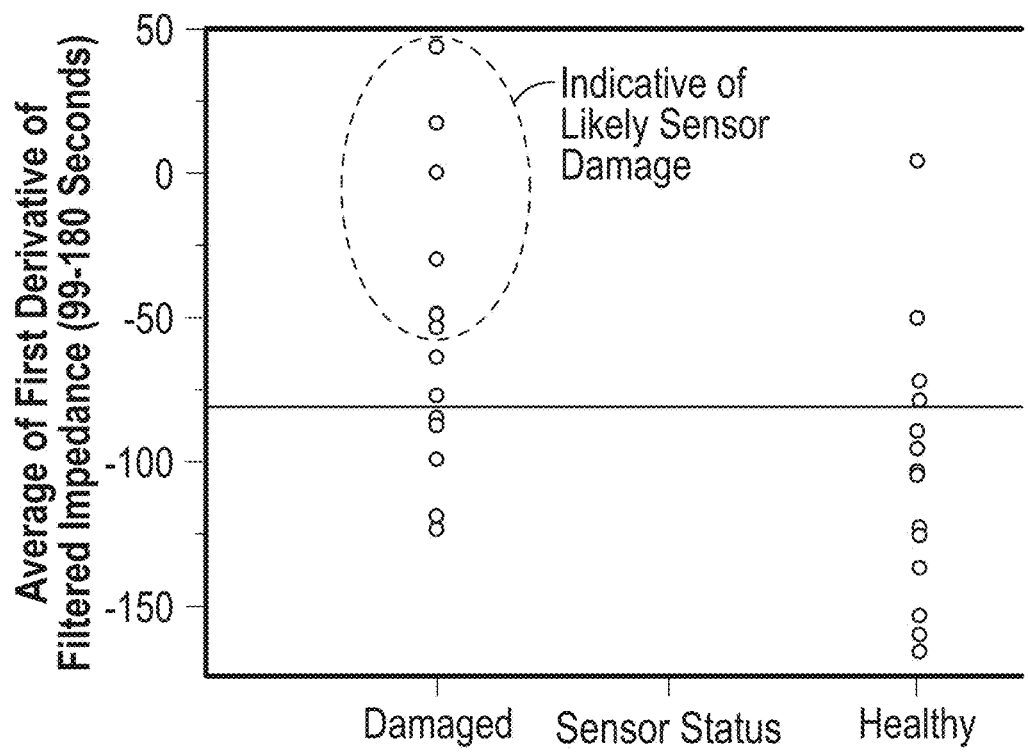
FIG. 25I is a graph that shows the average of the first derivative of filtered impedance for a plurality of damaged and healthy sensors.

FIGS. 25F and 25G show the second derivative of impedance plotted against time for healthy sensors (25F) and damaged sensors (25G), respectively. FIG. 25H shows these groups of second derivative data on the same chart.

Figure 25J:
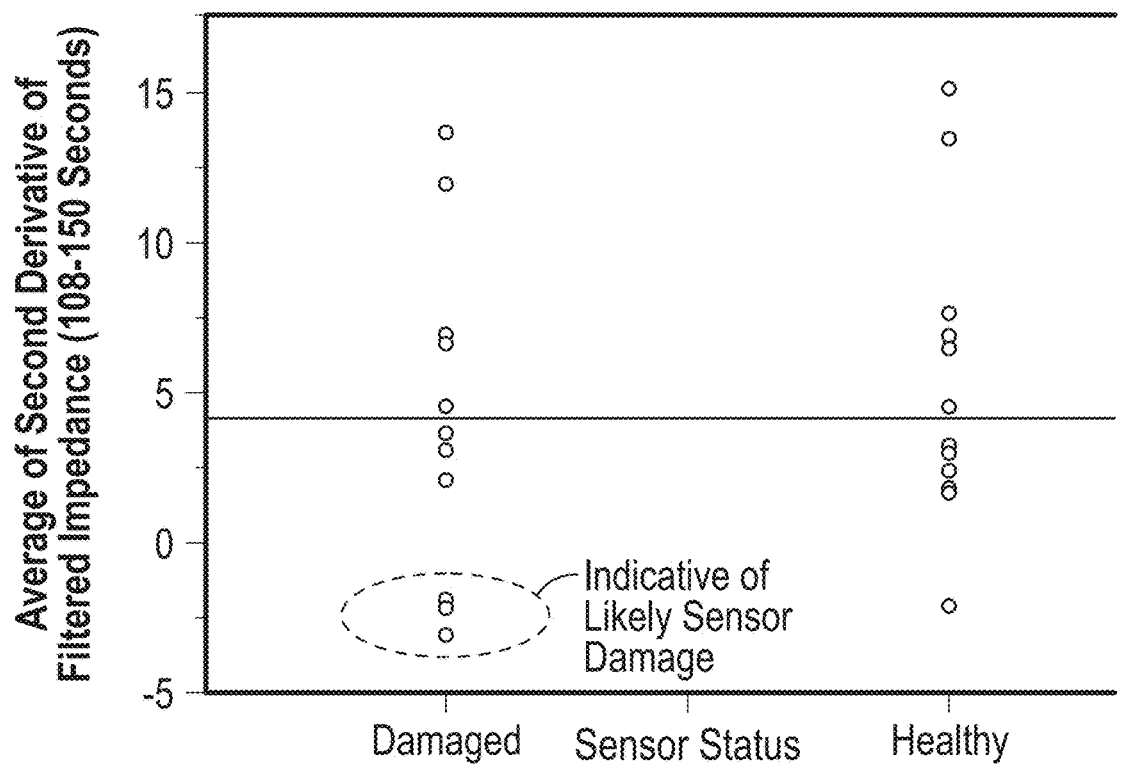
FIG. 25J is a graph that shows the average of the second derivative between 108 seconds and 150 seconds.

Differences in features of the second derivative vs. time plot for healthy and damaged sensors may be used to differentiate healthy sensors from damaged sensors. FIG. 25J shows the average of the second derivative between 108 seconds and 150 seconds. Sensors with a low average are more likely to be damaged.

In another example, the variability in the second derivative over a specified time period (e.g., 108 seconds to 150 seconds, or 100 seconds to 180 seconds) may be assessed as an indicator of sensor damage. A more variable signal indicates a sensor is likely healthy, and a less variable signal indicates that a sensor is likely damaged. This may be a result of interactions within the membrane in healthy sensors, and the relatively smaller impact of such interactions in a damaged membrane, in which more direct access to an electrode may be possible, due to membrane damage.

In some examples, a curve-fitting technique may be used to distinguish healthy sensors from damaged sensors.

In some examples, a curve-fitting technique may be applied to impedance vs. time, first derivative of impedance vs. time, second derivative impedance vs. time, or dual-frequency impedance vs. time. In some examples, a fitted curve or function may be applied to a template or model to determine a sensor's health status (e.g., to declare the sensor state as healthy or unhealthy, or characterize an amount of damage based on a model or a plurality of templates or models corresponding to a spectrum of damage levels). In some examples, one or more parameters (e.g., membrane resistance and pseudo membrane capacitance) extracted from a fitting (e.g., determined function) may be used to distinguish healthy sensors from damaged sensors.

Figure 26:
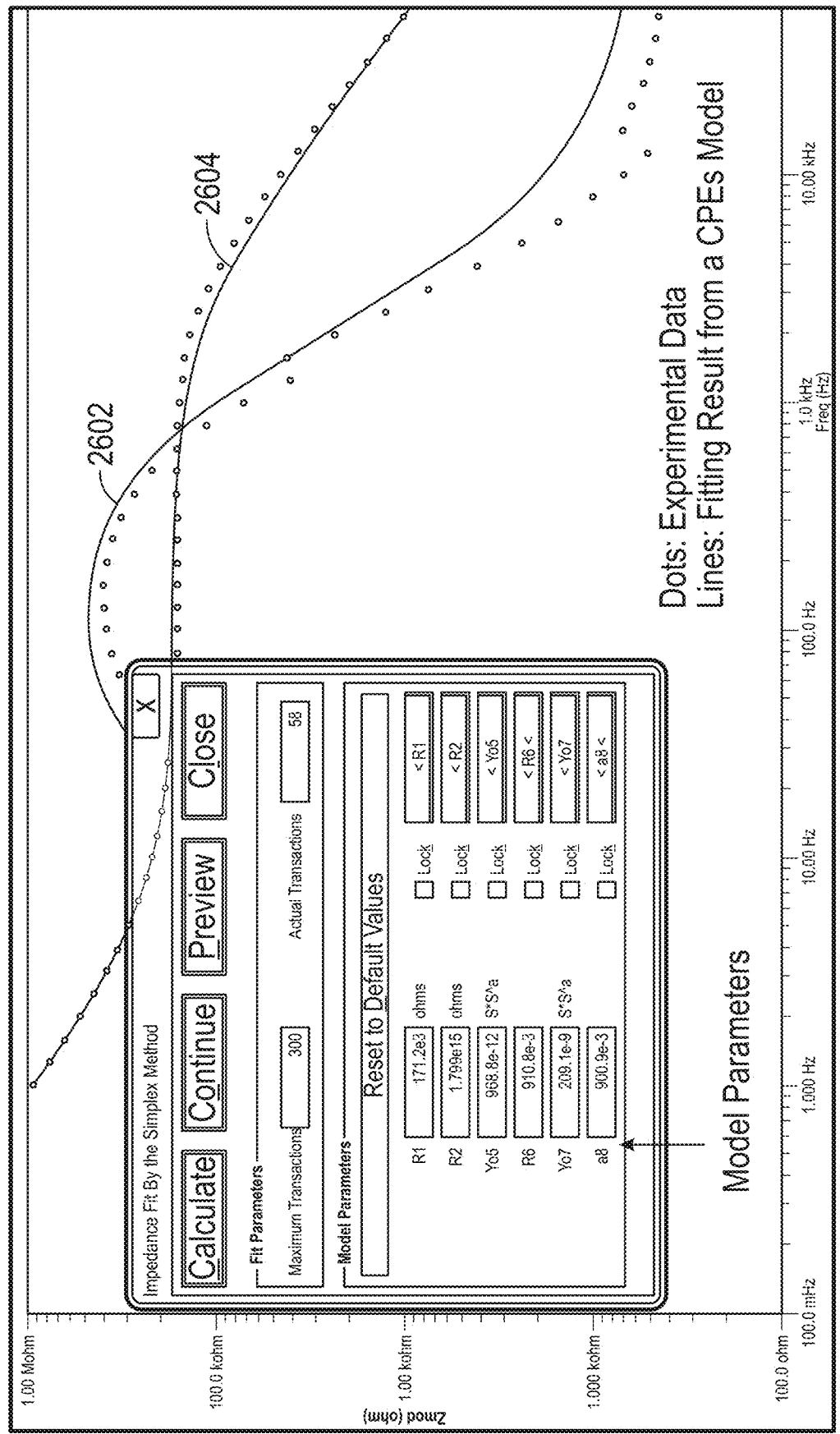
FIG. 26 shows an example curve-fitting for impedance and frequency data.

In some examples, a curve-fitting technique may be applied to an impedance spectroscopy data set (e.g., impedance at a plurality of frequencies). FIG. 26 shows an example curve-fitting, where dots indicate data from sensor testing (e.g., determined impedance values at various frequencies) and lines 2602, 2604 indicate fitted model for the sensor data. Software and a model may be used to determine a fit for the measured sensor data.

Figure 27:
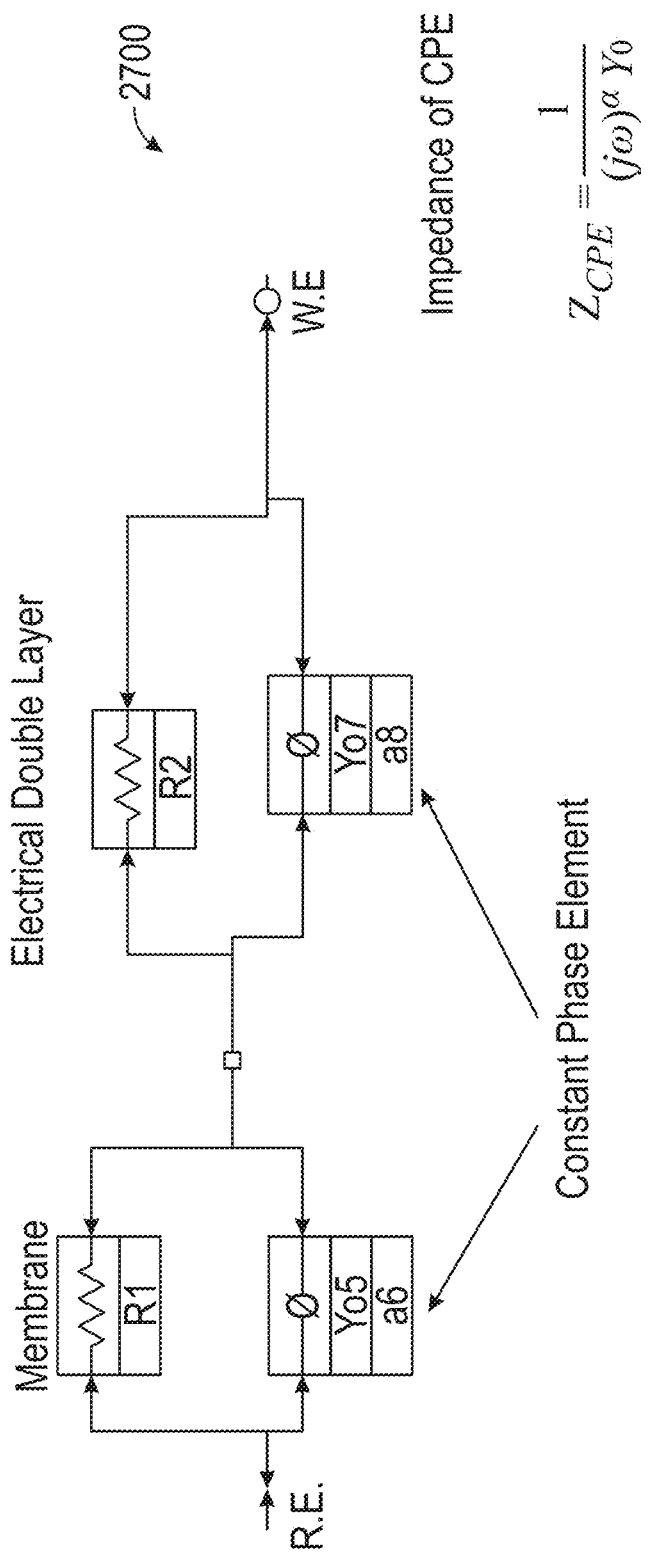
FIG. 27 is a schematic illustration of a constant-phase element (CPE) model.

In some examples, a constant-phase element model may be used to fit impedance spectroscopy data. A capacitor in an electrochemical sensor system may not behave ideally. For example, the double-layer capacitor (described above) formed by a membrane of an analyte sensor may behave according to a constant-phase element model, as opposed to a capacitor. FIG. 27 is a schematic illustration of a constant-phase element (CPE) model 2700, where R is resistance, Yo is a "pseudo" capacitance, and alpha is an exponent that equals 1 for a capacitor. A sensor may be tested to determine impedance across a range of frequencies, a fit may be determined (e.g., using a model), and the sensor may be declared healthy if one or more or a combination of the fitted parameters satisfies one or more health conditions. For example, the tested sensor may be declared healthy based upon a comparison of one or more parameter values to one or more respective thresholds. In some examples, a slightly damaged sensor may be identified based on a condition, and either approved for use, or compensated based on a measure of potential damage such as one or more of the model parameters.

Eight sensors were fitting using the CPE model explained above, where two sensors (denoted A and B) were healthy (undamaged), two sensors (denoted C and D) were badly damaged, and four sensors (E, F, G, and H) were slightly damaged.

Figure 28A:
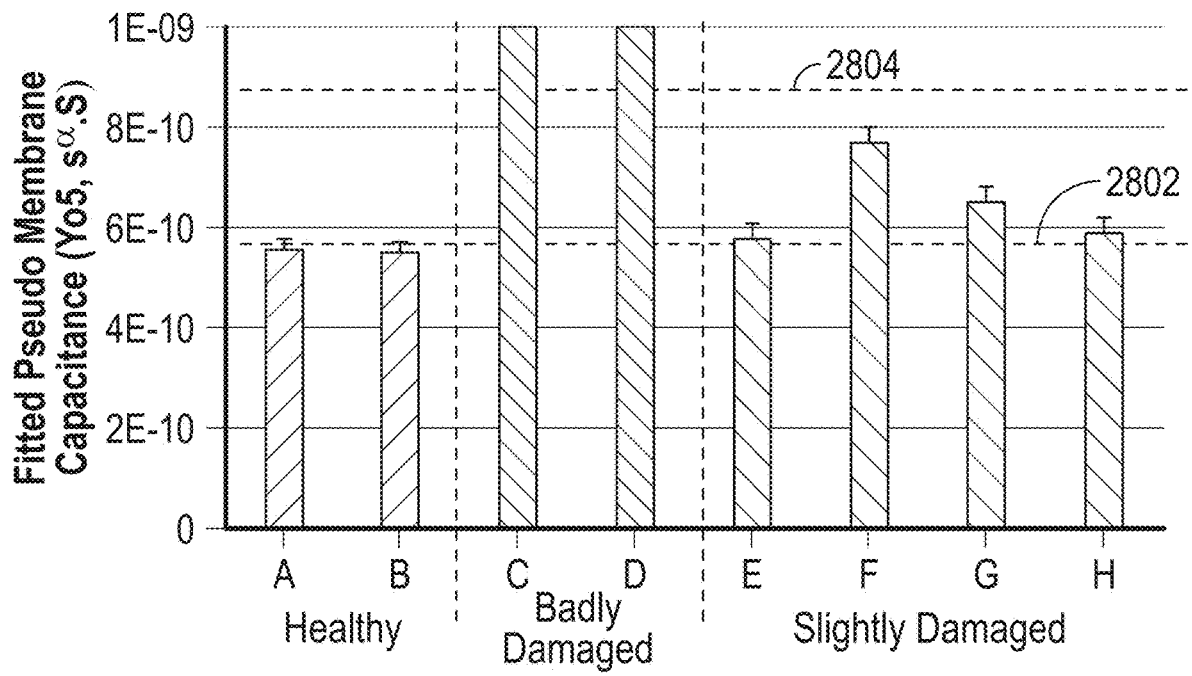
FIG. 28A is a chart that shows fitted pseudo membrane capacitance, determined using a CPE model, for eight sensors.

FIG. 28A shows fitted pseudo membrane capacitance for each of eight sensors, determined using the CPE model described above. The healthy sensors (sensors A and B) have the lowest fitted pseudo membrane capacitance in the group, the heavily damaged sensors (C and D) have the highest fitted pseudo membrane capacitance, and the slightly damaged sensors (E-H) have fitted pseudo membrane capacitance values between values for the healthy sensors and the badly damaged sensors, which indicates that the fitted pseudo membrane capacitance may be used to distinguish healthy sensors from damaged sensors. For example, a sensor may be tested, and a sensor status may be determined based on the fitted pseudo membrane capacitance relative to one or more thresholds, which may be determined from a population of tested sensors with known damage states (e.g., determined from a microscope inspection or protocol for inflicting damage, or both). In an example, a sensor may be declared healthy if the fitted pseudo membrane capacitance is below a first threshold 2802, a sensor may be declared badly damaged responsive to the fitted pseudo membrane capacitance being above a second threshold 2804, and a sensor may be declared slightly damaged (e.g., in need of appropriate compensation) if the fitted pseudo membrane capacitance is between the first and second thresholds 2802, 2804. In various examples, more or fewer threshold may be used, and a threshold may additionally or alternatively be applied to one or more of the other parameters represented in FIGS. 28A-E. In some examples, a probability of sensor damage may be determined based on one or more parameter values. In some examples, an estimate of an extent of sensor damage, or an amount of compensation, may be determined based on one or more parameters values. Such a probability or estimate may be used to determine whether to use a sensor (e.g., designate a sensor for removal from a production process, or indicate to a user to replace the sensor), or whether to apply compensation.

Figure 28B:
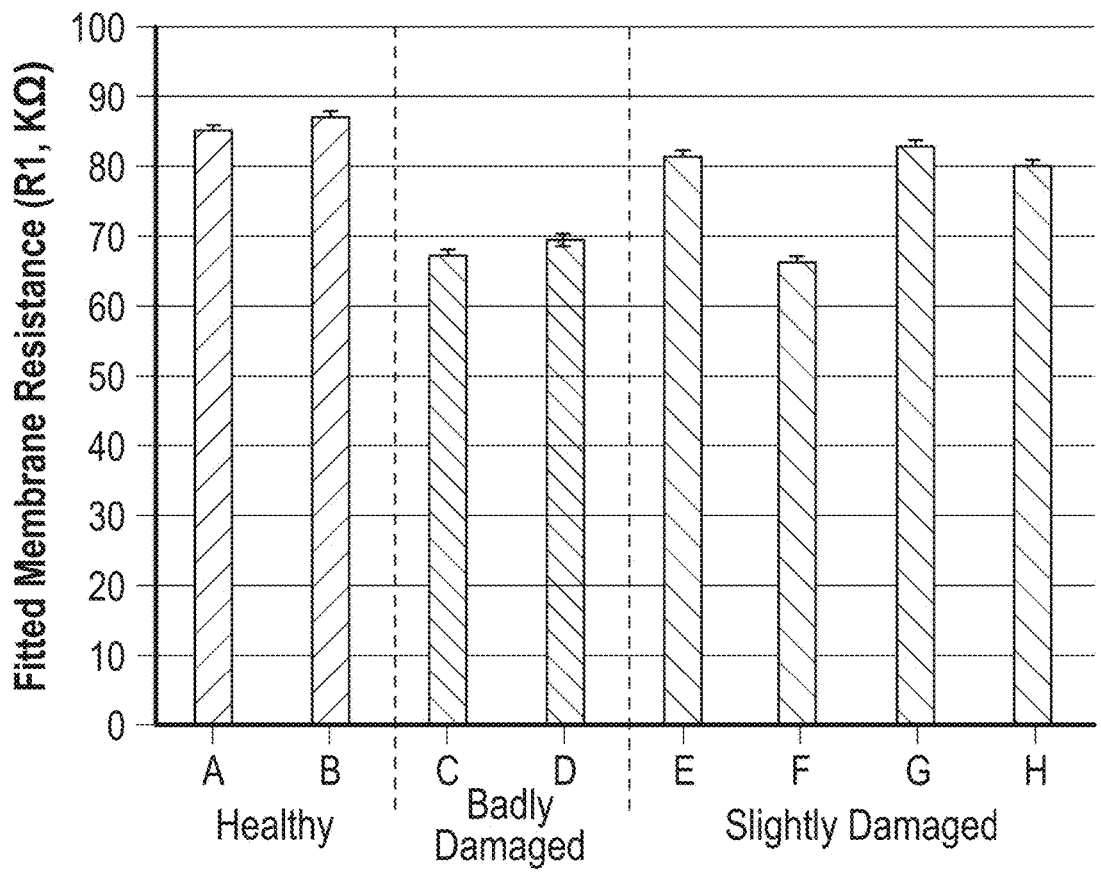
FIG. 28B is a chart that shows fitted membrane resistance for each of the eight sensors (also determined using the CPE model described above.)

FIG. 28B shows fitted membrane resistance for each of the eight sensors (also determined using the CPE model described above). The healthy sensors (sensors A and B) have a fitted membrane resistance that is significantly higher than the fitted membrane resistance of the heavily damaged sensors (C and D). The slightly damaged sensors (E, F, G, H) have an average fitted membrane resistance value that is between the values for the healthy sensors and the values for the badly damaged sensors. These relationships in fitted membrane resistance indicate that the fitted membrane resistance may be used to distinguish healthy sensors from damaged sensors. For example, a sensor may be tested to determine impedance across a range of frequencies, a fit may be determined (e.g., using a model), and the sensor may be declared healthy if the fitted membrane resistance satisfies a health condition. For example, the tested sensor may be declared healthy responsive to the fitted membrane resistance exceeding 82 kiloohms. In some examples, a slightly damaged sensor may be identified based on a fitted membrane resistance condition (e.g., R1 between two thresholds), and slightly damaged sensor may be approved for use or compensated (e.g., compensated based on a measure of potential damage, such as the fitted membrane resistance value, or another model parameter, or combination or parameters).

Figure 28C:
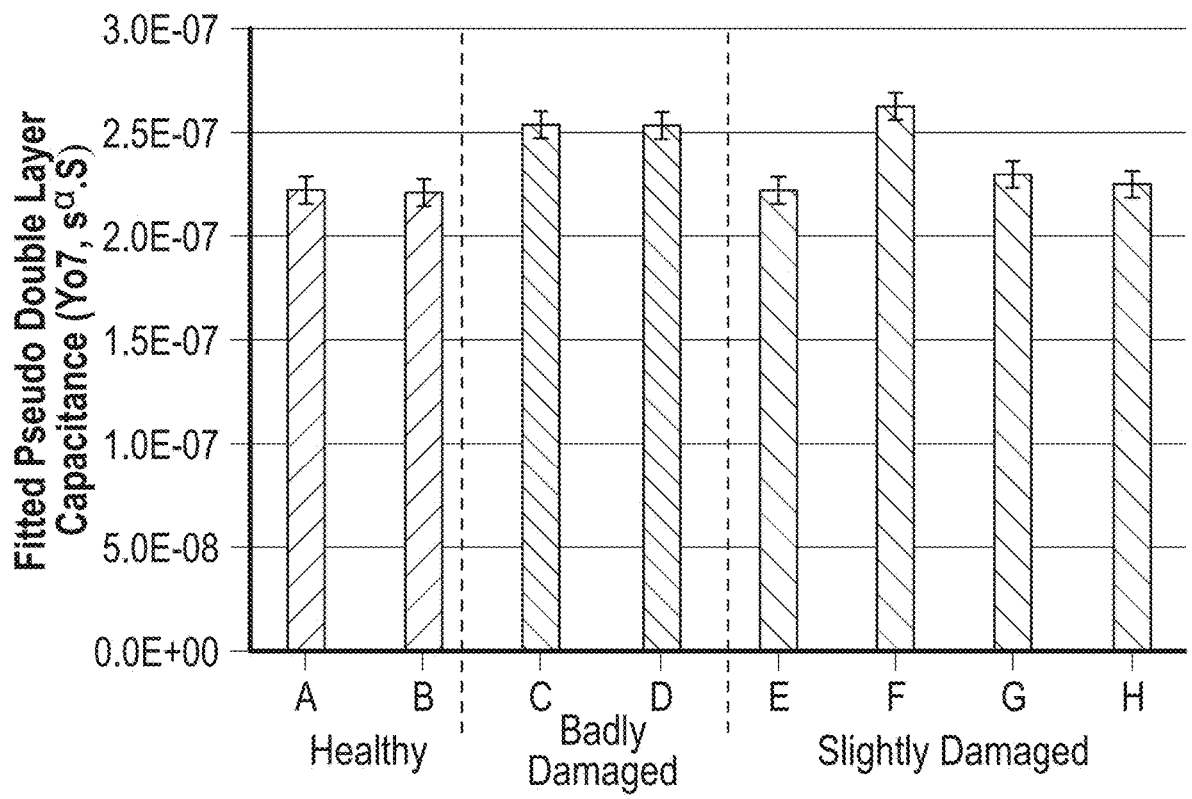
FIG. 28C is a chart that shows fitted pseudo double layer capacitance for the eight sensors.

FIG. 28C shows fitted pseudo double layer capacitance for the eight sensors. The healthy sensors (sensors A and B) have a fitted pseudo double layer capacitance that is lower than fitted pseudo double layer capacitance of the heavily damaged sensors (C and D). The slightly damaged sensors have fitted pseudo double layer capacitance values that are between the values for the healthy sensors and the values badly damaged sensors, which indicates that the fitted pseudo double layer capacitance may be used to distinguish healthy sensors from damaged sensors.

Figure 28D:
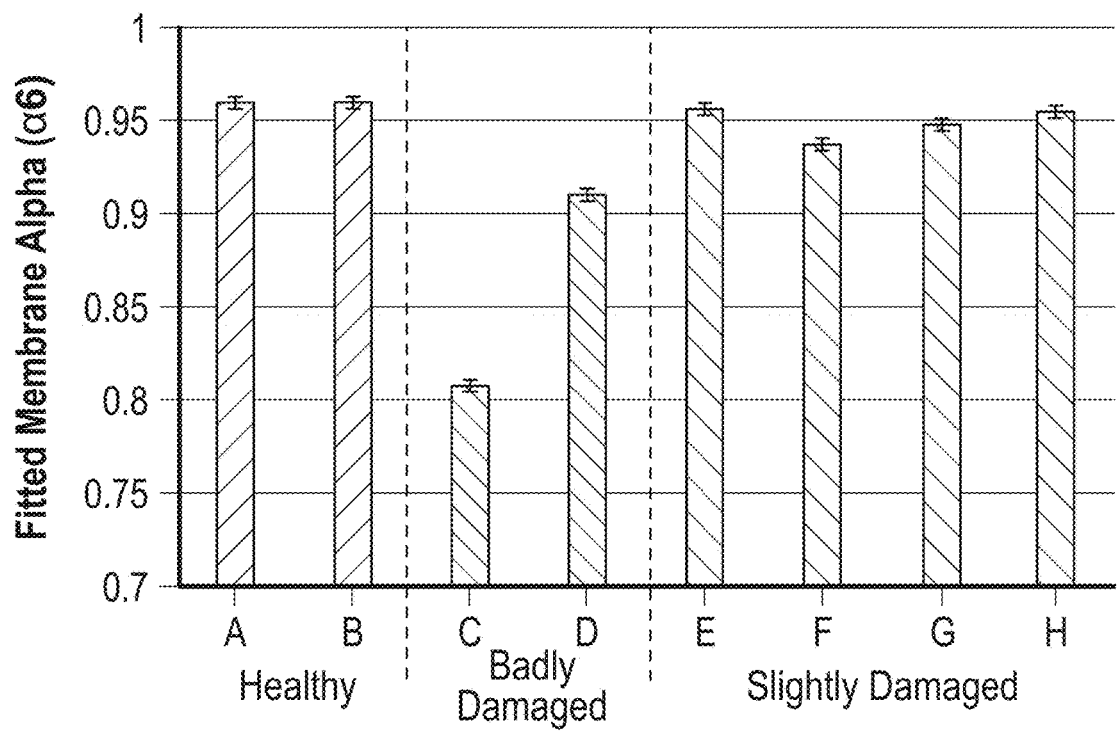
FIG. 28D is a chart that shows fitted membrane alpha for the eight sensors.

FIG. 28D shows fitted membrane alpha for the eight sensors. The healthy sensors (sensors A and B) have fitted membrane alpha values that are higher than the values for the heavily damaged sensors (C and D). The slightly damaged sensors have fitted membrane alpha values that are between values for the healthy sensors and the badly damaged sensors, which indicates that the fitted membrane alpha may be used to distinguish healthy sensors from damaged sensors.

Figure 28E:
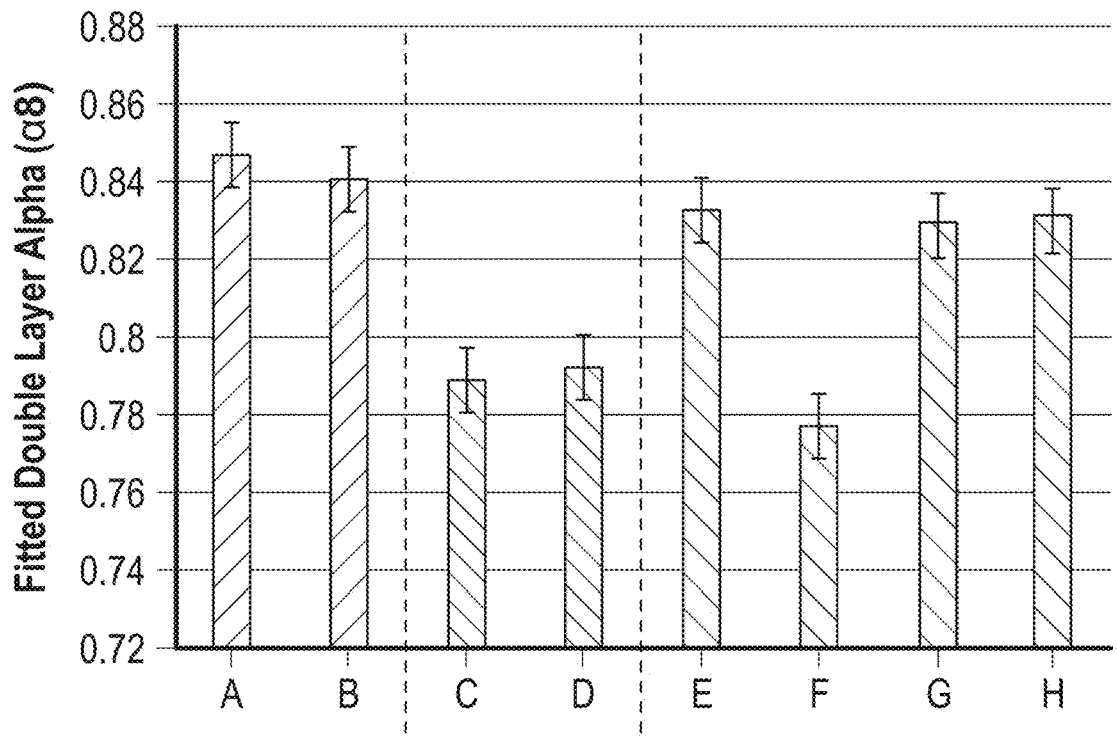
FIG. 28E is a chart that shows fitted double layer alpha for the eight sensors.

FIG. 28E shows fitted double layer alpha for the eight sensors. The healthy sensors (A and B) have fitted double layer alpha values that are significantly higher than the fitted double layer alpha values for the damaged sensors (C and D). The slightly damaged sensors have fitted double layer alpha values that are generally between the values for healthy and highly damaged sensors, with one sensor (sensor F) having a value that is lower than the highly damaged sensors.

In some examples, two or more of the parameters may be used in combination to ascertain whether a sensor is healthy, or damaged, or badly damaged. Using two or more sensors may increase the confidence in the classification of a particular sensor or reduce the likelihood of misclassification. For example, FIG. 28E suggests that sensor F is badly damaged, but the chart in FIG. 28A suggests it is slightly damaged. In some examples, the parameters may be weighted, e.g., the fitted pseudo membrane capacitance or fitted membrane resistance may be weighted more heavily than the other parameters in determining whether a sensor is damaged, or the extent of damage.

Figure 29:
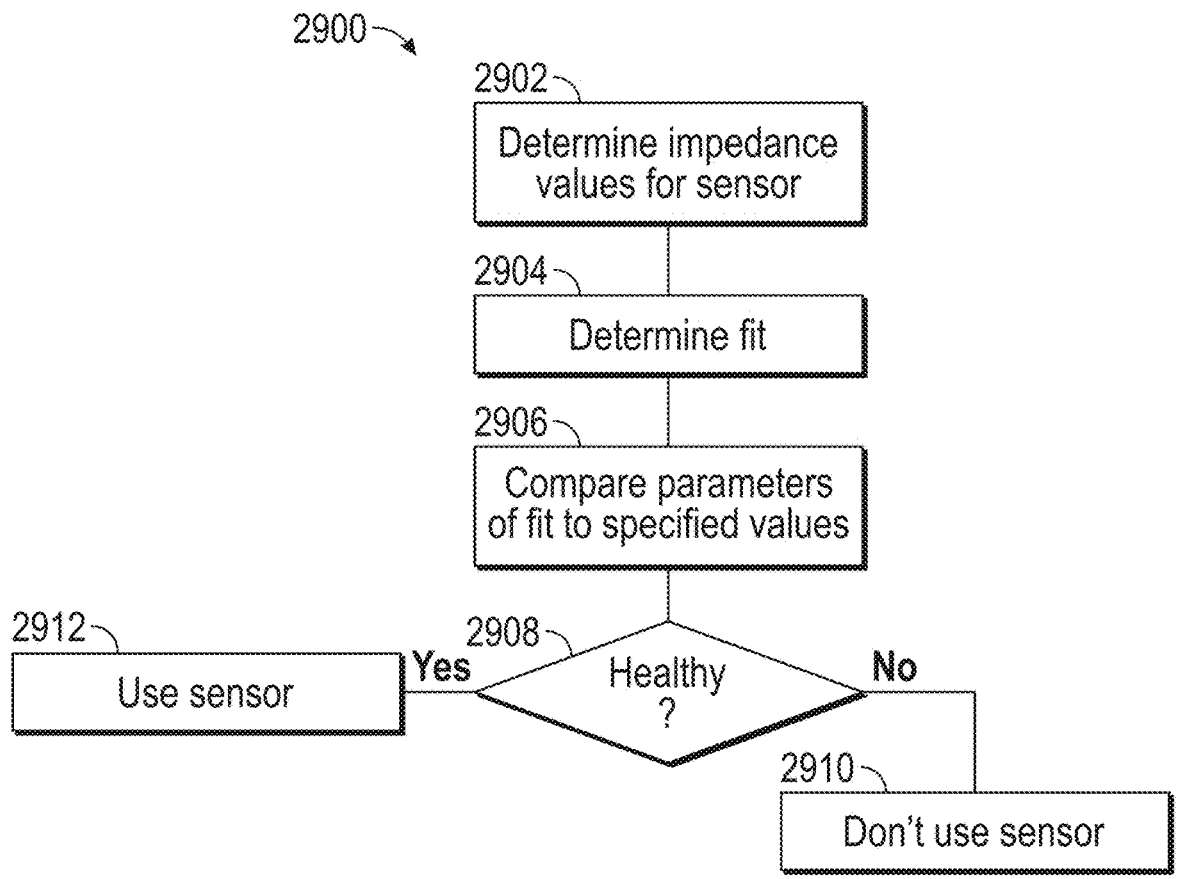
FIG. 29 is a flowchart illustration of a method of assessing a health of a sensor.

FIG. 29 is a flowchart illustration of a method 2900 of assessing a health of a sensor. At operation 2902, an impedance value is determined for a sensor. The impedance value may be determined, for example, by applying a voltage or voltage change, and measuring a current or current change, and using Ohm's law to determine impedance. In some examples, the method may include applying a plurality of signals at different frequencies and determining impedance for the different frequencies.

At operation 2904, a fit may be determined. For example, a fit may be determined for a relationship between impedance and frequency, as described in reference to FIG. 26. At operation 2906, a comparison is made to one or more specified values. For example, a comparison may be made against a reference value or a model or template. In some examples, the comparison may include a fitted parameter such as fitted pseudo membrane capacitance, fitted membrane resistance, fitted pseudo double layer capacitance, fitted membrane alpha, or fitted double layer alpha. In some examples, a comparison may be made for two or more parameters, which may increase a confidence that a sensor has been correctly characterized.

At operation 2908, a health determination may be made about the sensor. For example, the health determination may include a determination about whether the sensor is healthy, or not healthy (e.g., excessively damaged). In some examples, a sensor may be assigned a health status from three or more available classifications (e.g., healthy, slightly damaged, or extensively damaged). In some examples, a quantitative healthy assessment may be made. For example, a degree of damage of a sensor may be determined, based on one or more fit parameters.

At operation 2910, responsive to a determination that a sensor is not healthy, a sensor may be rejected. For example, a sensor may be removed from a manufacturing process (e.g., scrapped), or a user may be notified that the sensor should be replaced. At operation 2912, responsive to a determination that a sensor is healthy, it may be approved for use. In some examples, a sensor that is approved for use may be compensated based on a measured or determined parameter, such as one of the fitted parameters listed above, or based on a determined degree of damage. For example, sensor electronics may apply an adjusted sensitivity or sensitivity curve to compensate for the detected damage or abnormality characteristic in the sensor.

The method 2900 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine a health state of a sensor membrane (e.g., determine an amount of damage or abnormality) and avoid reliance on inaccurate sensor readings from an unhealthy (e.g., excessively damaged) sensor.

Estimated Sensor Sensitivity Methods and MARD Improvements

In various examples, impedance may be used alone, or in combination with one or more other factors, to determine a sensor sensitivity ($m_r$). While impedance may be used as a surrogate for sensitivity, e.g., to account for drift, many factors may influence impedance. For example, fluctuations in temperature may introduce impedance fluctuations in an in vivo ionic environment. A sensitivity determination may be improved by combining additional information with impedance.

Any of the techniques described herein for determining an impedance parameter may be used to obtain an estimated impedance parameter. For example, an impedance parameter may be determined using an impulse-response method to measure membrane impedance. In an example, impedance may be determined based on an integrated pulse-current (PI) as driven by a square wave pulse supplied by sensor electronics. The relationship between integrated pulse-current (PI) and membrane impedance ($R_{RL}$) is deterministic.

Using impedance alone, sensitivity may be determined based on the integrated pulse current using the following equation (denoted "IMPD"):

$$\hat{m}_t = PI \cdot (a_1 + a_2 \cdot \log(t))$$

In the equation above, and the other examples below, the values denoted ax (e.g., $a_1$, $a_2$, $a_3$, etc.) may be experimentally determined using a number of similar sensors.

Using impedance in combination with a calibration curve (CC) for the sensor (which may for example be an experimentally-determined relationship (e.g., slope) between analyte level and measured current), sensitivity may be determined based on the following equation (denoted "IMPD+CC"):

$$\hat{m}_t = PI \cdot (a_1 + a_2 \cdot \log(t)) \cdot \left(1 + \frac{a_3 \cdot CC + a_4}{100}\right)$$

In products made by Dexcom, the calibration curve (CC) may be a Calcheck slope determined for a particular sensor, or for a population of sensors.

Using impedance in combination with transmitter temperature, sensitivity ($m_t$) may be determined from the equation (denoted "IMPD+T"):

$$\hat{m}_t = PI \cdot (a_1 + a_2 \cdot \log(t) + a_3 \cdot T)$$

or from the equation:

$$\hat{m}_t = PI \cdot (a_1 + a_2 \cdot \log(t)) \cdot (a_3 + a_4 \cdot T)$$

Using impedance in combination with transmitter temperature (T) and a calibration slope (CC), sensitivity ($m_t$) may be determined from the equation (denoted "IMPD+T+CC"):

$$\hat{m}_t = PI \cdot (a_1 + a_2 \cdot \log(t) + a_3 \cdot T) \cdot \left(1 + \frac{a_4 \cdot CC + a_5}{100}\right)$$

or from the equation:

$$\hat{m}_t = PI \cdot (a_1 + a_2 \cdot \log(t)) + (a_3 + a_4 \cdot T) \cdot \left(1 + \frac{a_5 \cdot CC + a_6}{100}\right)$$

In another example, an empirical linear relationship may also be pursued without making any assumption about the underlying relationship between different physical variables, and sensitivity ($m_t$) may be determined from the equation:

$$\hat{m}_t = a_1 + a_2 \cdot CC + a_3 \cdot \log(t) + a_4 \cdot PI + a_5 \cdot T$$

In all the equations above, the integrated pulse-current PI may be replaced directly by RL membrane resistance (in unit of kΩ):

$$R_{RL}^{-1} \approx \frac{PI}{8541.6 - 147.6 \cdot PI}$$

Note that the inverse of membrane resistance (1/R) is conductance. Sensitivity ($m_t$) may be determined from the conductance equation (denoted "Cdut+T+CC"):

$$\hat{m}_t = R_{RL}^{-1} \cdot (a_1 + a_2 \cdot \log(t)) + (a_3 + a_4 \cdot T) \cdot \left(1 + \frac{a_5 \cdot CC + a_6}{100}\right)$$

In some examples, the conversion parameters in $R_{RL}^{-1}$ may be optimized empirically, and sensitivity ($m_t$) may be determined from the equation:

$$\hat{m}_t = a_1 + [a_2 \cdot CC + a_3] \cdot [1 - \exp(-a_4 \cdot t)] + \frac{PI}{a_5 \cdot PI + a_6} + a_7 \cdot T$$

In some examples, a temperature may be determined using impedance. Methods for determining a temperature (e.g., the temperature of a sensor working electrode) using are described, for example, in U.S. Patent Publication No. 2012/0262298 and U.S. Patent Application No. 62/620,775, both of which are incorporated by reference in their entirety. In some examples, a subcutaneous temperature (e.g., an estimate of an analyte sensor working electrode temperature) may be determined from a non-subcutaneous temperature sensor signal (e.g., transmitter temperature) using a partial differential equation (PDE) model. A PDE approach to temperature compensation may make the system more accurate, for example by accounting for the fact that the rate of change of temperature in external electronics (e.g., a CGM transmitter) is higher than the rate of change of temperature of subcutaneous tissue or fluids. In some examples, Green's function (GF) of the full PDE model may be used to filter a non-subcutaneous temperature (e.g., transmitter temperature (TTx)) linearly and causally, with the sensor working electrode temperature as the output. Because the PDE model assumes fixed parameters, it can be deemed a linear time-invariant (LTI) system, whose GF is also the impulse response function (IRF) of that LTI system. Two forms of GF can be obtained, one of which is by empirically solving a least-square fit for the IRF, and the second by a parametric fit to the empirical IRF which requires only three parameters. Both IRF solutions resulted in less than 0.1° C. difference from the sensor working electrode temperature predicted by solving the full PDE. Using Green's function may improve the performance of the sensor system (e.g., reduce power consumption or enable additional processing) because it avoids or reduces the need for a PDE solver (e.g., processor and software or firmware) in the sensor electronics. A PDE solver may consume significant power, increase cost of sensor electronics, or both.

Results of Experiments

Experiments were run to demonstrate the effectiveness of these approaches and the potential for improving the performance of an analyte sensor system. Based on forty-one (41) preliminary datasets, a Monte Carlo cross-validation procedure was performed on a commercially-available system (as a baseline) and four different techniques (described below) for improving the performance of an analyte sensor system. The results of the experiments are shown in FIGS. 30A-30F and show that the prediction errors of in vivo glucose sensitivity can be significantly improved using the combination of different physical measurements, such as impedance, temperature, and a calibration curve.

For a baseline comparison, a standard commercial factory-calibrated Dexcom G6 sensor system was used, without in vivo calibration.

A first technique based sensitivity drift compensation on impedance measurement alone using the relationship (IMPD) described above.

A second technique based sensitivity drift compensation on both impedance and calibration curve using the relationship (IMPD+CC) described above.

A third technique based sensitivity drift compensation on both impedance and temperature using the relationship (IMPD+T) described above.

A fourth technique based sensitivity drift compensation on impedance, temperature and a calibration curve, using the relationship (IMPD+CC+T) described above.

For the purpose of comparison, curves were also generated for a factory calibration approach with wedge parameters optimized locally using the same informal datasets as those used in training the other prototype algorithms ("FC Local").

FIGS. 30A to 30F show the cumulative distribution functions (CDF), for various metrics, from 1000 rounds of randomizations.

Figure 30A:
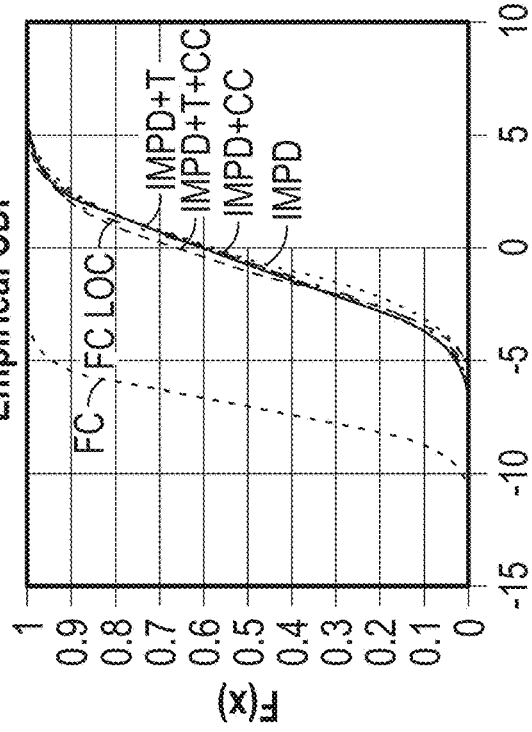
FIG. 30A shows empirical cumulative distribution function of the mean absolute relative difference (MARD) for a variety of compensation techniques.

FIG. 30A shows empirical cumulative distribution function of the mean absolute relative difference (MARD). The MARD is a measure of error. Thus, with respect to sensor system performance, a lower MARD is more desirable than a higher MARD, because the sensor data will be more accurate (e.g., include less error compared to a gold standard). The F(x) on the Y axis is the proportion of randomizations that produced a particular MARD.

Each of the drift compensation techniques provided a lower MARD than the baseline factory-calibrated (FC) sensor. The technique that used impedance, a calibration curve (CalCheck), and temperature produced the smallest MARD.

Figure 30C:
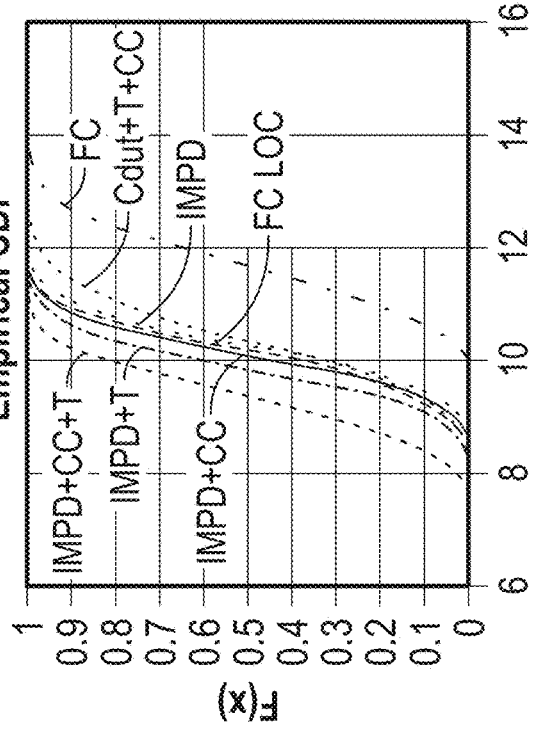
FIG. 30C shows the empirical cumulative distribution function of the relative distance (RD).
Figure 30B:
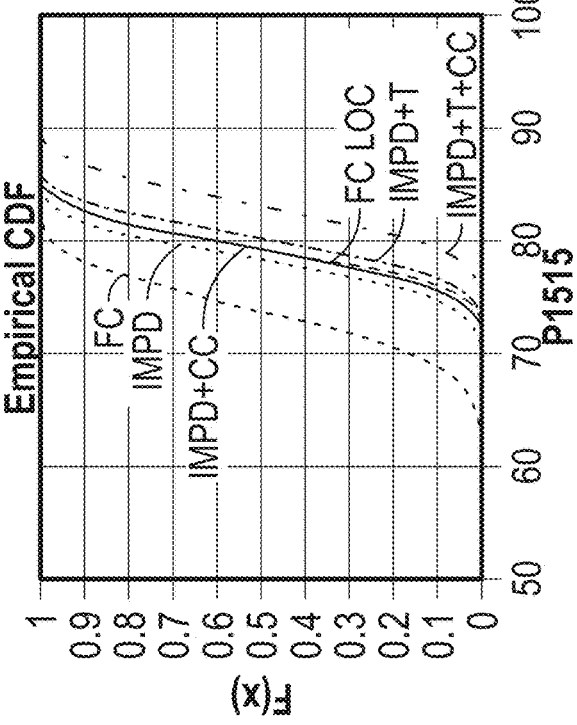
FIG. 30B shows the empirical cumulative distribution function of the mean relative difference (MRD).

FIG. 30B shows the empirical cumulative distribution function or the mean relative difference (MRD). An MRD value closer to zero is more desirable. The various improvement techniques produced highly clustered MRD values, and each technique represents an improvement over the factory-calibrated (FC) result.

FIG. 30C shows the empirical cumulative distribution function or the relative distance (RD). An RD value closer to zero is more desirable. The various improvement techniques produced highly clustered MRD values, and each technique represents an improvement over the factory-calibrated (FC) result.

Figure 30D:
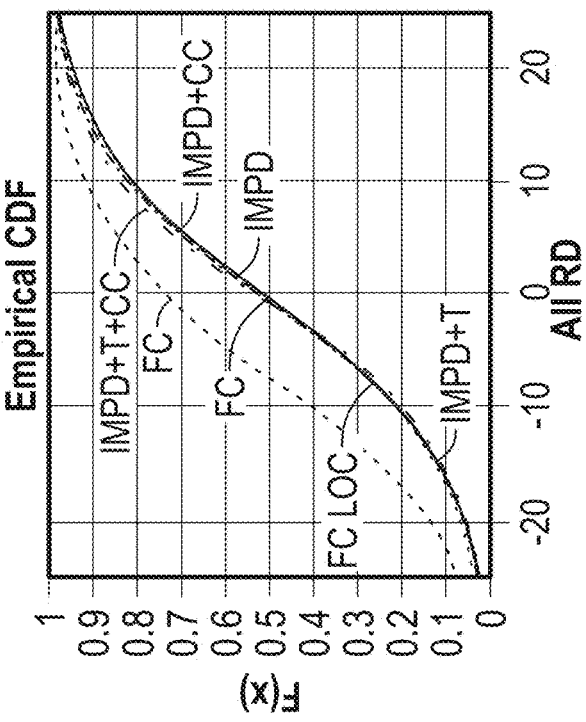
FIGS. 30D, 30E, and 30F show the empirical cumulative distribution function for p1515, p2020, and p4040.
Figure 30E:
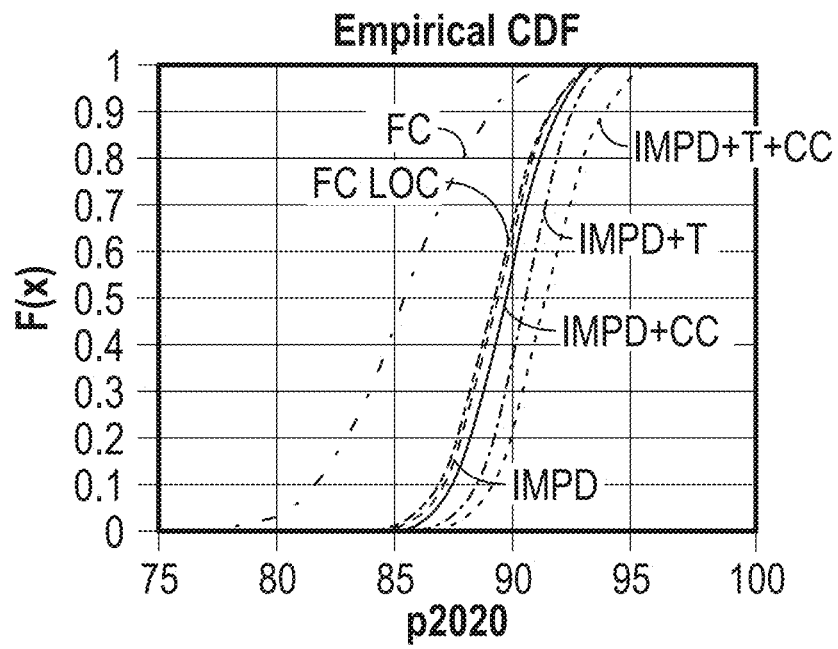
Figure 30F:
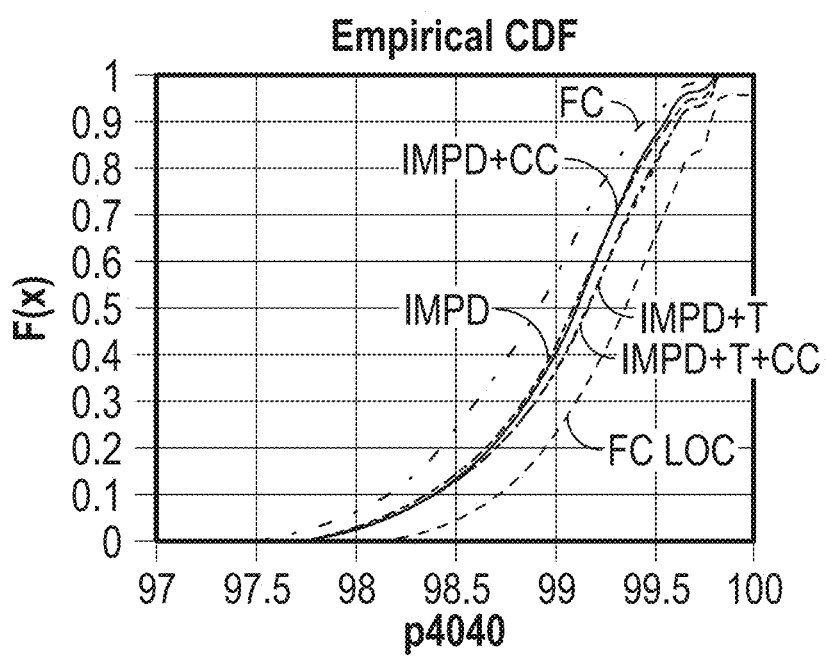

FIGS. 30D, 30E, and 30F show the empirical cumulative distribution function for p1515, p2020, and p4040. The charts indicate the percentage of randomizations that will fall within respective fifteen percent (±15% for FIG. 30D), twenty percent (±20% for FIG. 30E), or forty percent (±15% for FIG. 30F), of an actual blood glucose value. A higher value is better, as it indicates that a larger percentage of sensors will fall within a specified error range. Each of the four techniques improved the performance of the analyte sensor system. FIG. 30G provides data that shows the performance improvement achieved by various compensation techniques described above.

Using a compensation technique to account for factors such as temperature, in vivo environment changes, and damage may improve sensor performance (e.g., lower the MARD for a sensor or a sensor population), or may improve manufacturing yields (e.g., a smaller percentage of sensors may fail a performance test), or both.

FIGS. 31 to 38 are flowchart illustrations that may be performed by sensor electronics (e.g., sensor electronics 106 in FIGS. 1 and 2) coupled to a sensor (e.g., sensor 104 in FIG. 1 or sensor 34 in FIGS. 3A-3B).

Figure 31:
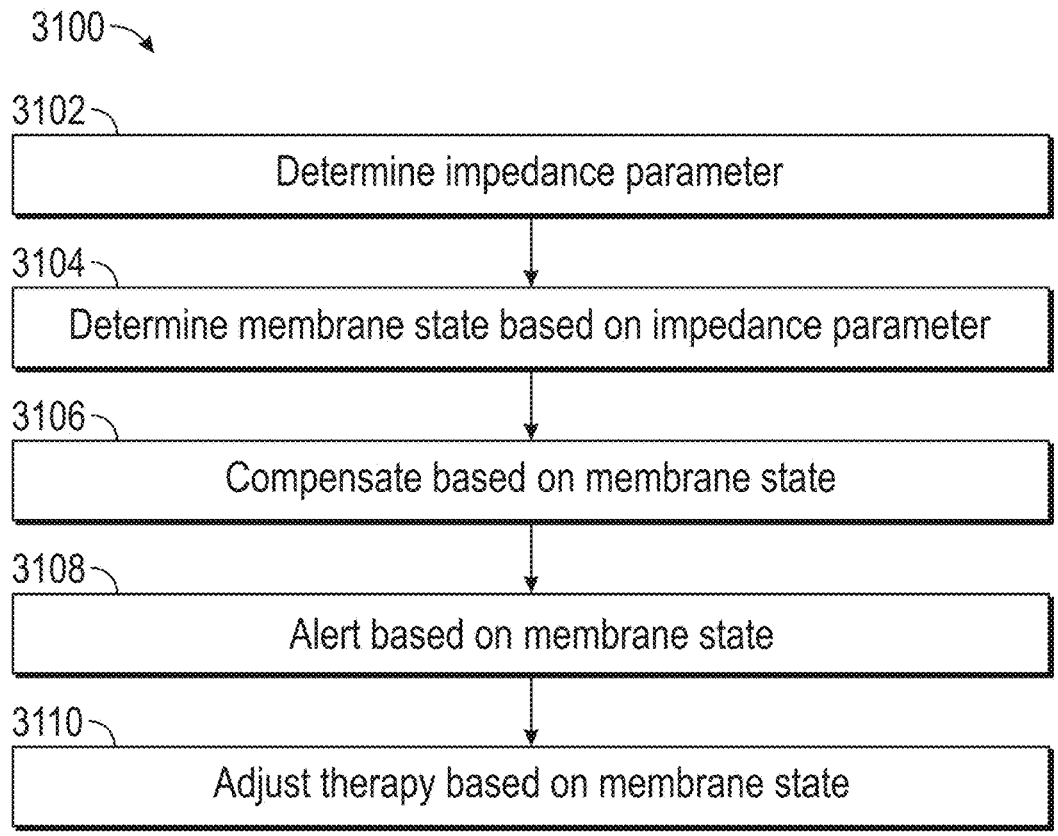
FIG. 31 is a flowchart illustration of a method of assessing sensor membrane integrity using sensor electronics.

FIG. 31 is a flowchart illustration of a method 3100 of assessing sensor membrane integrity using sensor electronics. The method may include, at operation 3102, determining an impedance parameter of an analyte sensor.

The method 3100 may include, at operation 3104, determining an integrity state of the analyte sensor membrane based on the impedance parameter. Determining the integrity state may include determining whether the membrane has damage or a significant abnormality. Determining the membrane state may include determining whether an impedance condition has been satisfied. For example, it may be determined that a sensor membrane is excessively damaged or abnormal in response to an impedance parameter that is below a specified threshold. In some examples, determining the membrane integrity state may include determining a level of membrane damage or abnormality.

In some examples, the determined impedance parameter may be an impedance of the analyte sensor after hydration, or a determined impedance of a membrane portion of an analyte sensor after hydration, e.g., using methods described above. The method may include determining the impedance parameter based on a measurement a specified time after hydration of the sensor. In some examples, the specified time may between 5 and 600 seconds after hydration. Hydration may include, for example, insertion of a sensor in a bath, or insertion of a sensor in a host. In some examples, the impedance parameter may be determined based on a measurement after a measured parameter has reached a steady state condition (e.g., responsive to detecting that impedance has stabilized, which may correlate with a time that the membrane has become sufficiently hydrated or other processes at the working electrode or an insertion site have sufficiently progressed).

In some examples, the impedance parameter may be a derivative (e.g., first derivative or second derivative) of impedance with respect to time. The membrane integrity state may be determined, for example, based on a shape of a first derivative vs. time curve or second derivative vs. time curve, or basted on one or more values of a first derivative or a second derivative.

In some examples, the membrane integrity state may be determined based at least in part on a fitted membrane resistance determined using a constant phase element model. In various examples, determining a membrane integrity state may include performing a template match, determining a best fit from a plurality of templates, or using dynamic time warping, or any combination thereof.

In some examples, the impedance parameter may be determined at a specified frequency. For example, the impedance parameter may be determined at a frequency above 50 Hz. In some examples, the impedance parameter may be determined at a frequency between 50 Hz and 3,000 Hz. In some examples, the comparison between the impedance at the frequency and the impedance at the second frequency is a difference between the impedance at the first frequency and the impedance at the second frequency. As described above, the difference in frequency is referred to as the "dual frequency impedance." The first frequency and second frequency may provide a relatively pronounced impedance difference. For example, the frequencies may be specified to accentuate the impedance difference, e.g., provide a relatively large difference, compared to selection of other adjacent frequencies. In some examples, the comparison includes determining an existence or amount of a kickback in a dual frequency impedance vs. time relationship, e.g., kickback may be detected when a dual frequency impedance reaches a low point and then rises to a generally steady value that is larger than the low point.

In some examples, the determined impedance parameter may be based on a comparison (e.g., a difference) of an impedance at a first frequency and an impedance at a second frequency. The comparison between an impedance at the first frequency and the impedance at the second frequency may become stable at a time after hydration that is earlier than the impedance at the first frequency or the impedance at the second frequency (or both) becomes stable, which may allow for an earlier assessment of the state of the membrane. For example, a damaged membrane may be more quickly identified after insertion into a host, which may allow for earlier notification of a user that the sensor should be replaced.

The method 3100 may include, at operation 3106, compensating an estimated analyte concentration level based at least in part on a determined level of membrane damage or abnormality. For example, an estimated analyte concentration level may be compensated by adjusting a sensitivity value based on the determined level of membrane damage or abnormality as indicated by an impedance parameter. The method 3100 may include, at operation 3308, alerting a user based on a membrane state. For example, a system may declare an alert or raise a "replace sensor" alarm" responsive to a membrane state that suggests a problem (e.g., damage) with a membrane.

The method 3100 may also include, at operation 3110, changing a therapy responsive to a determined membrane state. For example, a system may generate a recommended insulin dosage that is changed (e.g., reduced) based on the membrane state, or an insulin pump may change an insulin dosing regimen or scheme based on the membrane state.

The method 3100 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine a state of a sensor membrane (e.g., determine an amount of damage or abnormality) and avoid reliance on inaccurate sensor readings from an excessively damaged sensor, or determine an estimated analyte concentration level more accurately than conventional methods based on knowledge of the membrane state.

Figure 32:
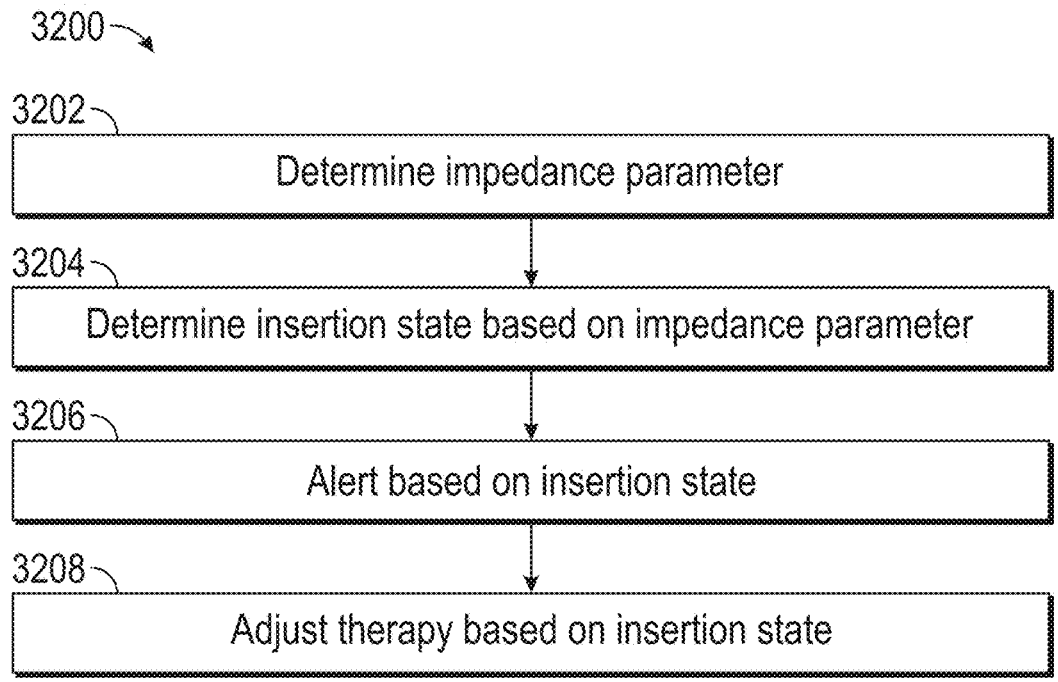
FIG. 32 is a flowchart illustration of a method of operating analyte sensor that may include determining an impedance parameter of an analyte sensor.

FIG. 32 is a flowchart illustration of a method 3200 of operating analyte sensor that may include, at operation 3202, determining an impedance parameter of an analyte sensor. In some examples, the impedance parameter may be a sensor impedance or membrane impedance, which may be determined using any of the methods described herein (e.g., using a measured current, a known voltage applied by sensors electronics, and Ohm's law).

The method 3200 may include, at operation 3204, determining an insertion state of the analyte sensor based on the impedance parameter. In some examples, determining an insertion state may include detecting a dislodgment of a sensor from an insertion position in a host. In some examples, determining the insertion state may include detecting that a sensor has been at least partially pulled out of an initial insertion position. Dislodgment may be detected, for example, based upon an increase in impedance.

The method 3200 may include, at operation 3206, alerting a user based on an insertion state (e.g., delivering a message on a receiver or smart device such as "Sensor has dislodged").

The method 3200 may include, at operation 3208, altering a therapy responsive to a determined membrane state. For example, a system may generate a recommended insulin dosage that is changed (e.g., reduced) based on the membrane state, or an insulin pump may change an insulin dosing regimen or scheme based on the membrane state (e.g., the pump may not rely on sensor data, or rely on sensor data from prior to a sensor withdrawal event).

The method 3200 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an insertion state of a sensor and avoid reliance on inaccurate sensor readings from a dislodged sensor or determine an estimated analyte concentration level more accurately than conventional methods based on knowledge of the insertion state.

Figure 33:
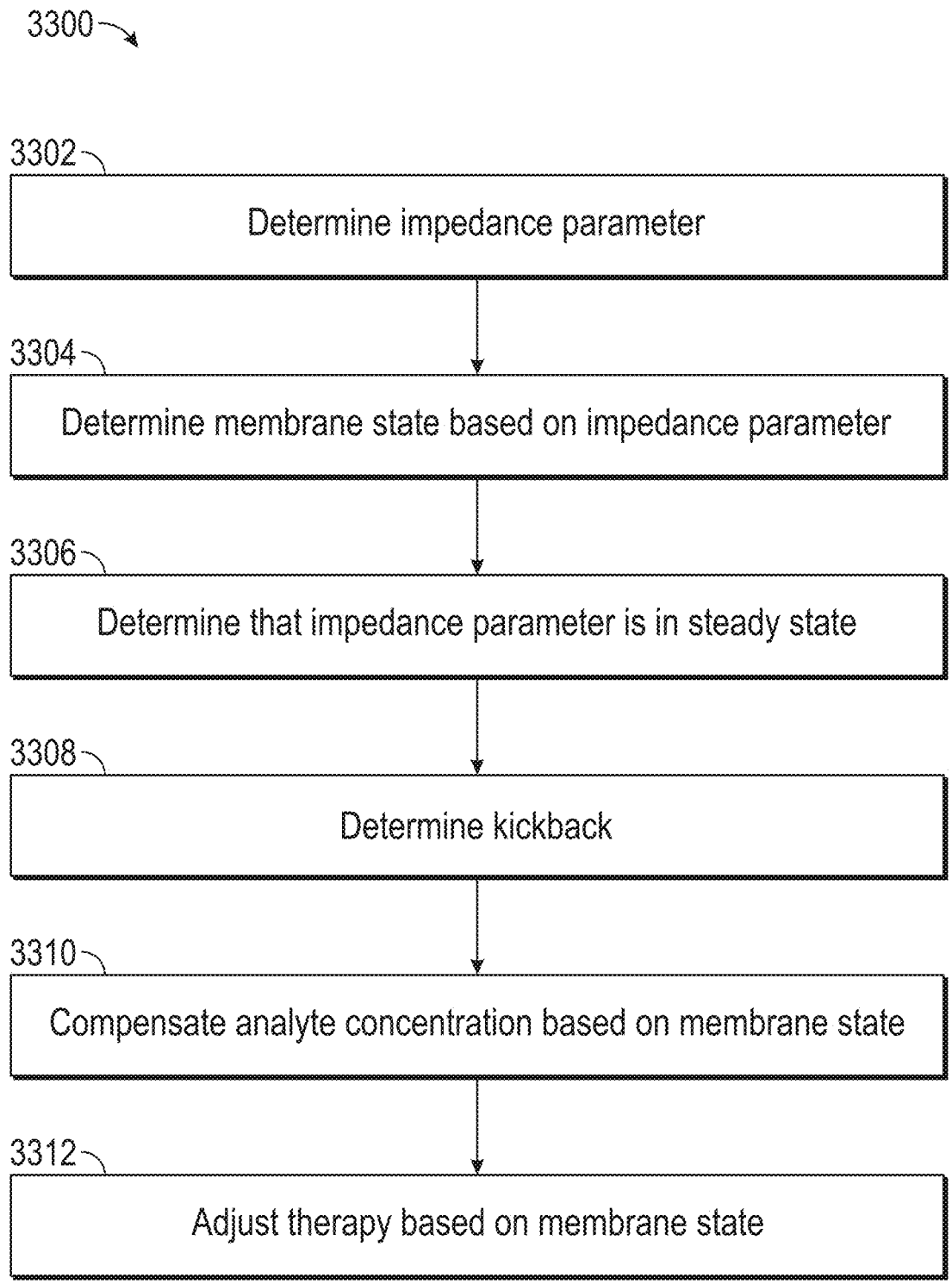
FIG. 33 is a flow chart illustration of a method of compensating an analyte sensor system that may be executed by sensor electronics.

FIG. 33 is a flow chart illustration of a method 3300 of compensating an analyte sensor system that may be executed by sensor electronics. The method 3300 may include, at operation 3302, determining an impedance parameter of an analyte sensor. In various examples, the impedance parameter may be an estimated membrane impedance, an impedance at a specified frequency, a dual frequency impedance, a first derivative of impedance with respect to time, or a second derivative of impedance with respect to time.

The method 3300 may include, at operation 3304, determining a membrane state based on the impedance parameter. For example, sensor electronics may determine the impedance parameter, and apply logic, compare the impedance parameter to a threshold or condition, or one or more impedance parameters to a model to determine a membrane state.

The method 3300 may include, at operation 3306, determining that the impedance parameter is in a steady state. For example, sensor electronics may compare a plurality of sequential impedance parameter values or perform statistical analysis or other analysis to assess a stability of the impedance parameter.

The method 3300 may include, at operation 3308, determining an existence or amount of a kickback in a dual frequency impedance vs. time relationship.

The method 3300 may include, at operation 3310, compensating an analyte concentration level based on the membrane state. For example, sensor electronics may use the membrane state or the steady state impedance parameter to compensate a sensor sensitivity, e.g., to account for drift or sensor-to-sensor variations in impedance. In some examples, sensor electronics may determine an amount of compensation based on the existence or amount of kickback.

The method 3300 may include, at operation 3312, adjusting a therapy based on the determined membrane state. For example, a system may generate a recommended insulin dosage that is changed (e.g., reduced) based on the membrane state, or an insulin pump may change an insulin dosing regimen or scheme based on the membrane state.

In some examples, a system may declare an alert or raise a "replace sensor" alarm" responsive to determination of a membrane state. For example, the system may raise an alert responsive to determination that a sensor is damaged.

The method 3300 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an estimated analyte concentration level more accurately than conventional methods.

Figure 34:
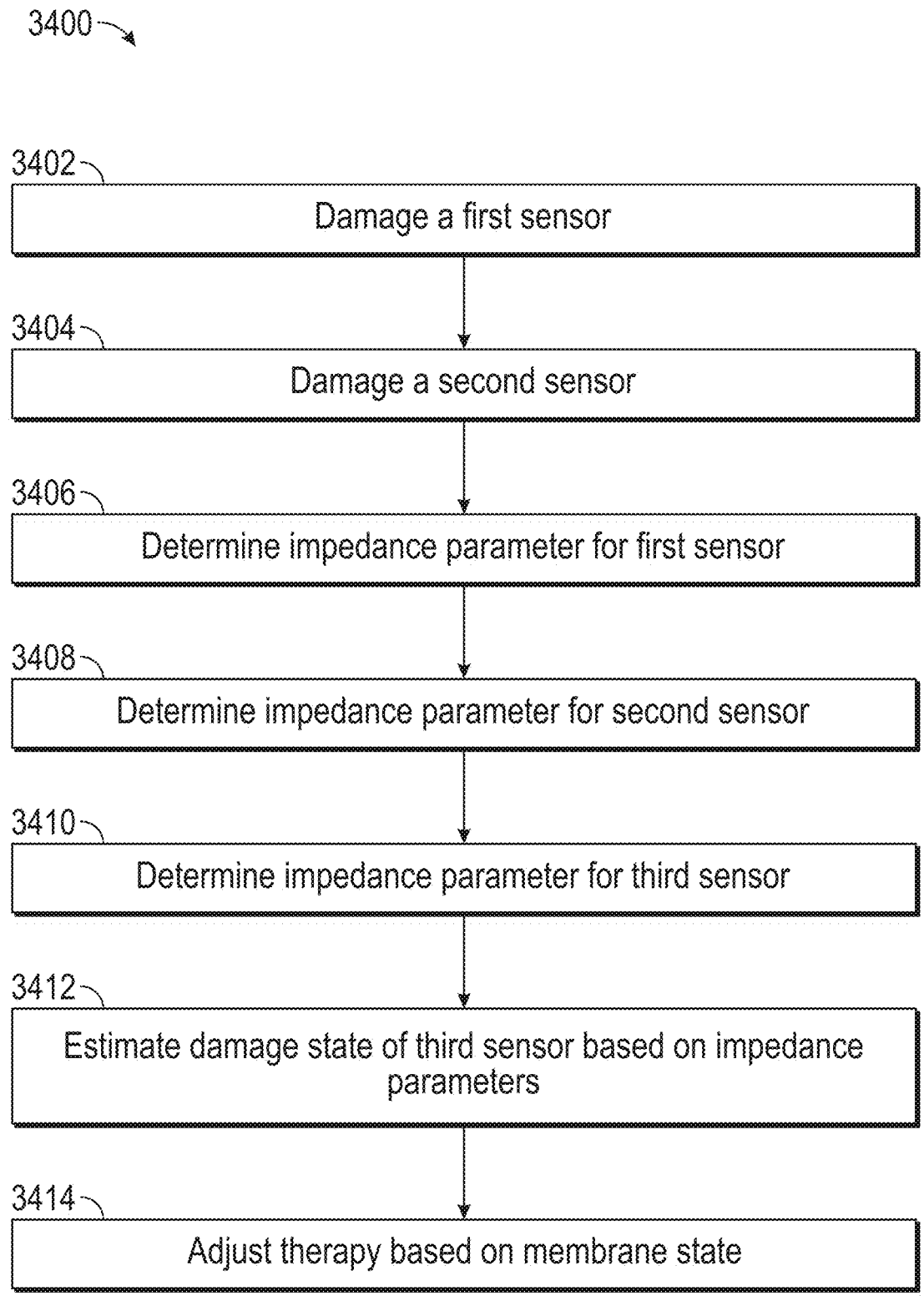
FIG. 34 is a flow chart illustration of a method of calibrating damage to impedance in a population of analyte sensors.

FIG. 34 is a flow chart illustration of a method 3400 of calibrating damage to impedance in a population of analyte sensors. The method 3400 may include, at operation 3402, damaging a first sensor; and at operation 3404, damaging a second sensor. The method 3400 may further include, at operation 3406, determining an impedance parameter for the first sensor using a first process, and, at operation 3408, determining an impedance parameter for the second sensor using a second process, wherein the second process is different than the first process. In an example, damaging the first sensor includes scratching the first sensor against an abrasive surface a specified number of times, and damaging the second sensor includes scratching the second sensor against an abrasive surface a specified number of times. For example, a first sensor may be scratched three times, and a second sensor may be scratched eight times, and it may be inferred from the process that the second sensor is more damaged that the first sensor.

The method 3400 may further include, at operation 3410, determining an impedance parameter for a third sensor. The method 3400 may further include, at operation 3412, estimating a damage state of the third sensor based at least in part on the determined impedance parameter for the first sensor, the determined impedance parameter for the second sensor, and the determined impedance parameter for the third sensor. In some examples, the method 3400 may include determining a damage curve based at least in part on the determined impedance parameter for the first sensor and the determined impedance parameter for the second sensor and estimating the damage state of the third sensor based upon the determined impedance parameter for the third sensor and the damage curve. In some examples, each of a plurality of sensors (e.g., five, ten, or twenty sensors) may be scratched a different number of times to provide a continuum of degrees of damage for comparison against a characteristic of a sensor of interest (e.g., the third sensor). At operation 3414, a therapy may be adjusted based on a membrane state. For example, delivery of insulin may be adjusted based on a membrane state, which may for example be received from an analyte sensor system via a wired or wireless communication connection.

The method 3400 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., by estimating a damage state the damage state to identify excessively damaged sensors, or determine an accurate estimated analyte concentration level more accurately than conventional methods.

Figure 35:
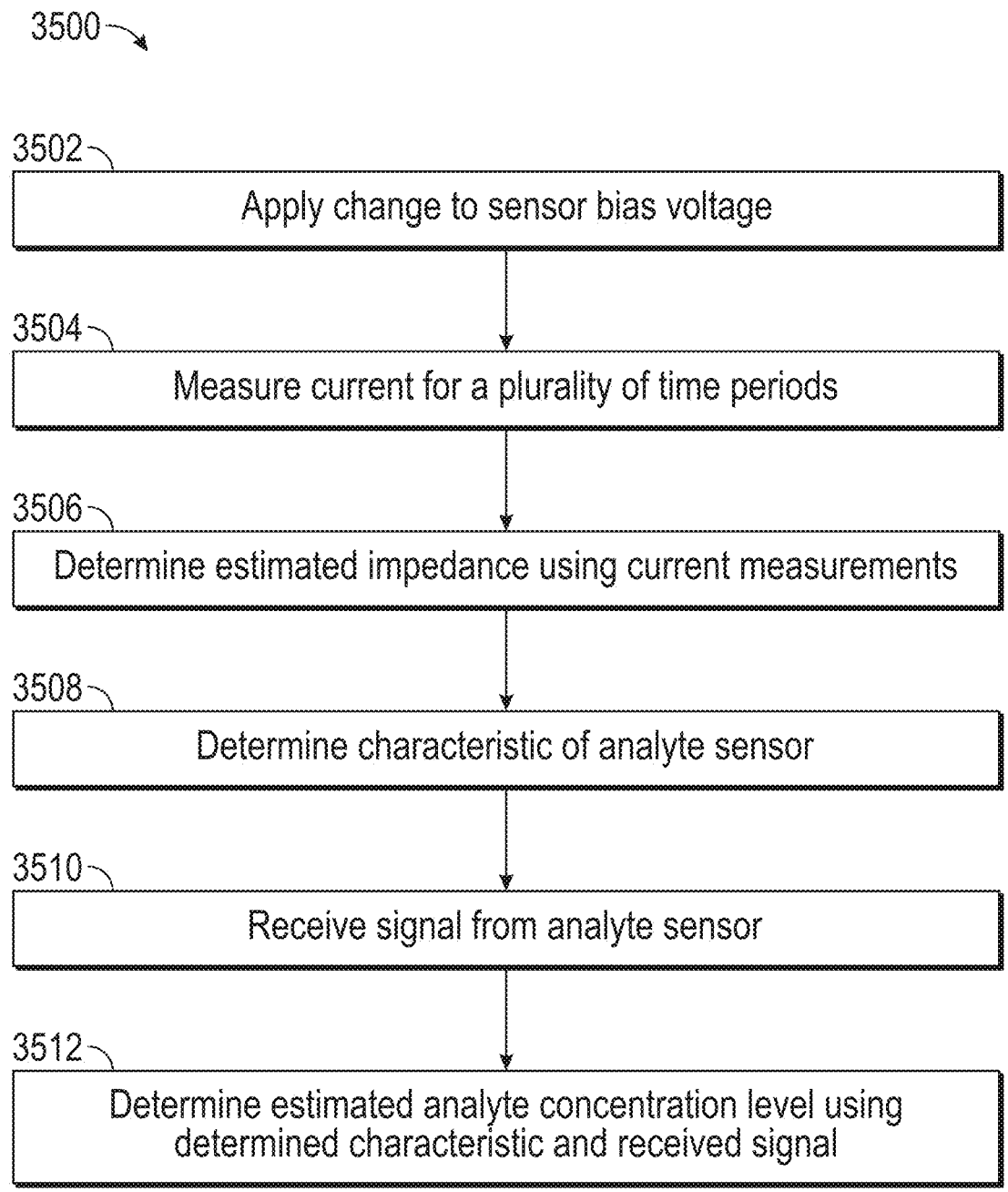
FIG. 35 is a flowchart illustration of a method of operating an analyte sensor system using sensor electronics.

FIG. 35 is a flowchart illustration of a method 3500 of operating an analyte sensor system using sensor electronics. The method 3500 may include, at operation 3502, applying a change to an analyte sensor bias voltage. In some examples, applying a change may include applying a step in the bias voltage, for example as described in reference to FIGS. 5A to 5C.

The method 3500 may include, at operation 3504, measuring a current value for each of a plurality of time periods after application of the bias voltage change, for example as described in reference to FIG. 5D. Measuring the current may include, for example, integrating a charge over each of the specified time periods.

The method 3500 may include, at operation 3506, determining an estimated impedance of using the current values for the plurality of time periods. In some examples, determining an impedance may include fitting a curve using the determined currents for the plurality of time periods, and determining the impedance based on the fitted curve. Fitting the curve may include fitting an exponential curve, wherein the exponential curve accounts for the impact of double-layer capacitance on the measured current response.

The method 3500 may include, at operation 3508, determining a characteristic of the analyte sensor using the estimated impedance. Determining a characteristic of the analyte sensor may include, for example, determining a sensitivity of the analyte sensor to an analyte concentration. The method 3500 may include compensating for sensor drift using the determined impedance or the determined sensitivity.

In some examples, determining a characteristic of the analyte sensor may include determining a level of damage or abnormality of the sensor.

In some examples, determining a characteristic of the analyte sensor includes determining a compensation factor for the sensor.

The method 3500 may include, at operation 3510, receiving from the analyte sensor a signal indicative of an analyte concentration.

The method 3500 may include, at operation 3512, determining an estimated analyte concentration level using the determined characteristic of the analyte sensor and the received signal.

The method 3500 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., by determining impedance more accurately than conventional methods and using the determined impedance to determine a more accurate estimated analyte concentration level.

Figure 36:
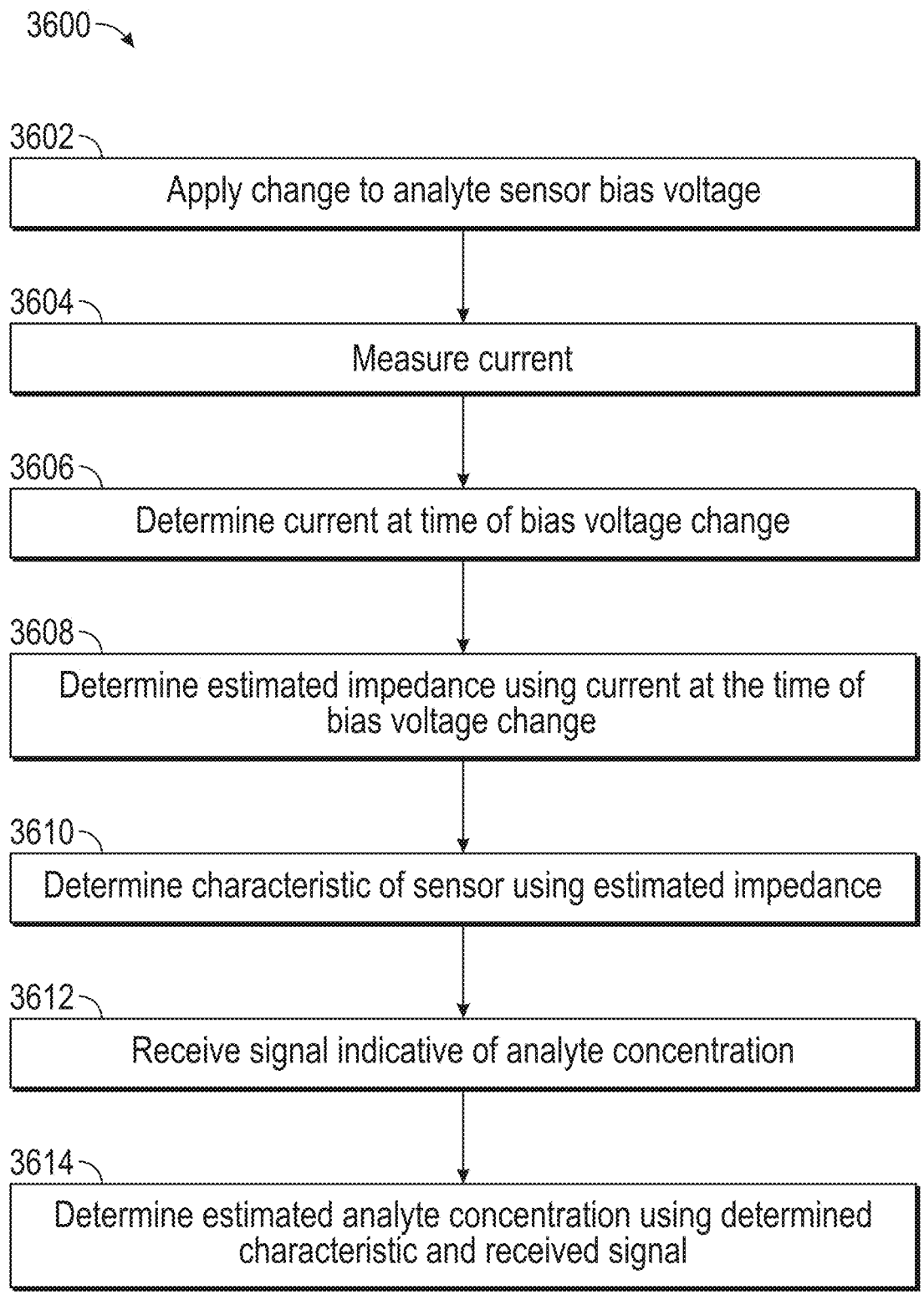
FIG. 36 is a flow chart illustration of a method of operating an analyte sensor system using sensor electronics to correct for an error from double-layer capacitance of a sensor membrane.

FIG. 36 is a flow chart illustration of a method 3600 of operating an analyte sensor system using sensor electronics to correct for an error from double-layer capacitance of a sensor membrane. The method 3600 may include, at operation 3602, applying a change to an analyte sensor bias voltage, for example as described in reference to FIGS. 5A to 5C.

The method 3600 may include, at operation 3604, measuring a current value for each of a plurality of time periods after application of the bias voltage change. The method 3600 may include, at operation 3606, determining a current at the time of the bias voltage change using the current values for the plurality of time periods. For example, a curve may be extrapolated using current values measured after the bias voltage change to determine a current at the time of the bias voltage change, which may allow for more accurate determination of an impedance, by accounting for a membrane capacitance, as described in reference to FIGS. 8A to 8D. In some examples, the method 3600 may include fitting the current values for the plurality of time periods to an exponential curve and extrapolating the fitted curve to determine the current at the time of the bias voltage change, for example as described in reference to FIGS. 8C and 8D.

The method 3600 may include, at operation 3608, determining an estimated impedance using the determined current at the time of the bias voltage change. The method 3600 may include, at operation 3610, determining a characteristic of the analyte sensor using the estimated impedance. In some examples, determining the characteristic of the analyte sensor may include determining a sensor sensitivity. In some examples, a sensor sensitivity may be updated to account for drift by applying the change to the bias voltage at a second time, measuring the currents for a second plurality of time periods, extrapolating to determine the current at the second time, determining the estimated impedance based on the current at the second time, and determining the characteristic of the sensor at the second time based on the estimated impedance at the second time.

The method 3600 may include, at operation 3612, receiving from the analyte sensor a signal indicative of an analyte concentration. The method 3600 may include, at operation 3614, determining an estimated analyte concentration level using the determined characteristic of the analyte sensor and the received signal.

The method 3600 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an impedance of or characteristic of a sensor more accurately than conventional methods, which may allow for more accurate determination of estimated analyte concentration methods.

Figure 37:
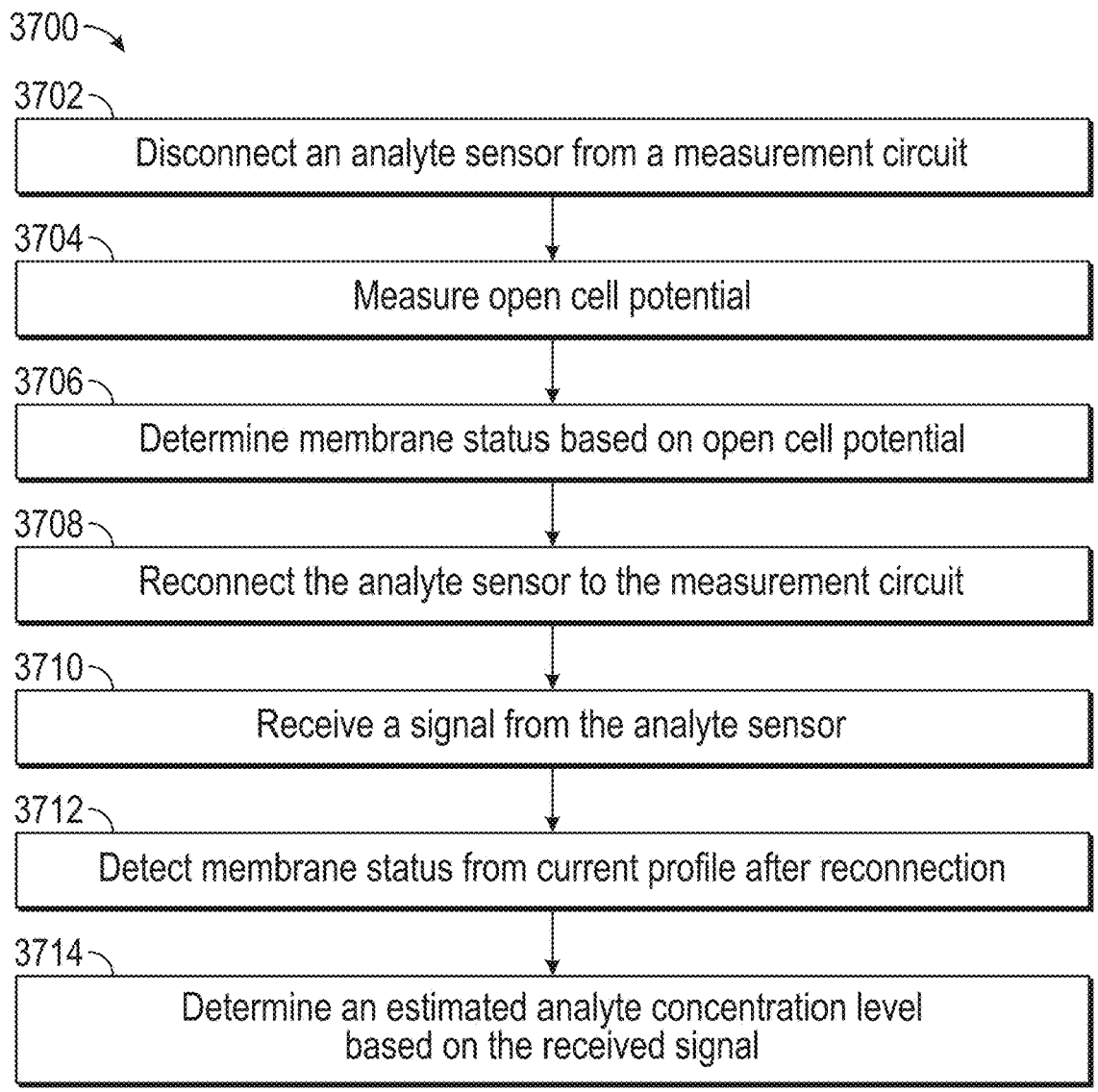
FIG. 37 is a flowchart illustration of a method that may include disconnecting an analyte sensor from a measurement circuit.

FIG. 37 is a flowchart illustration of a method 3700 that may include, at operation 3702, disconnecting an analyte sensor from a measurement circuit.

The method 3700 may include, at operation 3704, measuring one or more open cell potentials during the accumulation period. The method 3700 may include, at operation 3706, determining a membrane status based on one or more open cell potentials. In various examples, the membrane status may include an interference status (e.g., interference from acetaminophen), or a damage or abnormality status. For example, an abnormality or damage in a sensor membrane may be detected based upon an impedance characteristic (e.g., estimated sensor impedance, estimated membrane impedance, a first derivative of impedance, a second derivative impedance, or a fitted curve) determined from the one or more open cell potentials, or from a shape of an open cell vs. time curve.

The method 3700 may include, at operation 3708, reconnecting the analyte sensor to the measurement circuit after an accumulation period. The method 3700 may include using a gate circuit to disconnect and reconnect the analyte sensor.

The method 3700 may include, at operation 3710, receiving a signal from the analyte sensor, wherein the signal is indicative of an amount of charge accumulated on the analyte sensor during the accumulation period. Disconnecting and reconnecting (e.g., gating) an analyte sensor may improve the performance of a sensor system, for example because charge from an analyte reaction may increase during an accumulation period, resulting in a larger detectable current signal, whereas sources of interference or noise (e.g., acetaminophen) may not grow during the accumulation period. In some examples, the disconnection and reconnection of the analyte sensor improves a signal to interference ratio of the analyte sensor, as described above in the section titled "Gated Amperometric Detection."

The method 3700 may include, at operation 3712, determining a membrane status based on the analyte signal received after reconnection of the analyte sensor to the measurement circuit. In some examples, the method 3700 may include monitoring a current profile after reconnecting the analyte sensor and detecting a membrane status (e.g., membrane fault) using the current profile. In some examples, the method 3700 may include determining an impedance characteristic and detecting a membrane fault responsive to the impedance characteristic satisfying a fault condition (e.g., impedance characteristic below a threshold or resembling a damage template curve). In various examples, the impedance characteristic may be an estimated membrane impedance, a first derivative of impedance, a second derivative impedance, or a fitted curve.

The method 3700 may include, at operation 3714, determining an estimated analyte concentration level based on the received signal.

The method 3700 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to improve the signal to noise ration of a sensor system, or avoid reliance on inaccurate sensor readings from a sensor that has a damaged or abnormal membrane, or to determine an estimated analyte concentration level more accurately than conventional methods, based on one or more of the factors mentioned above.

Figure 38:
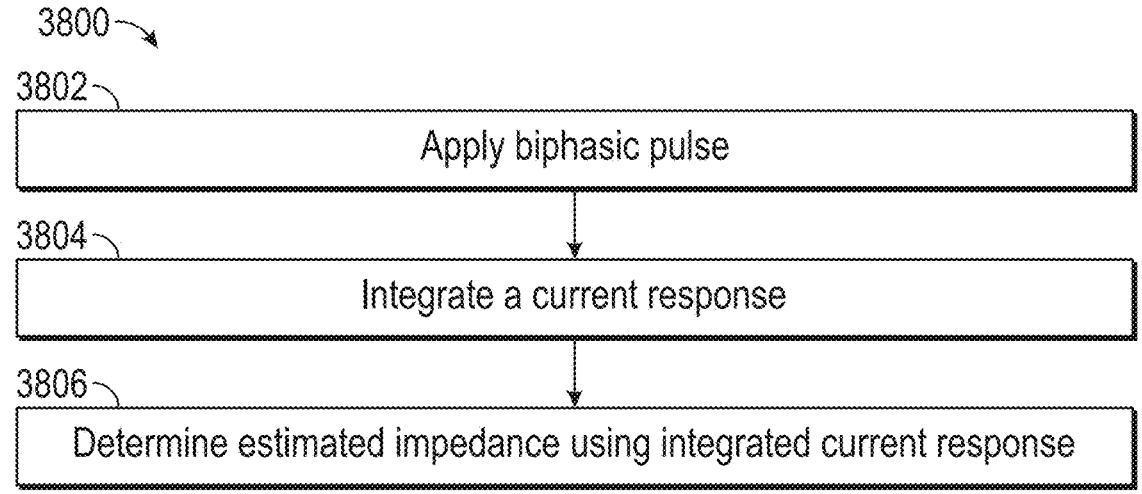
FIG. 38 is a flowchart illustration of a method that may include applying a biphasic pulse to a continuous analyte sensor circuit.

FIG. 38 is a flowchart illustration of a method 3800 that may include, at operation 3802, applying a biphasic pulse to a continuous analyte sensor circuit. The method 3800 may include, at operation 3804, integrating a current response to the biphasic pulse, e.g., as described in reference to FIG. 9. The method 3800 may include, at operation 3806, determining an estimated impedance using the integrated current response, for example as shown in FIG. 9 and described in reference thereto. As described in various examples above, the estimated impedance may be used to detect a sensor membrane status or compensate for drift.

The method 3800 may be performed by sensor electronics (e.g., sensor electronics 106 in FIGS. 1 and 2) that are coupled to a sensor (e.g., sensor 104 in FIG. 1 or sensor 34 in FIGS. 3A-3B) to improve the performance of an analyte sensor system, e.g., to determine an impedance, detect a sensor membrane status (e.g., membrane fault), or determine an estimated analyte concentration level more accurately than conventional methods.

In some examples, the method 3700 or method 3800 may include compensating a sensor sensitivity using the determined impedance. In some examples, the method may include determining impedance using a signal at a frequency that avoid an effect of a double-layer membrane capacitance on the impedance. In some examples, the compensation may be based on impedance and one or more additional factors, such as temperature, a calibration curve (e.g., factory-determined calibration curve), or any combination thereof. In some examples, the compensation may use a transmitter temperature, and the transmitter temperature may be filtered using Greene's function.

In various examples, the method 3700 or 3800 may include determining the humidity of an environment of the sensor based at least in part on a determined impedance. For example, the method may include detection of humidity during transportation of the sensor or during storage of the sensor, or both. In some examples, the performance or operation of a sensor may be affected the humidity environment. In some examples, the method 3700 or method 3800 may include compensating a sensor sensitivity based upon the determined humidity and may optionally include declaring an alert based upon a determined humidity. For example, the method 3700 or 3800 may include delivering an alert using a smart device to alert a user that a sensor should not be used due to excessive humidity exposure.

The response of an analyte sensor to different bias voltages can provide information about the analyte sensor, including, for example, a stage of life of the analyte sensor. As described herein, an analyte sensor, such as the analyte sensor 34 shown in FIGS. 3A-3C, includes at least a working electrode and a reference electrode. The reference electrode may be formed of a material that is depleted during use of the analyte sensor, such as silver chloride. As the silver chloride or other similar material at the reference electrode is depleted, the electrochemical response of the analyte sensor changes. For example, as the reference electrode is depleted, its potential may change. This can affect the sensor current, leading to less accurate readings.

In some examples, the stage of life of an analyte sensor can be detected using the current response of the analyte sensor to a set of bias voltages. The set of bias voltages can include at least one voltage that is less than an operational voltage of the analyte sensor. When a bias voltage is applied to the analyte sensor, the analyte sensor produces a corresponding sensor current. The set of sensor currents produced by the sensor in response to a set of bias voltages is referred to as a current response.

The current response provides information about the stage of life of the sensor. For example, as the reference electrode is depleted, the current response of the sensor drops, first at bias voltages less than the operational bias voltage and increasing until the sensor is no longer usable at the bias voltage. The point at which the current response ceases to rise and flattens out or plateaus can correspond to the sensor's stage of life. This is shown in FIG. 39.

Figure 39:
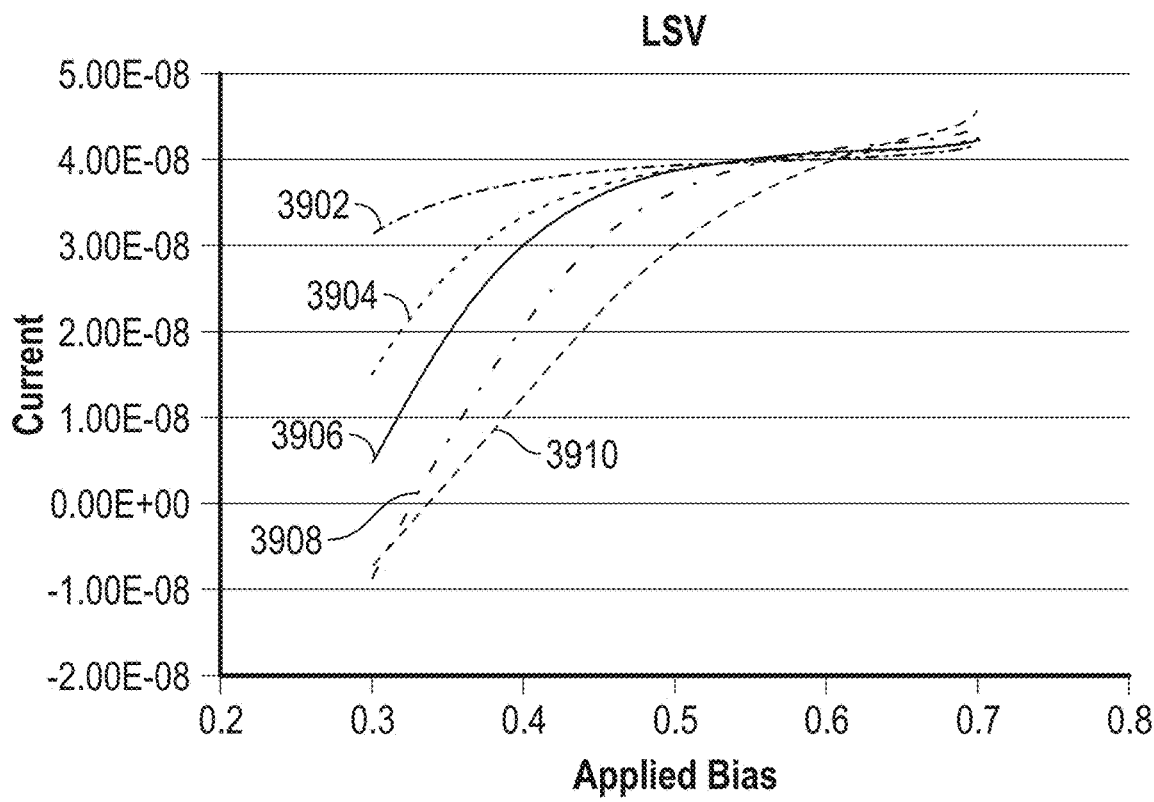
FIG. 39 is a graph that shows current responses of an analyte sensor, such as the analyte sensor 34 of FIGS. 3A-3C, at different stages of life.

FIG. 39 is a graph that shows current responses 3902, 3904, 3906, 3908, 3910 of an analyte sensor, such as the analyte sensor 34 of FIGS. 3A-3C, at different stages of life. The graph of FIG. 39 includes a horizontal or x-axis showing bias voltage applied to the analyte sensor and a vertical or y-axis showing analyte sensor current.

In the example of FIG. 39, the operating bias voltage of the analyte sensor is about 0.6 V. The set of bias voltages applied to generate the current responses 3902, 3904, 3906, 3908, 3910 in this example ranges from about 0.3 V to about 0.7 V. In some examples, the set of bias voltages includes a number of discrete voltages that can be applied in any order. In other examples, the set of bias voltages is applied by continuously sweeping the bias voltage of the sensor between a low bias voltage and a high bias voltage. In this example, the low bias voltage is about 0.3 V and the high bias voltage is about 0.6 V.

The current responses 3902, 3904, 3906, 3908, 3910 describe the analyte sensor at different stages of life. The current response 3902 describes the analyte sensor a first stage of life of the analyte sensor when the reference electrode has not been significantly depleted. As shown, the current response 3902 rises slightly between about 0.3 V and 0.45 V and then plateaus through the operational bias voltage of 0.6 V.

The current response 3904 describes the analyte sensor at a second stage of life at which the reference electrode is more depleted than at the current response 3902. The current response 3904 rises between about 0.3 V and 0.48 V and then plateaus. The current response 3906 describes the analyte sensor at a third stage of life at which the reference electrode is more depleted than at the current response 3904. The current response 3906 rises from about 0.3 V and 0.5 V and then plateaus. The current response 3908 describes the analyte sensor at a fourth stage of life at which the reference electrode is more depleted than at the current response 3906. The current response 3908 rises from about 0.3 V to 0.55 V and then plateaus.

The current response 3910 describes the analyte sensor at a fifth stage of life at which the reference electrode is more depleted than at the current response 3908. The current response 3910 begins rising at 0.3 V and does not plateau. For example, the current response 3910 may indicate an end-of-life for the sensor.

As shown in FIG. 9, the point at which a current response stops rising correlates to the stage of life of the sensor. Various examples described herein utilize this correlation to detect and respond to an analyte sensor's stage of life.

Figure 40:
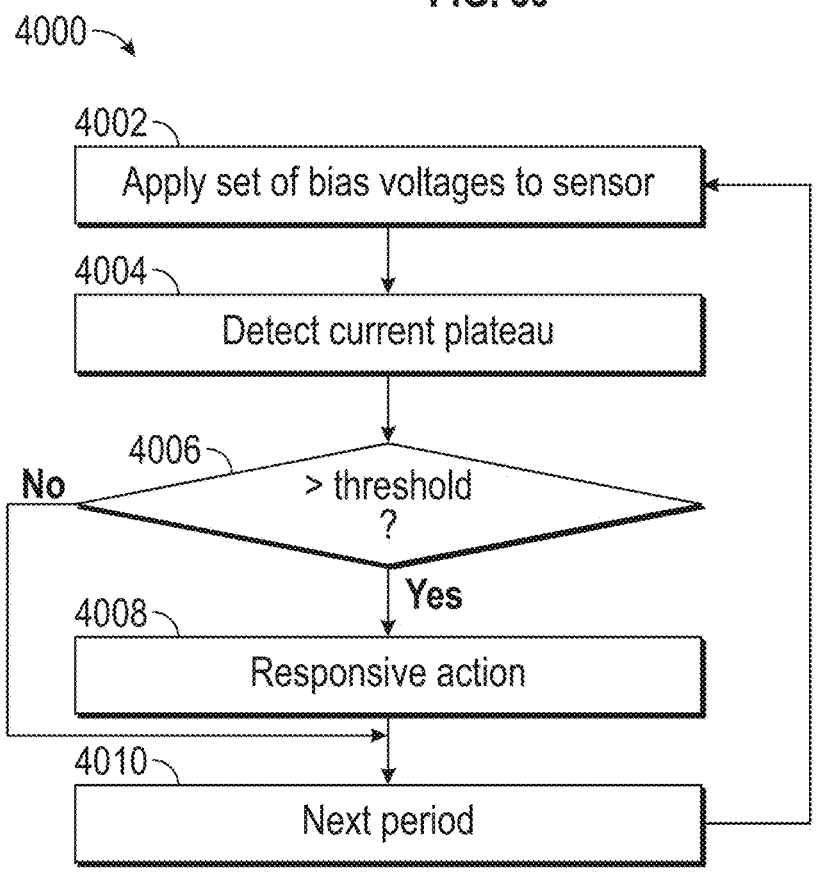
FIG. 40 is a flowchart illustration of an example method for determining properties of an analyte sensor by applying a set of bias voltages.

FIG. 40 is a flowchart illustration of an example method 4000 for determining properties of an analyte sensor by applying a set of bias voltages. The method 4000 can be executed by or at the direction of any suitable device such as, for example, sensor electronics, such as sensor electronics 106 of FIG. 1.

At operation 4002, the device applies a set of bias voltages to the analyte sensor. The set of bias voltages can include at least one bias voltage below an operating bias voltage of the sensor. In some examples, the set of bias voltages also includes at least one bias voltage above the operating bias voltage of the sensor. The set of bias voltages can be applied discretely (e.g., one at a time) and/or can be applied continuously (e.g., from low to high or from high to low). Applying the set of bias voltages yields a current response. For example, each bias voltage results in a corresponding sensor current that is generated when the bias voltage is applied. The set of bias voltages can be applied close enough in time that the sensor current would not be expected to change due to changes in analyte concentration. For example, the set of bias voltages can be applied within about one second per 100 mV of bias voltage.

At operation 4004, the device determines a plateau bias voltage for the current response. The plateau bias voltage can be the bias voltage at which the rise in a current response stops. The plateau bias voltage can be detected in a number of different ways. In some examples, the plateau bias voltage is determined by finding the lowest bias voltage at which the analyte sensor current is above a current threshold. Referring to the example of FIG. 39, for example, the current threshold could be 40 nA. The lowest bias voltage resulting in a sensor current greater than 40 nA may be considered the plateau voltage. In some examples, the device finds the plateau bias voltage, at least in part, by identifying the bias voltage at which the current response first has a slope of about zero.

At operation 4006, the device determines if the plateau bias voltage determined at operation 4004 is greater than a bias voltage threshold. Referring again to FIG. 39, the higher the plateau bias voltage, the later the stage of life of the analyte sensor. If the plateau bias voltage is not greater than the threshold, it indicates that the sensor is at an early stage of life and can continue operating. Accordingly, the device continues to a next period 4010 and then re-applies the set of bias voltages at operation 4002.

On the other hand, if the plateau bias voltage is greater than the threshold, it indicates that the analyte sensor is at an advanced enough stage of life to prompt a responsive action. Various different types of responsive actions can be executed. In some examples, the responsive action includes deriving a stage of life for the analyte sensor and displaying the stage of life at a user interface accessible to the host or other user, such as the user interface 252 of the peripheral device 250 and/or the user interface 272 of the medical device 270 described herein. The stage of life can be based on the plateau bias voltage. For example, higher plateau bias voltages can correspond to a more advanced stage of life. In some examples, the stage of life is indicated by a number of hours, days, weeks, etc. until the sensor's end of life. In some examples, different values for the plateau bias voltage are correlated to corresponding stages of life, for example, at a look-up table or other suitable data structure at the sensor electronics, peripheral device, medical device, or other suitable device.

In some examples, the responsive action can include applying a compensation to the sensor current to determine a compensated analyte compensation. The responsive action can also include ending a session for the analyte sensor. Ending a session for the analyte sensor can include, for example, ceasing to provide a bias voltage to the sensor, ceasing to report readings from the analyte sensor and/or indicating at a user interface that the session for the current session is complete.

In some examples, the selected responsive action is determined based on the value of the plateau bias voltage. For example, if the plateau bias voltage is greater than a selected threshold and/or no current plateau is detected, the responsive action can include ending the sensor session. If the plateau bias voltage is lower than the threshold, the responsive action can include compensating the analyte sensor and/or waiting until a next measurement.

In many analyte sensors, process variations in the manufacture of the sensor can lead to variations in sensitivity from sensor to sensor. For example, variations in temperature during manufacture, variations in humidity during manufacture, differences in material properties from lot-to-lot, and other factors can lead differences in sensitivity.

Various examples described herein are directed to sensors and techniques for manufacturing sensors that reduce sensor-to-sensor variations by trimming sensor components. For example, a sensor can be manufactured with an associated trim circuit. The trim circuit can include an amplifier including at least one adjustable component. For example, an analyte sensor that generates a current indicating analyte concentration can include a trim circuit that includes a current amplifier tunable by at least one resistor. After a sensor including a trim circuit is manufactured, the adjustable component or components are trimmed to cause the sensor to have a desired sensitivity.

Figure 41:
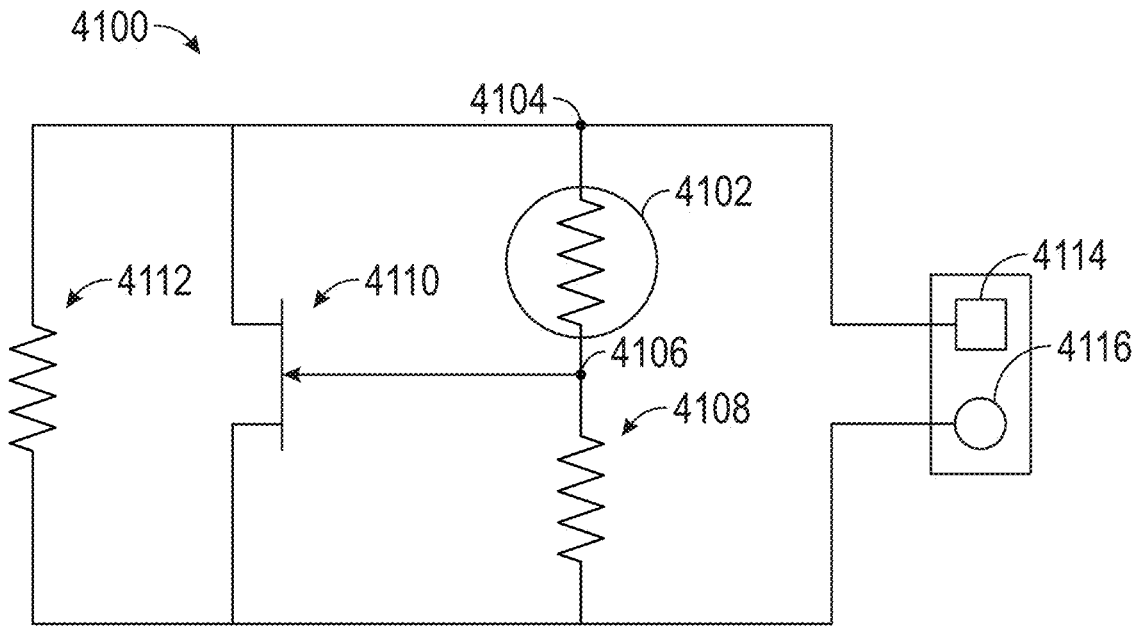
FIG. 41 is a schematic illustration of one example of an analyte sensor circuit including an analyte system and a trim circuit.

FIG. 41 is a schematic illustration of one example of an analyte sensor circuit 4100. The circuit 4100 includes an analyte sensor 4102. The analyte sensor 4102 comprises a working electrode 4104 and a reference electrode 4106. The analyte sensor 4102 can be arranged, for example, in the manner of the analyte sensor 34 of FIG. 3. For example, when a bias voltage is applied across the electrodes 4104, 4106 of the analyte sensor 4102 generates an electric current between the electrodes 4104, 4106. The electric current is related to the concentration of analyte at the analyte sensor 4102, for example, by a sensitivity as described herein.

The analyte sensor circuit 4100 also includes a trim circuit including field effect transistor (FET) 4110 and resistors 4112 and 4108. The FET 4110 and resistors 4112, 4108 operate as a current amplifier that amplifies the current generated by the analyte sensor. For example, current generated by the analyte sensor 4102 causes a voltage drop across the resistor 4108 that is mirrored between the gate and the source of the FET 4110. This, in turn, causes the FET 4110 to conduct current that may be proportional to the voltage drop between the gate and source. The FET 4110 can be any suitable type of FET such as, for example, a metal oxide semiconductor FET (MOSFET), junction gate FET (JFET), etc.

In some examples, the components of the analyte sensor circuit 4100 are integrated. For example, the components of the analyte sensor circuit 4100 may be fabricated on and/or connected to a common substrate, such as a semiconductor substrate. The analyte sensor 4102 may be soldered or otherwise coupled to the common substrate.

The analyte sensor circuit 4100 can include connectors 4114, 4116 that connect the analyte sensor circuit 4100 to sensor electronics or other suitable hardware for connecting the analyte sensor circuit 4100 to sensor electronics and/or another suitable device or devices. For example, a bias voltage can be provided across connectors 4114, 4116. Also, in some examples, sensor current generated by the analyte sensor 4102 is sensed across connectors 4114, 4116.

In some examples, the effective drain-source resistance of the FET 4110 (e.g., when the FED 4110 is fully on) is larger than the effective resistance of the analyte sensor 4102, which may be on the order of tens of megaohms. For example, the drain-source resistance of the FET 4110 may be more than one and one-half times the resistance of analyte sensor 4102. Selecting the FET 4110 with a drain-source resistance larger than the effective resistance of the analyte sensor 4102 may prevent the source current of the FET 4110 from dominating the current of the analyte sensor 4102.

In some examples, because the effective drain-source resistance of the FET 4110 is high for the reasons set forth above, the full-scale gate voltage may not need to be large. Accordingly, the resistor 4108 can be small. The resistor 4108 may also be selected to be small enough to prevent the effective bias voltage across the analyte sensor 4102 from falling outside of the value necessary for driving the sensor 4102.

In some examples, the FET 4110 is selected with low gate leakage current. For example, a high gate leakage current could cause significant portions of the sensor current to bypass the resistor R2, failing to generate sufficient potential to turn on the FET 4110.

The resistors 4112 and 4108 of the analyte sensor circuit 4100 can be physically modified to achieve a desired sensitivity and/or offset for the analyte sensor system 4100. For example, modifying the resistance of resistor 4108 can affect the gain of the FET 4110, modifying the current at the terminals 4114, 4116 for similar current generated by the analyte sensor 4102. This may modify the effective sensitivity of the analyte sensor circuit 4100. Similarly, modifying the resistance of the resistor 4112 changes a current through the resistor 4112 for a given bias voltage. Current generated by the analyte sensor 4102 can be in addition to the current at the resistor 4112. In this way, modifying the resistance of the resistor 4112 changes the offset of the analyte sensor system 4100.

Figure 42:
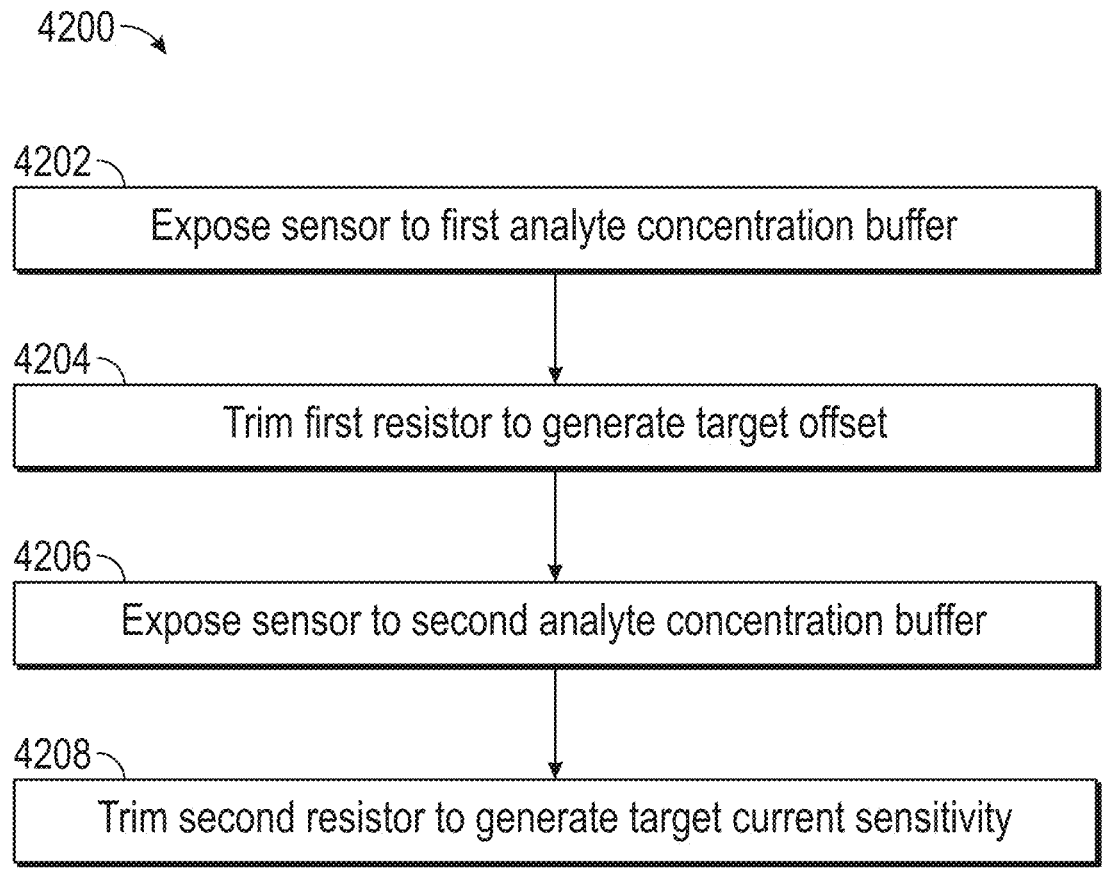
FIG. 42 is a flowchart illustration of an example method for tuning the analyte sensor circuit of FIG. 41.

FIG. 42 is a flowchart illustration of an example method for tuning the analyte sensor circuit 4100 of FIG. 41. At operation 4202, the analyte sensor 4102 is exposed to a buffer material having a first analyte concentration. The first analyte concentration may be a low concentration. For example, the first concentration can be at or near the lowest concentration of a range of concentrations to be sensed by the analyte sensor circuit 4100 in use. In some examples, the first concentration is in a lowest 25% of the range. The current generated by the analyte sensor circuit 4100 in the presence of the first analyte concentration is measured.

At operation 4204, the resistor 4112 is trimmed based on the current measured at operation 4202. Trimming the resistor 4112 can include applying laser trimming, lithography, or another suitable method to remove a portion of the material making up the resistor 4112. The resistor 4112 can be trimmed to cause the measured current at the first concentration to have a desired value. For example, the resistor 4112 can be trimmed to cause the measured current at the first concentration to be greater than zero. In some examples, the analyte sensor circuit 4100 is again exposed to the buffer at the first analyte concentration after trimming to verify that the desired current has been achieved. If the desired current has not been achieved, the resistor 4112 can be further trimmed.

At operation 4206, the analyte sensor 4102 is exposed to a second buffer having a second concentration of analyte. The second concentration of analyte is greater than the first concentration and, in some examples, is at or near a highest concentration of a range of concentrations to be sensed by the analyte sensor circuit 4100 in use. The current generated by the analyte sensor 4102 at the second concentration is measured.

At operation 4208, the resistor 4108 is trimmed to achieve a desired sensitivity for the analyte sensor circuit 4100. Trimming the resistor 4108 can include applying laser trimming, lithography, or another suitable method to remove a portion of the material making up the resistor 4108. For example, the resistor 4108 may be trimmed to a resistance level that causes the current generated by the analyte sensor 4102 to be at a high end of an expected range.

When an analyte sensor is inserted into the skin of a host, the host will sometimes apply pressure to the skin at or around the insertion point. For example, the host may sit or lay in a manner that causes all or most of the host's weight to compress the skin against a chair, bed, floor, wall, or other surface. When the skin is compressed, it can sometimes restrict fluid flow to the compressed area. This can reduce the natural flow of the analyte to and from the sensor. As a result, the sensor may provide readings that are lower than the host's actual analyte concentration. When compression of the hosts skin causes an analyte sensor to provide an inaccurately low reading, it is referred to herein as a compression low.

Consider an example in which the analyte is glucose and the analyte sensor is a continuous glucose sensor. If the host lies on or otherwise applies pressure to the sensor insertion site, the continuous glucose sensor may alert the user to a perceived low glucose condition although such a condition may not actually exist. This can reduce the trust of the host in the continuous glucose sensor. Also, if the compression low occurs while the host is sleeping, the continuous glucose sensor may awaken the user unnecessarily.

Various examples are directed to detecting and responding to compression lows in analyte sensors. In some examples, sensor electronics 106 (FIG. 1) or another suitable device is programmed to monitor analyte concentration values generated by an analyte sensor as well as the measured impedance of the sensor membrane. A compression low may be accompanied by a reduction in the membrane impedance. The device can be programmed to detect a compression low if the analyte concentration drops at a rate of change greater than a rate of change threshold while the resistance of the sensor membrane also drops.

Figure 43:
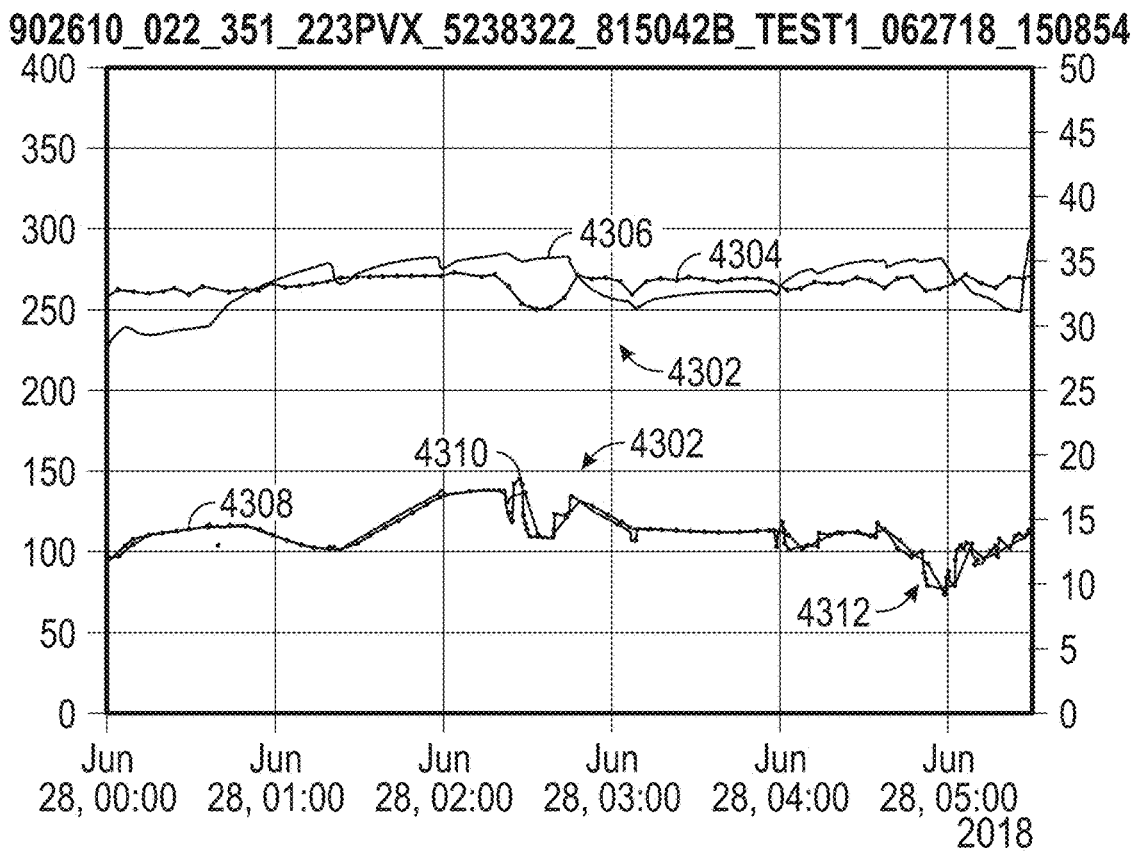
FIG. 43 is a diagram including various curves showing an example compression low in a continuous glucose sensor.

FIG. 43 is a diagram including various curves showing an example compression low 4302 in a continuous glucose sensor. Although FIG. 43 describes a continuous glucose sensor, similar effects are believed to be exhibited by other types of analyte sensors. The curve 4308 shows glucose concentration values returned by the sensor at five (5) minute intervals. A curve 4310 shows glucose concentration values returned by the sensor at thirty (30) second intervals. A curve 4306 shows a temperature at the sensor. A curve 4304 shows membrane impedance, for example, measured using the technique described herein with reference to FIGS. 5A-5F.

At the compression low 4302, the glucose concentration value curves 4308 and 4310 exhibit a drop. The membrane impedance curve 4304, as shown, exhibits a corresponding drop. Note that at a second low glucose event 4312 not caused by compression, there is no corresponding drop in the membrane impedance curve 4304.

Figure 44:
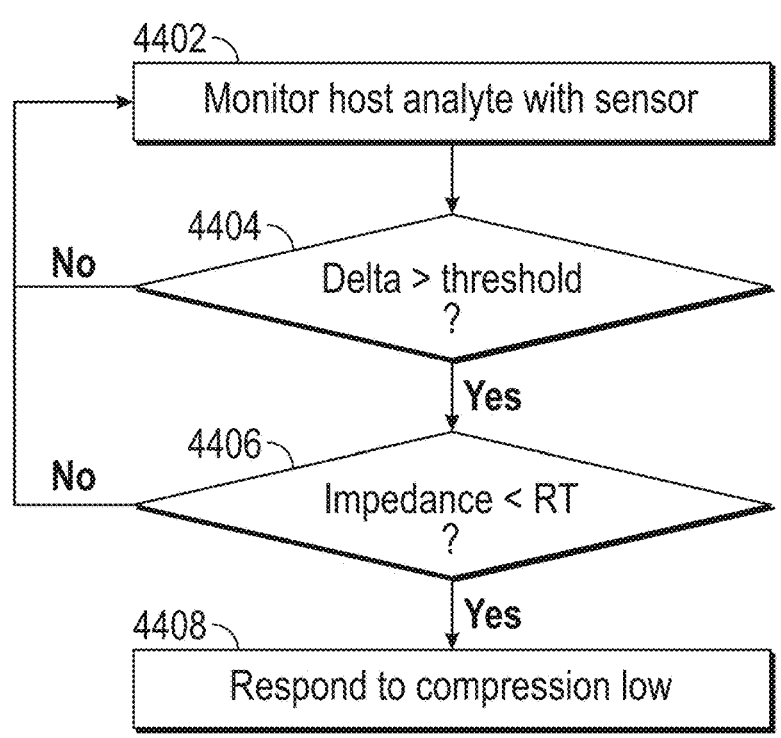
FIG. 44 is a flowchart illustration of an example method for detecting and responding to compression lows in an analyte sensor.

FIG. 44 is a flowchart illustration of an example method 4400 for detecting and responding to compression lows in an analyte sensor. The method 4400 can be executed by sensor electronics 106 (FIG. 1) or another suitable device associated with an analyte sensor. At operation 4402, the device monitors an analyte concentration at a host with the analyte sensor. This can include, for example, monitoring the current signal generated by an analyte sensor, such as the sensor 34 of FIGS. 3A-3C. Monitoring the analyte concentration at a host can also include applying a sensitivity to the generated current signal to determine an analyte concentration. In some examples, the analyte concentration is measured periodically (e.g., every 30 seconds, every 5 minutes).

At operation 4404, the device determines if a rate of reduction in the analyte concentration level is greater than a threshold. For example, the threshold can indicate a highest rate of reduction in the analyte expected in the host. If the rate of reduction is not greater than the threshold, it may indicate that the analyte concentration readings generated by the sensor are not the result of a compression low. The device can continue to monitor the host's analyte concentration at operation 4402.

If the rate of reduction in the analyte concentration level is greater than the threshold, then the device may, at operation 4406, determine if the membrane impedance at the sensor meets a membrane impedance condition. The impedance of the sensor membrane can be determined, for example, using any of the devices or methods described herein.

In some examples, the membrane impedance condition is met when the membrane impedance is less than a threshold impedance. Also, in some examples, the membrane impedance condition is met if a rate of reduction in the membrane impedance is greater than an impedance rate threshold. In some examples, the membrane impedance condition is met if the value of the membrane impedance is less than the threshold impedance and the rate of reduction in the membrane impedance is greater than the impedance rate threshold. In some examples, the membrane impedance condition is met if the value of the membrane impedance is less than the threshold impedance or if the rate of reduction in the membrane impedance is greater than the impedance rate threshold.

If the membrane impedance condition is not met, then a compression low may not be occurring. The device may continue to monitor the host's analyte concentration at operation 4402. If the membrane impedance condition is met, then a compression low may be occurring. The device responds to the compression low at operation 4408.

The device can respond to the compression low in any suitable manner. In some examples, the device responds to the compression low by suspending the reporting of analyte concentration values from the sensor at a user interface, such as the user interface 252 or the user interface 272 described herein. In some examples, the device responds by applying a correction factor to the analyte concentration values generated by the sensor until the compression low condition is no longer present. The device can detect that the compression low condition is no longer present, for example, by detecting an increase in the analyte concentration, an increase in the membrane impedance, or both.

Figure 45:
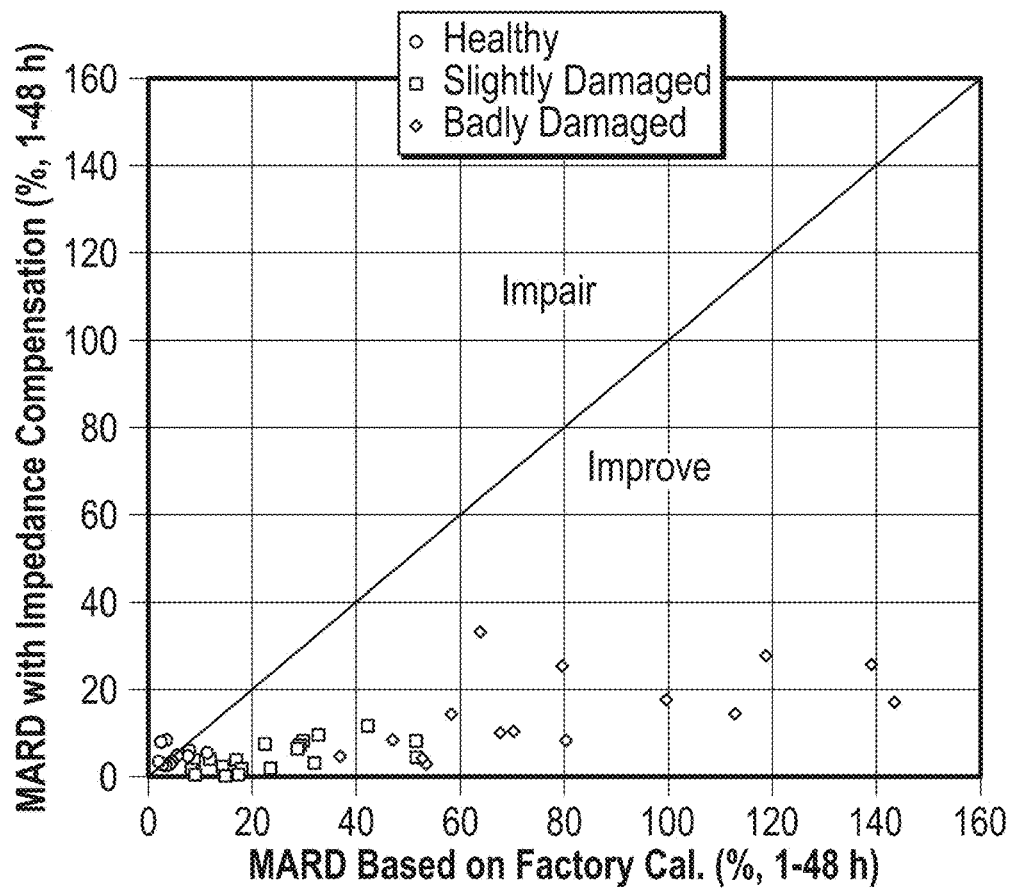
FIG. 45 is a plot showing example results of the experiment indicating a MARD with impedance compensation versus a MARD based on factory calibration.
Figure 46:
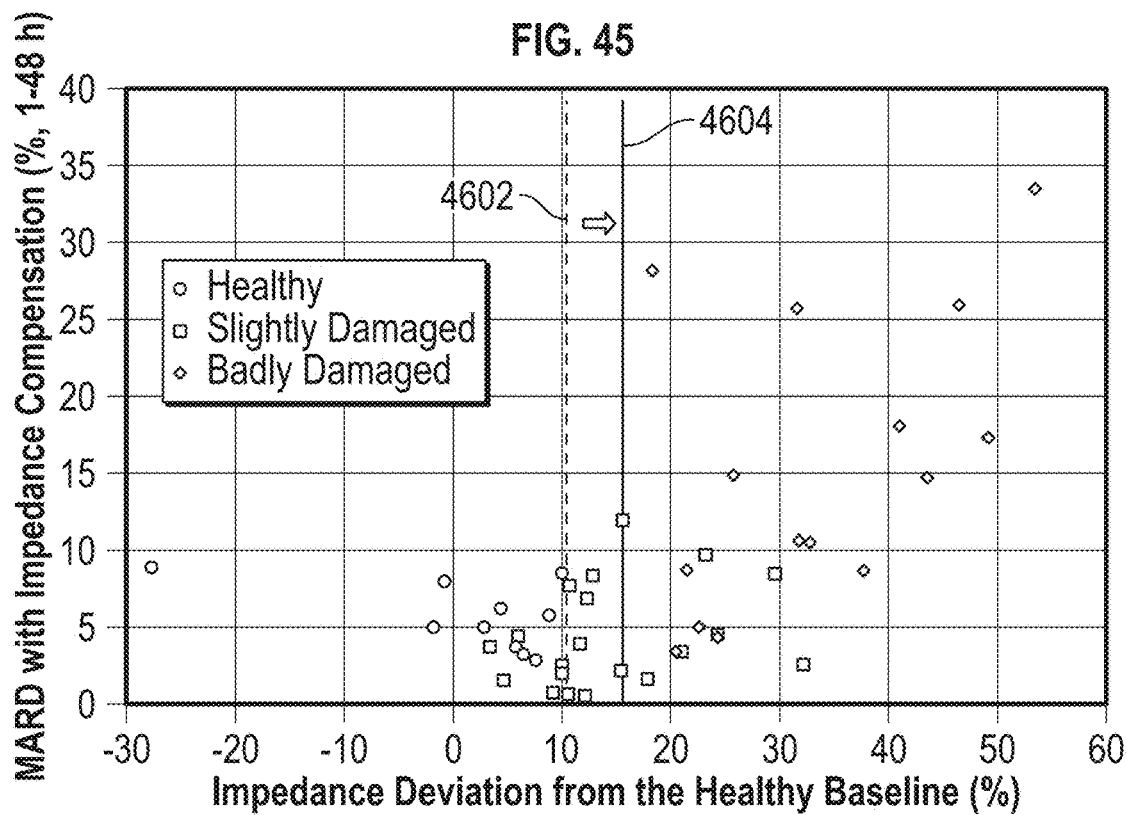
FIG. 46 is a plot showing example results of an experiment indicating sensor MARD with impedance compensation versus impedance deviation from a healthy baseline.
Figure 47:
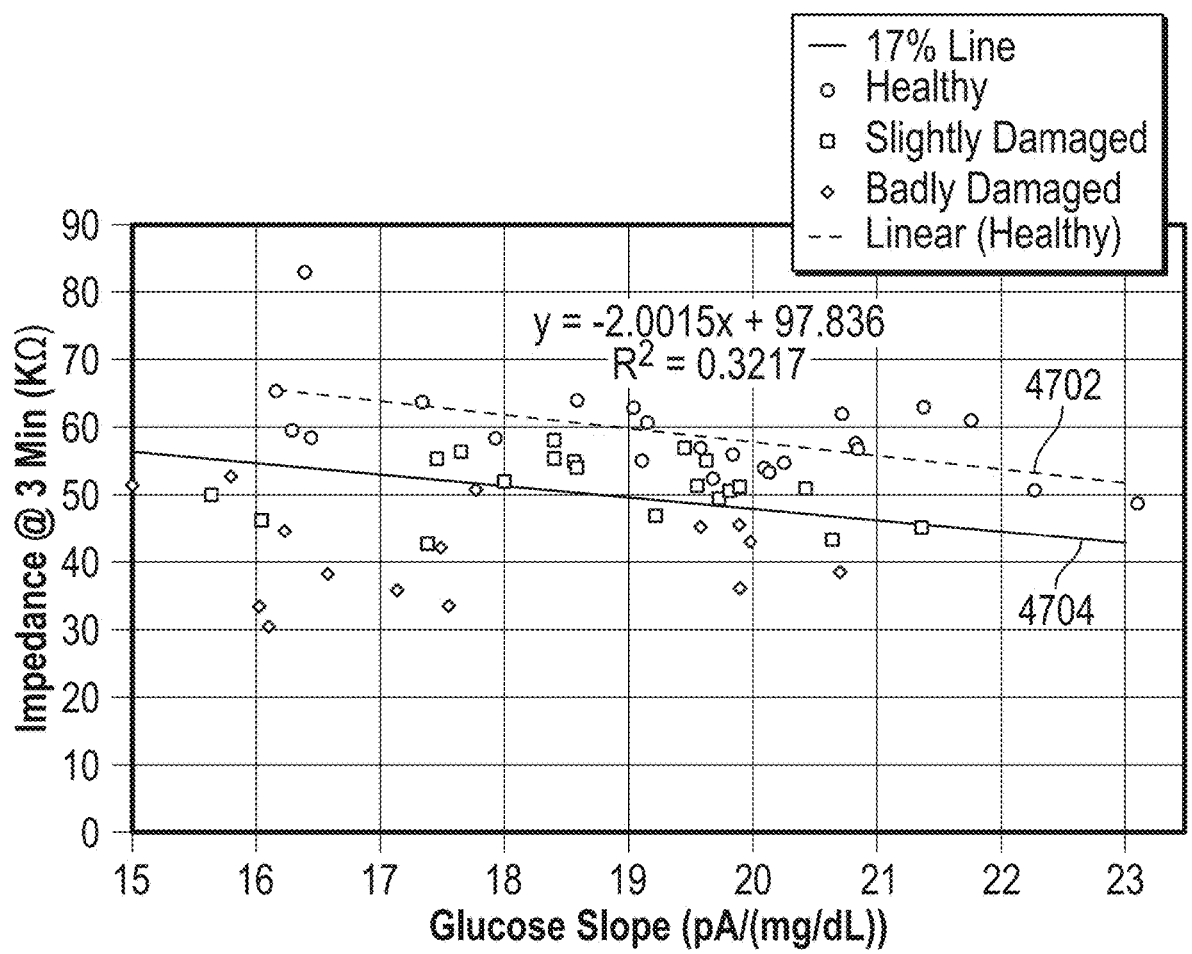
FIG. 47 is an example plot of an experiment described herein showing sensor impedance at three minutes from insertion versus glucose slope.

FIGS. 45-47 show results of additional experiments that were run to demonstrate the effectiveness of using impedance compensation to compensate for damaged sensors. Dexcom G6 sensor systems were used, both with and without impedance compensation. When used without impedance compensation, a standard commercial factory calibration was used. When used with impedance compensation, the impedance compensation was determined using the technique described herein with respect to FIGS. 30A-30G, although it is believed that similar results can be achieved with any suitable impedance compensation technique.

The experiments described by FIGS. 45-47 were run with a set of sensors that were healthy, a set of sensors that were slightly damaged, and a set of sensors that were badly damaged. Referring to the scale introduced herein with respect to FIGS. 12D-12H, sensors that were healthy had a damage level of 0. Sensors that were slightly damaged had a damage level between 1 and 4. Sensors that were badly damaged had a damage level greater than 5.

FIG. 45 is a plot showing example results of the experiment indicating a MARD with impedance compensation versus a MARD based on factory calibration. On the horizontal axis, which shows MARD based on factory calibration, it will be observed that sensors that health sensors generally exhibited a MARD of less than 10. Slightly damaged sensors generally exhibited a MARD of less than 50, with badly damaged sensors exhibiting MARDs of around 40 and above. The vertical axis shows sensor MARDs for the indicated sensors with impedance compensation. As shown, all of the healthy and slightly damaged sensors show MARDs of about 10 or less, which may be suitable for use.

FIG. 46 is a plot showing example results of an experiment indicating sensor MARD with impedance compensation versus impedance deviation from a healthy baseline. Impedance deviation from the healthy baseline is a threshold describing how much lower the impedance of a sensor can be than the healthy baseline impedance before the sensor is unsuitable for use. FIG. 46 shows a first threshold 4602. As shown, all of the healthy sensors to the left of the first threshold 4602 have a MARD of less than 10. With compensation, however, slightly damaged sensors above the first threshold 4602 also have a MARD of less than 10. Accordingly, the use of impedance compensation, as described herein, may make it possible to increase sensor yield by utilizing a higher, second threshold 4604 that passes more sensors. For example, sensors with impedance deviations less than the second threshold 4604 may exhibit acceptable MARDs (e.g., less than 10). This allows slightly damaged sensors that might otherwise have been discarded to be used and provide suitable accuracy.

FIG. 47 is an example plot of the experiment described herein showing sensor impedance at three minutes from insertion versus glucose slope. The glucose slope indicates a relationship between sensor current (in picoamps) and the corresponding glucose concentration at the sensor (in mg/dL).

FIG. 47 also shows a healthy line 4702 that indicates a threshold for passing sensors. For example, sensors within a threshold distance of the healthy line 4702 are passed for use while sensors that are more than a threshold distance are not passed and may be discarded. In the example experiment described by FIG. 47, the use of impedance adjusted sensitivity allowed the healthy line to be shifted by 17% to generate a 17% line 4704. Sensors within the threshold of the 17% line exhibit acceptable accuracy and may be passed for use.

Each of these non-limiting examples in any portion of the above description may stand on its own or may be combined in various permutations or combinations with one or more of the other examples.

The above detailed description includes references to the accompanying drawings, which form a part of the detailed description. The drawings show, by way of illustration, specific embodiments in which the subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," "third," etc., are used merely as labels, and are not intended to impose numerical requirements on their objects.

Geometric terms, such as "parallel", "perpendicular", "round", or "square" are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the subject matter should be determined with reference to the claims, along with the full scope of equivalents to which such claims are entitled.

What is claimed is:

1. An analyte sensor system, comprising:
   an analyte sensor comprising a working electrode and a reference electrode, the reference electrode comprising a material that is depleted during use of the analyte sensor; and
   a hardware device in communication with the analyte sensor, wherein the hardware device is configured to perform operations comprising:
   applying a first bias voltage to the working electrode of the analyte sensor, the first bias voltage less than an operational bias voltage of the working electrode of the analyte sensor;
   measuring a first current at the analyte sensor when the first bias voltage is applied;
   applying a second bias voltage to the working electrode of the analyte sensor;
   measuring a second current at the analyte sensor when the second bias voltage is applied;
   detecting a plateau bias voltage using the first current and the second current, wherein the plateau bias voltage is the bias voltage at which a current response stops;
   determining if the plateau bias voltage is greater than a plateau bias voltage threshold; and
   executing, in response to determining that the plateau bias voltage is greater than the plateau bias voltage threshold, a responsive action at the analyte sensor.

2. The analyte sensor system of claim 1, wherein applying the first bias voltage and applying the second bias voltage comprises continuously sweeping the first bias voltage and the second bias voltage of the analyte sensor along a range including the first bias voltage and the second bias voltage.

3. The analyte sensor system of claim 1, wherein detecting the plateau bias voltage comprises determining that the first current is less than a current threshold.

4. The analyte sensor system of claim 1, the operations further comprising:
   determining a current response of the analyte sensor using the first current and the second current, wherein detecting the plateau bias voltage comprises determining a bias voltage at which a slope of the current response is about zero.

5. The analyte sensor system of claim 1, the operations further comprising:
   determining stage of life data for the analyte sensor using the plateau bias voltage; and
   displaying the stage of life data at a user interface.

6. The analyte sensor system of claim 1, wherein the responsive action comprises applying a compensation to a third sensor current generated by the analyte sensor.

7. The analyte sensor system of claim 1, wherein the responsive action comprises:
   ceasing to provide a bias current to the analyte sensor; and
   displaying at a user interface an indication that a sensor session for the analyte sensor is ended.

8. The analyte sensor system of claim 1, wherein the analyte sensor is a glucose sensor.

9. The analyte sensor system of claim 1, wherein the analyte sensor is a transcutaneous sensor.

10. A method of operating an analyte sensor, comprising:
    applying a first bias voltage to a working electrode of the analyte sensor, the first bias voltage less than an operational bias voltage of the working electrode of the analyte sensor;
    measuring a first current at the analyte sensor when the first bias voltage is applied;
    applying a second bias voltage to the working electrode of the analyte sensor;
    measuring a second current at the analyte sensor when the second bias voltage is applied;
    detecting a plateau bias voltage using the first current and the second current;
    determining if the plateau bias voltage is greater than a plateau bias voltage threshold; and
    executing, in response to determining that the plateau bias voltage is greater than the plateau bias voltage threshold, a responsive action at the analyte sensor.

11. The method of claim 10, wherein applying the first bias voltage and applying the second bias voltage comprises continuously sweeping the first bias voltage and the second bias voltage of the analyte sensor along a range including the first bias voltage and the second bias voltage.

12. The method of claim 10, wherein detecting the plateau bias voltage comprises determining that the first current is less than a current threshold.

13. The method of claim 10, further comprising:
    determining a current response of the analyte sensor using the first current and the second current, wherein detecting the plateau bias voltage comprises determining a bias voltage at which a slope of the current response is about zero.

14. The method of claim 10, further comprising:
    determining stage of life data for the analyte sensor using the plateau bias voltage; and
    displaying the stage of life data at a user interface.

15. The method of claim 10, wherein the responsive action comprises applying a compensation to a third sensor current generated by the analyte sensor.

16. The method of claim 10, wherein the responsive action comprises:
    ceasing to provide a bias current to the analyte sensor; and
    displaying at a user interface an indication that a sensor session for the analyte sensor is ended.

17. The method of claim 10, wherein the analyte sensor is a glucose sensor.

18. The method of claim 10, wherein the analyte sensor is a transcutaneous sensor.

\* \* \* \* \*